US012805186B2

(12) United States Patent
Lu et al.

(10) Patent No.: US 12,805,186 B2
(45) Date of Patent: Nov. 17, 2026

(54) BENZOXAZOLE DERIVATIVE AND ELECTROLUMINESCENT APPLICATION THEREOF

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Tingting Lu, Shanghai (CN); Wenpeng Dai, Shanghai (CN); Wei Gao, Shanghai (CN); Yi Liu, Shanghai (CN)

(73) Assignees: WUHAN TIANMA MICROELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 1003 days.

(21) Appl. No.: 18/067,737

(22) Filed: Dec. 19, 2022

(65) Prior Publication Data

US 2023/0139051 A1 May 4, 2023

(30) Foreign Application Priority Data

Jul. 26, 2022 (CN) ........................ 202210883191.5

(51) Int. Cl.

| | |
|---|---|
| ***C07D 498/04*** | (2006.01) |
| ***C09K 11/06*** | (2006.01) |
| ***H10K 85/30*** | (2023.01) |
| ***H10K 85/60*** | (2023.01) |
| *H10K 50/16* | (2023.01) |
| *H10K 101/30* | (2023.01) |

(52) U.S. Cl.

CPC ......... *H10K 85/654* (2023.02); *C07D 498/04* (2013.01); *C09K 11/06* (2013.01); *H10K 85/30* (2023.02); *H10K 85/615* (2023.02); *H10K 85/626* (2023.02); *H10K 85/657* (2023.02); *C09K 2211/1018* (2013.01); *H10K 50/16* (2023.02); *H10K 2101/30* (2023.02)

(58) Field of Classification Search

CPC .................................................... C07D 498/04

See application file for complete search history.

(56) References Cited

FOREIGN PATENT DOCUMENTS

| | | | |
|---|---|---|---|
| CN | 112851649 | A | 5/2021 |
| CN | 113429395 | A | 9/2021 |
| CN | 113501824 | A | 10/2021 |
| KR | 20200100972 | A | 8/2020 |
| WO | 2015020399 | A1 | 2/2015 |
| WO | 2015190718 | A1 | 12/2015 |

OTHER PUBLICATIONS

Office Action of Chinese Patent Application No. 202210883191.5 Mailed Mar. 25, 2023.

*Primary Examiner* — Bruck Kifle

(74) *Attorney, Agent, or Firm* — KILPATRICK TOWNSEND & STOCKTON LLP

(57) ABSTRACT

In the benzoxazole derivatives provided by the present disclosure, by defining the structure of the benzoxazole group and introducing at least two aromatic groups between the benzoxazole group and the triazine group, the two electron withdrawing groups in the benzoxazole and triazine can be effectively separated, avoiding the energy level drop caused by the proximity of the two electron withdrawing groups, and the triplet energy level of the molecule can be effectively adjusted, and the whole molecule has appropriate HOMO and LUMO values, to effectively improve the electron transport ability, and provide the benzoxazole derivatives with high electron mobility, excellent thermal stability and film stability, which is beneficial to improving luminous efficiency, formula I

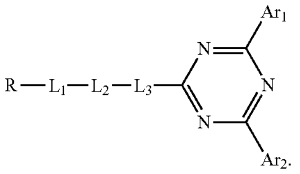

2 Claims, No Drawings

BENZOXAZOLE DERIVATIVE AND ELECTROLUMINESCENT APPLICATION THEREOF

CROSS REFERENCE TO RELATED APPLICATIONS

This application claims the priority of Chinese Patent Application No. 202210883191.5, filed with the China National Intellectual Property Administration on Jul. 26, 2022, and titled with "BENZOXAZOLE DERIVATIVE AND ELECTROLUMINESCENT APPLICATION THEREOF", which is hereby incorporated by reference.

FIELD

The present disclosure relates to the field of organic electroluminescent materials, and in particular to a benzoxazole derivative and an electroluminescent application thereof.

BACKGROUND

The electron transport material used in traditional electroluminescent devices is Alq3, but the electron mobility of Alq3 is relatively low (about $10^{-6}$ $cm^2/Vs$), which makes the electron transport and hole transport of the device unbalanced. With the commercialization and practical application of electroluminescent devices, ETL materials with higher transport efficiency and better performance are expected, in the field of which researchers have done a lot of exploratory work.

The glass transition temperature of current materials is low, generally lower than 85 °C. When the device is running, the Joule heat generated will lead to molecular degradation and changes in molecular structure, resulting in low efficiency and poor thermal stability of the panel. The materials are easy to be crystallized after a long time, and the intermolecular charge transition mechanism thereof will be different from the mechanism of the amorphous thin film under the normal operation, resulting in a decrease in the performance of electron transport.

It is of very important practical application value to design and develop stable and efficient electron transport materials and/or electron injection materials that can have both high electron mobility and high glass transition temperature, and are effectively doped with metal Yb or Liq, to reduce threshold voltage, improving efficiency of device, and prolonging lifetime of device.

SUMMARY

In view of this, the problem to be solved by the present disclosure is to provide a benzoxazole derivative and an electroluminescent application thereof, which can effectively improve the lifetime and efficiency of the device.

The present disclosure provides a benzoxazole derivative having the structure as shown in formula I:

formula I

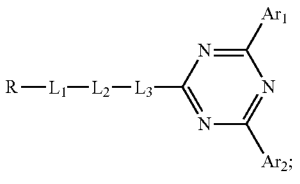

R has any of the following structures:

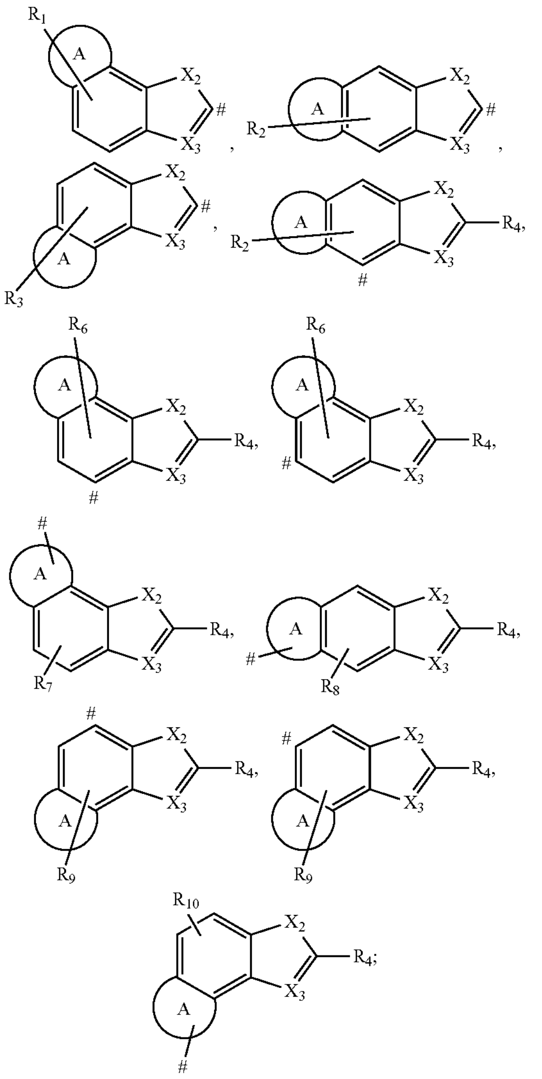

A is

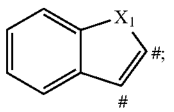

$X_1$, $X_2$, $X_3$ are independently selected from the group consisting of N, O, S or Si;

$R_1$, $R_2$, $R_3$, $R_4$, $R_5$, $R_6$, $R_7$, $R_8$, $R_9$, $R_{10}$ are independently selected from the group consisting of H, D, halogen, cyano, substituted or unsubstituted aryl or heteroaryl;

$L_1$, $L_2$, $L_3$ are independently selected from the group consisting of single bonds, substituted or unsubstituted aryl or heteroaryl, and at least two of $L_1$, $L_2$, and $L_3$ are not single bonds;

$Ar_1$ and $Ar_2$ are independently selected from the group consisting of substituted or unsubstituted aryl or heteroaryl;

# indicates the linking site.

The present disclosure provides an organic light-emitting device, the organic light-emitting device includes an anode, a cathode, and an organic thin film layer located between the anode and the cathode, and the organic thin film layer includes an electron transport layer, and the electron transport layer includes at least one of the above-mentioned benzoxazole derivatives.

The present disclosure provides a display panel comprising the above organic light-emitting device.

DETAILED DESCRIPTION

The present disclosure provides a benzoxazole derivative having a structure as shown in formula I.

formula I

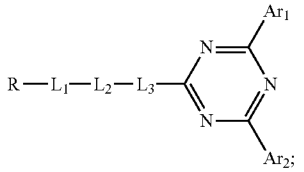

R has any of the following structures:

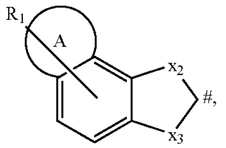

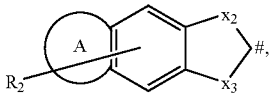

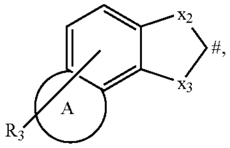

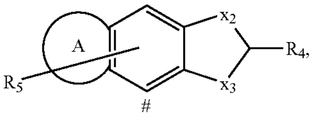

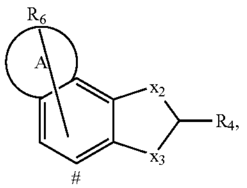

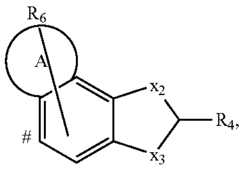

-continued

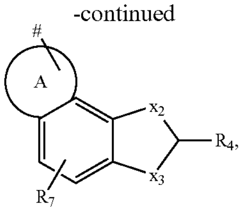

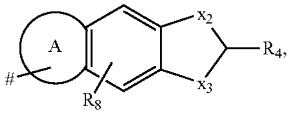

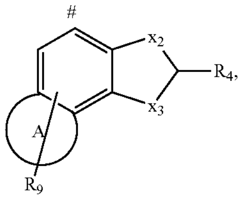

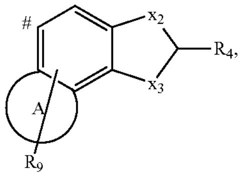

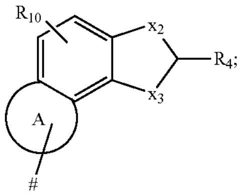

A is

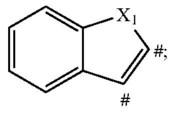

$X_1$, $X_2$, $X_3$ are independently selected from the group consisting of N, O, S or Si;

$R_1$, $R_2$, $R_3$, $R_4$, $R_5$, $R_6$, $R_7$, $R_8$, $R_9$, $R_{10}$ are independently selected from the group consisting of H, D, halogen, cyano, substituted or unsubstituted aryl or heteroaryl;

$L_1$, $L_2$, $L_3$ are independently selected from the group consisting of single bonds, substituted or unsubstituted aryl or heteroaryl, and at least two of $L_1$, $L_2$, and $L_3$ are not single bonds;

$Ar_1$ and $Ar_2$ are independently selected from the group consisting of substituted or unsubstituted aryl or heteroaryl;

# indicates the linking site.

In one embodiment, the substituents of the $R_1$, $R_2$, $R_3$, $R_4$, $R_5$, $R_6$, $R_7$, $R_8$, $R_9$, $R_{10}$, $L_1$, $L_2$, $L_3$, $Ar_1$ and $Ar_2$ are independently selected from the group consisting of D, halogen, cyano, aryl or heteroaryl.

In one embodiment, the $X_2$ is O, and the $X_3$ is N.

In one embodiment, the $X_1$ is O.

In one embodiment, the R has any of the following structures:

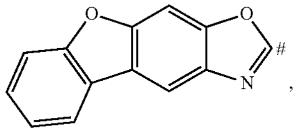
,
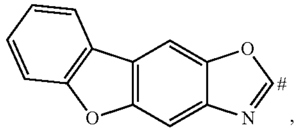
,
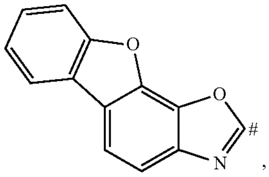
,
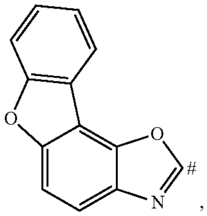
,
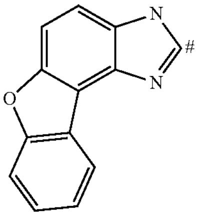
,
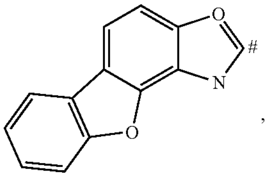
,
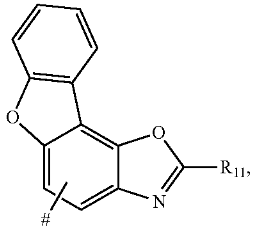

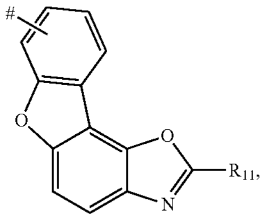

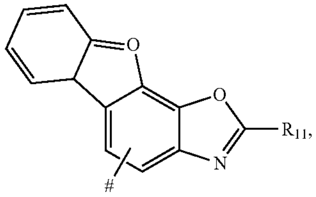

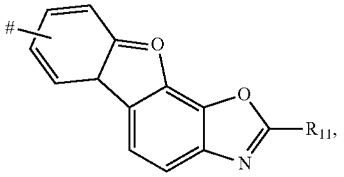

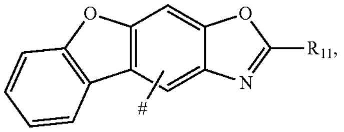

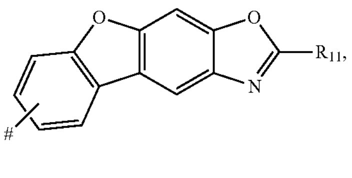

-continued

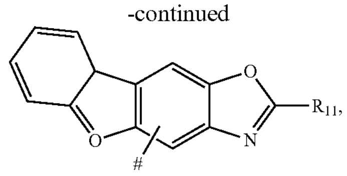

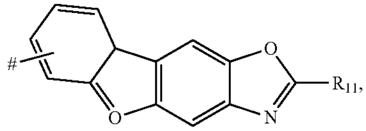

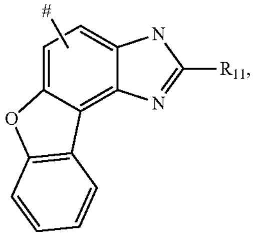

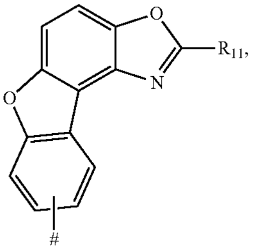

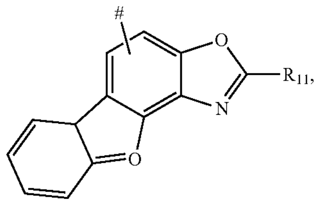

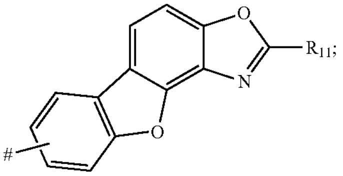

$R_{11}$ is selected from the group consisting of H, D, halogen, cyano, substituted or unsubstituted aryl or heteroaryl;

# is the linking site.

In one embodiment, the $R_{11}$ is selected from the group consisting of H, D, halogen, cyano, substituted or unsubstituted monocyclic aryl, monocyclic heteroaryl, fused aryl formed by the fusion of 2~3 aromatic rings, heteroaryl formed by the fusion of 2~3 aromatic rings and heteroaromatic rings, and heteroaryl formed by the fusion of 2~3 heteroaromatic rings.

In one embodiment, the monocyclic aryl is phenyl.

In one embodiment, the monocyclic heteroaryl is a five-membered or six-membered heteroaryl having 1~3 N atoms.

In one embodiment, the aromatic ring fused to form the fused aryl is a benzene ring.

In one embodiment, the aromatic ring fused to form the heteroaryl is a benzene ring.

In one embodiment, the heteroaromatic ring fused to form the heteroaryl is a five-membered or six-membered heteroaryl having 1~3 N atoms.

In one embodiment, the $R_{11}$ is selected from the group consisting of H, D, halogen, cyano, substituted or unsubstituted phenyl, pyridyl, pyrimidinyl, pyrazinyl, pyridazinyl, naphthyl, anthracenyl, phenanthryl, quinolinyl, isoquinolinyl, quinoxalinyl, quinazolinyl or 1,5-naphthyridinyl.

In one embodiment, the $R_1$, $R_2$, $R_3$, $R_4$, $R_5$, $R_6$, $R_7$, $R_8$, $R_9$, $R_{10}$ are independently selected from the group consisting of H, D, halogen, cyano, substituted or unsubstituted monocyclic aryl, monocyclic heteroaryl, fused aryl formed by the fusion of 2~3 aromatic rings, heteroaryl formed by the fusion of 2~3 aromatic rings and heteroaromatic rings, and heteroaryl formed by the fusion of 2~3 heteroaromatic rings.

In one embodiment, the monocyclic aryl is phenyl.

In one embodiment, the monocyclic heteroaryl is a five-membered or six-membered heteroaryl having 1~3 N atoms.

In one embodiment, the aromatic ring fused to form the fused aryl is a benzene ring.

In one embodiment, the aromatic ring fused to form the heteroaryl is a benzene ring.

In one embodiment, the heteroaromatic ring fused to form the heteroaryl is a five-membered or six-membered heteroaryl having 1~3 N atoms.

In one embodiment, the $R_1$, $R_2$, $R_3$, $R_4$, $R_5$, $R_6$, $R_7$, $R_8$, $R_9$, $R_{10}$ are independently selected from the group consisting of H, D, halogen, cyano, substituted or unsubstituted phenyl, pyridyl, pyrimidinyl, pyrazinyl, pyridazinyl, naphthyl, anthracenyl, phenanthryl, 1,10-phenanthrolinyl, quinolinyl, isoquinolinyl, quinoxalinyl, quinazolinyl or 1,5-naphthyridinyl.

In one embodiment, the $L_1$, $L_2$, $L_3$ are independently selected from the group consisting of single bonds, substituted or unsubstituted monocyclic aryl, monocyclic heteroaryl, fused aryl formed by the fusion of 2~3 aromatic rings, heteroaryl formed by the fusion of 2~3 aromatic rings and heteroaromatic rings, and heteroaryl formed by the fusion of 2~3 heteroaromatic rings, and at least two of $L_1$, $L_2$, and $L_3$ are not single bonds.

In one embodiment, the monocyclic aryl is phenyl.

In one embodiment, the monocyclic heteroaryl is a five-membered or six-membered heteroaryl having 1~3 N atoms.

In one embodiment, the aromatic ring fused to form the fused aryl is a benzene ring.

In one embodiment, the aromatic ring fused to form the heteroaryl is a benzene ring.

In one embodiment, the heteroaromatic ring fused to form the heteroaryl is a five-membered or six-membered heteroaryl having 1~3 N atoms.

In one embodiment, the $L_1$, $L_2$, $L_3$ are independently selected from the group consisting of single bonds, substituted or unsubstituted phenyl, pyridyl, pyrimidinyl, pyrazinyl, pyridazinyl, naphthyl, anthracenyl, phenanthryl, 1,10-phenanthrolinyl, quinolinyl, isoquinolinyl, quinoxalinyl, quinazolinyl or 1,5-naphthyridinyl, and at least two of $L_1$, $L_2$ and $L_3$ are not single bonds.

In one embodiment, two or three of the $L_1$, $L_2$, and $L_3$ are not single bonds.

In one embodiment, the $Ar_1$ and $Ar_2$ are independently selected from the group consisting of substituted or unsubstituted monocyclic aryl, monocyclic heteroaryl, fused aryl formed by the fusion of 2~3 aromatic rings, heteroaryl formed by the fusion of 2~3 aromatic rings and heteroaromatic rings, and heteroaryl formed by the fusion of 2~3 heteroaromatic rings, and at least two of $L_1$, $L_2$, and $L_3$ are not single bonds.

In one embodiment, the monocyclic aryl is phenyl.

In one embodiment, the monocyclic heteroaryl is a five-membered or six-membered heteroaryl having 1~3 N atoms.

In one embodiment, the aromatic ring fused to form the fused aryl is a benzene ring.

In one embodiment, the aromatic ring fused to form the heteroaryl is a benzene ring.

In one embodiment, the heteroaromatic ring fused to form the heteroaryl is a five-membered or six-membered heteroaryl having 1~3 N atoms.

In one embodiment, the $Ar_1$ and $Ar_2$ are independently selected from the group consisting of substituted or unsubstituted phenyl, pyridyl, pyrimidinyl, pyrazinyl, pyridazinyl, naphthyl, anthracenyl, phenanthryl, 1,10-phenanthrolinyl, quinolinyl, isoquinolinyl, quinoxalinyl, quinazolinyl or 1,5-naphthyridinyl.

In one embodiment, the benzoxazole derivative has any of the following structures:

A1

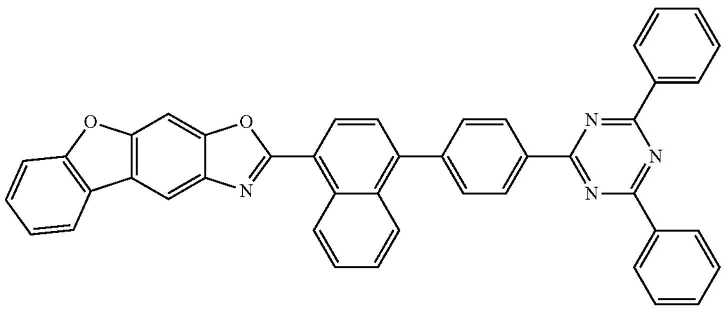

A2

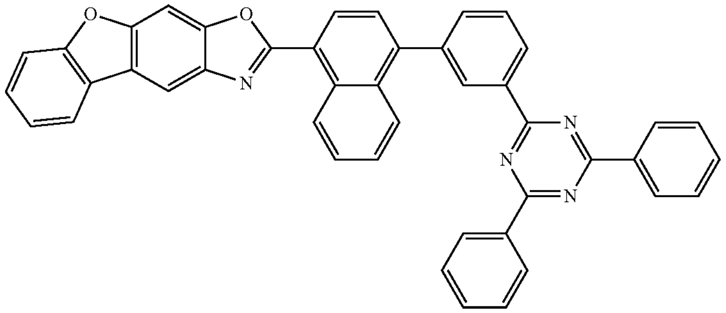

-continued
A3
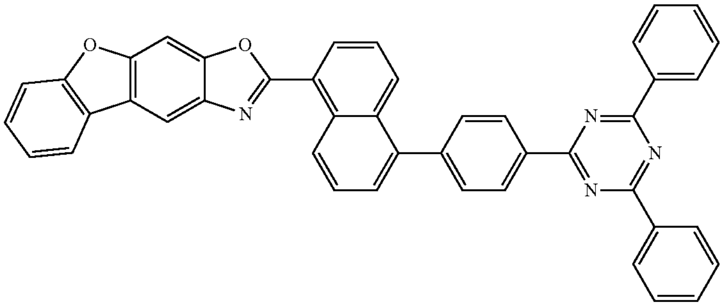
A4
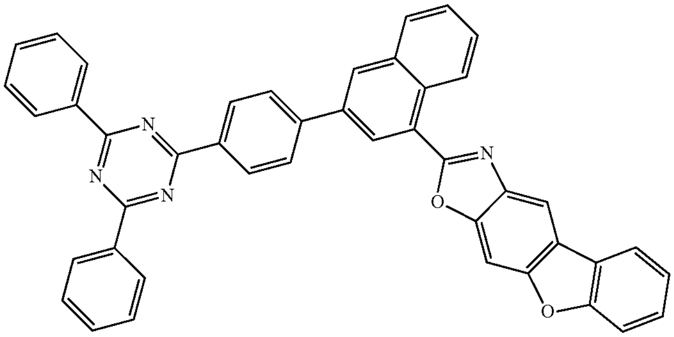
A5
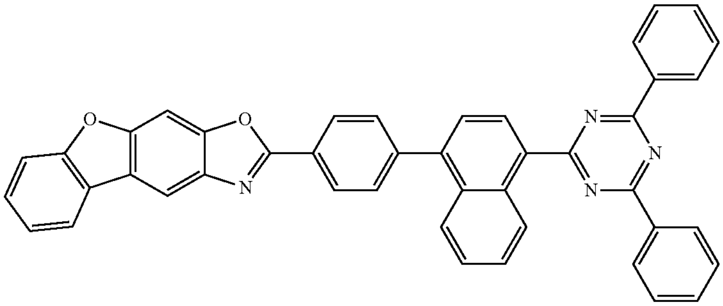
A6
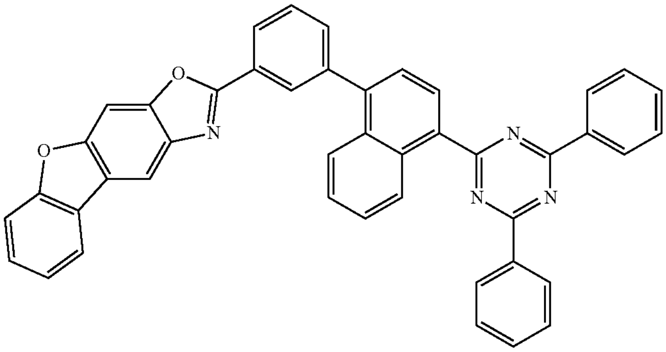
A7
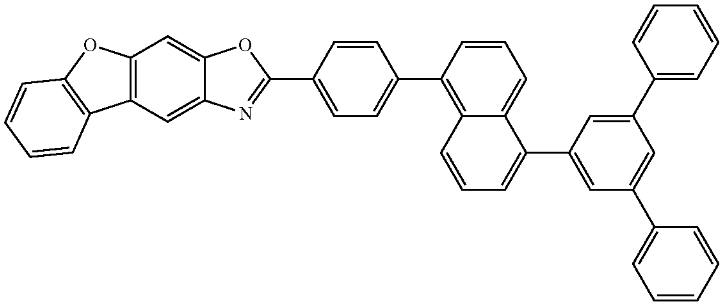

-continued
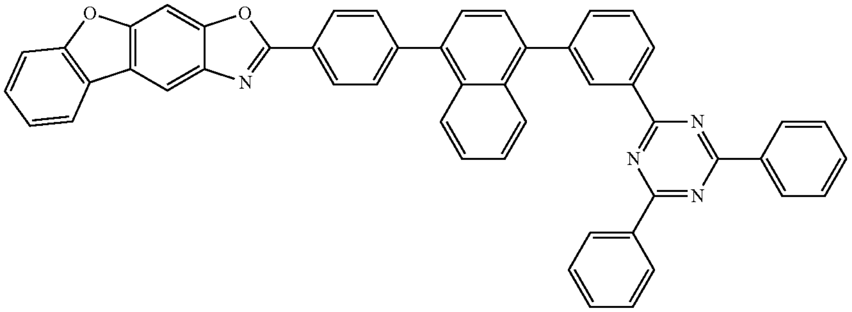
A8
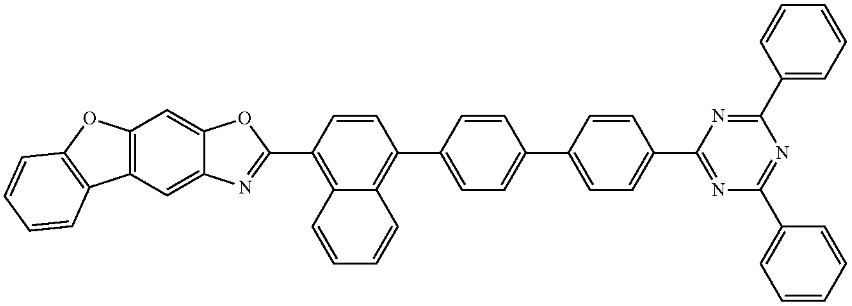
A9
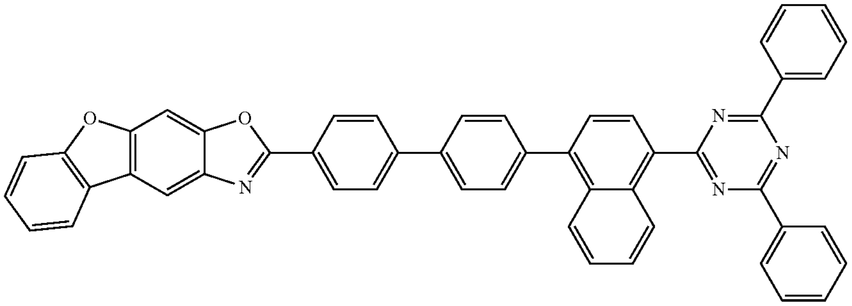
A10
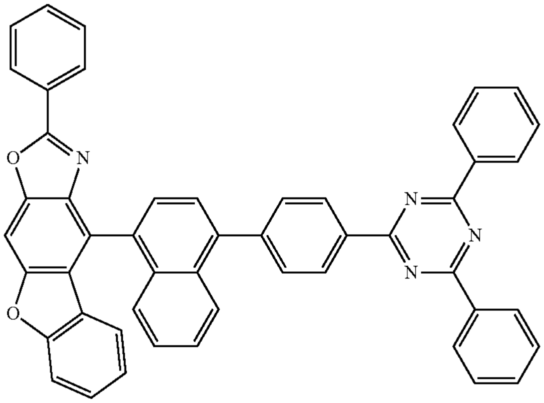
A11

-continued
A12
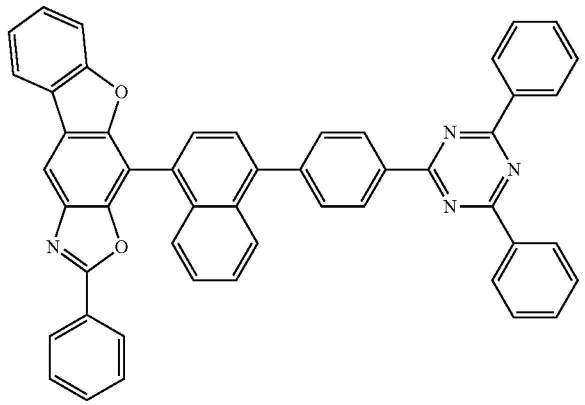
A13
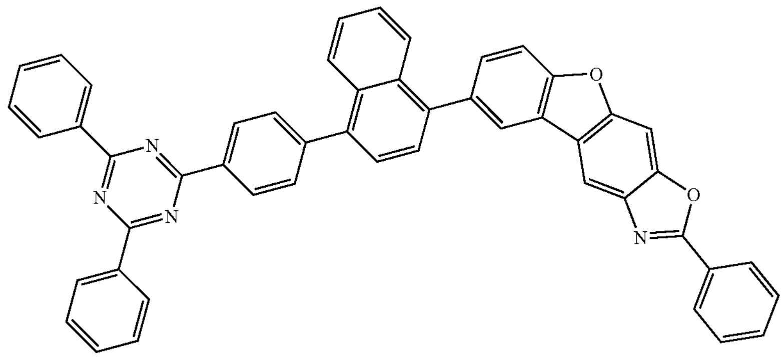
A14
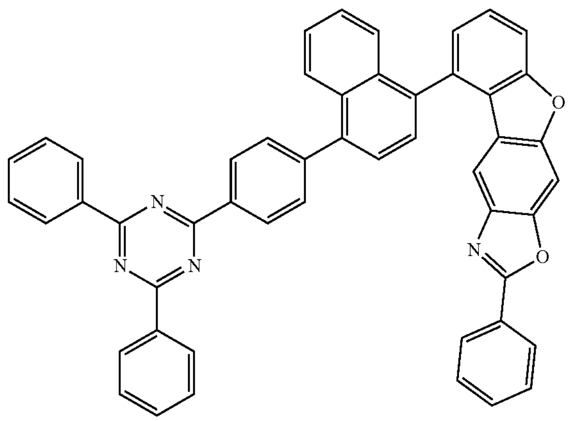
A15
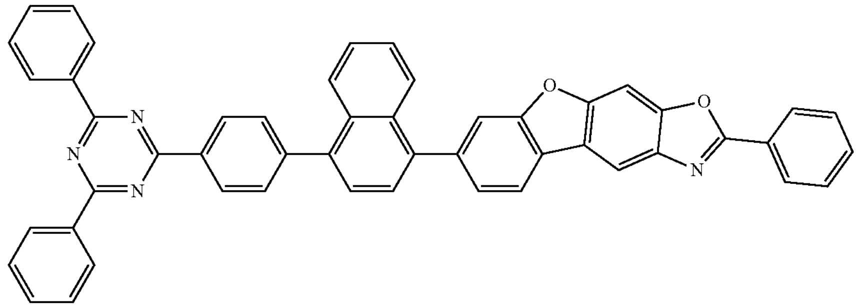

-continued
A16
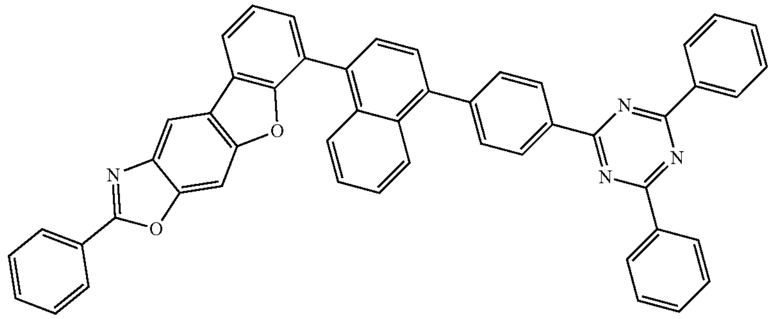
A17
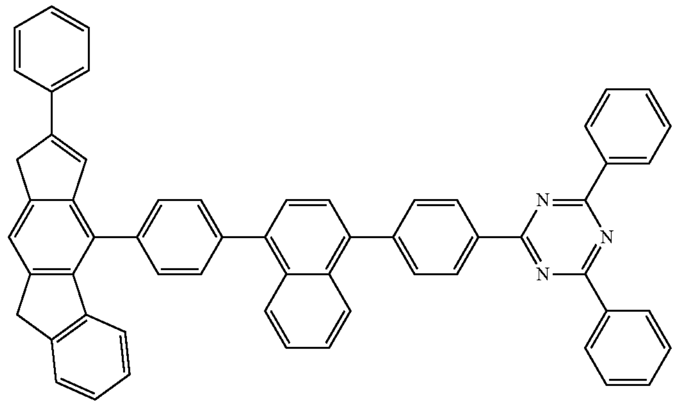
A18
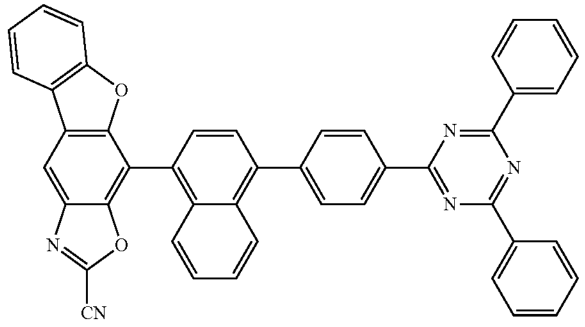
A19
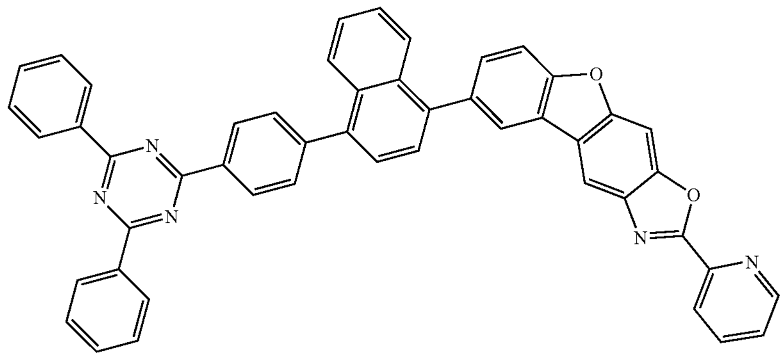

-continued
A20
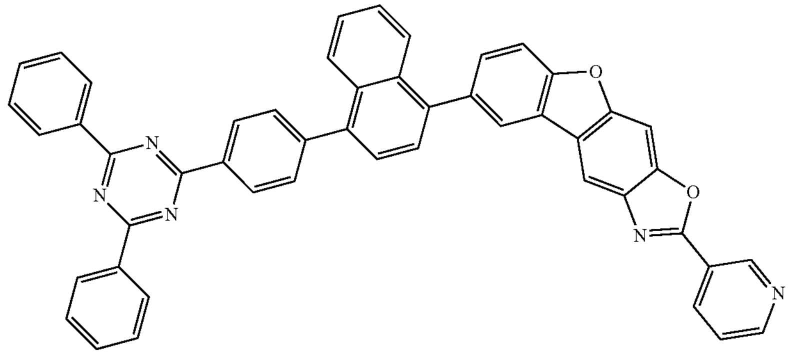
A21
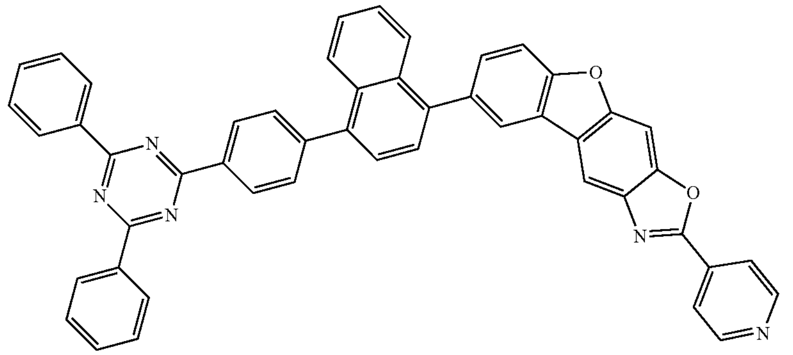
A22
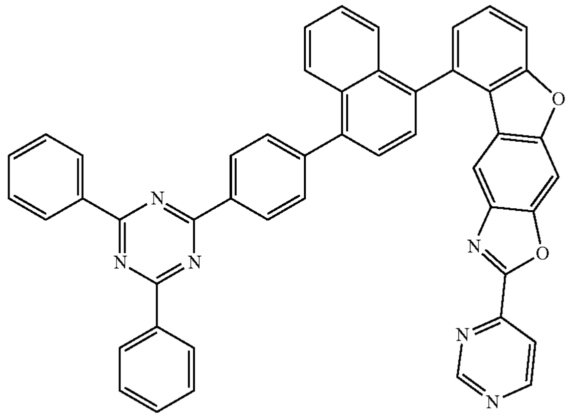
A23
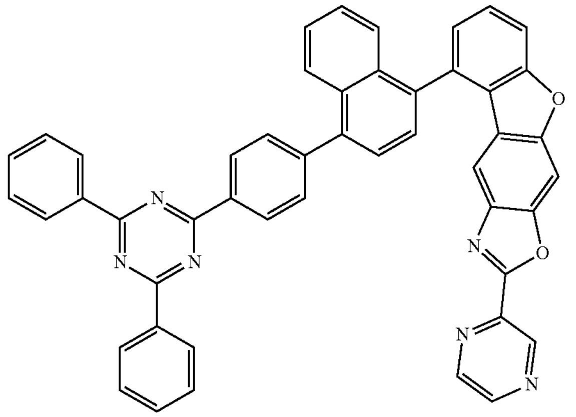

-continued
A24
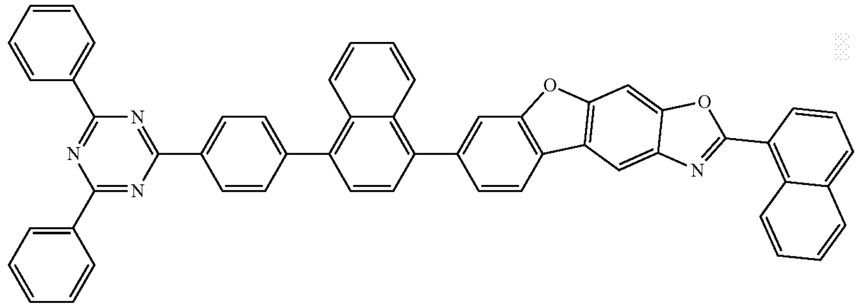
A25
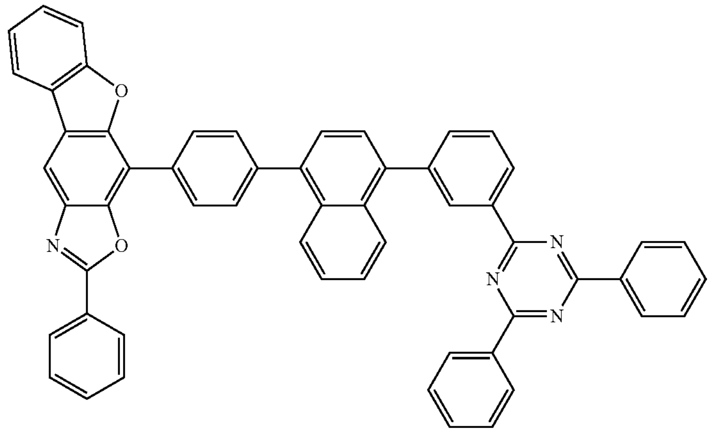
A26
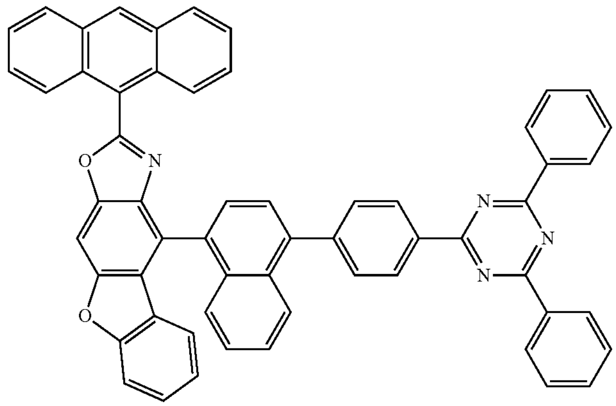
A27
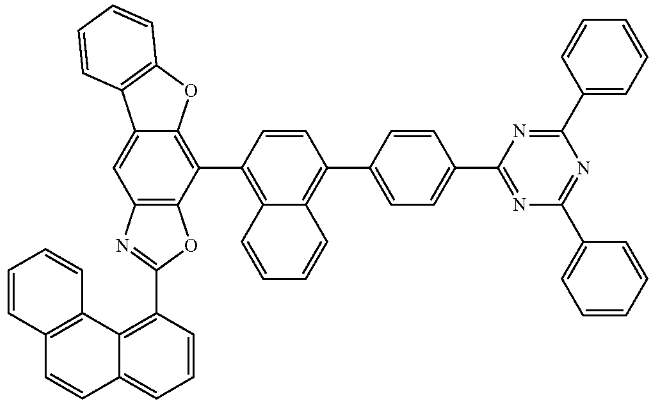

-continued
A28
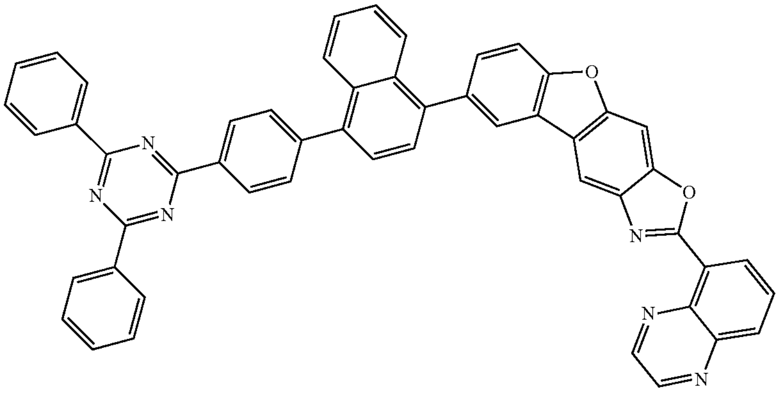
A29
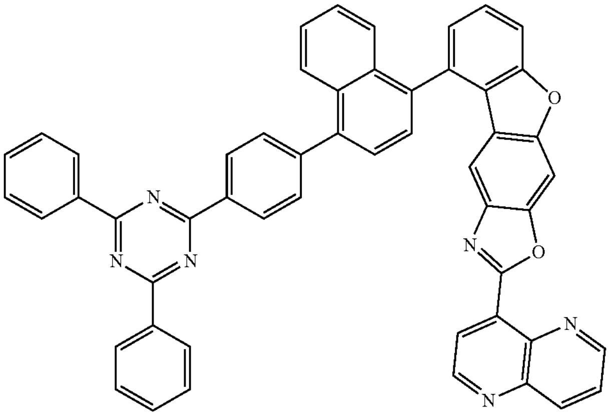
A30
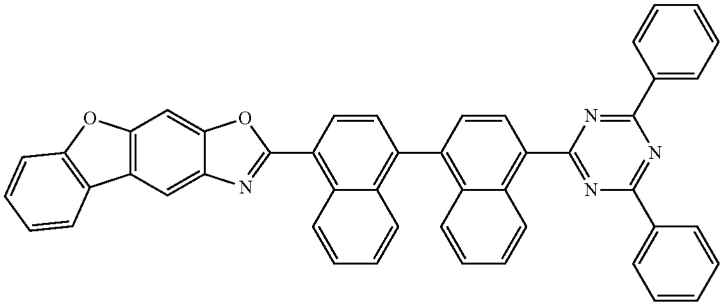
A31
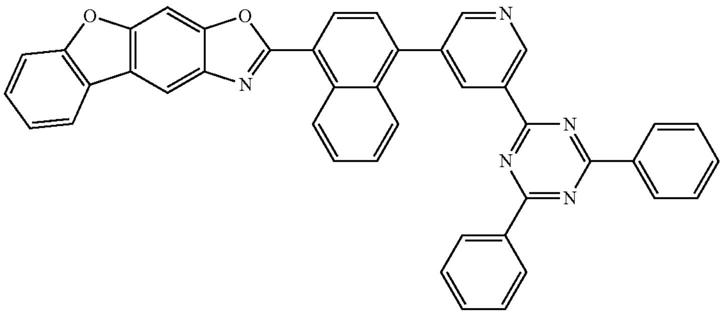

-continued
A32
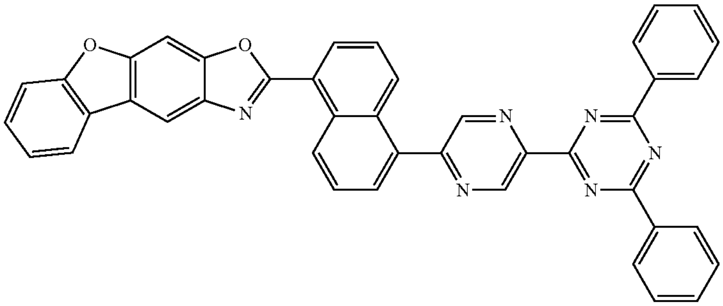
A33
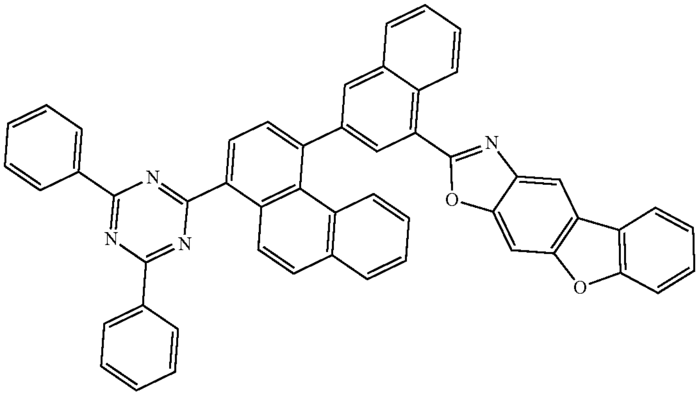
A34
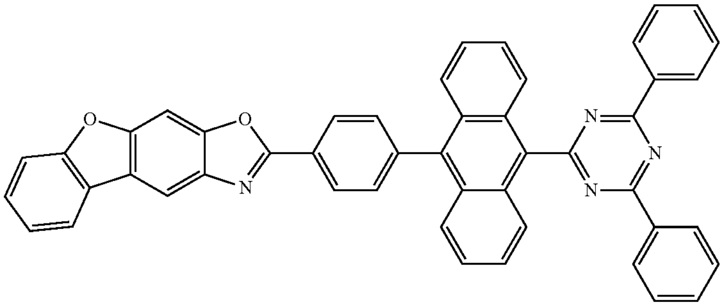
A35
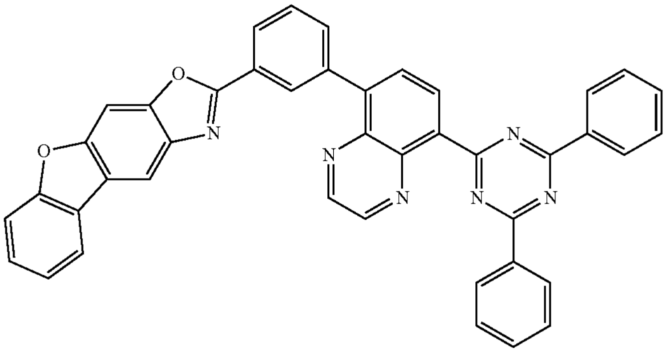

-continued
A36
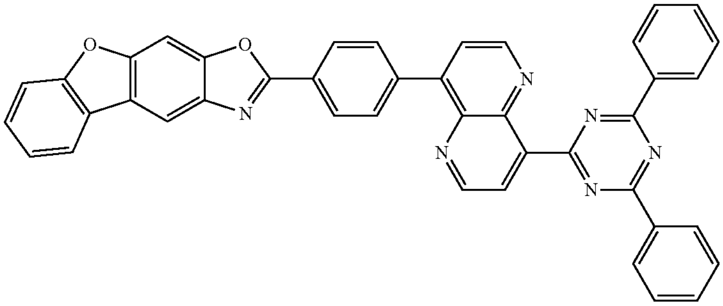
A37
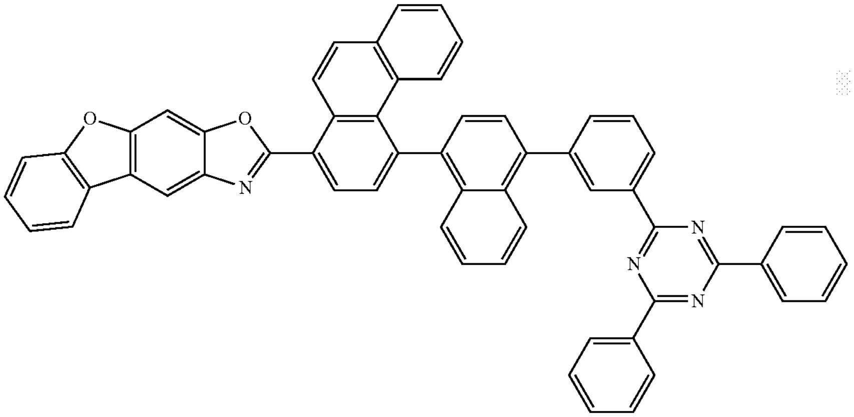
A38
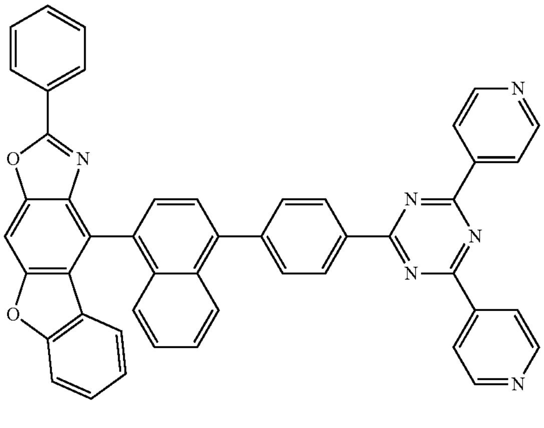
A39
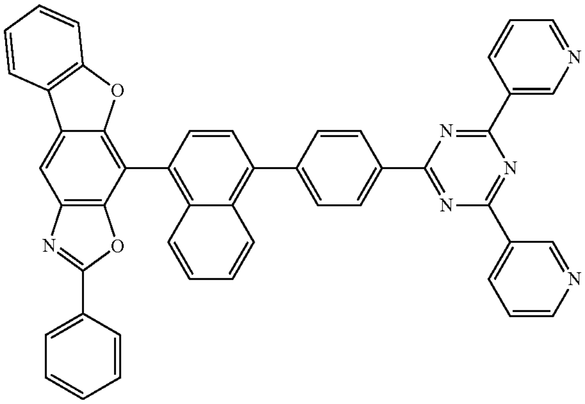

-continued
A40
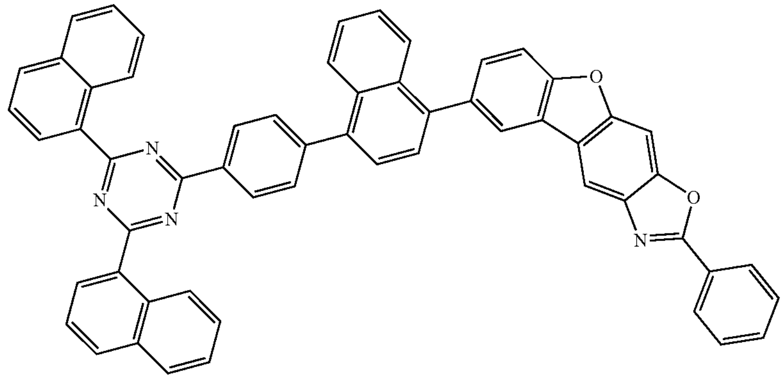
A41
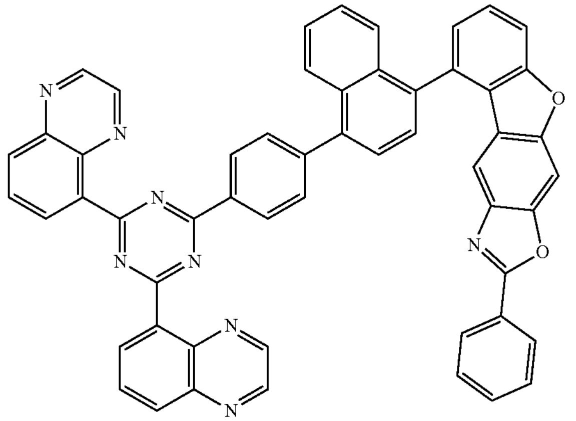
A42
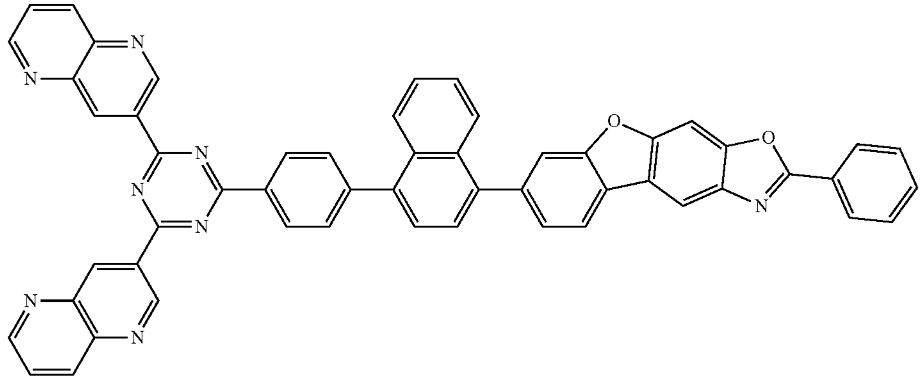
A43
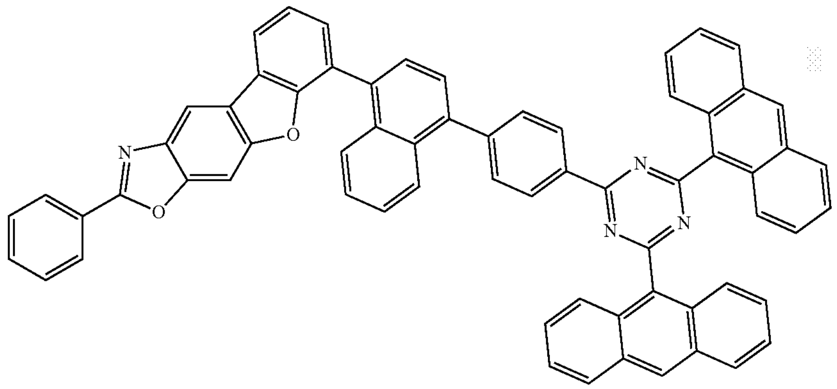

-continued
A44
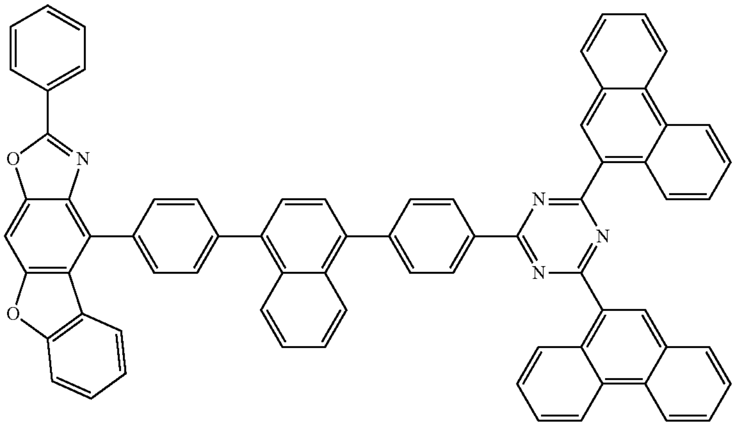
A45
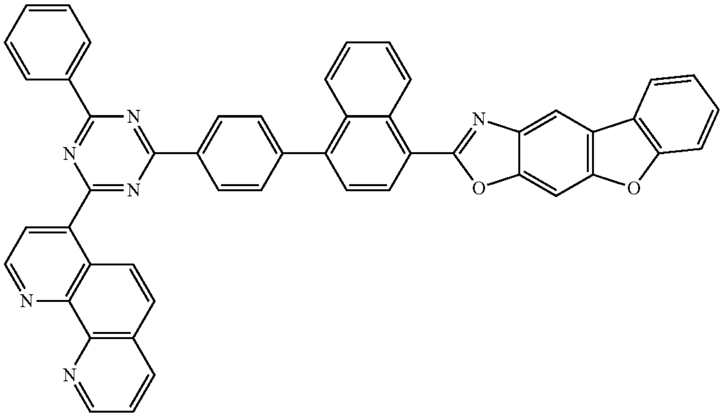
A46
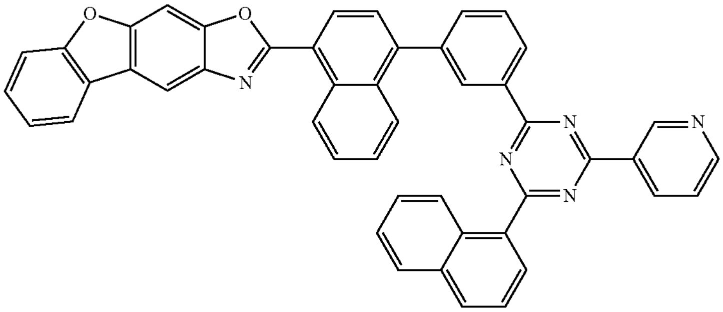
A47
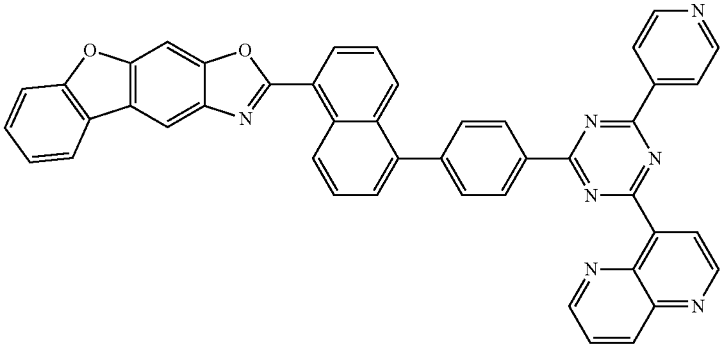

-continued
A48
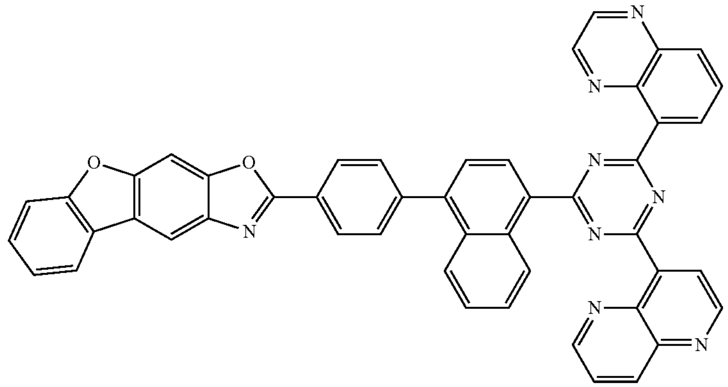
B1
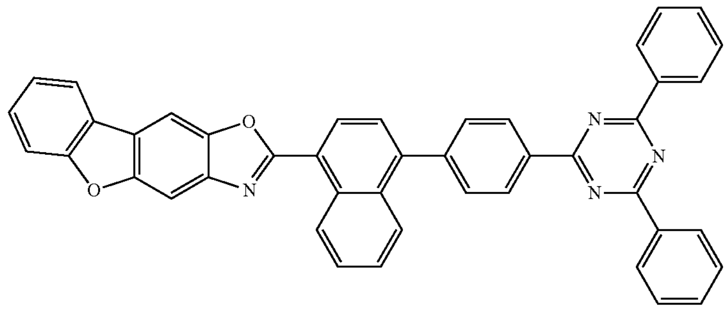
B2
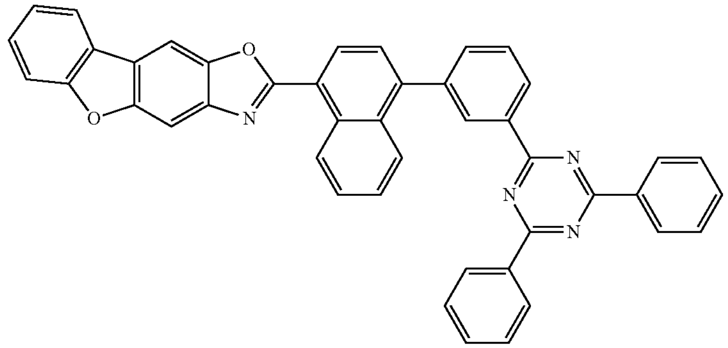
B3
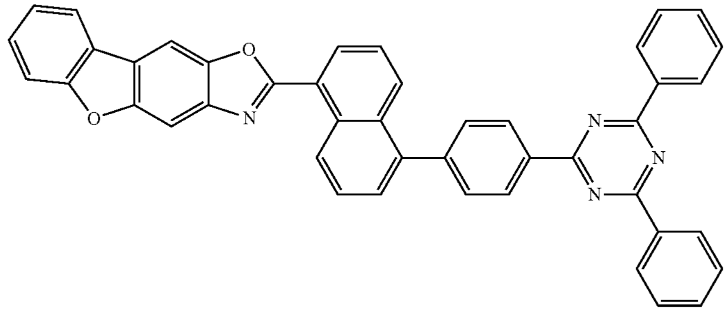

-continued
B4
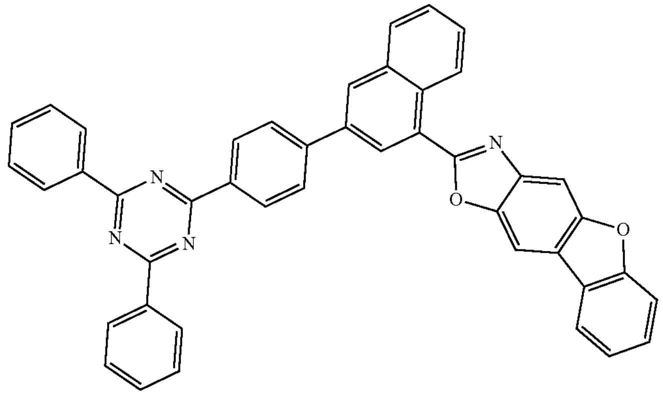
B5
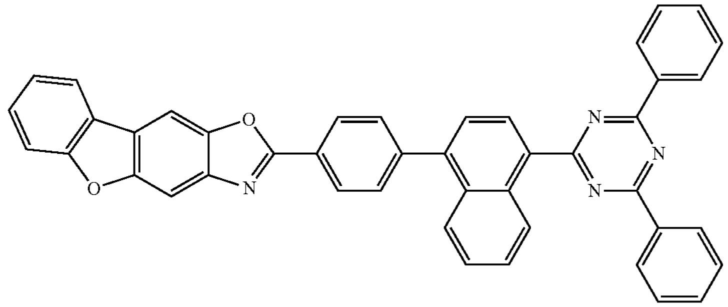
B6
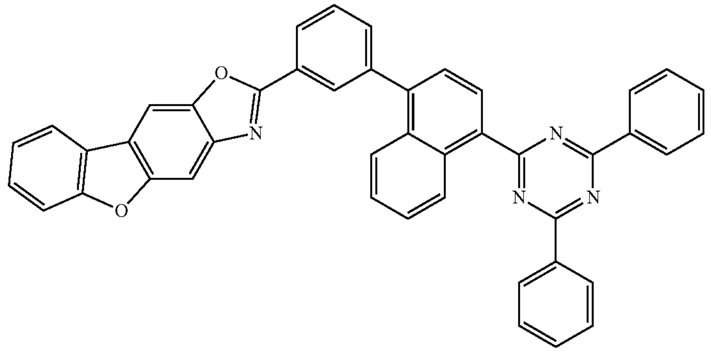
B7
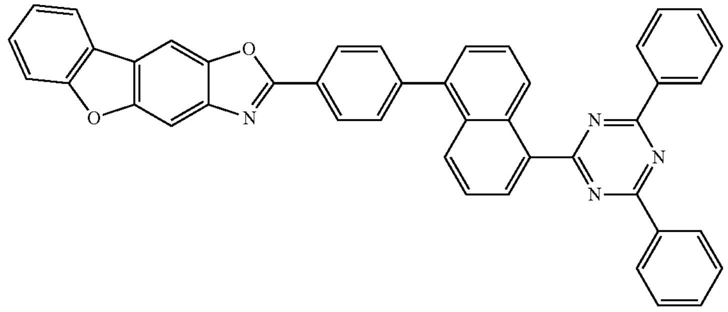

-continued
B8
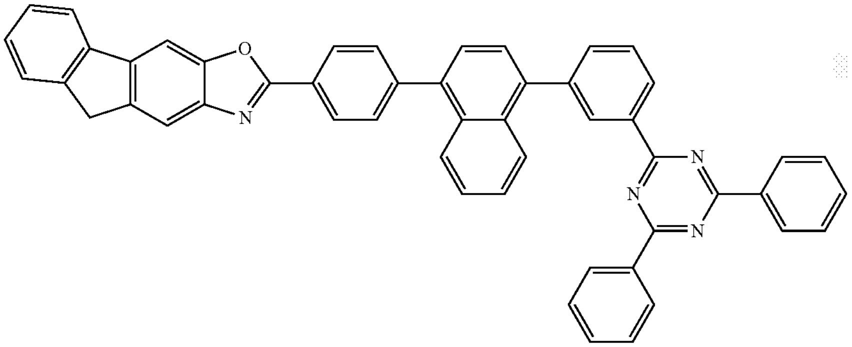
B9
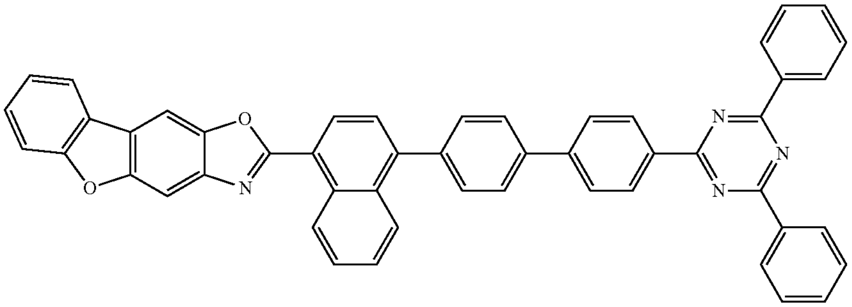
B10
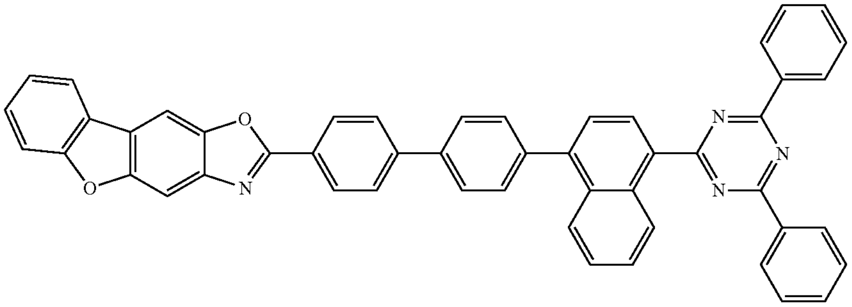
B11
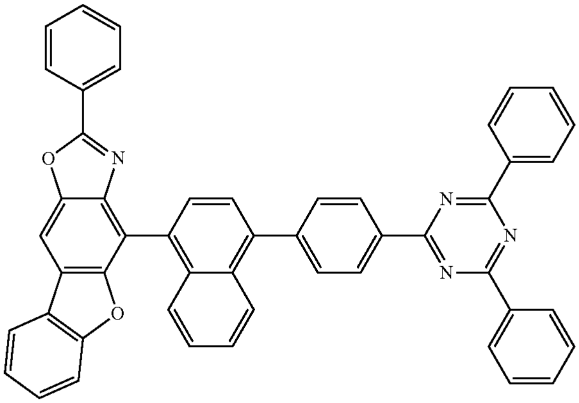

-continued
B12
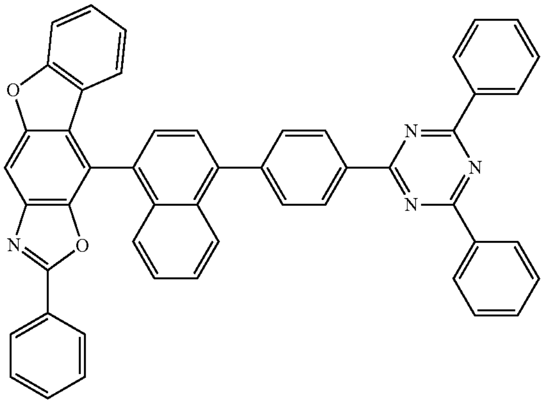
B13
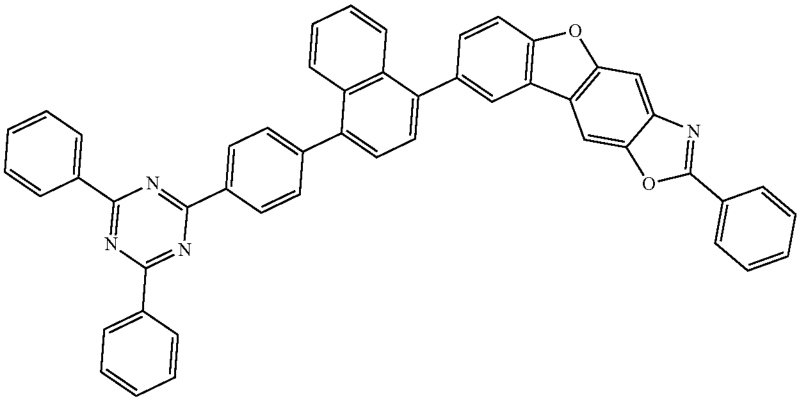
B14
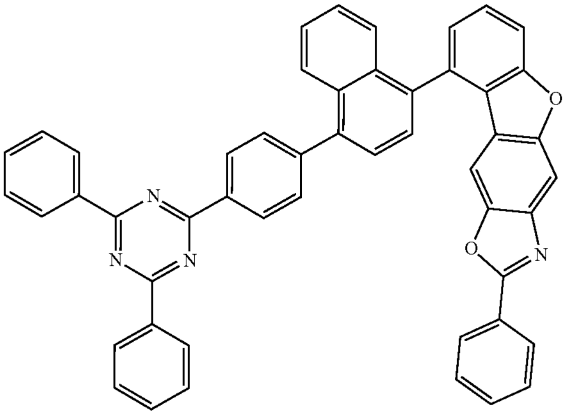
B15
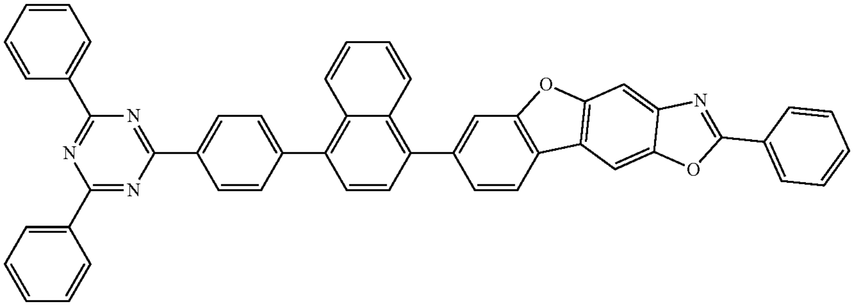

-continued
B16
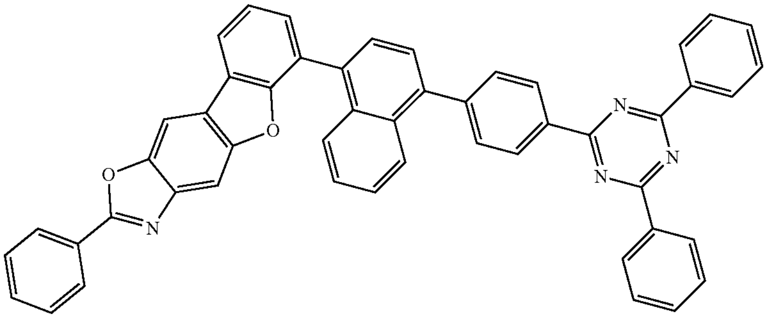
B17
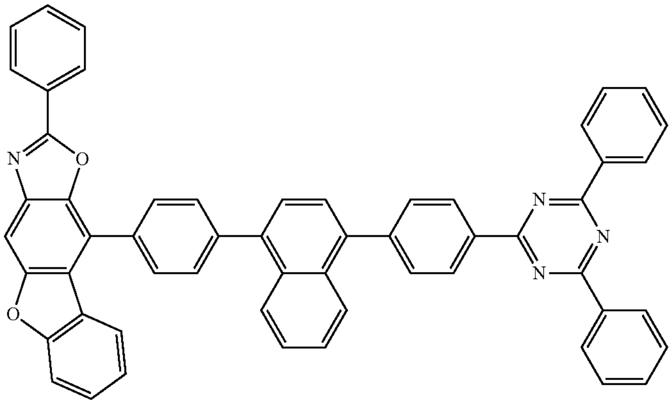
B18
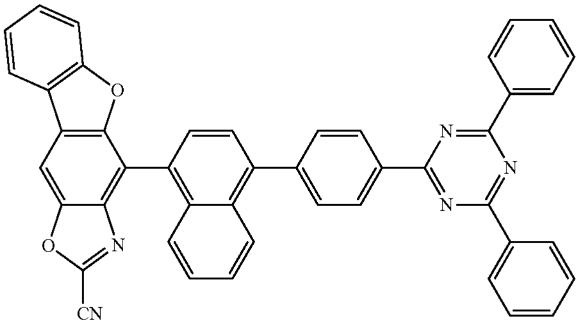
B19
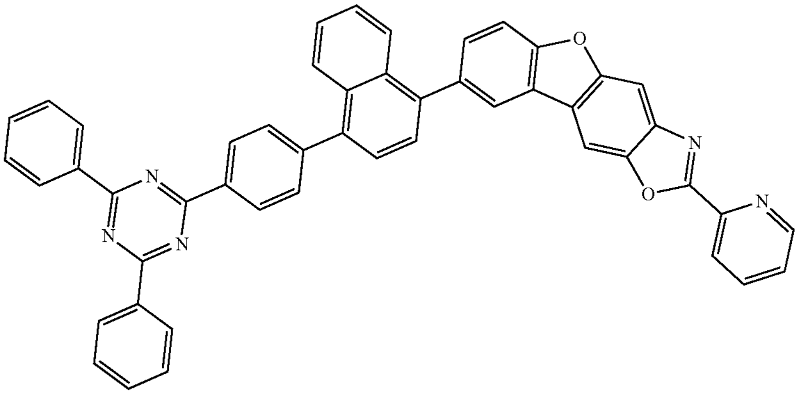

-continued
B20
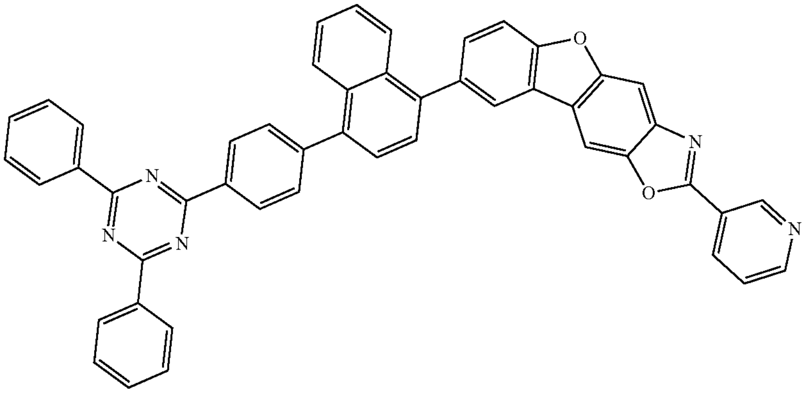
B21
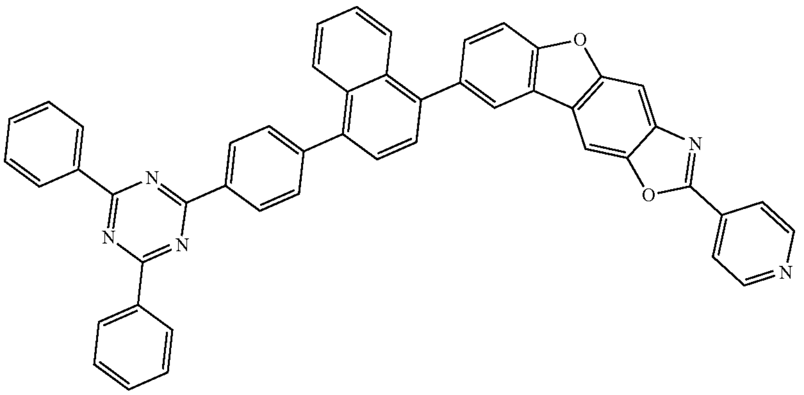
B22
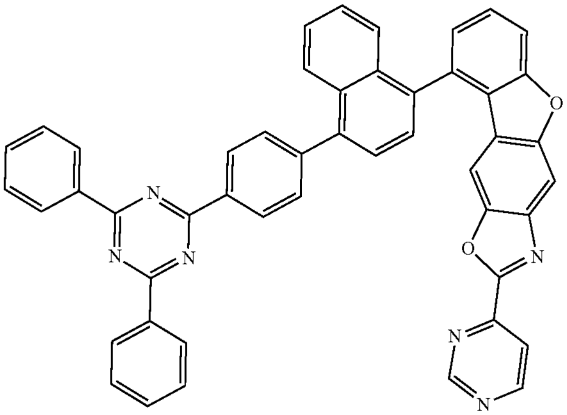
B23
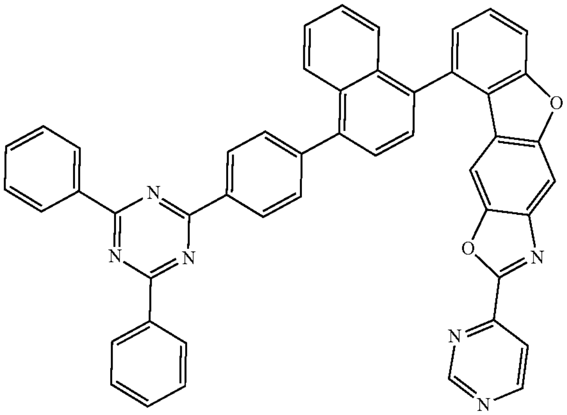

-continued
B24
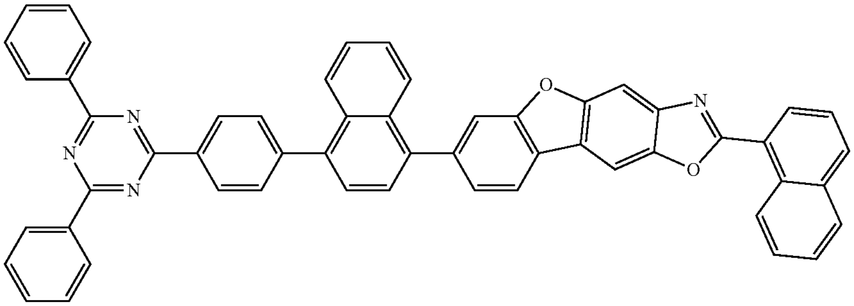
B25
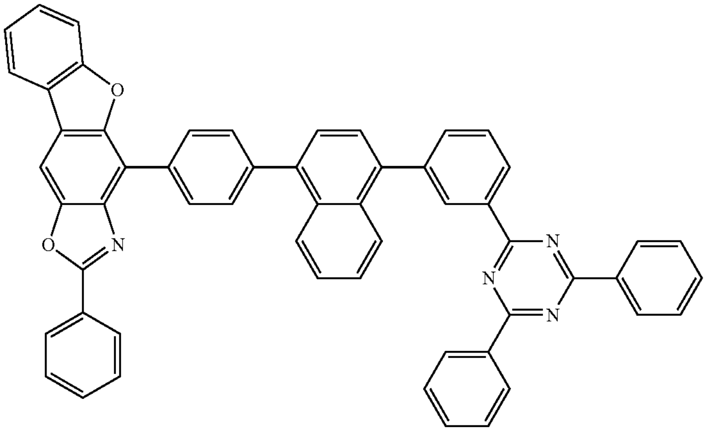
B26
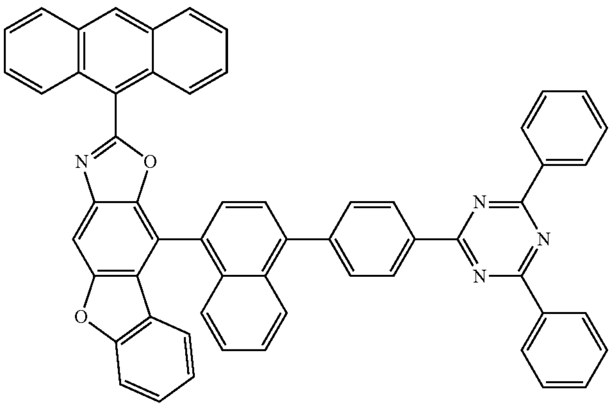
B27
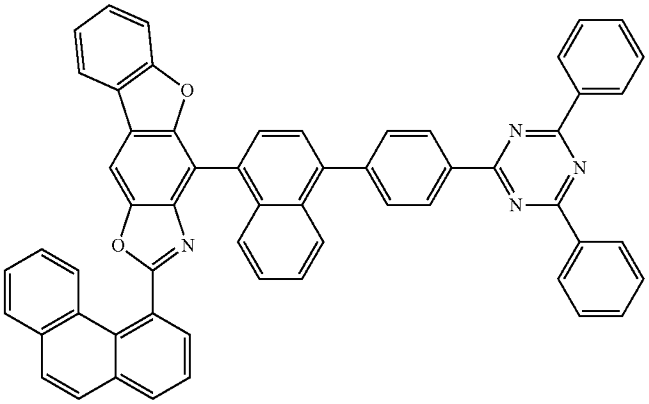

-continued
B28
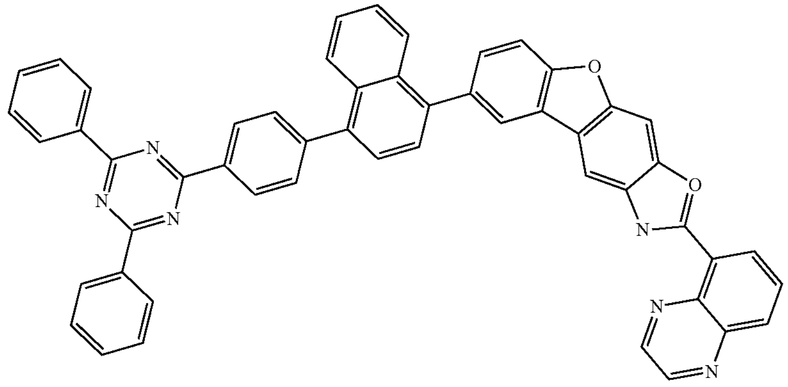
B29
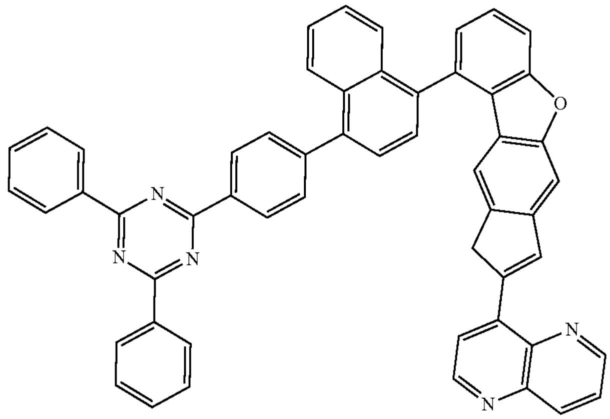
B30
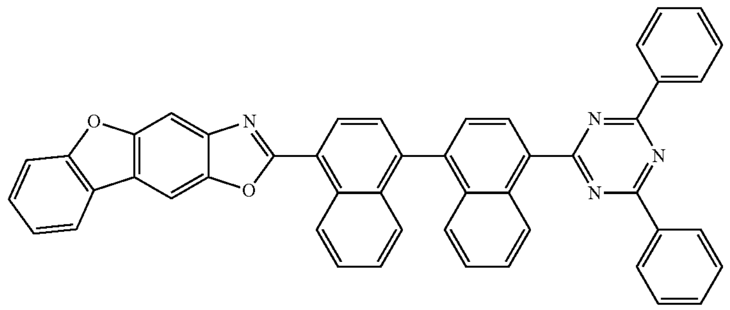
B31
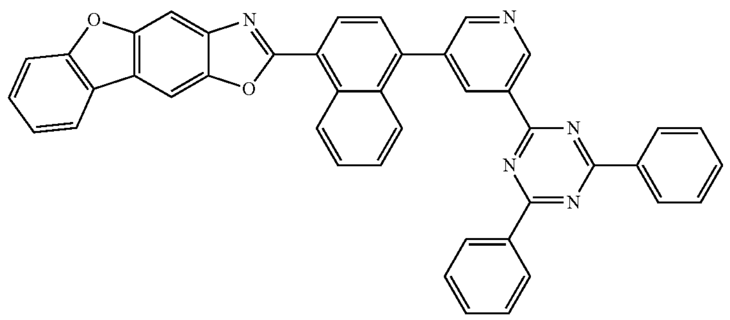

-continued
B32
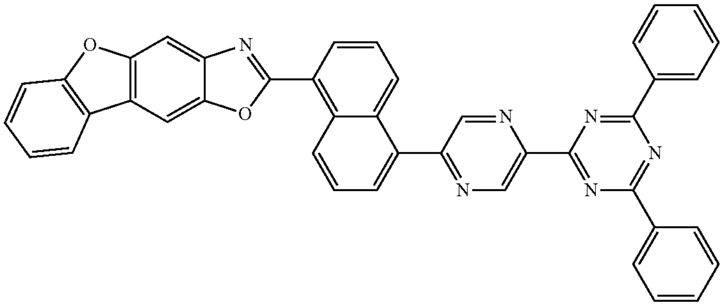
B33
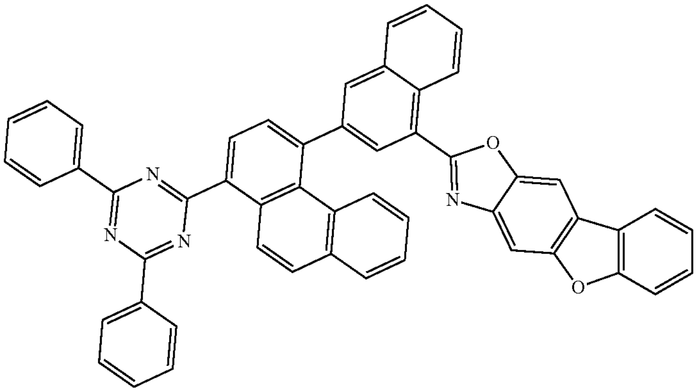
B34
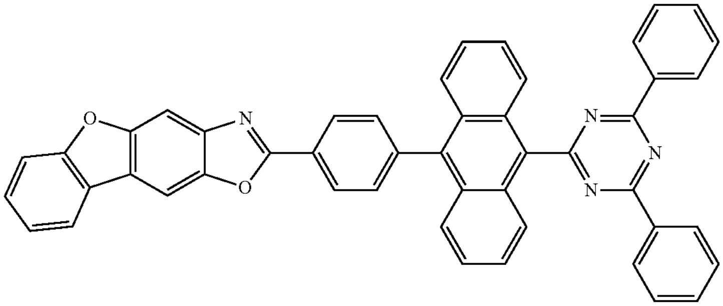
B35
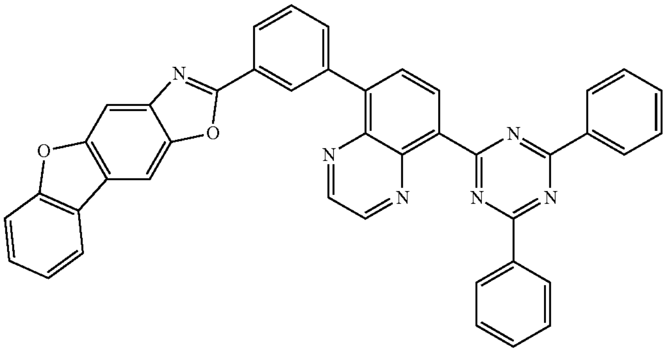

-continued
B36
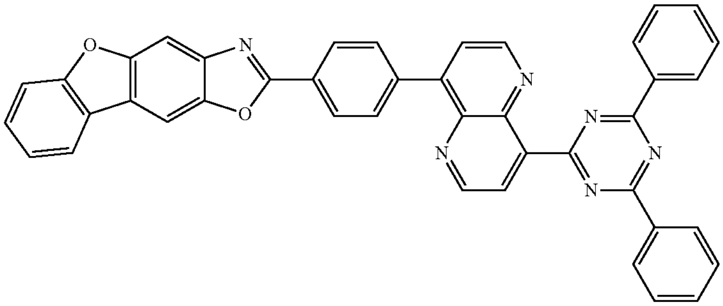
B37
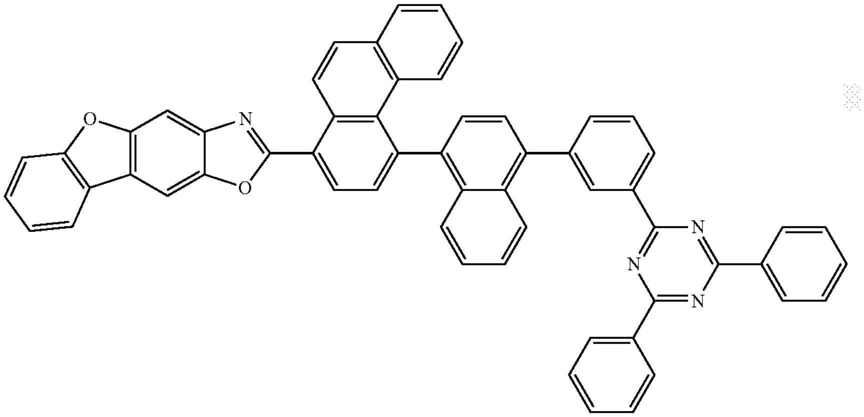
B38
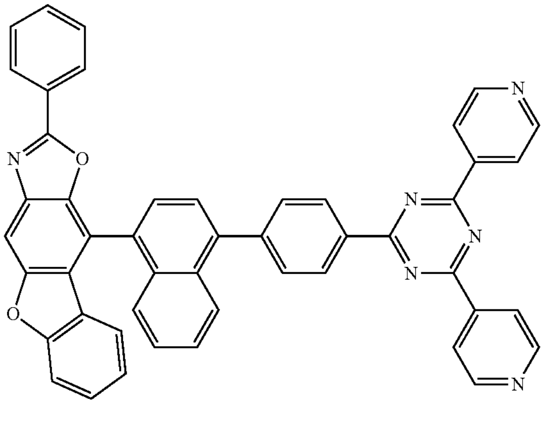
B39
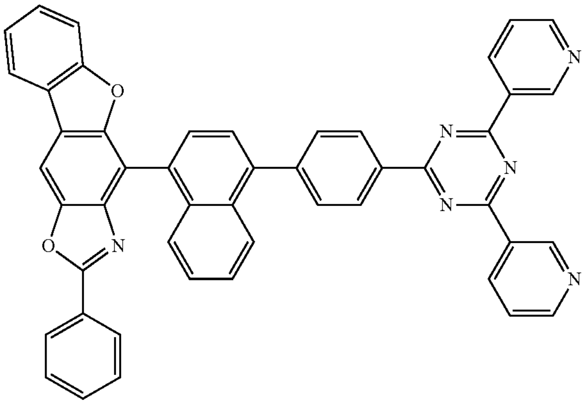

-continued
B40
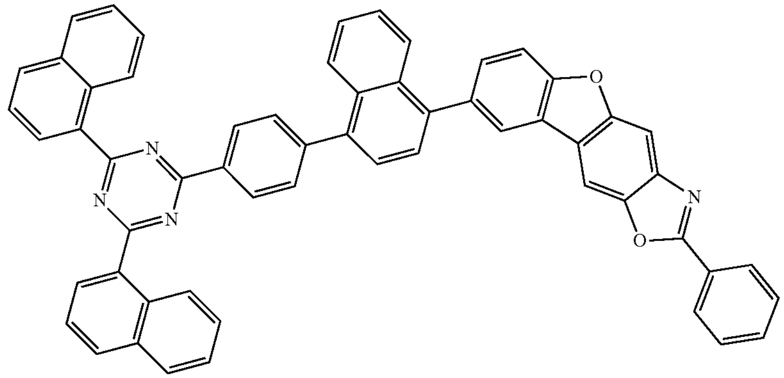
B41
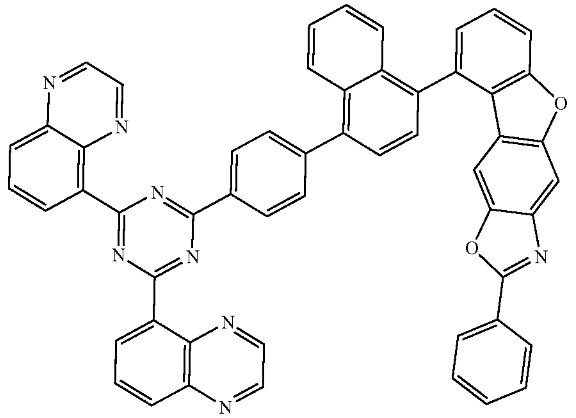
B42
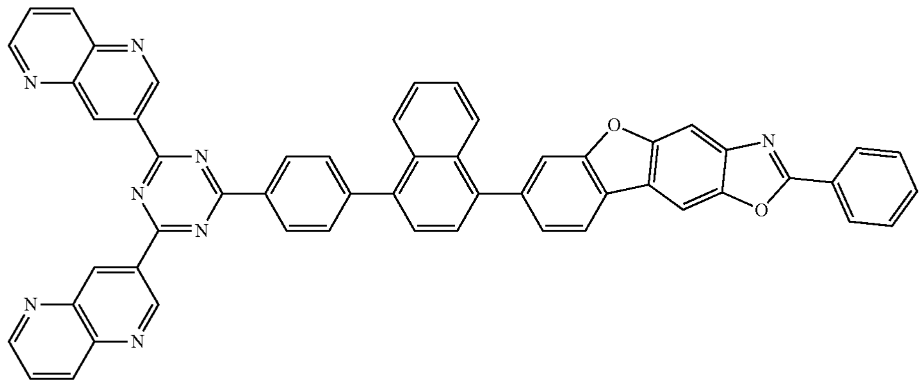
B43
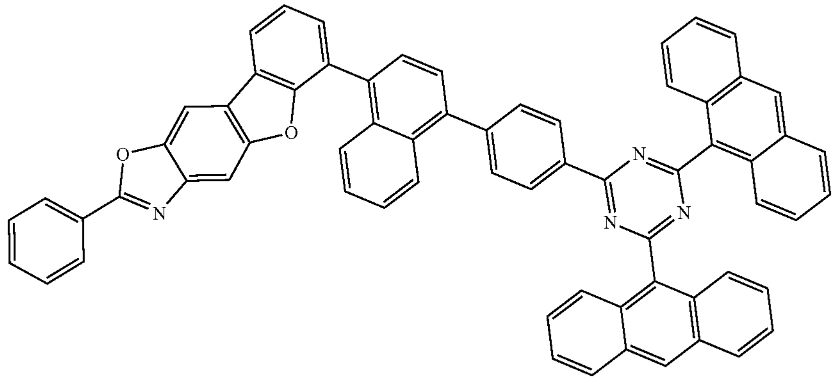

-continued
B44
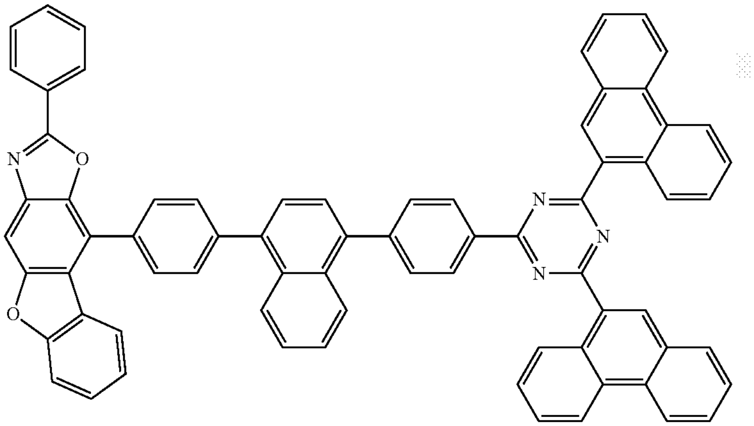
B45
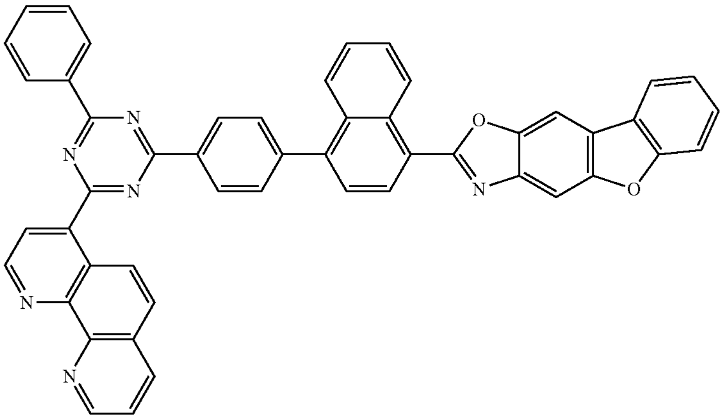
B46
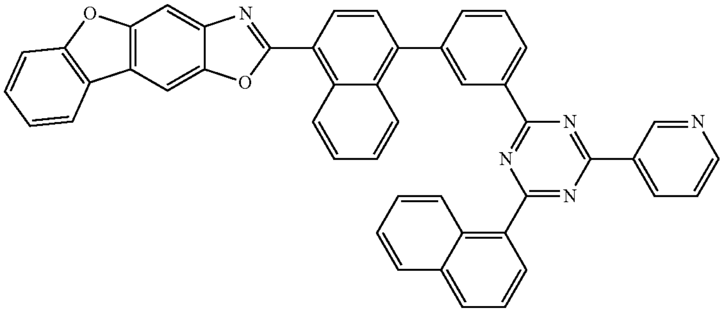
B47
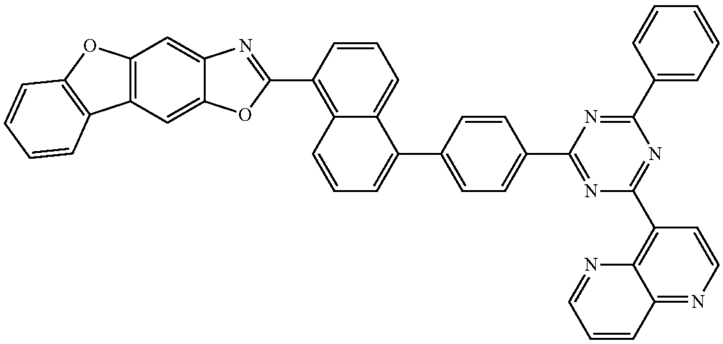

-continued
B48
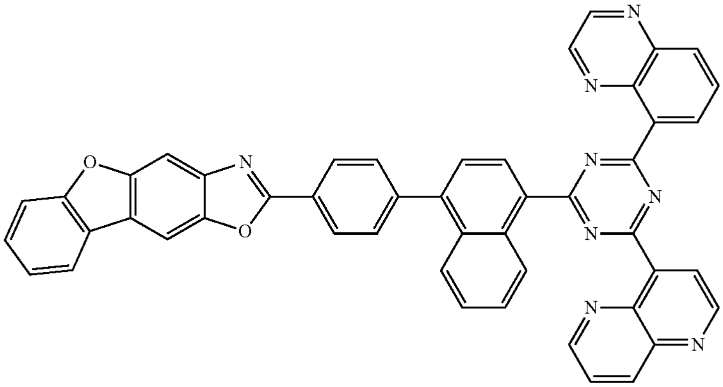
C1
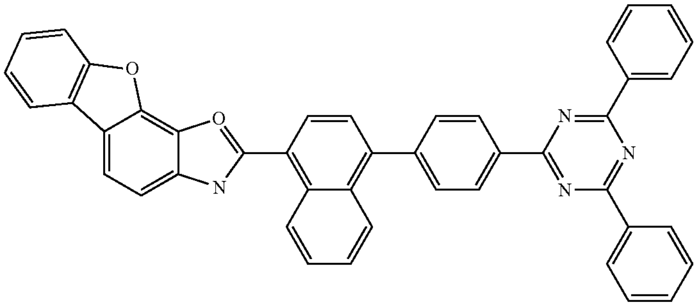
C2
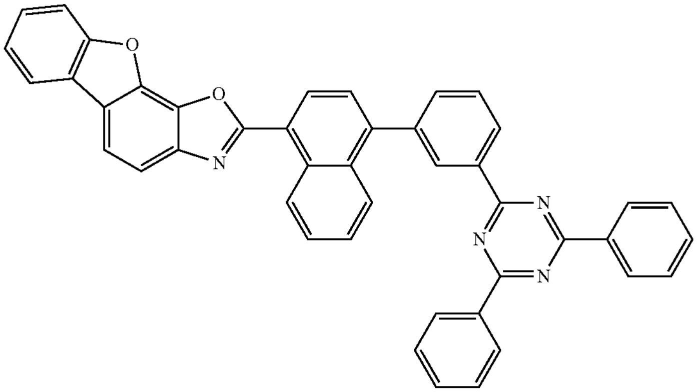
C3
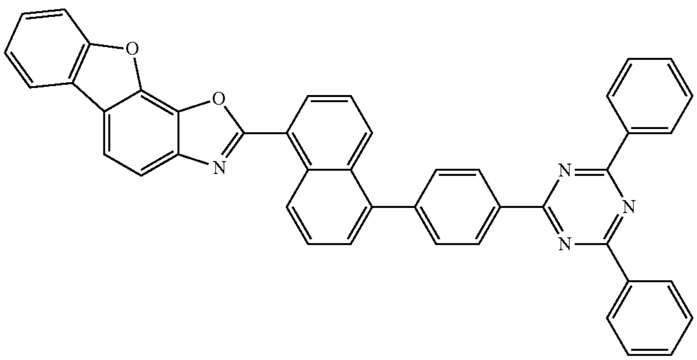

-continued
C4
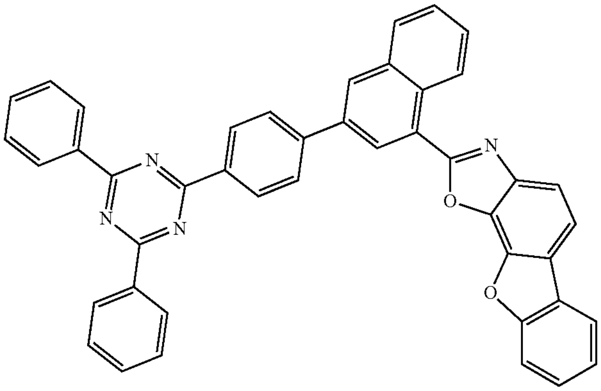
C5
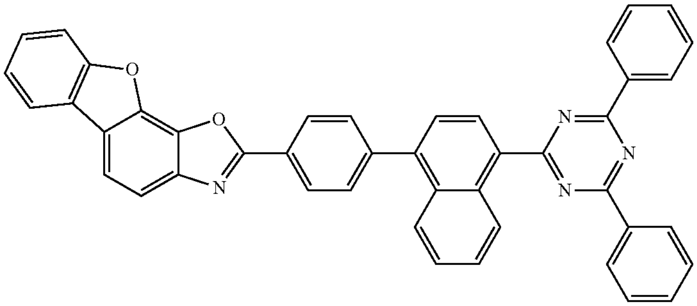
C6
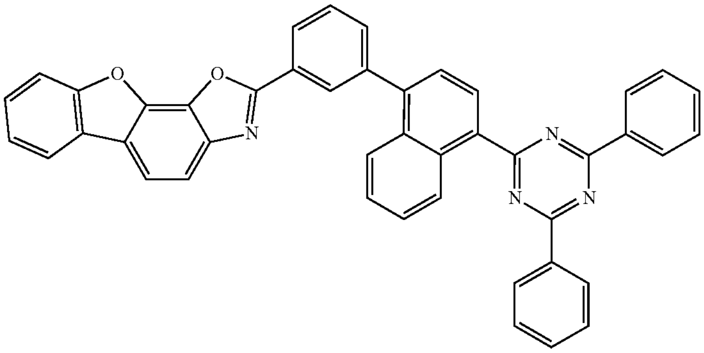
C7
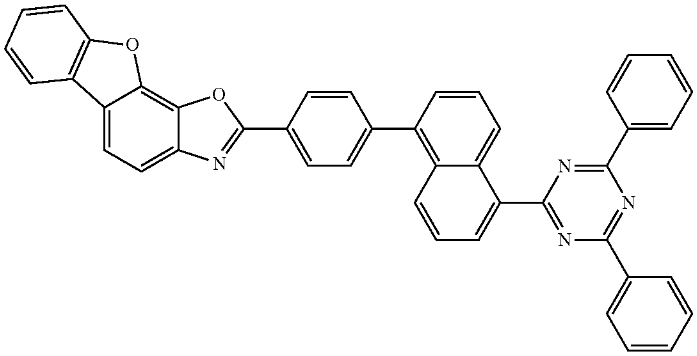

-continued
C8
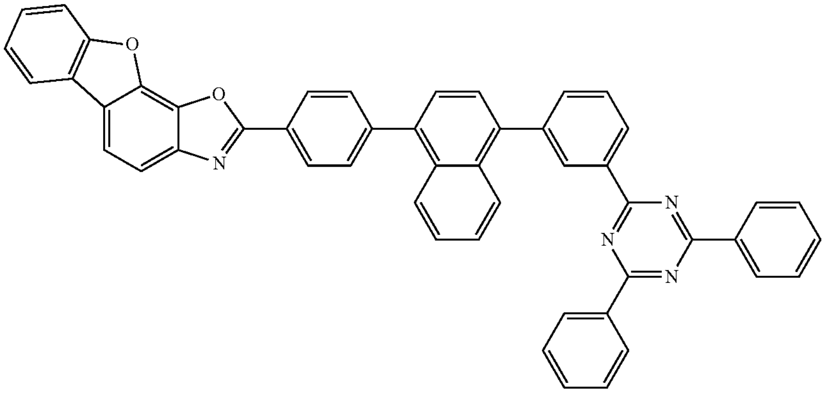
C9
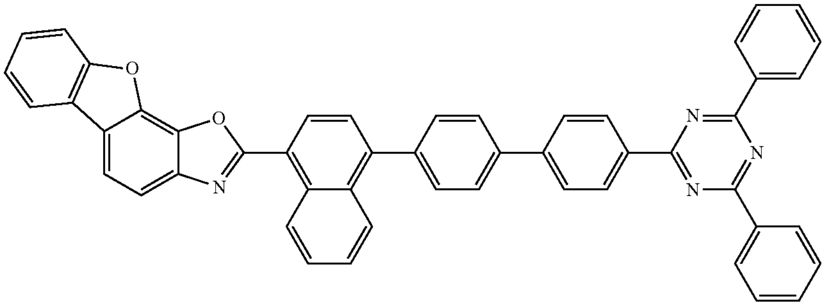
C10
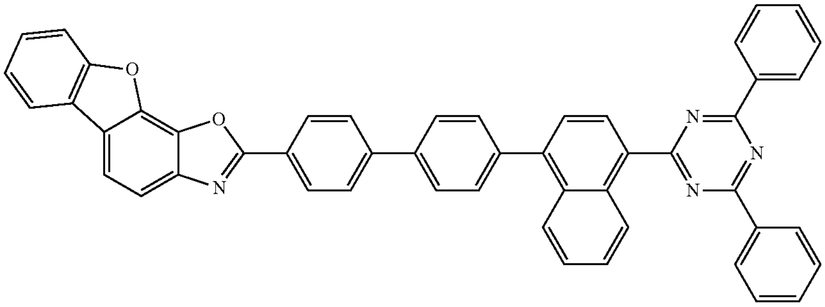
C11
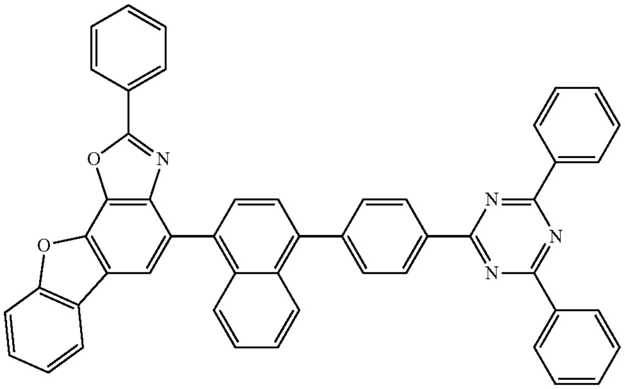

-continued
C12
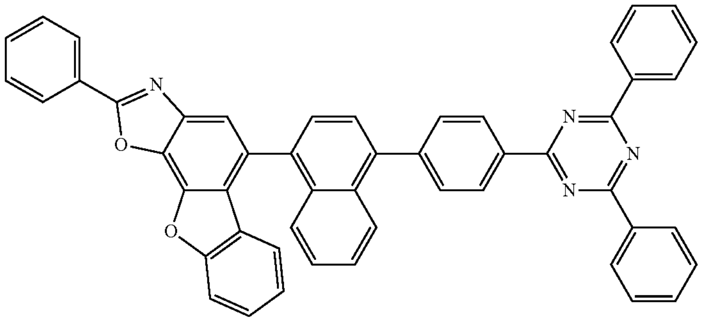
C13
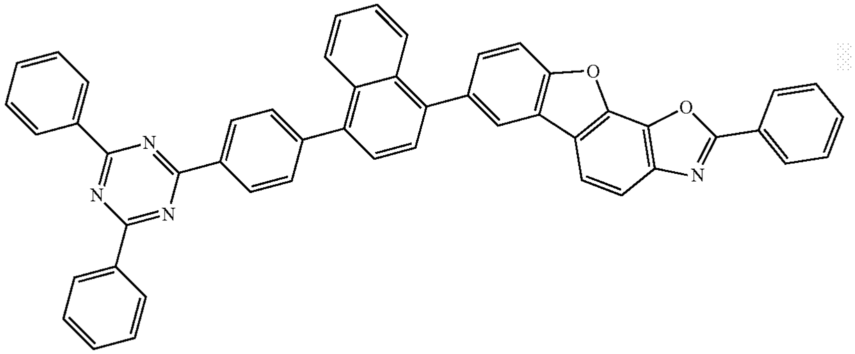
C14
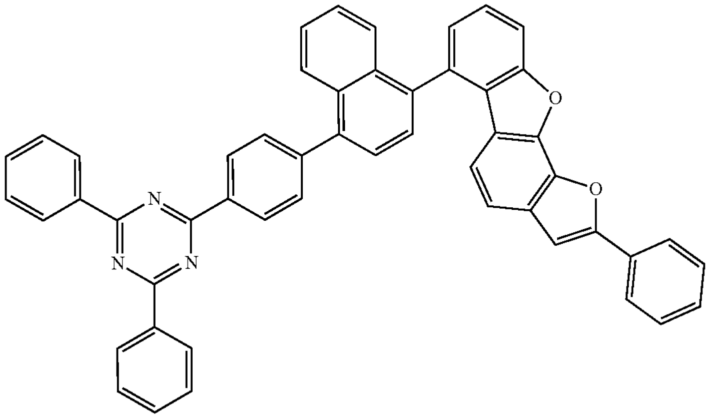
C15
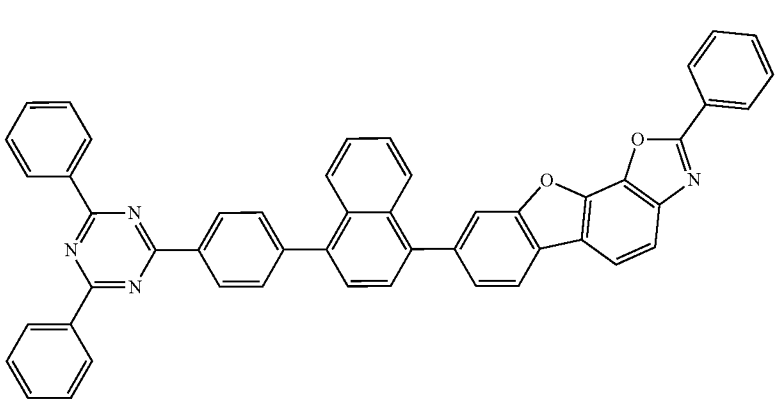

-continued
C16
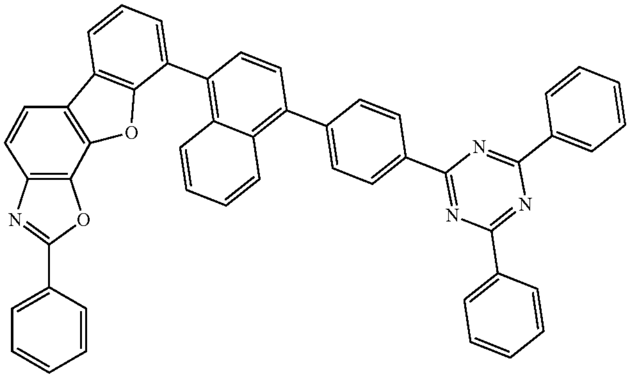
C17
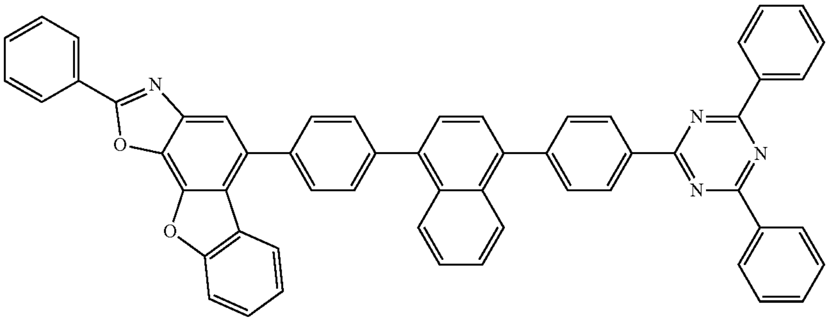
C18
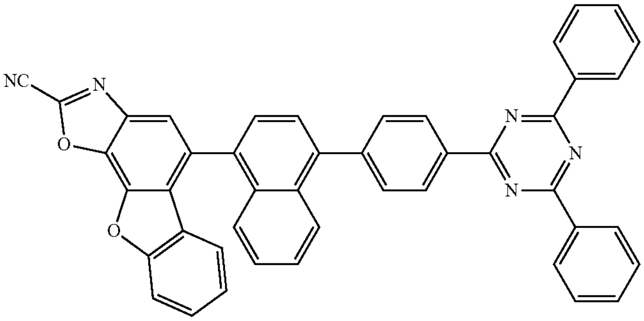
C19
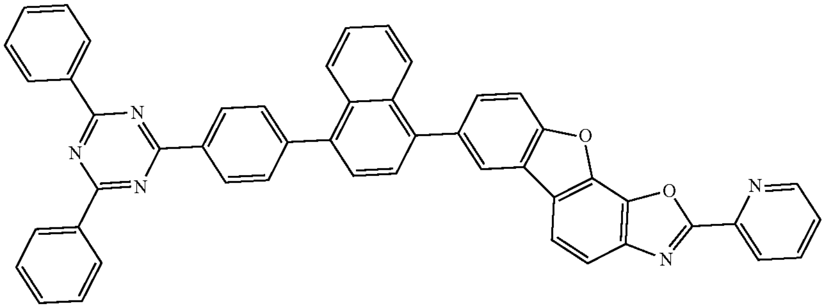

-continued
C20
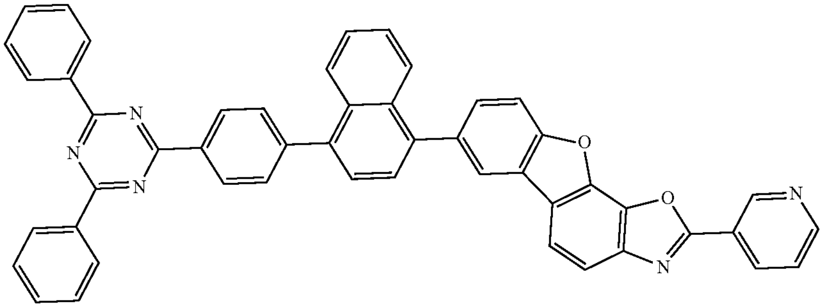
C21
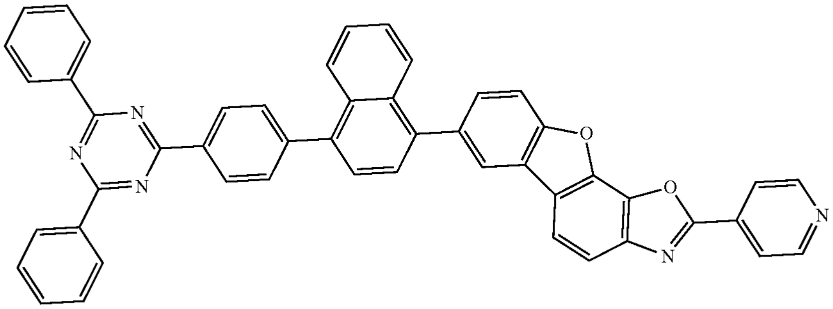
C22
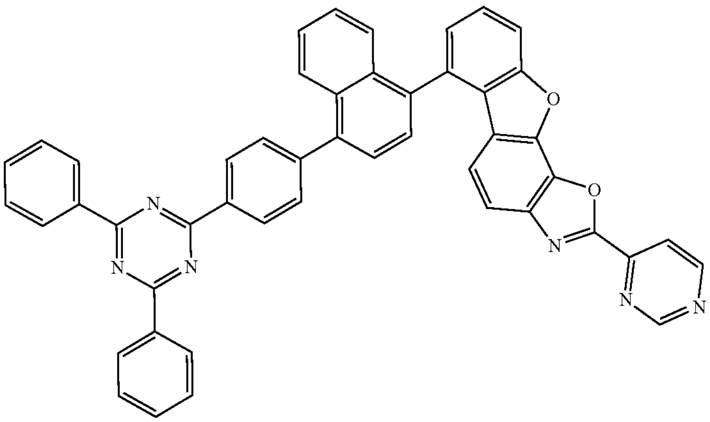
C23
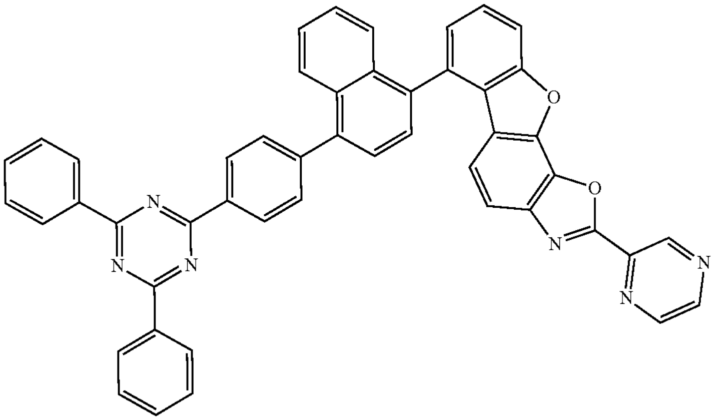

-continued
C24
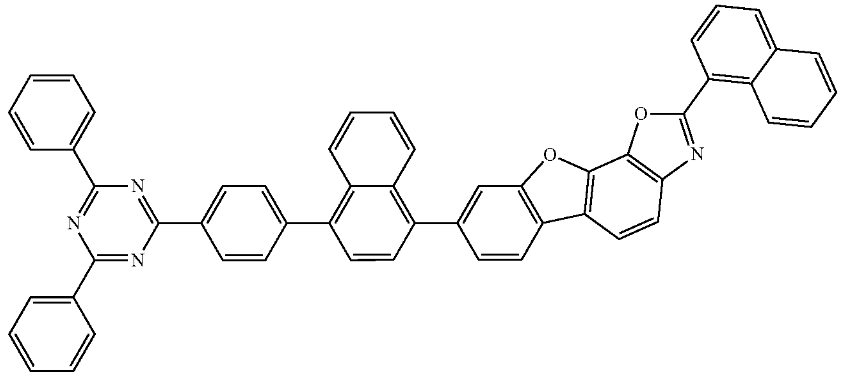
C25
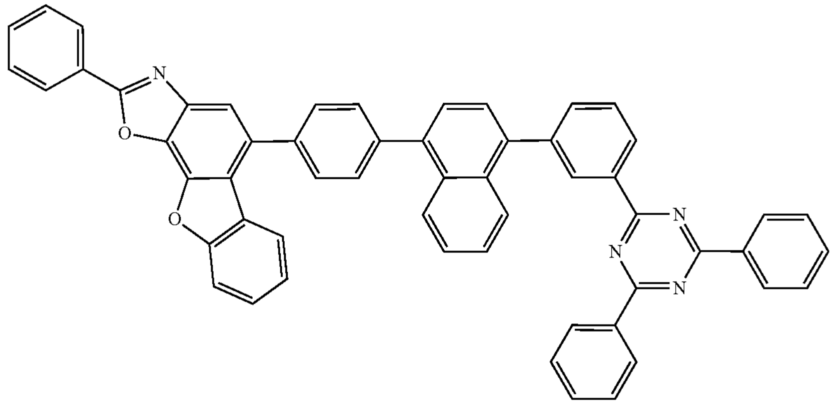
C26
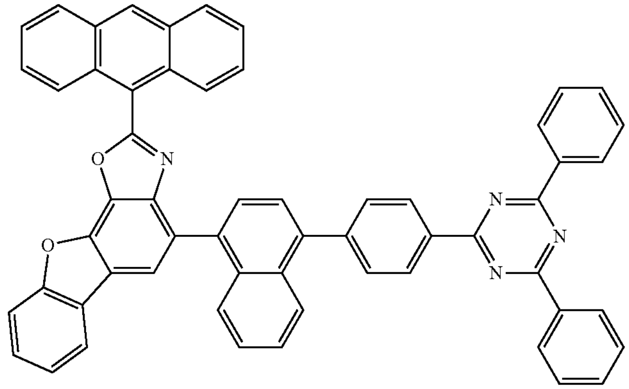
C27
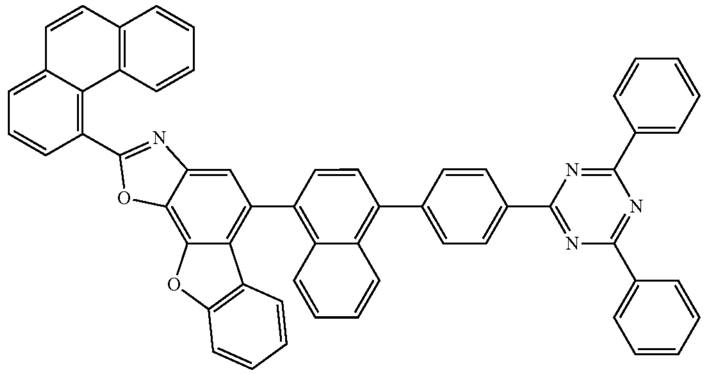

-continued
C28
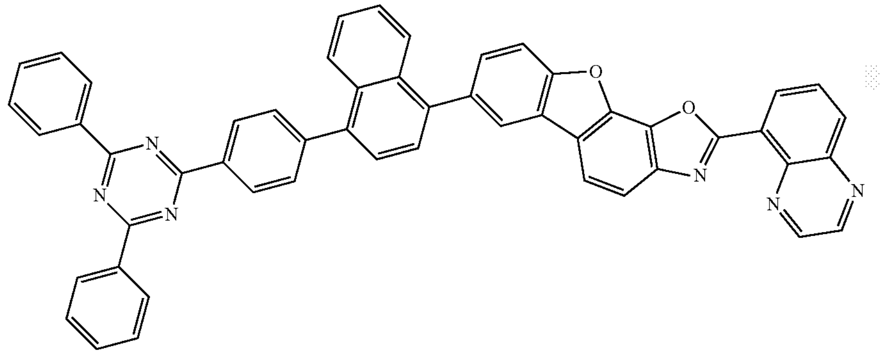
C29
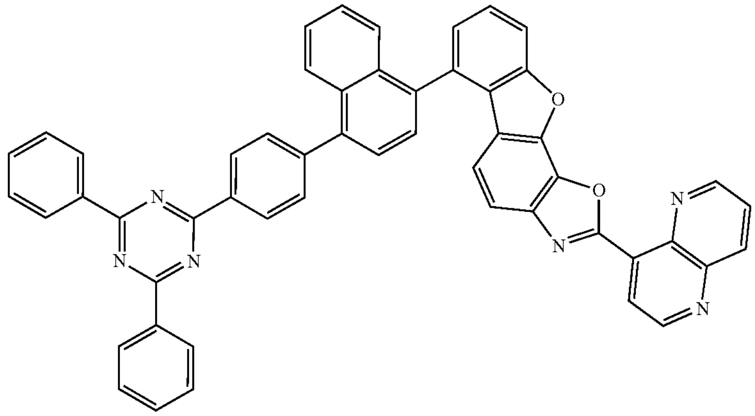
C30
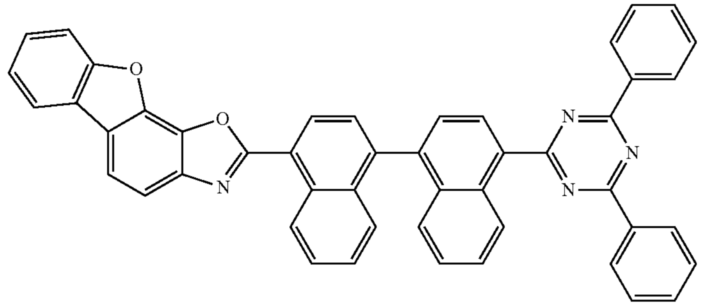
C31
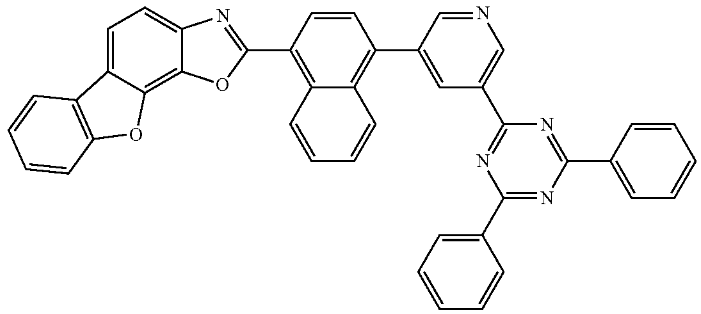

-continued
C32
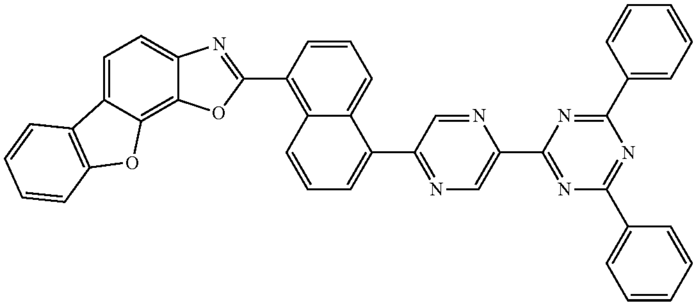
C33
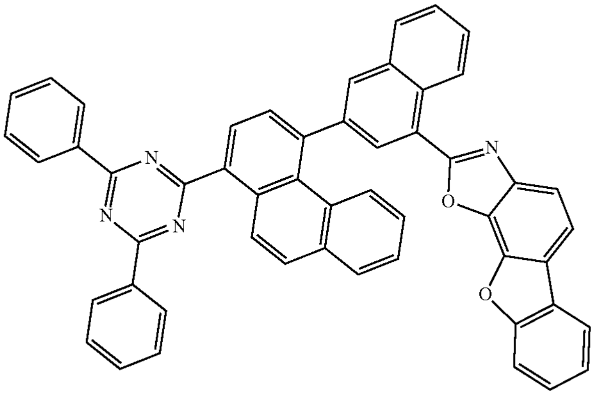
C34
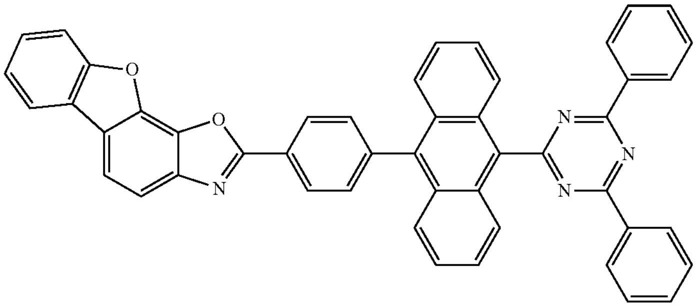
C35
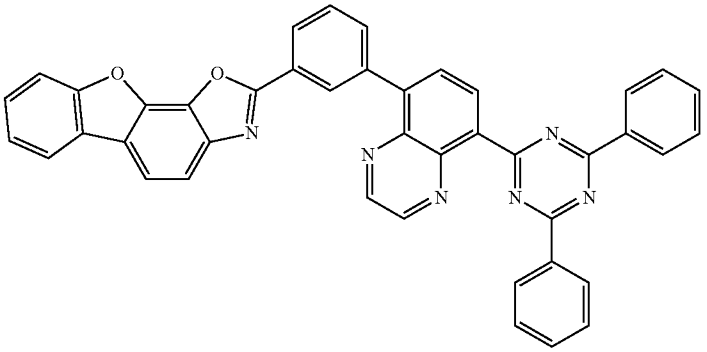

-continued
C36
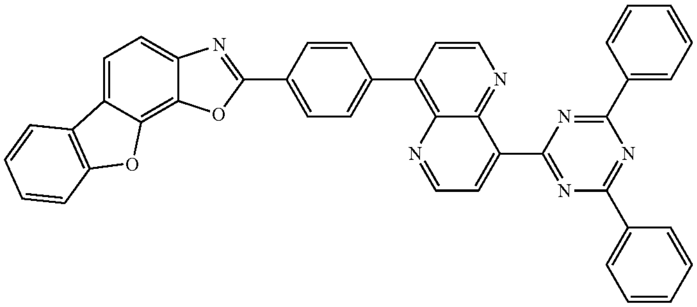
C37
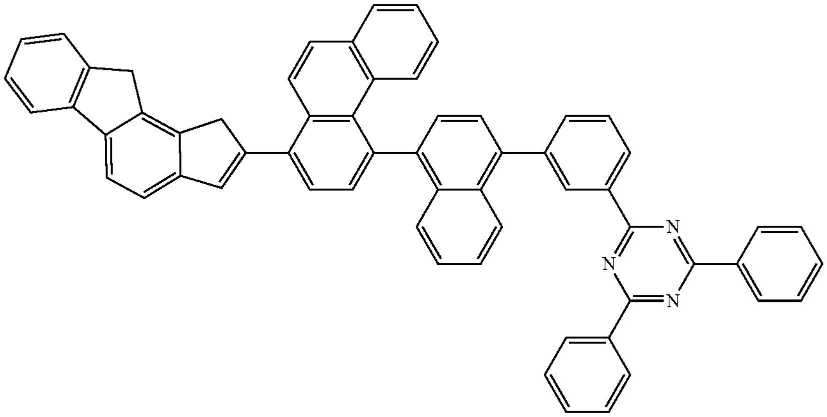
C38
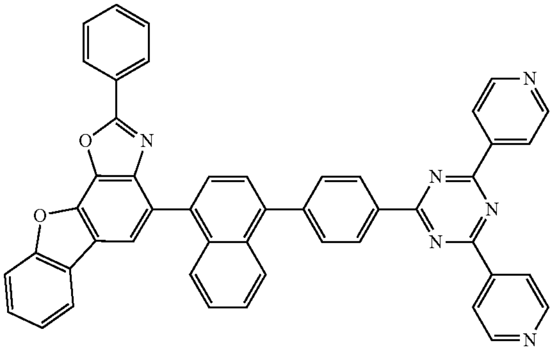
C39
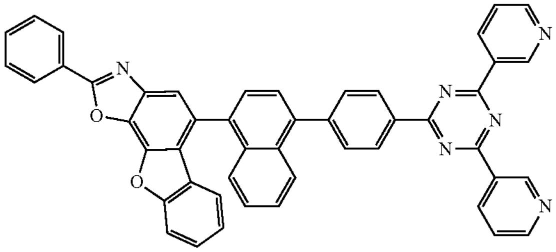
C40
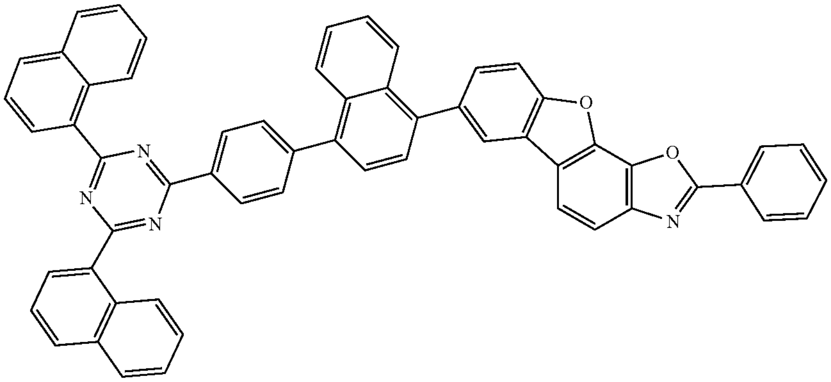

-continued
C41
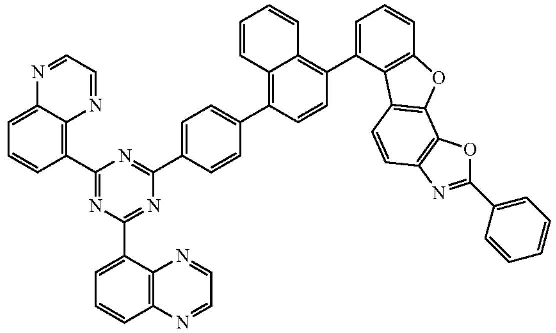
C42
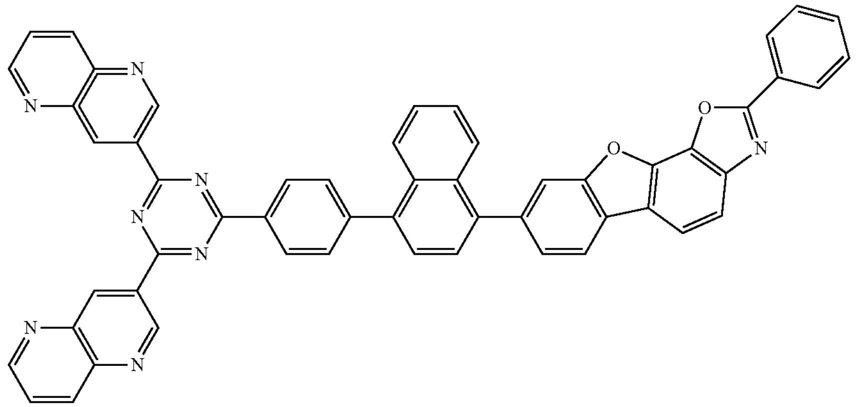
C43
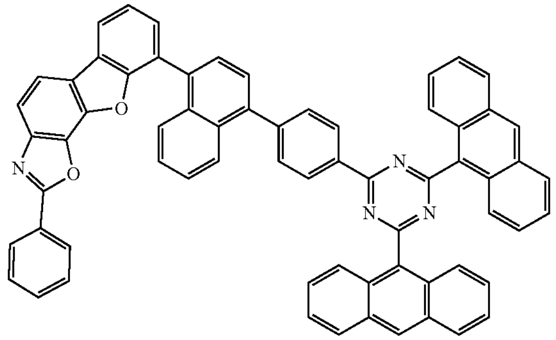
C44
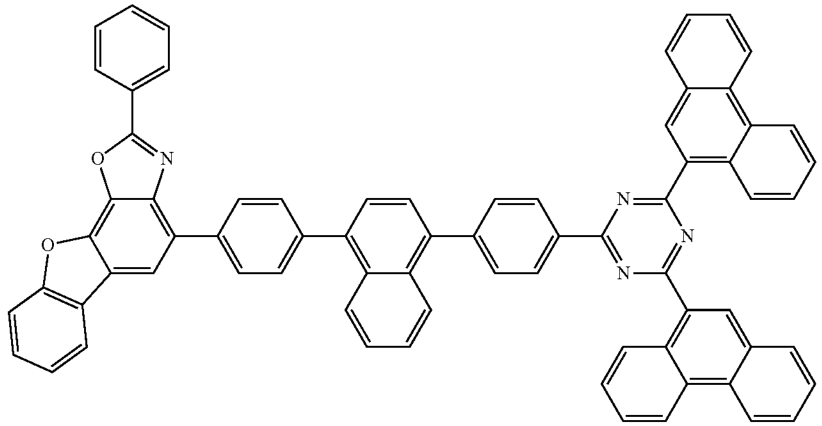

-continued
C45
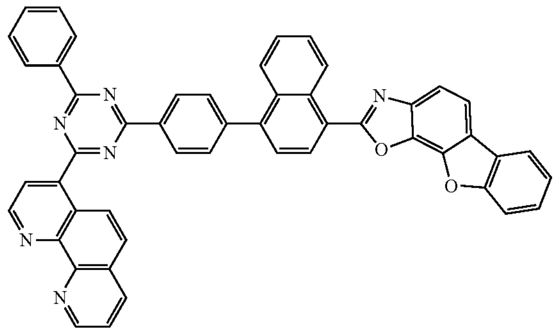
C46
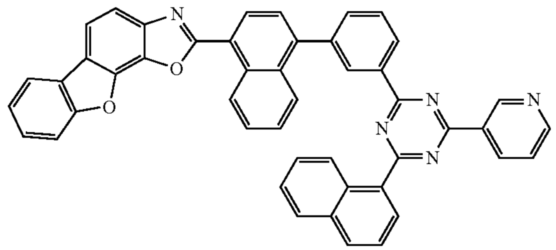
C47
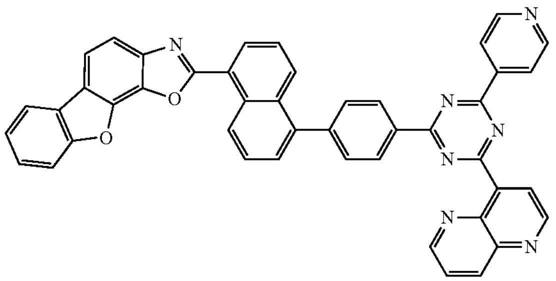
C48
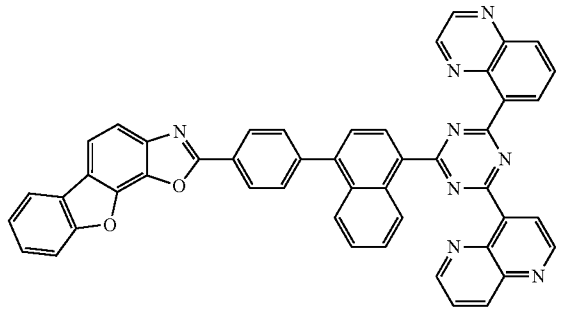
D1
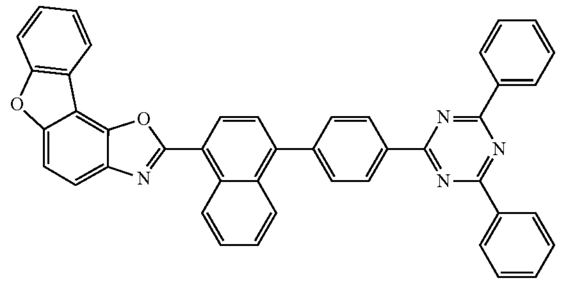
D2
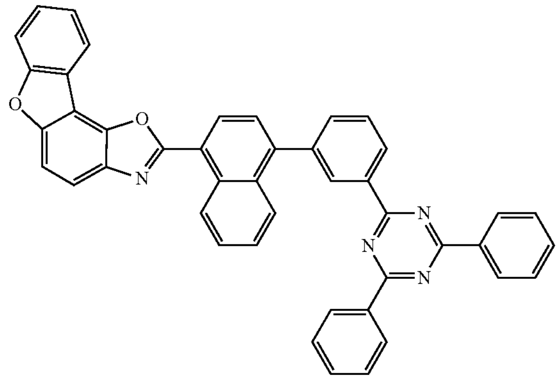
D3
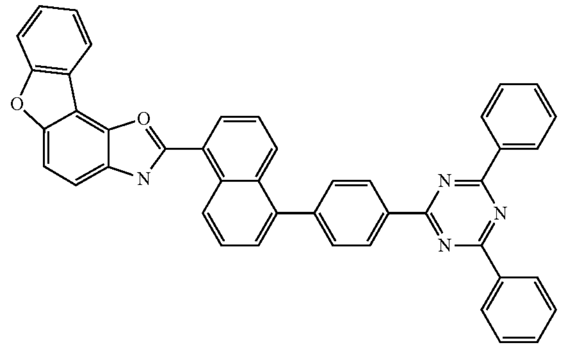

-continued
D4
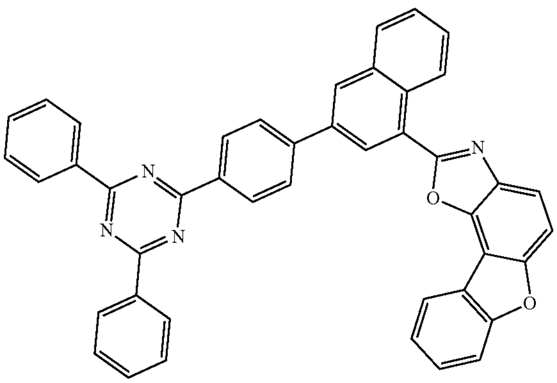
D5
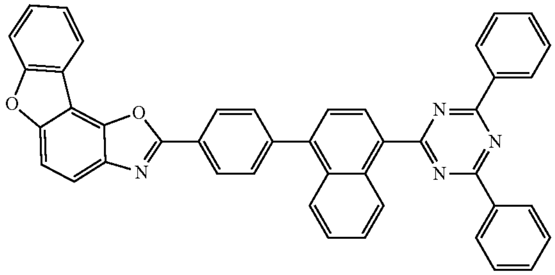
D6
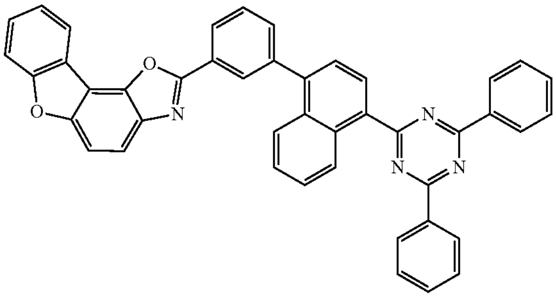
D7
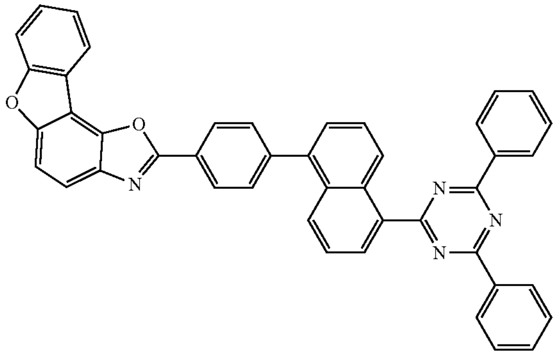
D8
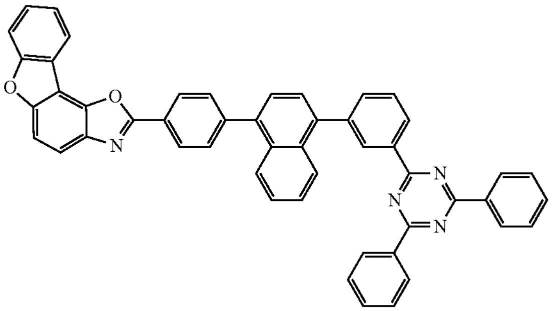
D9
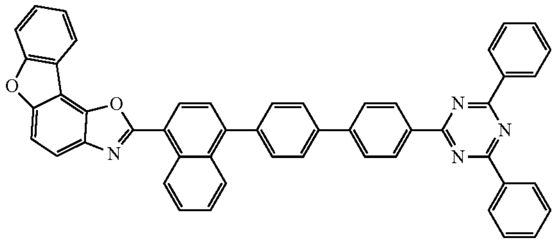
D10
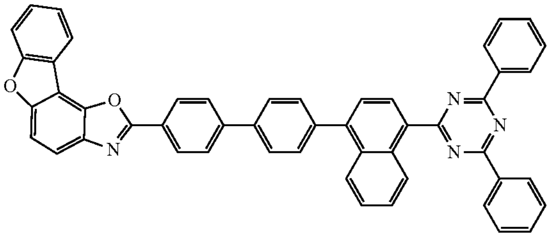
D11
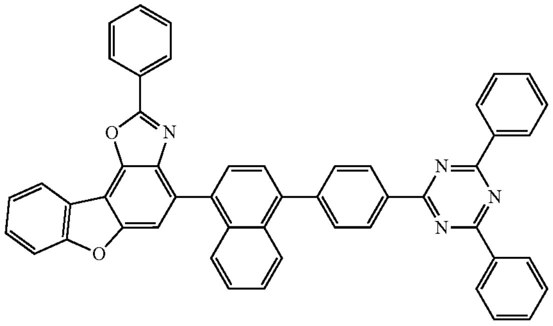

-continued
D12
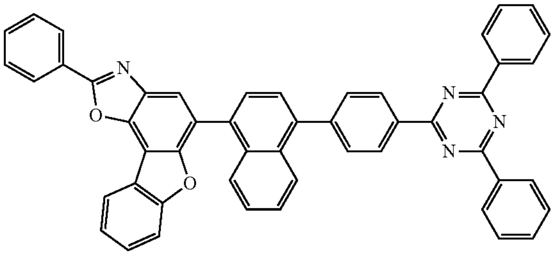
D13
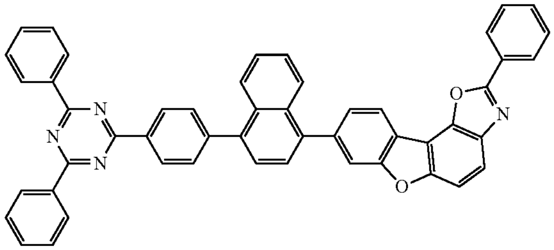
D14
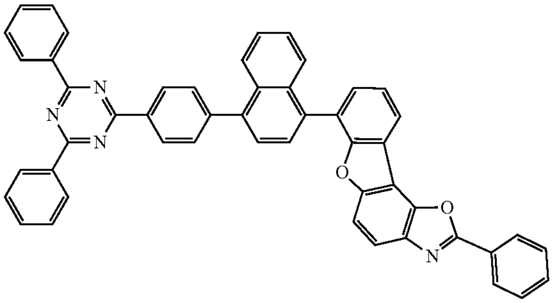
D15
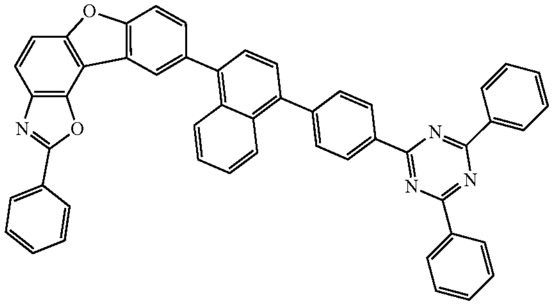
D16
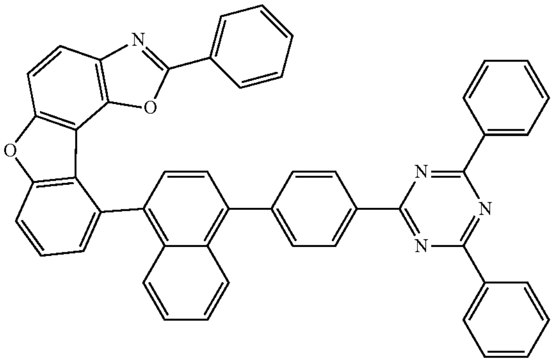
D17
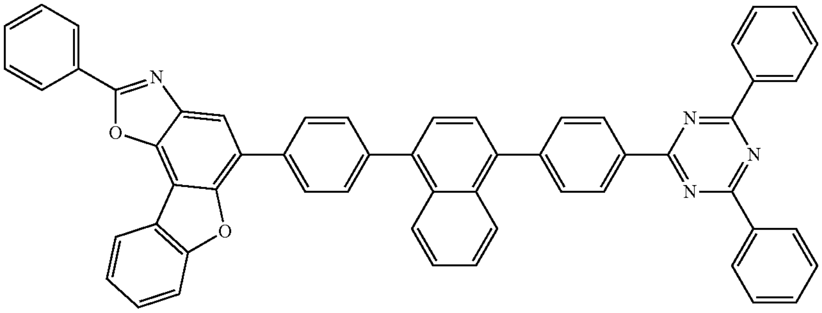
D18
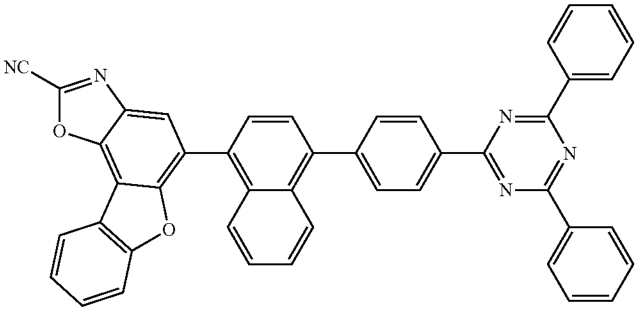

-continued
D19
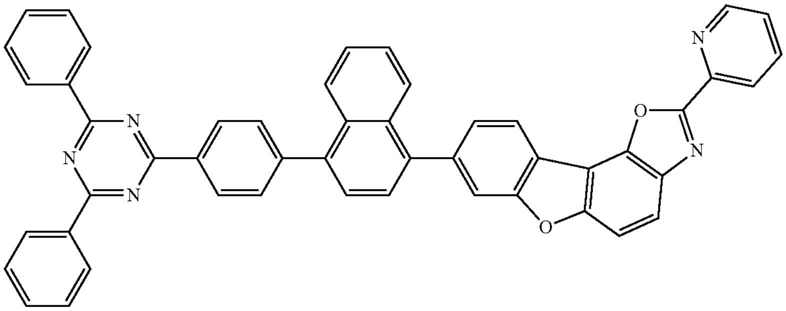
D20
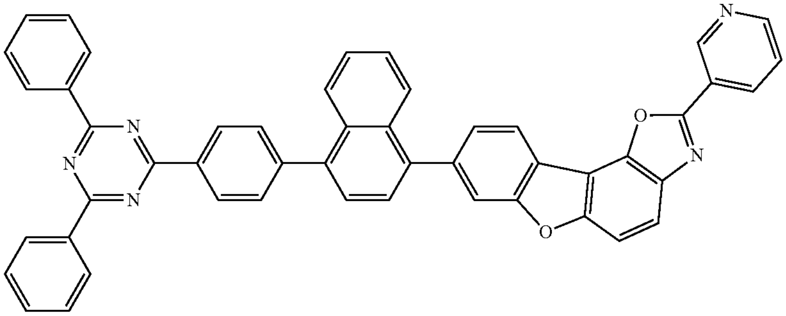
D21
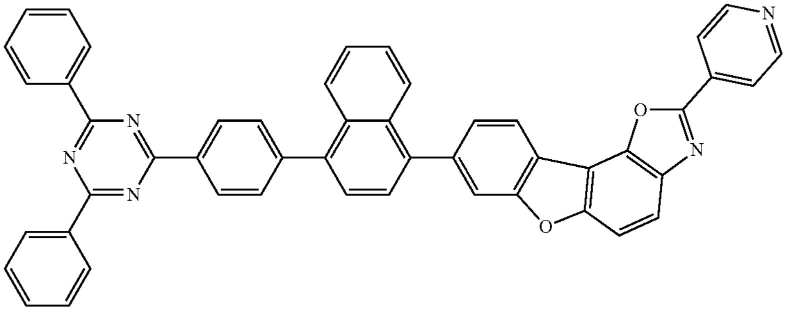
D22
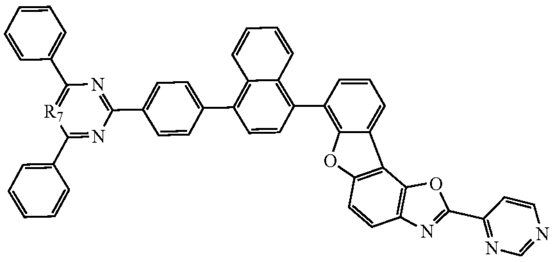
D23
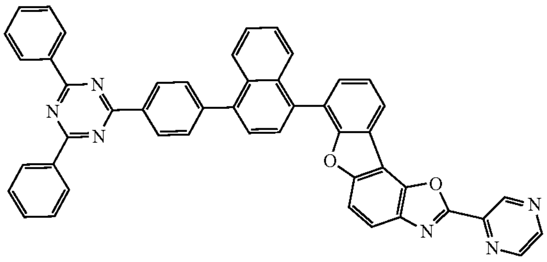
D24
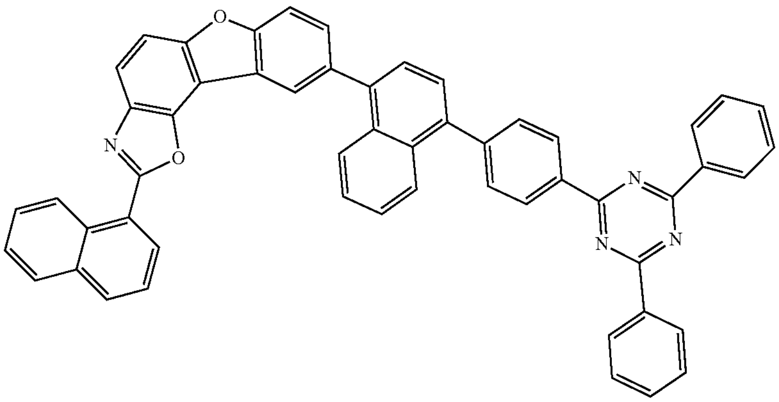

-continued
D25
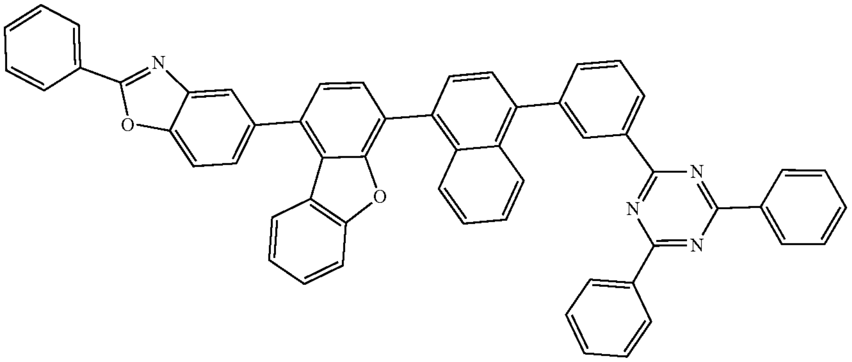
D26
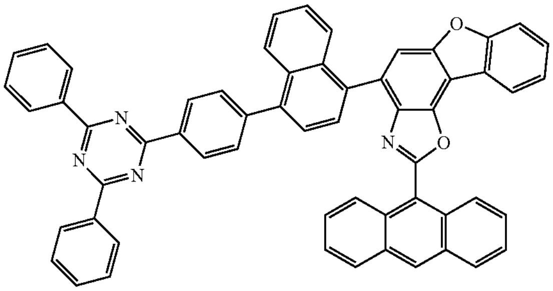
D27
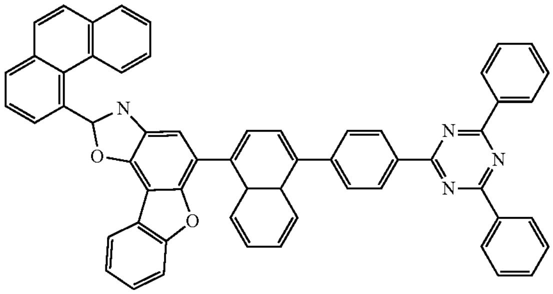
D28
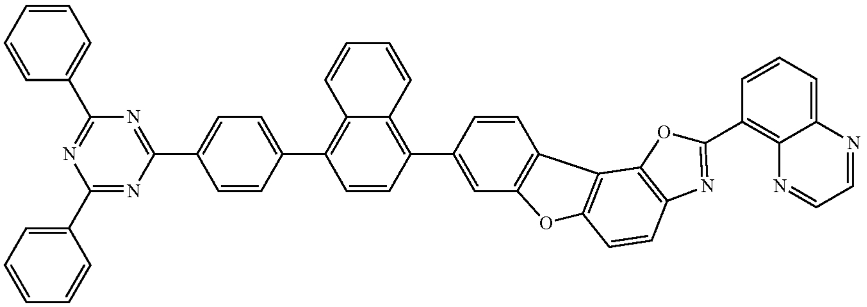
D29
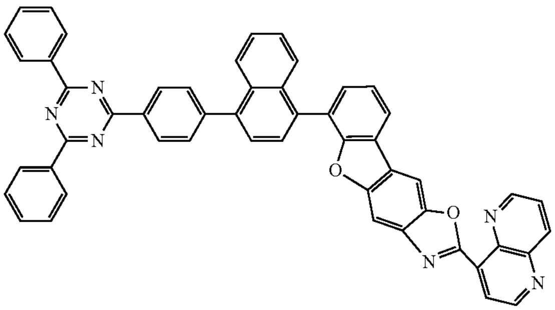
D30
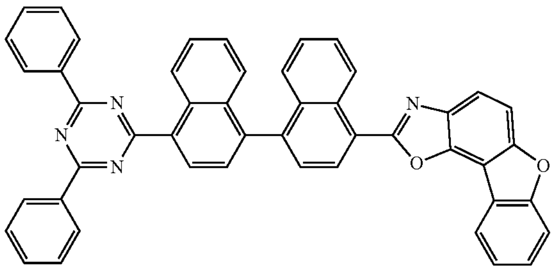
D31
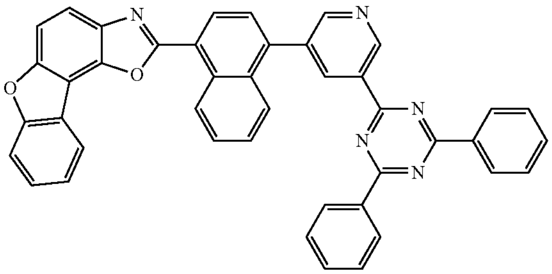
D32
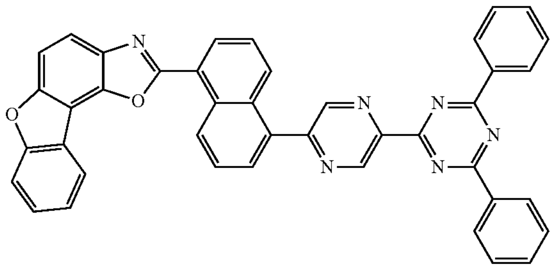

-continued
D33
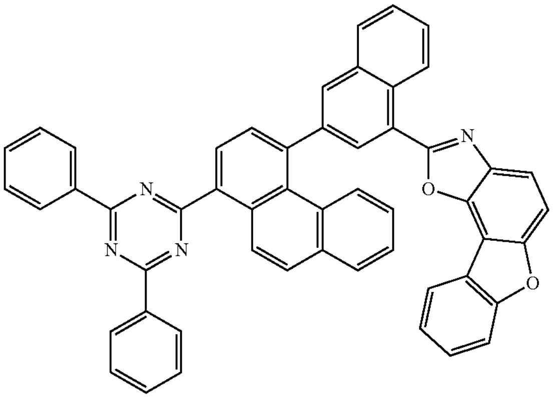
D34
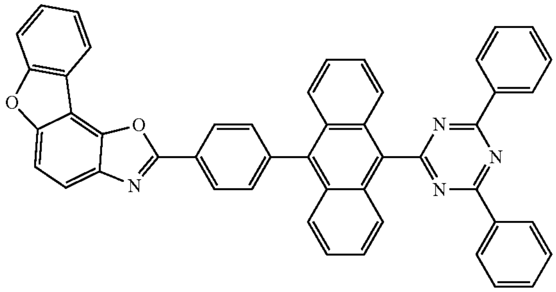
D35
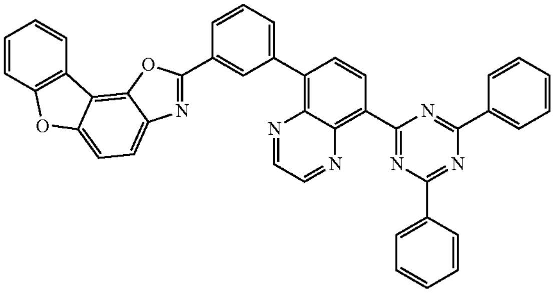
D36
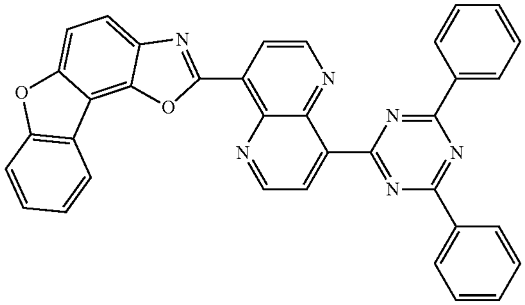
D37
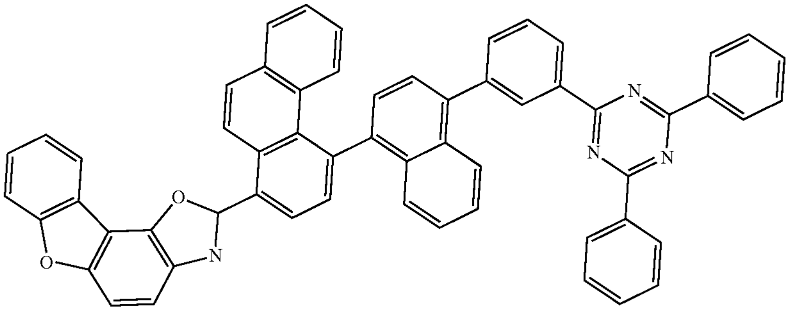
D38
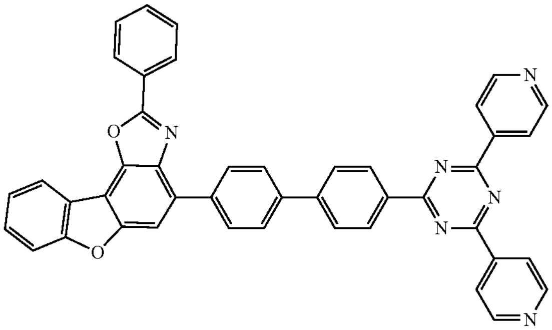
D39
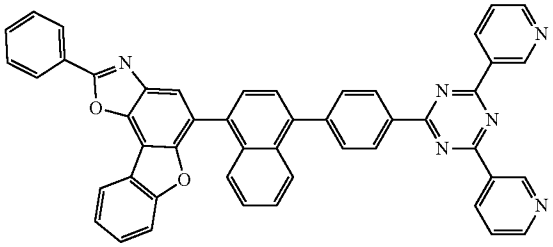

-continued
D40
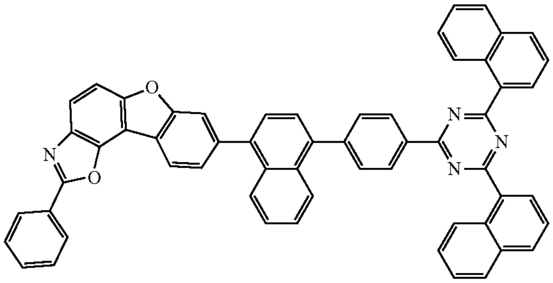
D41
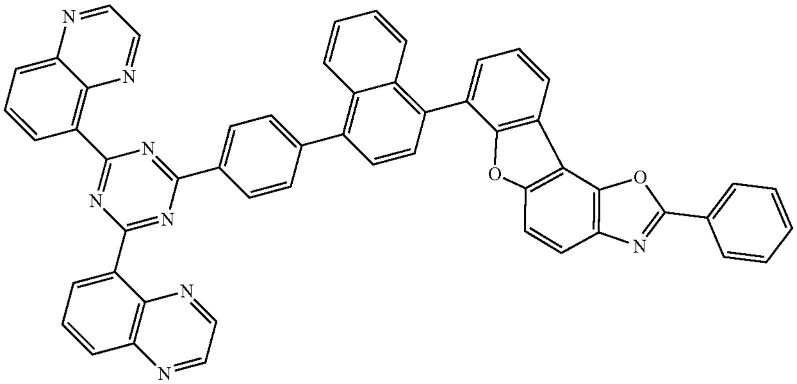
D42
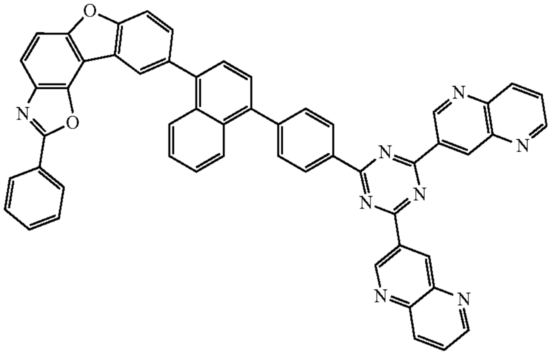
D43
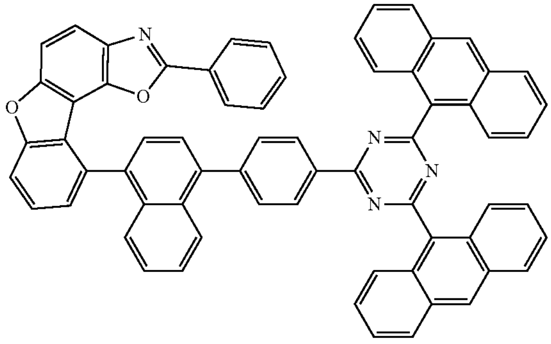
D44
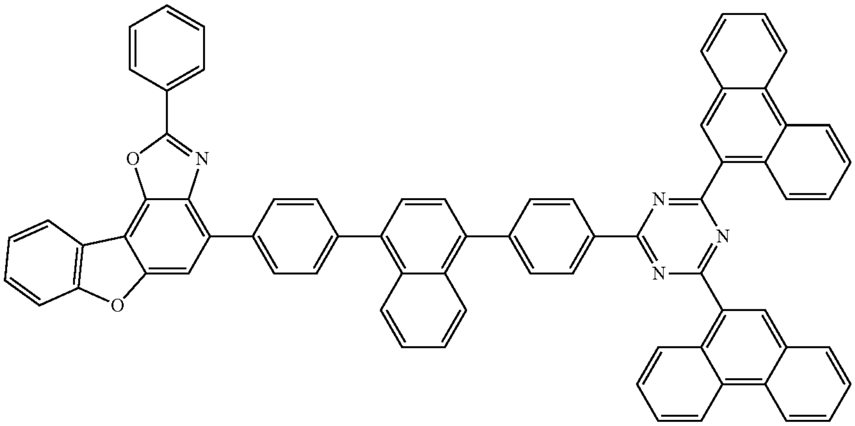

-continued
D45
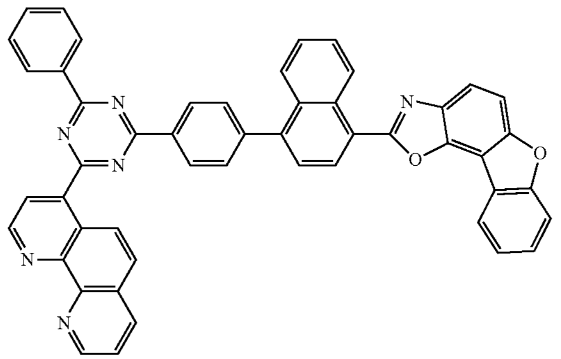
D46
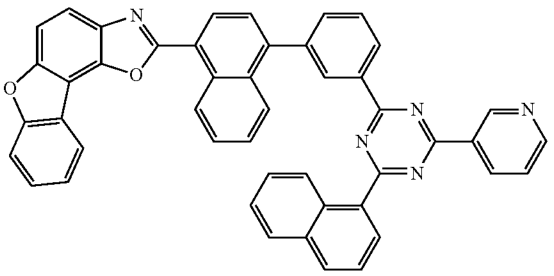
D47
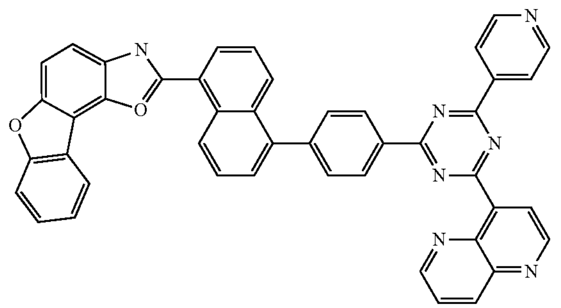
D48
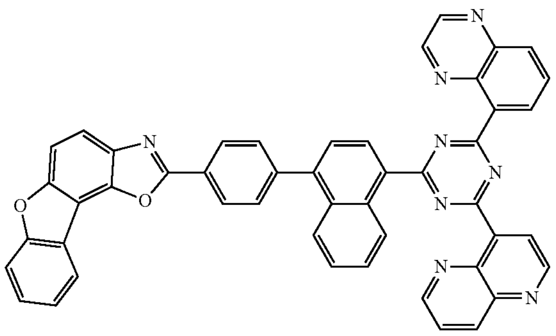
E1
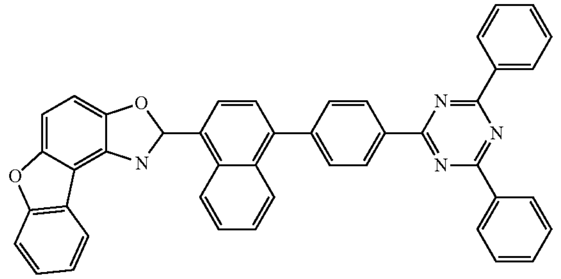
E2
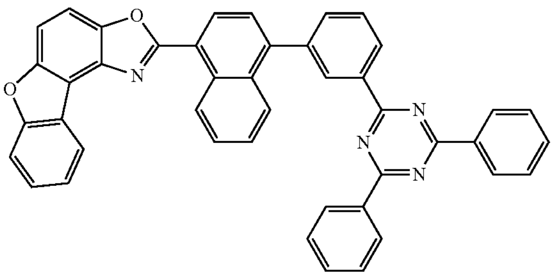
E3
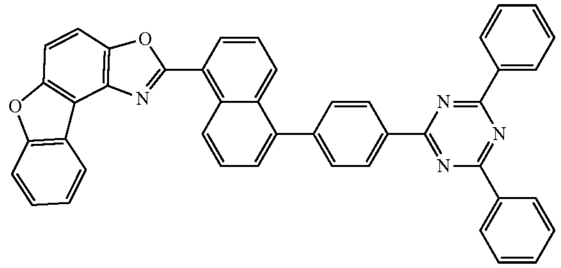
E4
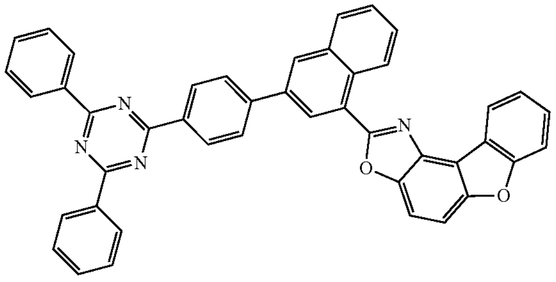
E5
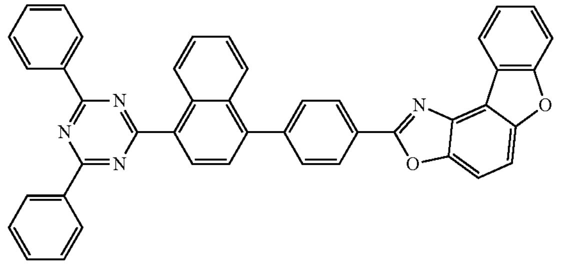
E6
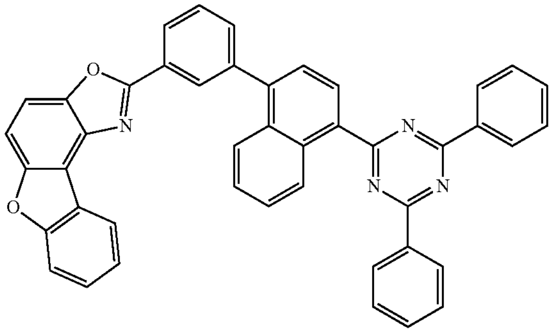

-continued
E7
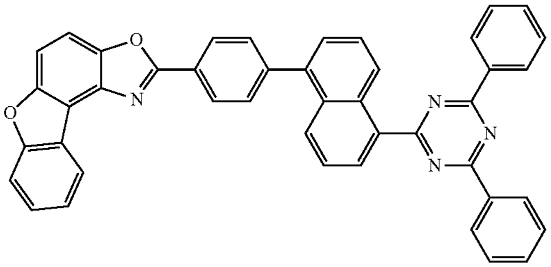
E8
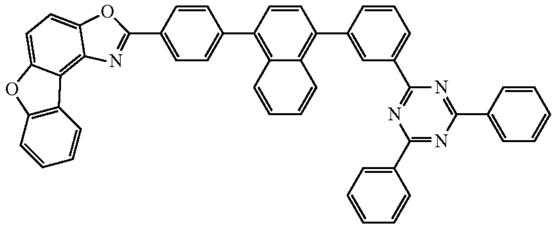
E9
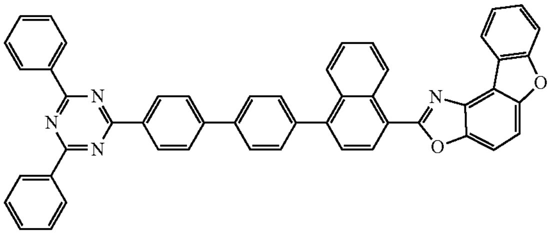
E10
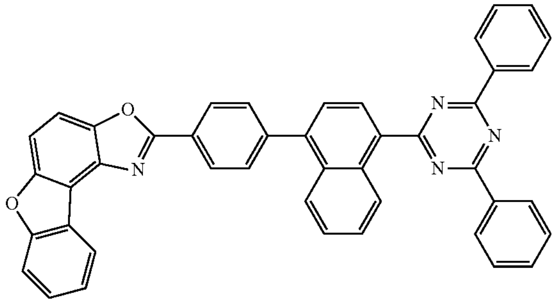
E11
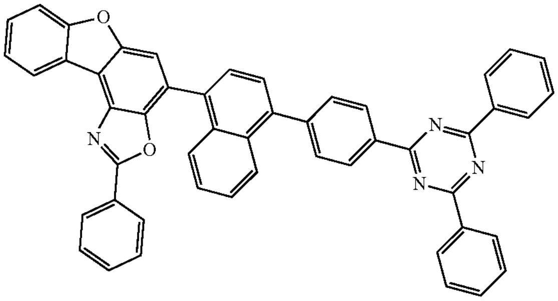
E12
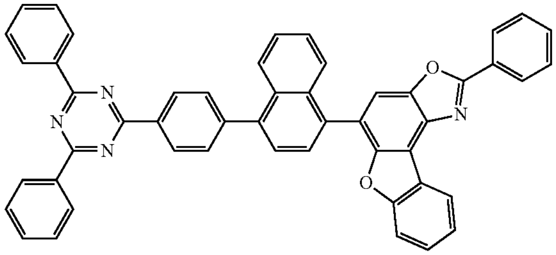
E13
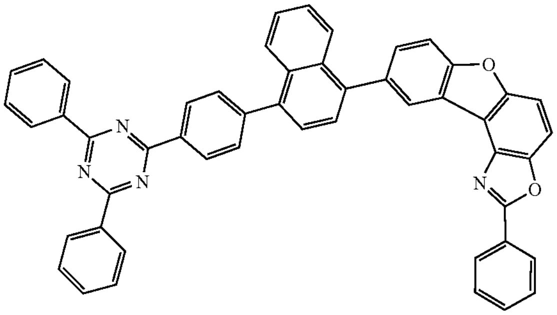
E14
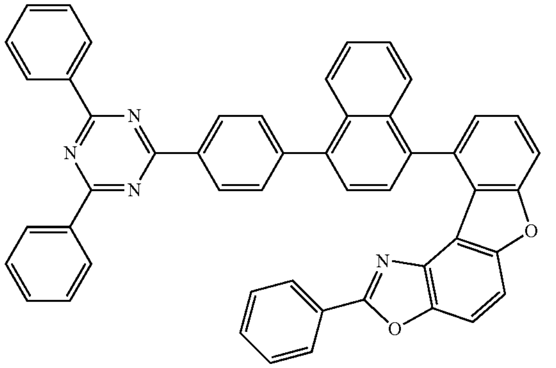

-continued
E15
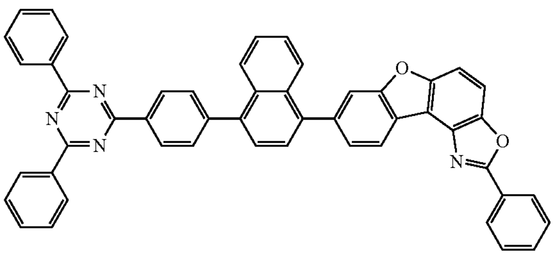
E16
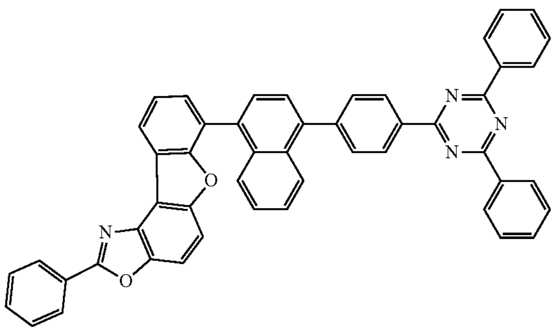
E17
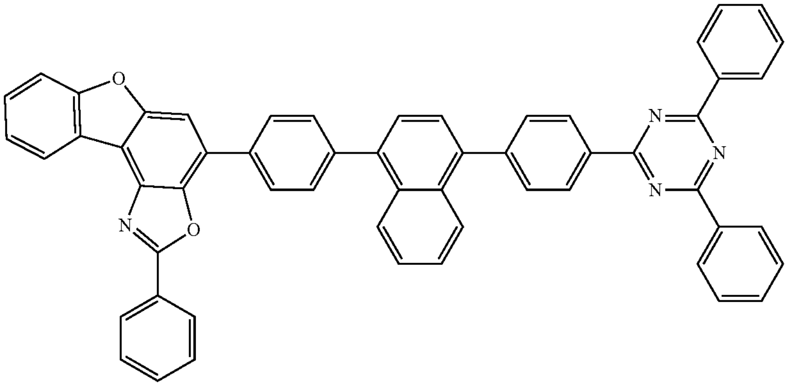
E18
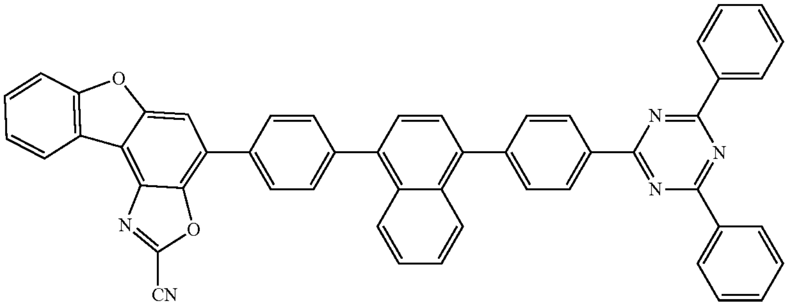
E19
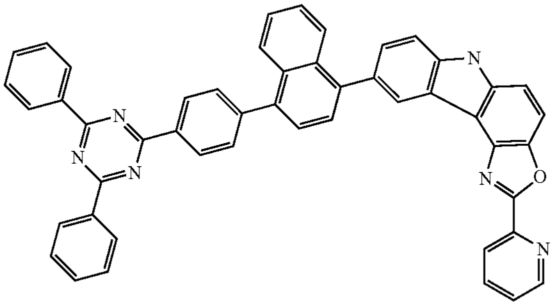
E20
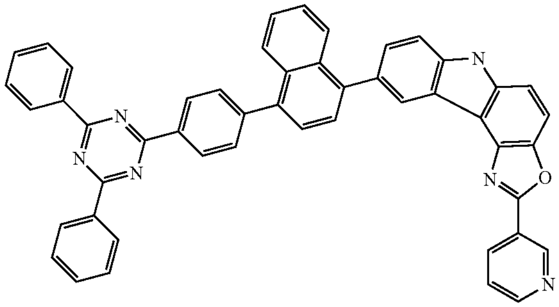

-continued
E21
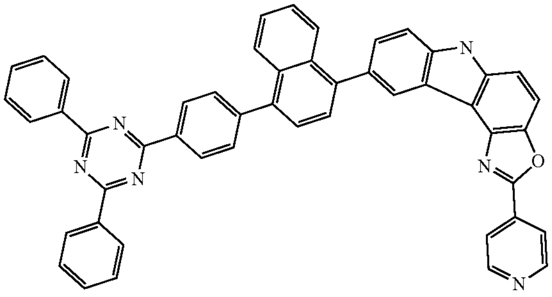
E22
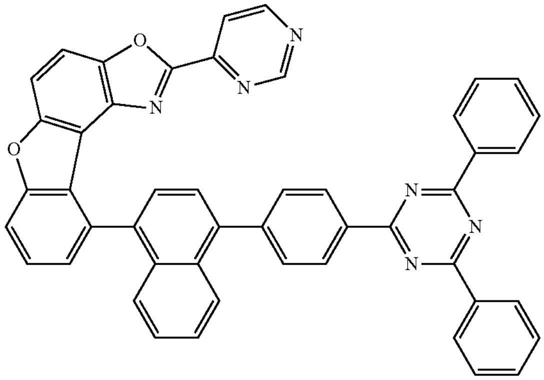
E23
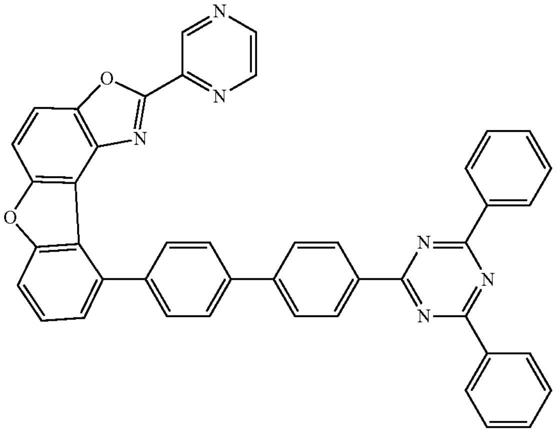
E24
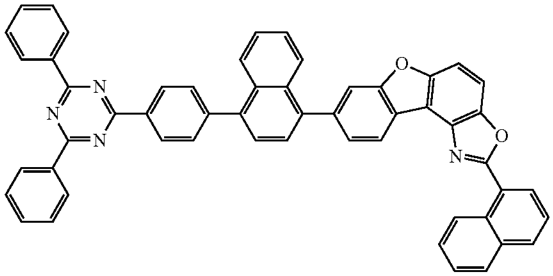
E25
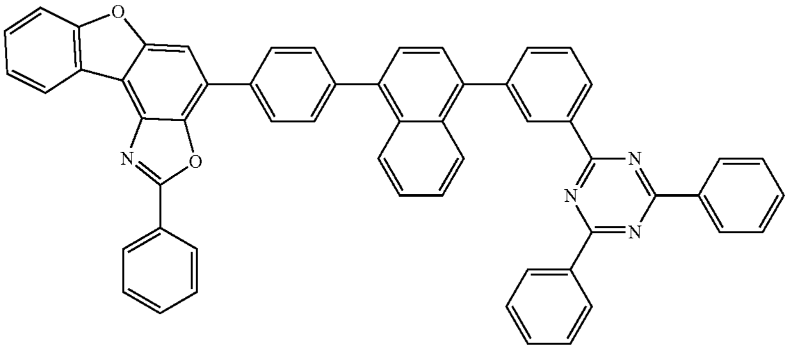
E26
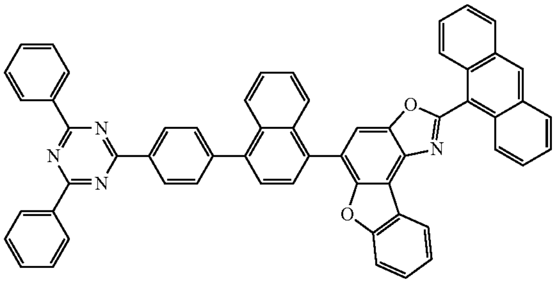
E27
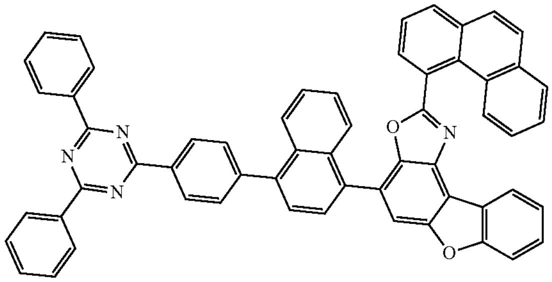

-continued
E28
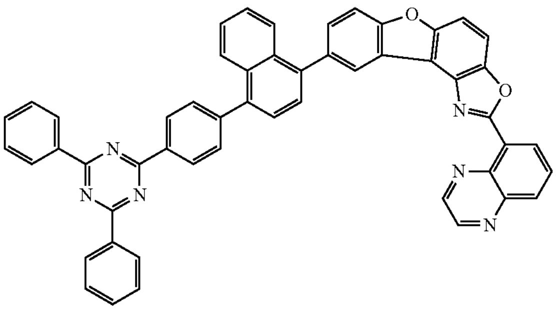
E29
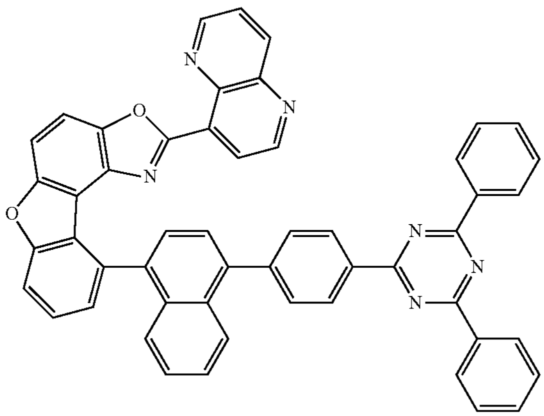
E30
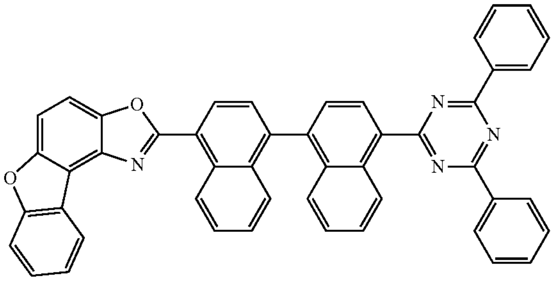
E31
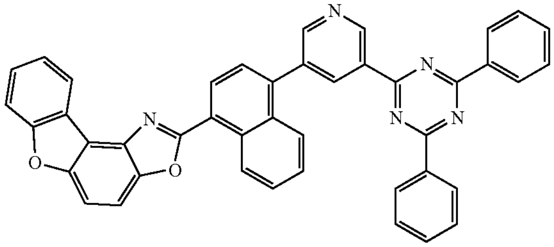
E32
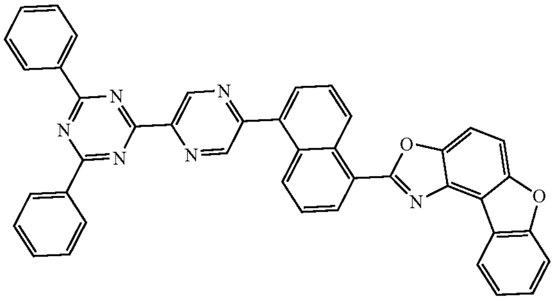
E33
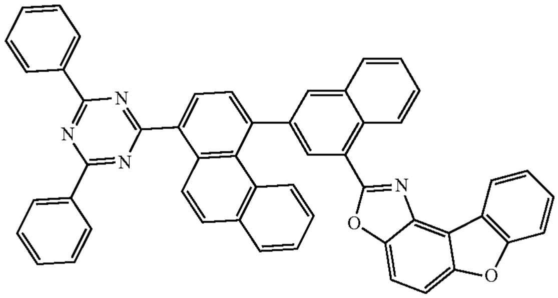
E34
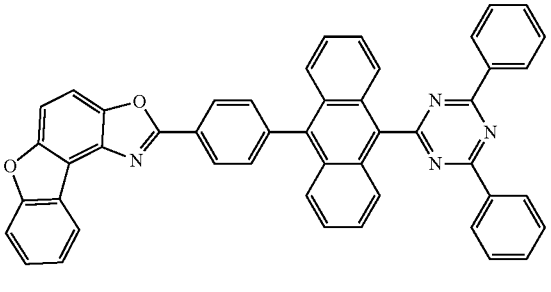
E35
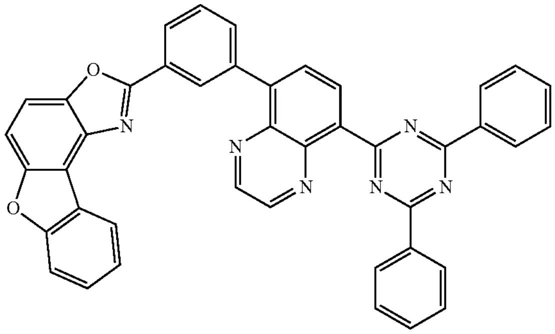

-continued
E36
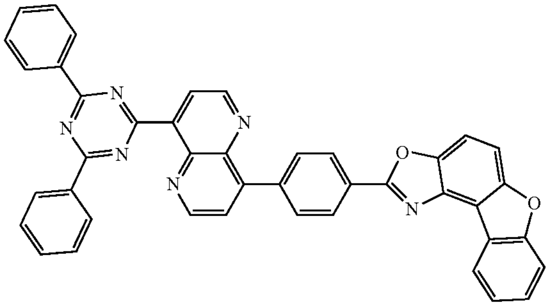
E37
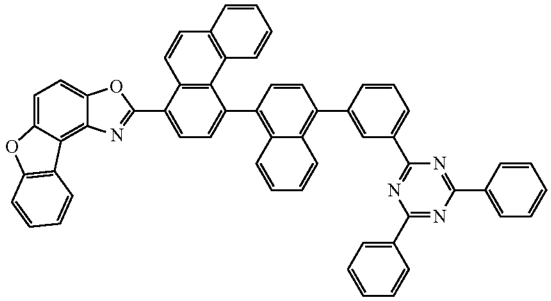
E38
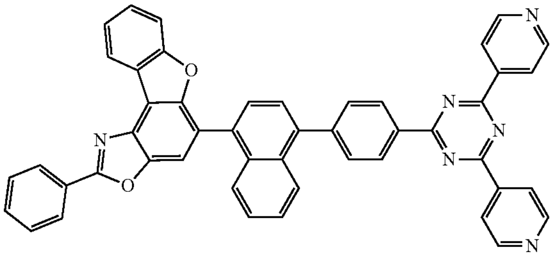
E39
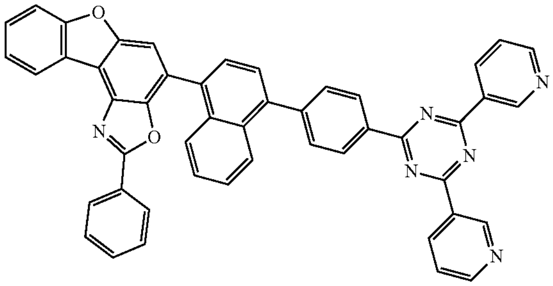
E40
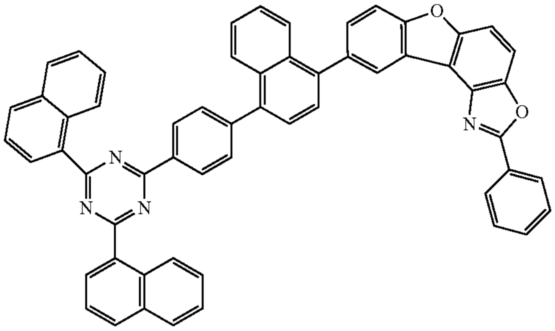
E41
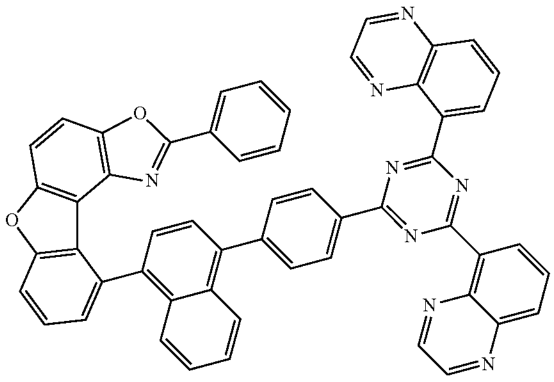
E42
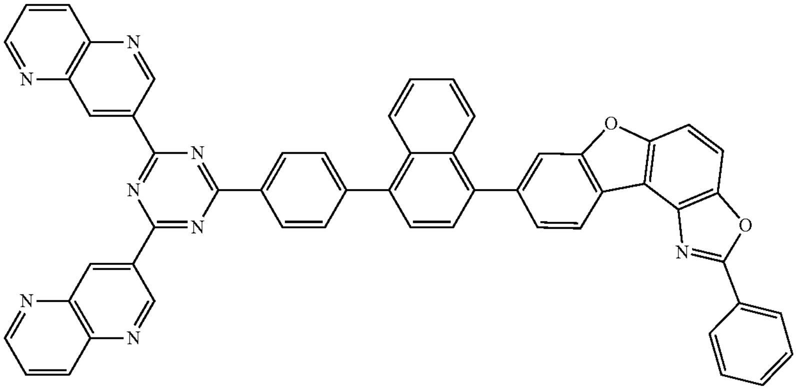

-continued
E43
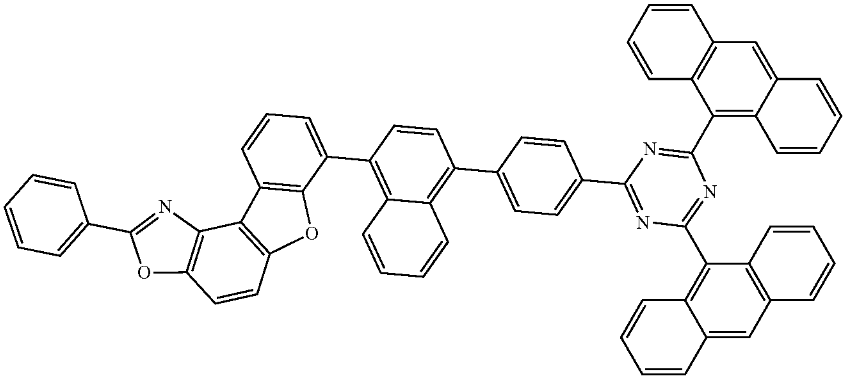
E44
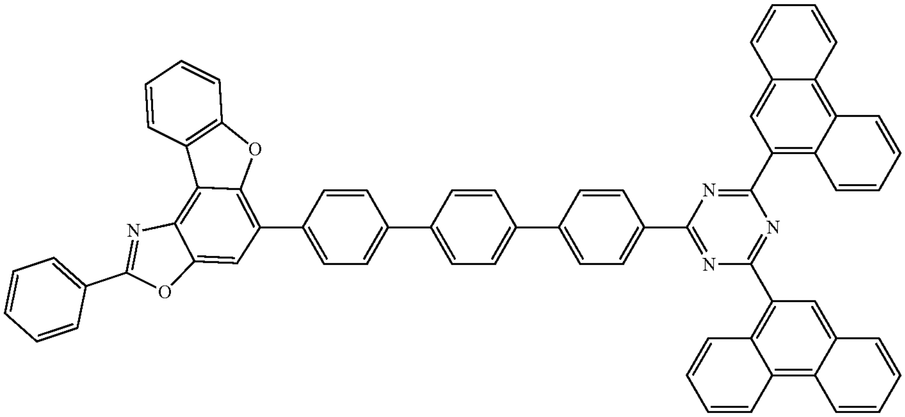
E45
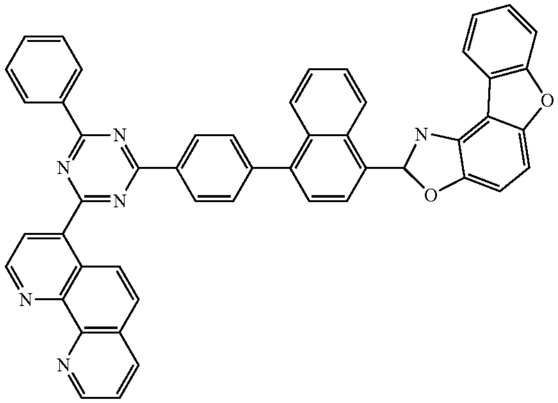
E46
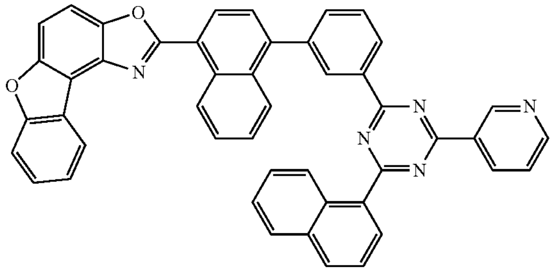
E47
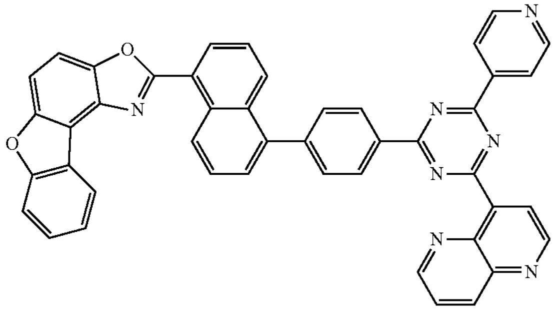
E48
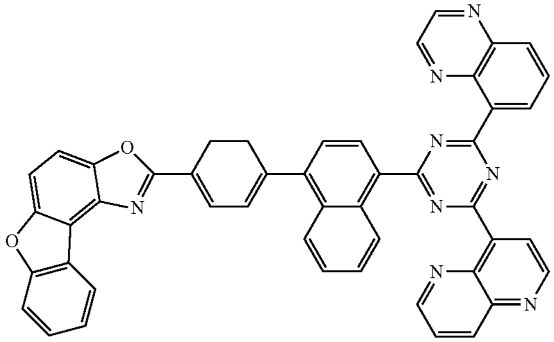

-continued
F1
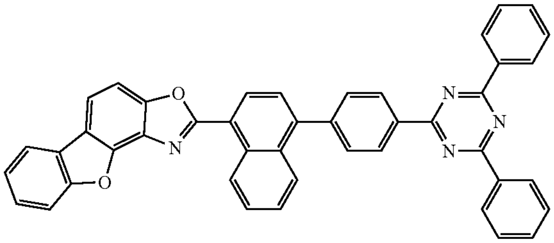
F2
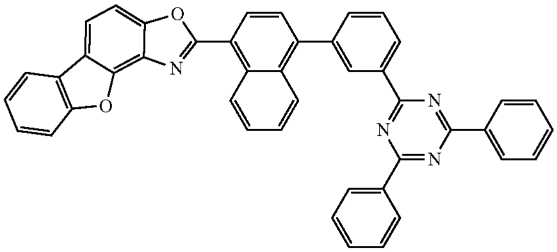
F3
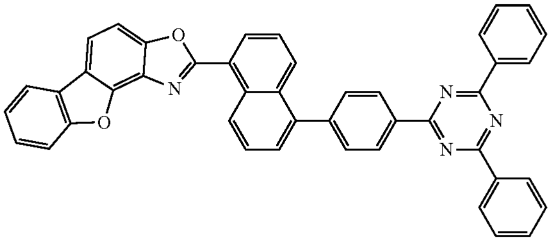
F4
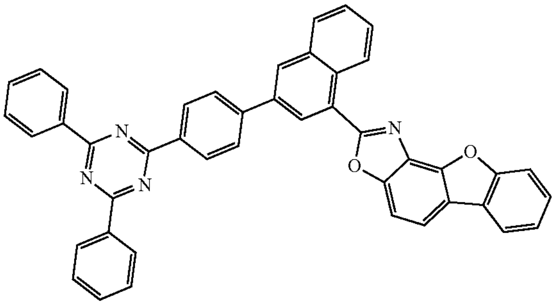
F5
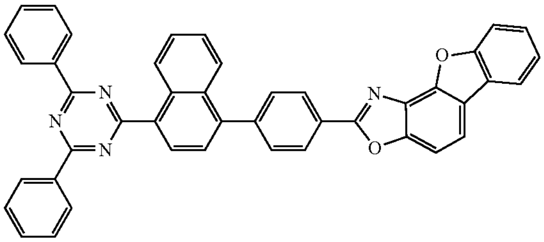
F6
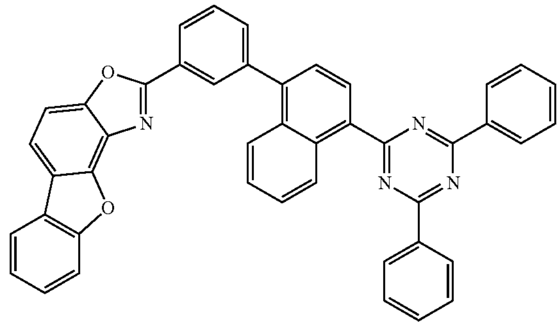
F7
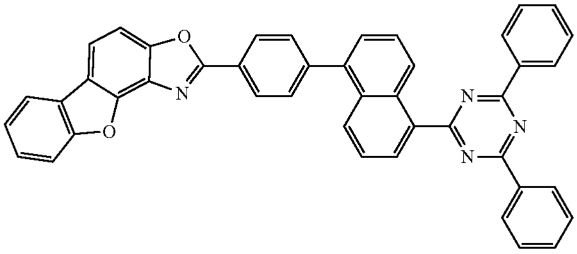
F8
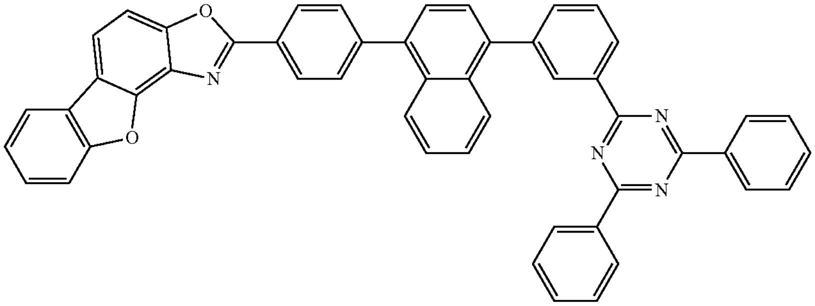

-continued
F9
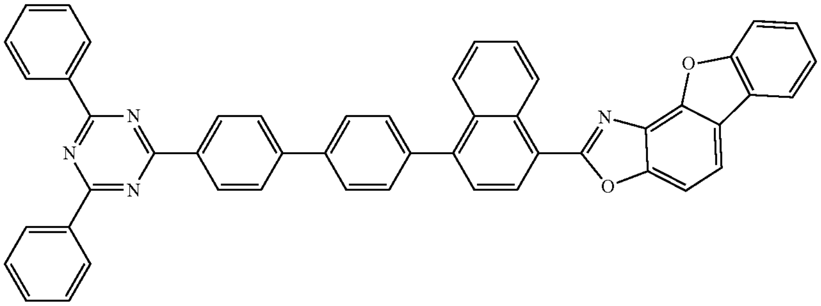
F10
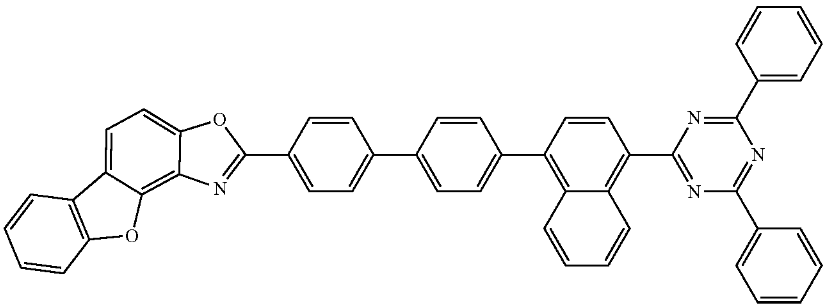
F11
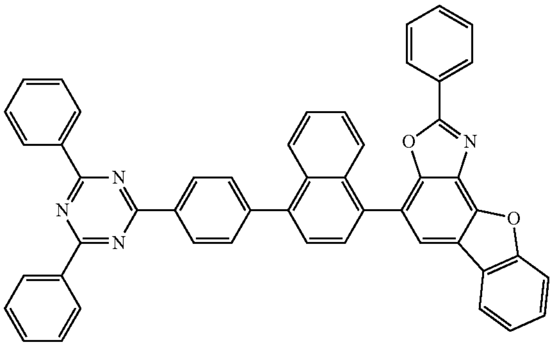
F12
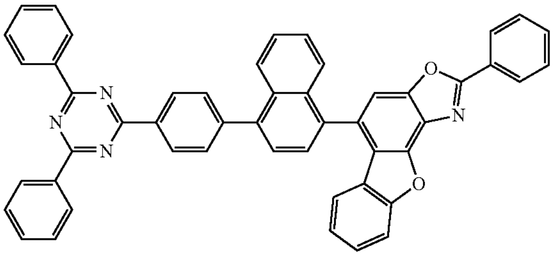
F13
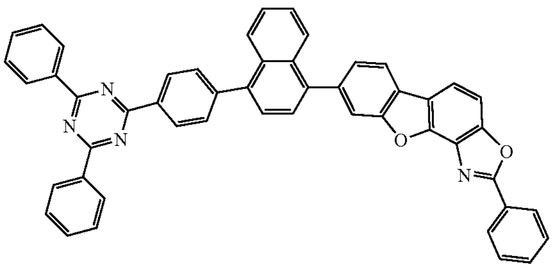
F14
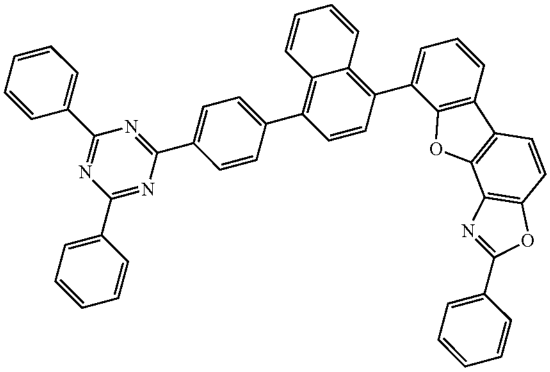

-continued
F15
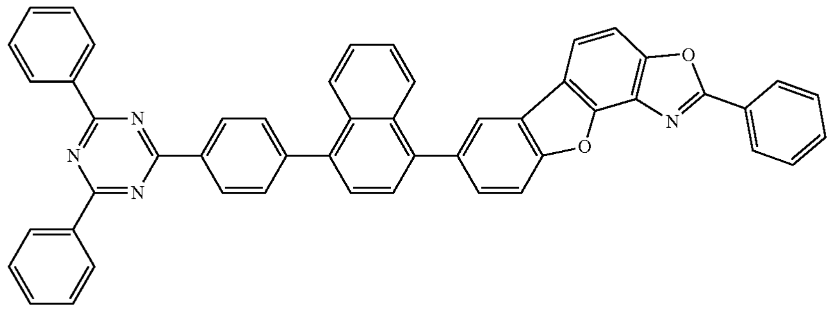
F16
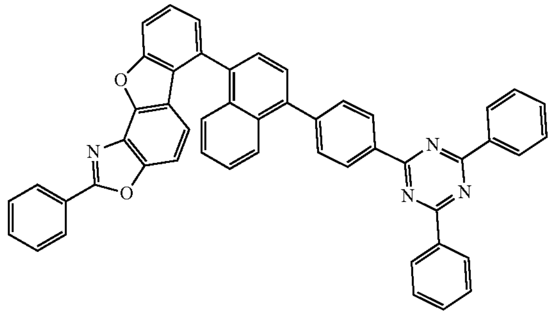
F17
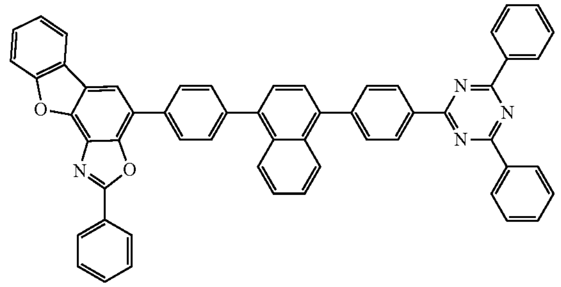
F18
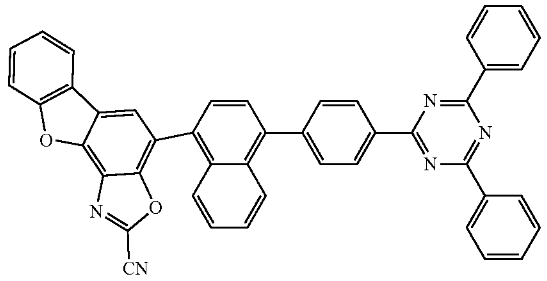
F19
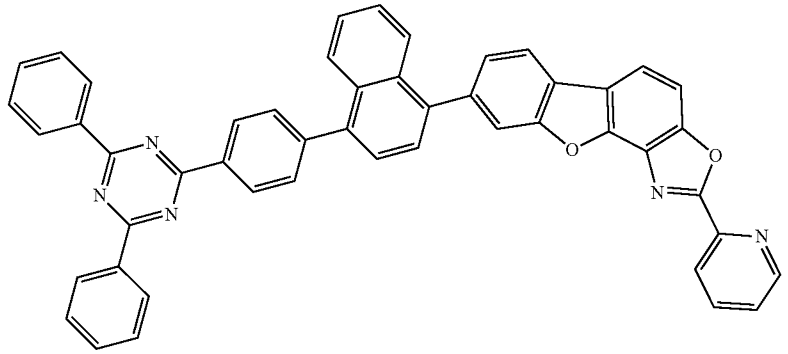
F20
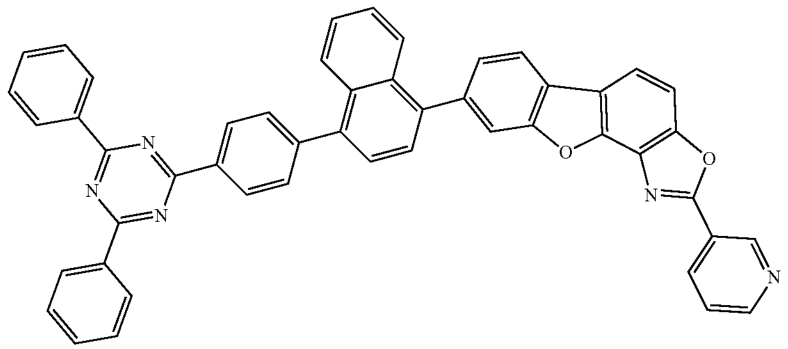

-continued
F21
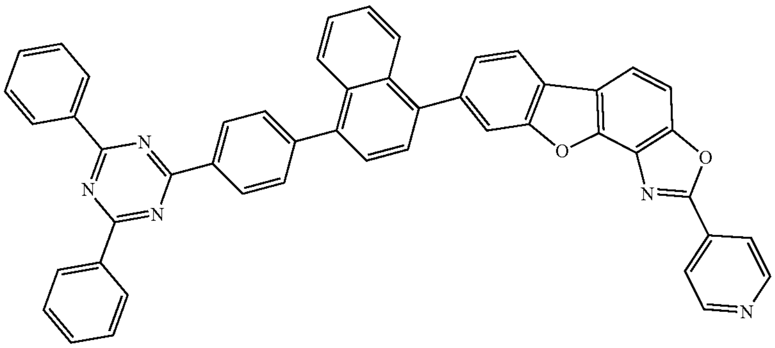
F22
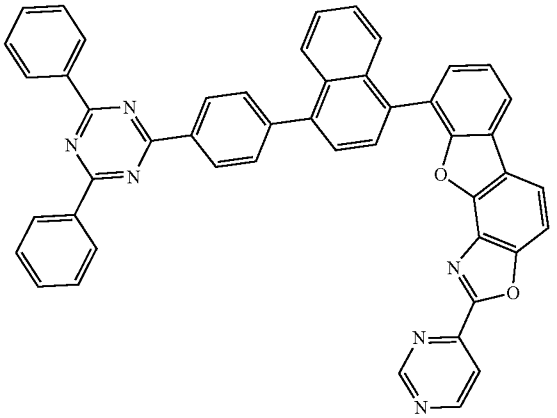
F23
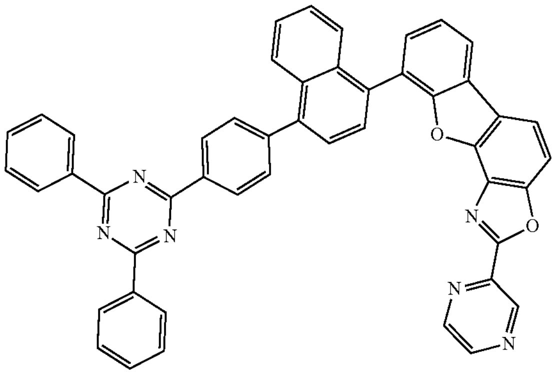
F24
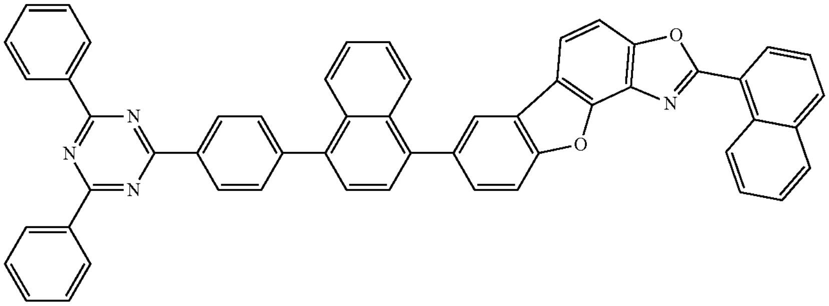
F25
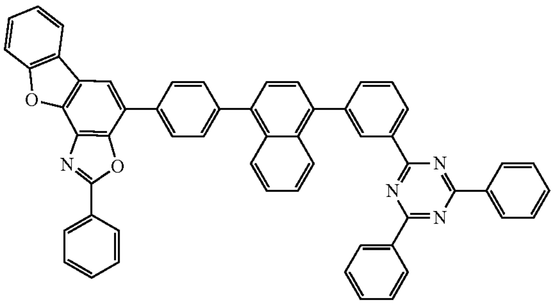
F26
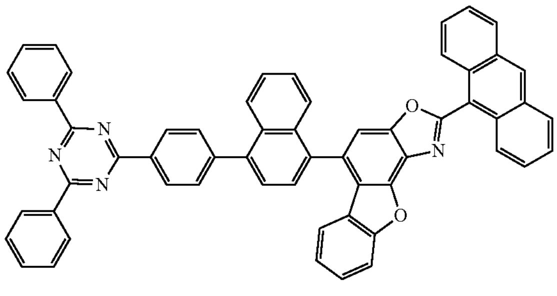

-continued
F27
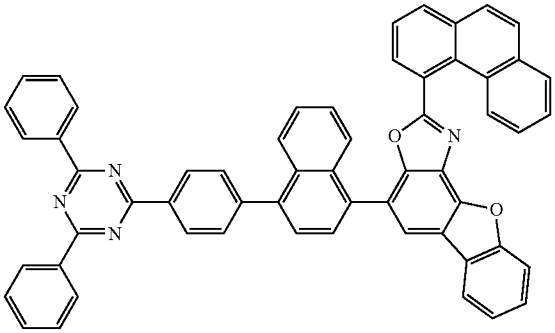
F28
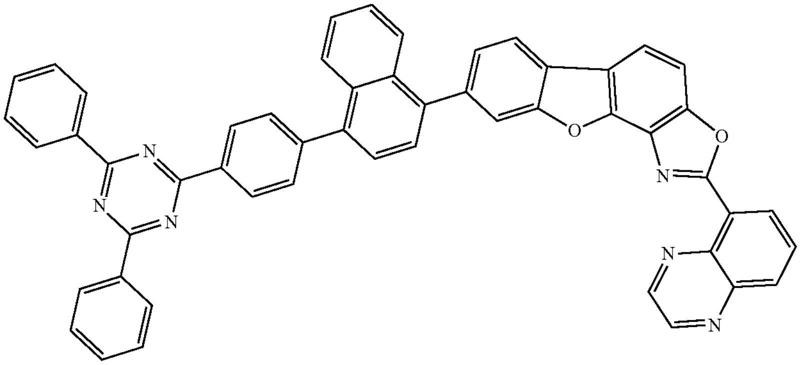
F29
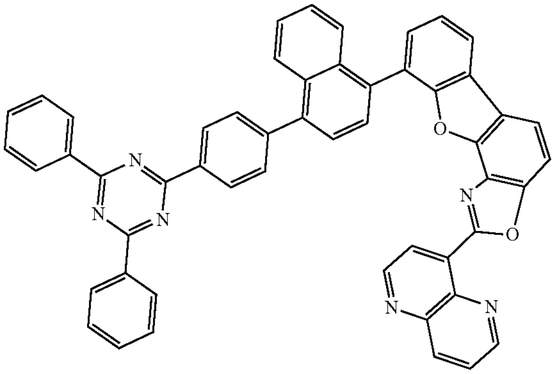
F30
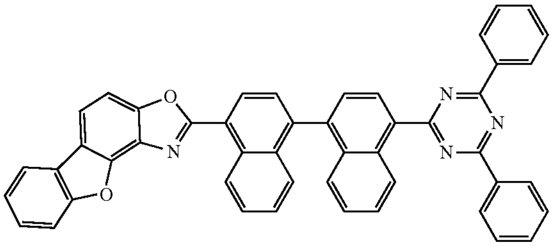
F31
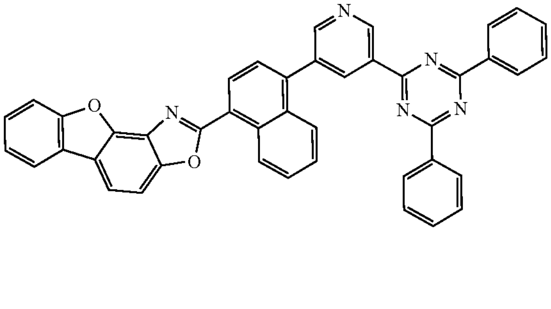
F32
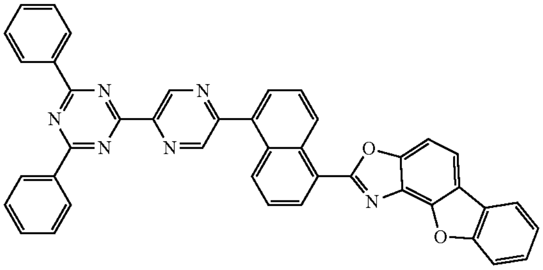

-continued
F33
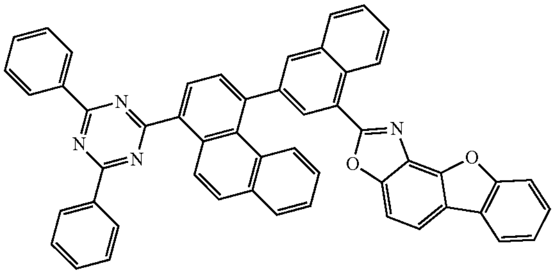
F34
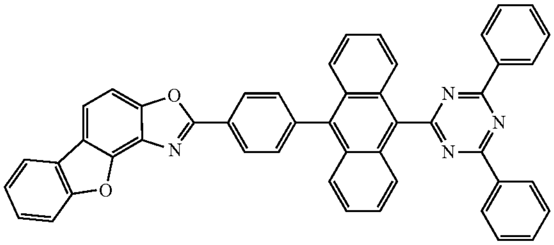
F35
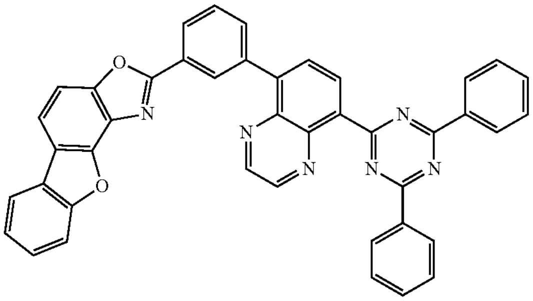
F36
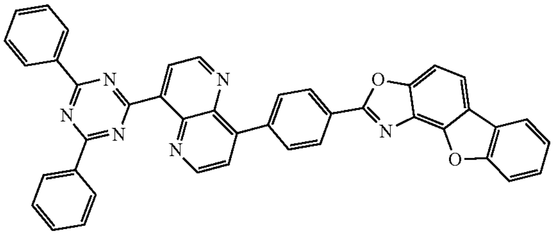
F37
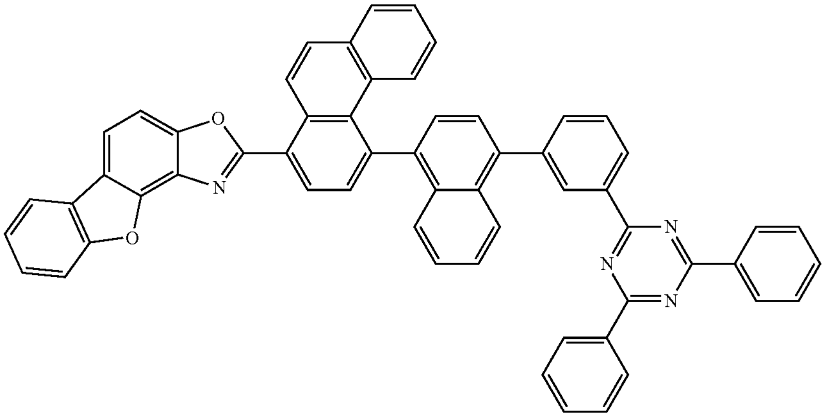
F38
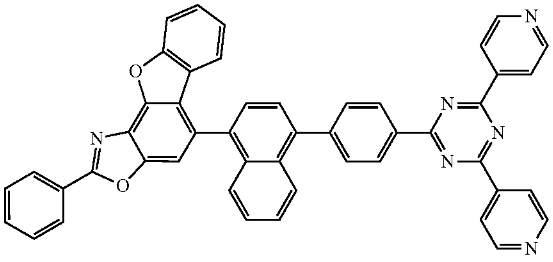
F39
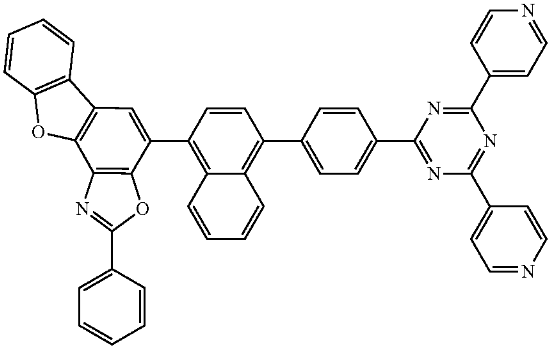

-continued
F40
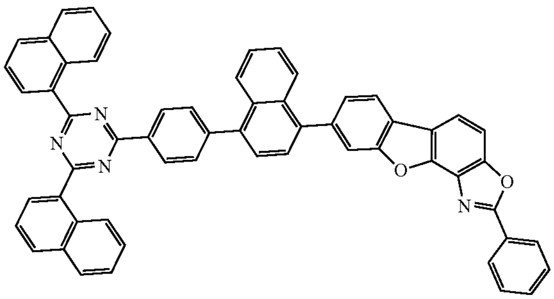
F41
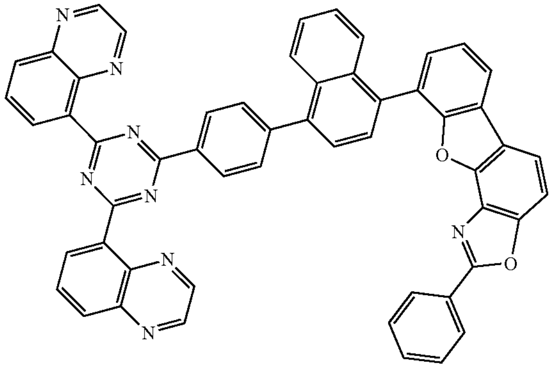
F42
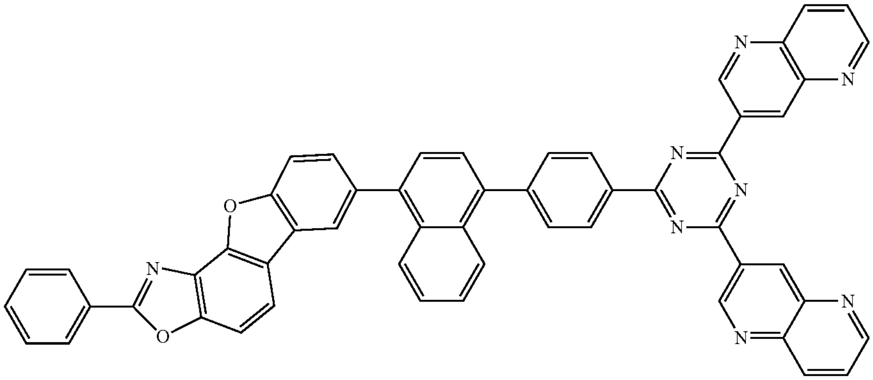
F43
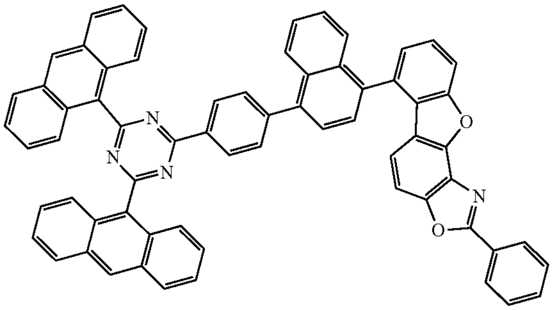
F44
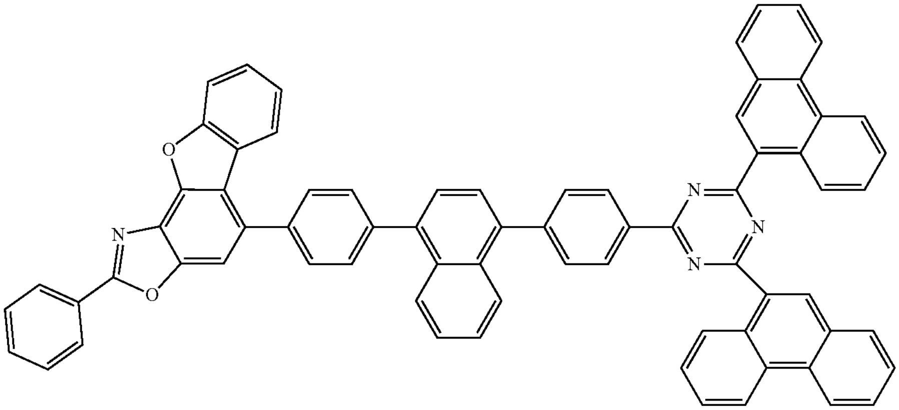

-continued

F45

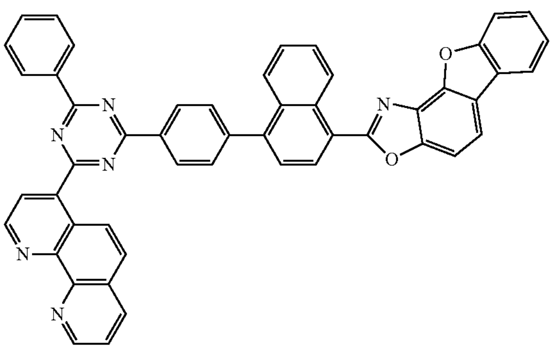

F46

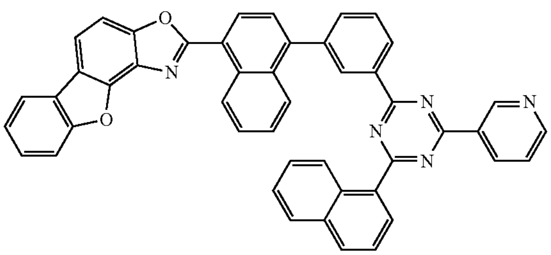

F47

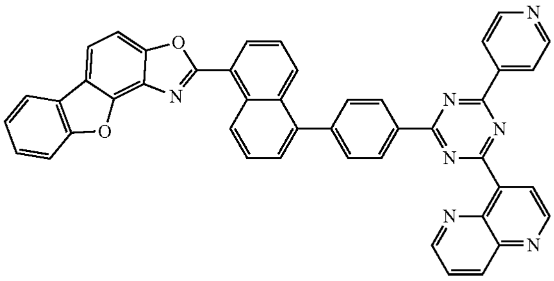

F48

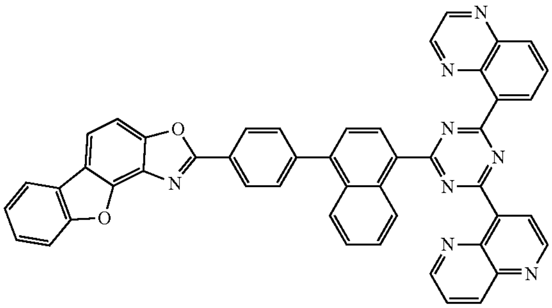

The present disclosure provides an organic light-emitting device comprising an anode, a cathode, and an organic thin film layer located between the anode and the cathode, and the organic thin film layer includes an electron transport layer, and the electron transport layer includes at least one of the above-mentioned benzoxazole derivatives.

In one embodiment, the electron transport layer includes the benzoxazole derivative and LiQ.

The above-mentioned LiQ refers to 8-hydroxyquinolino-lato-lithium.

The present disclosure provides a display panel comprising the above organic light-emitting device.

The organic light-emitting device provided by the present disclosure can be an organic light-emitting device well known to those skilled in the art. In one embodiment of the present disclosure, the organic light-emitting device includes a substrate plate, an ITO anode, a first hole transport layer, a second hole transport layer, an electron blocking layer, a light-emitting layer, a first electron transport layer, a second electron transport layer, a cathode (magnesium-silver electrode, the mass ratio of magnesium-silver is 1:9) and a capping layer (CPL).

In one embodiment of the present disclosure, the anode material of the organic light-emitting device can be selected from the group consisting of metals-copper, gold, silver, iron, chromium, nickel, manganese, palladium, platinum, etc. and alloys thereof; such as metal oxides-indium oxide, zinc oxide, indium tin oxide (ITO), indium zinc oxide (IZO); such as conductive polymers—polyaniline, polypyrrole, poly(3-methylthiophene). In addition to the above materials and combinations thereof that contribute to hole injection, materials known to be suitable for use as anodes are also included.

In one embodiment of the present disclosure, the cathode material of the organic light-emitting device can be selected from the group consisting of metals-aluminum, magnesium, silver, indium, tin, titanium, etc. and alloys thereof; such as multi-layer metal materials-LiF/Al, $LiO_2$/Al, $BaF_2$/Al; in addition to the above materials and combinations thereof that contribute to electron injection, materials known to be suitable for use as cathodes are also included.

In one embodiment of the present disclosure, the organic thin film layer in the organic photoelectronic device, such as the organic light-emitting device, includes at least one light-emitting layer (EML), and may also include other functional layers, comprising a hole injection layer (HIL), a hole transport layer (HTL), an electron blocking layer (EBL), a hole blocking layer (HBL), an electron transport layer (ETL), and an electron injection layer (EIL).

In one embodiment of the present disclosure, the organic light-emitting device is prepared according to the following method:

Forming an anode on a transparent or opaque smooth substrate plate, forming an organic thin layer on the anode, and forming a cathode on the organic thin layer.

In one embodiment of the present disclosure, known film forming methods such as vapor deposition, sputtering, spin coating, dipping, and ion plating can be used to form the organic thin layer.

The present disclosure provides a display device comprising the above-mentioned display panel.

In the present disclosure, an organic light-emitting device (OLED device) can be used in a display device, and the organic light-emitting display device can be a mobile phone display, a computer display, a TV display, a smart watch display, a smart car display panel, a VR or AR helmet display, displays of various smart devices, etc.

The following will clearly and completely describe the embodiments of the present disclosure. The described examples are only a part of the embodiments of the present disclosure, rather than all the embodiments. Based on the examples of the present disclosure, all other examples may be obtained.

Example 1 Preparation of Compounds

Preparation of A1

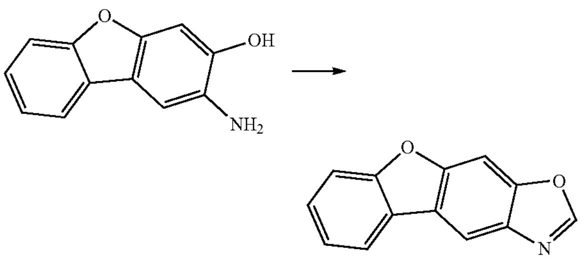

M1-1

2-amino-3-dibenzofuranol (20.0 g, 101 mmol) and triethyl formate (20 mL) were added to a reaction vessel. The obtained mixture was refluxed for 9 hours until the reaction was completed. Triethyl formate was then removed. The residue was separated by column chromatography to obtain M1-1 (18.06 g, 86%).

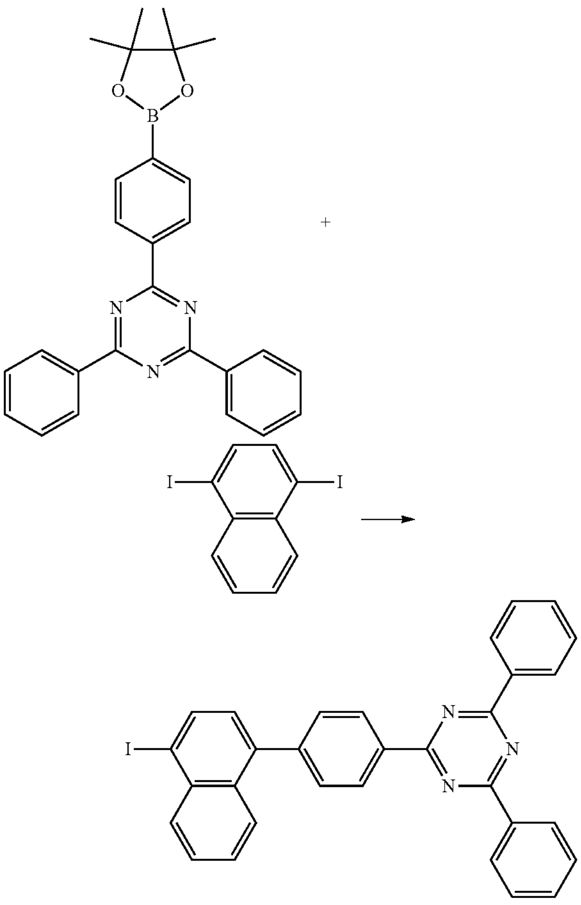

M1-2

Intermediate 2,4-diphenyl-6-[4-(4,4,5,5-tetramethyl-1,3,2-dioxaborolan-2-yl)phenyl]-1,3,5-triazine (8.7 g, 20.00 mmol), 1,4-diiodonaphthalene (7.6 g, 20.05 mmol), $Pd(PPh_3)_4$ (1.13 g, 0.98 mmol), and $K_2CO_3$ (8.11 g, 58.66 mmol) were mixed into 100 ml of toluene, 25 ml of $H_2O$ and 25 ml of EtOH under nitrogen gas stream, and the mixture was stirred at 110 °C for 4 hours. After the reaction was completed, the mixture was extracted with dichloromethane, added with $MgSO_4$, and filtered. After the solvent of the filtered organic layer was removed, the residue was subjected to column chromatography to obtain 9.54 g (yield: 85%) of the target compound M1-2.

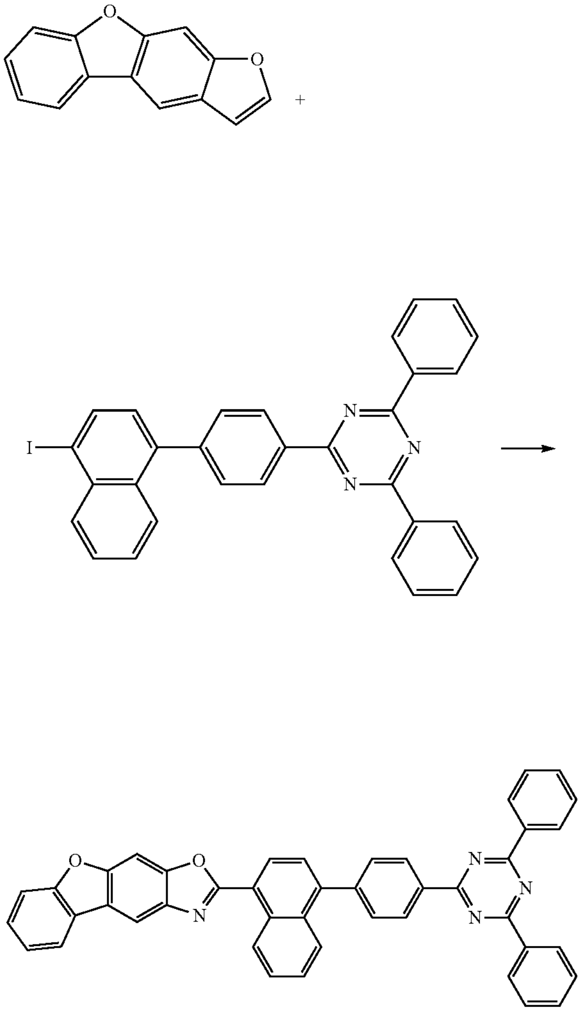

A1

Copper (I) thiophene-2-carboxylate (0.1 g, 0.5 mmol), 2,2'-bipyridine (0.1 g, 0.5 mmol), and lithium were added to tert-butoxide (2.0 g, 25 mmol) and dry N,N-dimethylformamide (50 ml, 0.2 M) with a magnetic stir bar under nitrogen atmosphere. After stirring for 5 minutes, the color of the solvent changed from light green to light yellow, and M1-1 (2.1 g, 10 mmol) and M1-2 (22.4 g, 40 mmol) were added to the mixture. The obtained solution was then irradiated with a blue LED and stirred at room temperature for 16 hours. The obtained suspension was filtered on a pad of silica gel using ethyl acetate as eluent and evaporated in vacuum. The residue was separated by column chromatography to obtain 5.14 g of product A1, (yield: 80%).

Preparation of A2

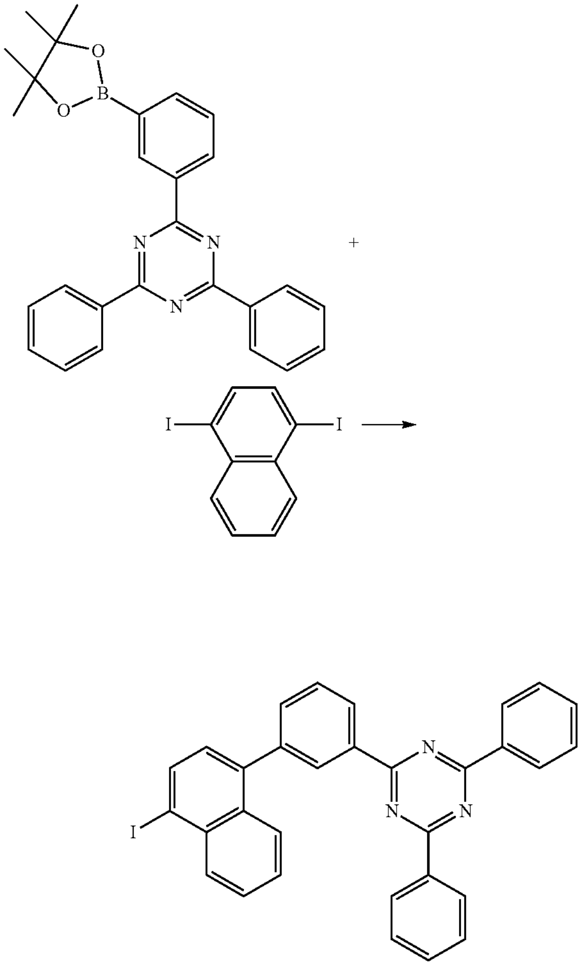

M2-1

M2-1 was prepared in the same way as M1-2, following the same preparation method of M1-2, using the same molar ratio, except that 2,4-diphenyl-6-[4-(4,4,5,5-tetramethyl-1,3,2-dioxaborolan-2-yl)phenyl]-1,3,5-triazine was replaced by 2,4-diphenyl-6-[3-(4,4,5,5-tetramethyl-1,3,2-dioxaborolan-2-yl)phenyl]-1,3,5-triazine.

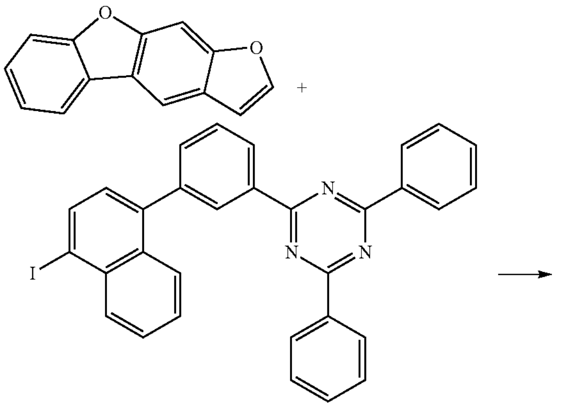

-continued

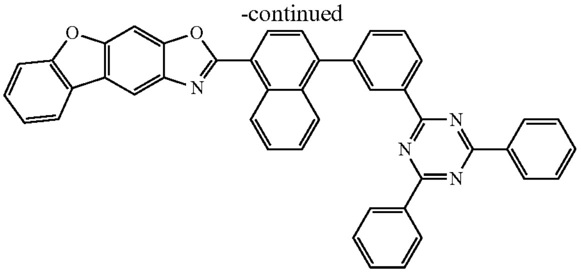

A2

A2 was prepared in the same way as A1, following the same preparation method of A1, using the same molar ratio, except that M1-2 was replaced by M2-1.

Preparation of A5

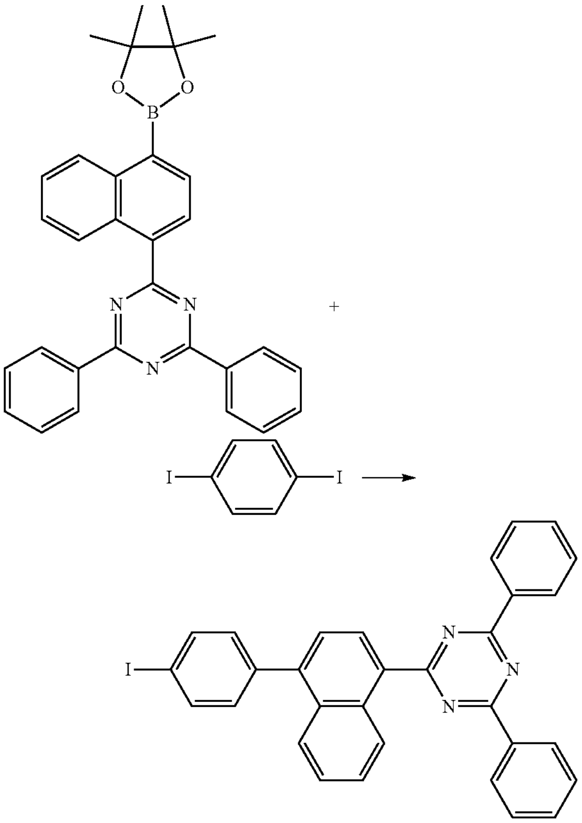

M3-1

M3-1 was prepared in the same way as M1-2, following the same preparation method of M1-2, using the same molar ratio, except that 1,4-diiodonaphthalene was replaced by 1,4-diiodobenzene, and 2,4-diphenyl-6-[4-(4,4,5,5-tetramethyl-1,3,2-dioxaborolan-2-yl)phenyl]-1,3,5-triazine was replaced with 2,4-diphenyl-6-[4-(4,4,5,5-tetramethyl-1,3,2-dioxaborolan-2-yl)-1-naphthyl]-1,3,5-triazine.

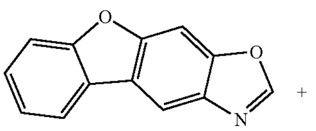

-continued

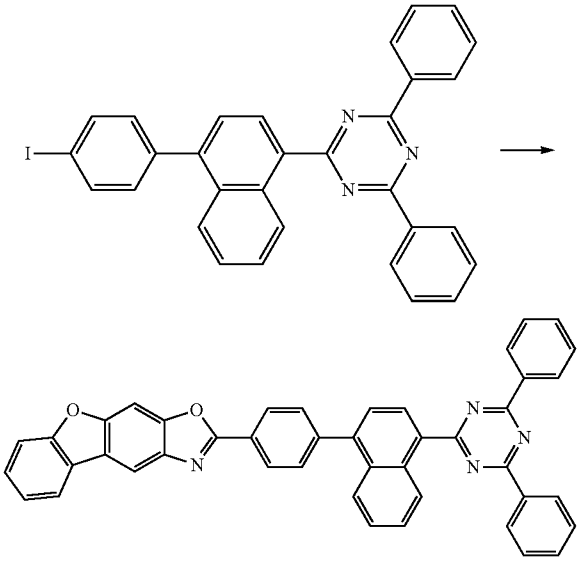

A5

A5 was prepared in the same way as A1, following the same preparation method of A1, using the same molar ratio, except that M1-2 was replaced by M3-1.

Preparation of A12

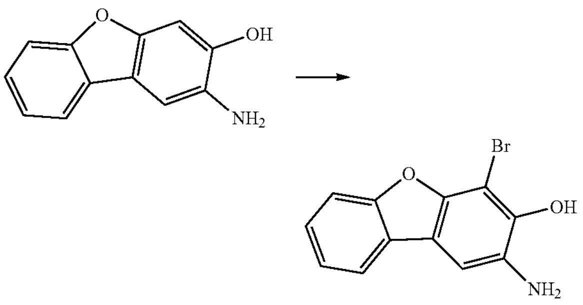

M4-1

100 ml of ethanol, 2-amino-3-dibenzofuranol (20.0 g, 101 mmol), NBS (2.5 g, 220 mmol) and copper nitrate (1.3 g, 10 mmol) were sequentially added in a reactor, and the mixture was stirred at room temperature for 0.5 h, then heated up to 50 °C and maintained for 3 h until the reaction was completed. Then the reaction solution was cooled to 20 °C, and poured into 100 ml of water, and the mixture was stirred for 2 h. The obtained mixture was suction filtered, and the filter cake was stirred with 100 ml of water at room temperature for 1 h. The mixture was suction filtered, and then dried at 50 °C to obtain M4-1 (23.3 g, 84%).

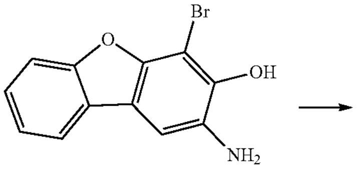

-continued

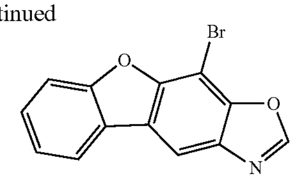

M4-2

M4-2 was prepared in the same way as M1-1, following the same preparation method of M1-1, using the same molar ratio, except that 2-amino-3-dibenzofuranol was replaced by M4-1.

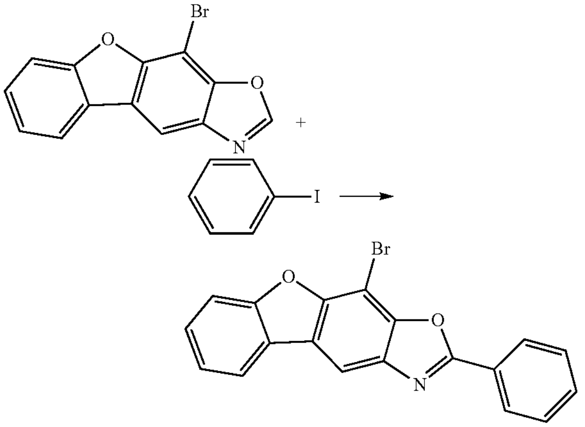

M4-3

M4-3 was prepared in the same way as A1, following the same preparation method of A1, using the same molar ratio, except that M1-2 was replaced with iodobenzene.

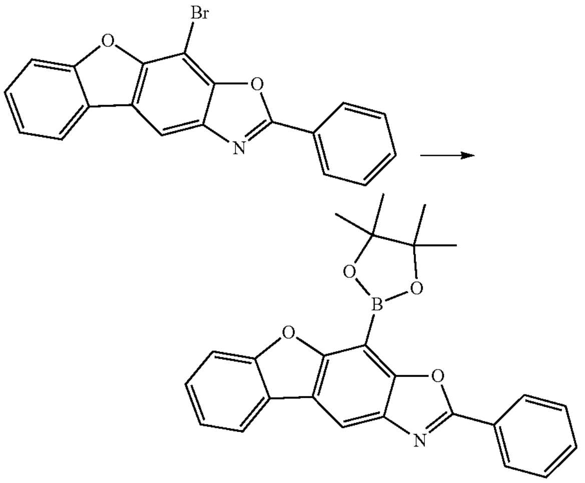

M4-4

Intermediate M4-3 (7.2 g, 19.55 mmol), pinacol bisborate (5.96 g, 23.46 mmol), $Pd(OAc)_2$ (0.13 g, 0.59 mmol), KOAc (3.84 g, 39.11 mmol) and 100 ml of toluene were mixed under nitrogen atmosphere, and the mixture was stirred at 100 °C for 8 hours. After the reaction was completed, the mixture was extracted with dichloromethane, added with $MgSO_4$, and the obtained mixture was filtered. After the solvent of the filtered organic layer was removed, the residue was subjected to column chromatography to obtain 7.2 g (yield: 88%) of intermediate M4-4.

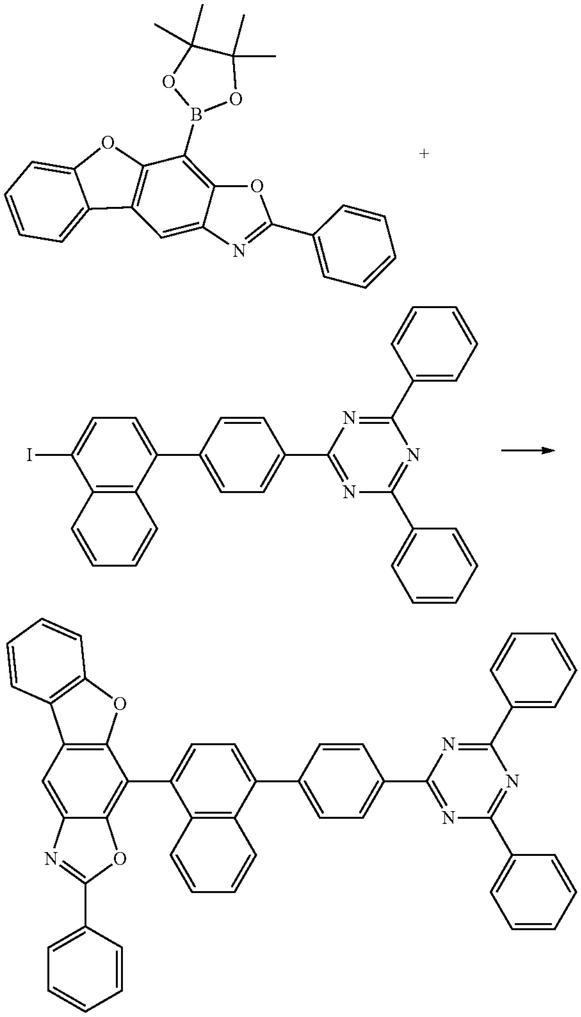

A12

Intermediates M4-4 (6.7 g, 20.0 mmol), M1-2 (11.2 g, 20.0 mmol), $Pd(PPh_3)_4$ (1.13 g, 0.98 mmol), $K_2CO_3$ (8.11 g, 58.66 mmol) were mixed into 100 ml of toluene, 25 ml of $H_2O$ and 25 ml of EtOH under nitrogen gas stream, and the mixture was stirred at 110 °C for 4 hours. After the reaction was completed, the mixture was extracted with dichloromethane, added with $MgSO_4$, and the obtained mixture was filtered. After the solvent of the filtered organic layer was removed, the residue was subjected to column chromatography to obtain 12.9 g (yield: 90%) of the target compound A12.

Preparation of A21

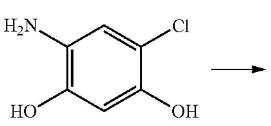

-continued

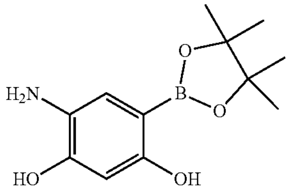

M5-1

M5-1 was prepared in the same way as M4-3, following the same preparation method of M4-3, using the same molar ratio, except that M4-2 was replaced with 4-amino-6-chloro-1,3-benzenediol.

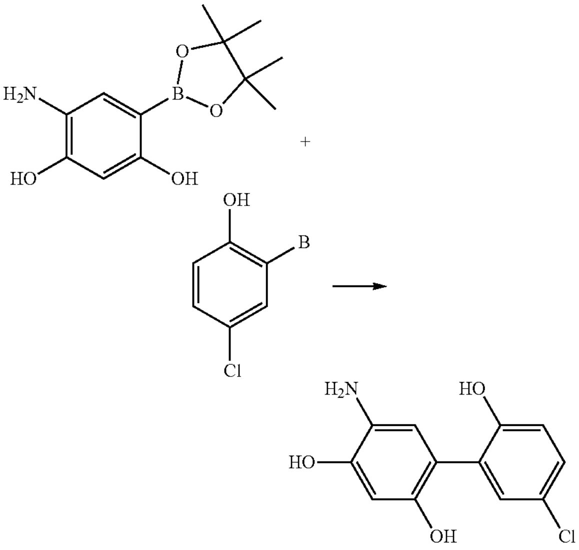

M5-2

M5-2 was prepared in the same way as A12, following the same preparation method of A12, using the same molar ratio, except that M4-3 was replaced by M5-1, and M1-2 was replaced by 2-bromo-4-chlorophenol.

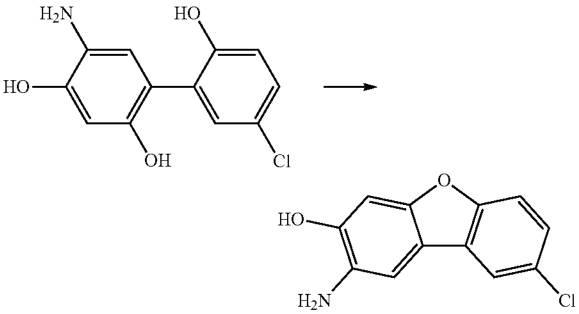

M5-3

M5-2 (5.0 g, 20 mmol) and 1,2-dichlorobenzene (250 mL) were added to a reactor. The reaction mixture was heated at 160 °C for 8 hours. After the reaction was completed, the organic substance was dissolved in chloroform (100 mL). After the solvent was removed, the crude compound was separated by column chromatography to obtain M5-3 (4.6 g, 77%).

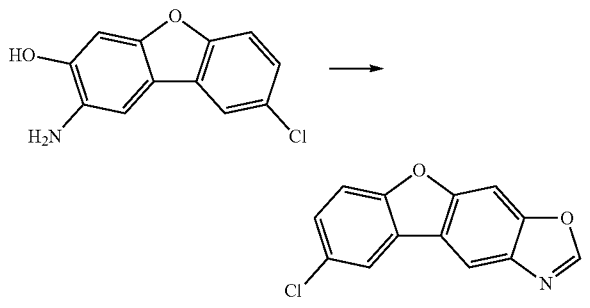

M5-4

M5-4 was prepared in the same way as M1-1, following the same preparation method of M1-1, using the same molar ratio, except that 2-amino-3-dibenzofuranol was replaced with M5-3.

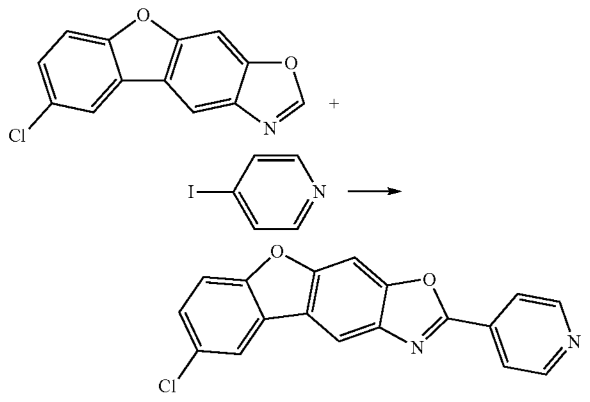

M5-5

M5-5 was prepared in the same way as A1, following the same preparation method of A1, using the same molar ratio, except that M1-1 was replaced by M5-4, and M1-2 was replaced by 4-iodopyridine.

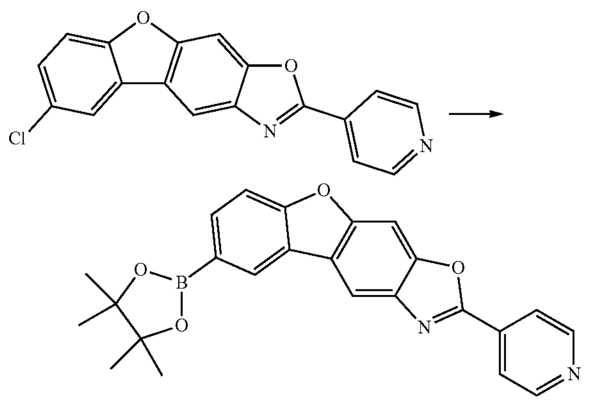

M5-6

M5-6 was prepared in the same way as M4-3, following the same preparation method of M4-3, using the same molar ratio, except that M4-2 was replaced by M5-5.

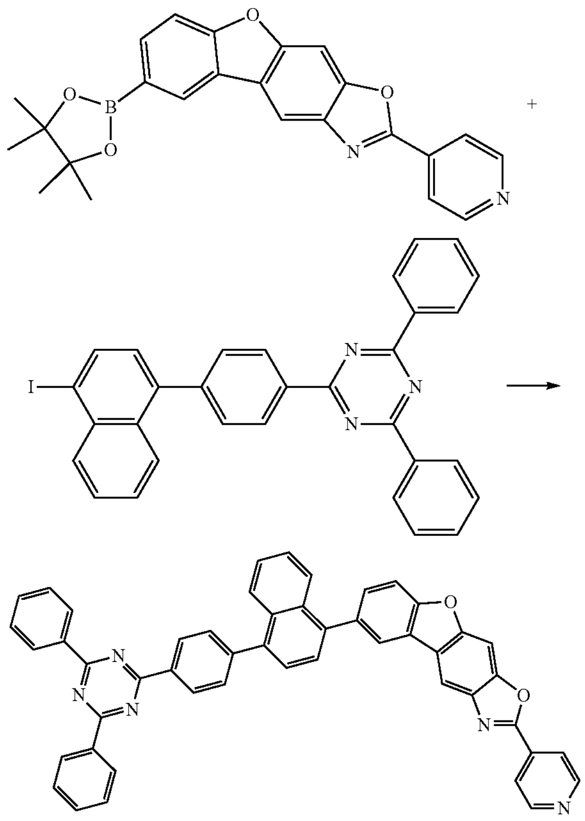

A21

A21 was prepared in the same way as A12, following the same preparation method of A12, using the same molar ratio, except that M4-4 was replaced by M5-6.

Preparation of A24

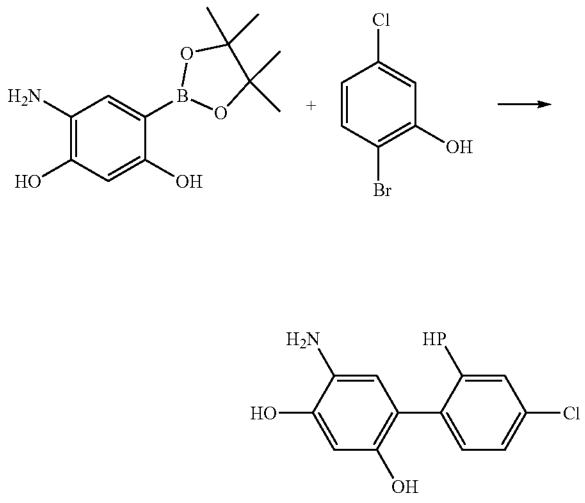

M6-1

M6-1 was prepared in the same way as A12, following the same preparation method of A12, using the same molar ratio, except that M4-3 was replaced by M6-1, and M1-2 was replaced by 2-bromo-5-chlorophenol.

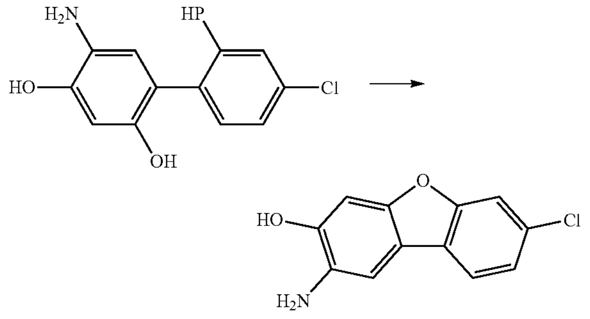

M6-2

M6-2 was prepared in the same way as M5-3, following the same preparation method of M5-3, using the same molar ratio, except that M5-2 was replaced by M6-1.

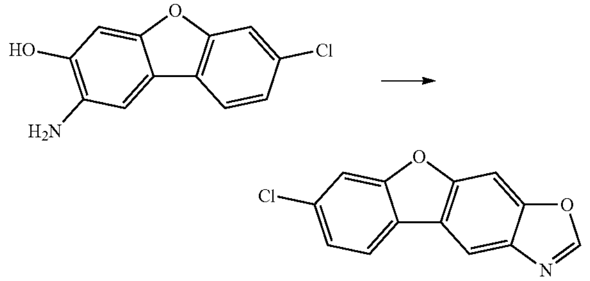

M6-3

M6-3 was prepared in the same way as M1-1, following the same preparation method of M1-1, using the same molar ratio, except that 2-amino-3-dibenzofuranol was replaced by M6-2.

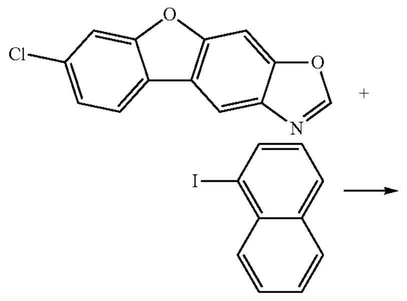

-continued

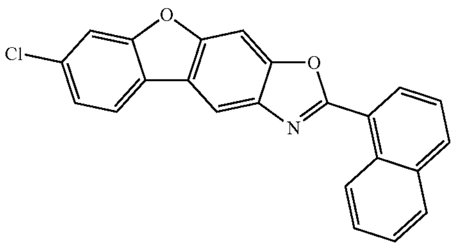

M6-4

M6-4 was prepared in the same way as A1, following the same preparation method of A1, using the same molar ratio, except that M1-1 was replaced by M6-3, and M1-2 was replaced by 1-iodonaphthalene.

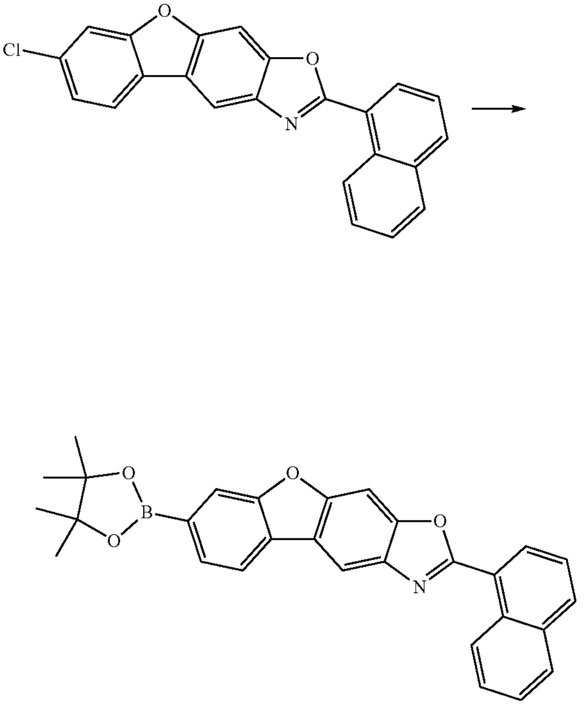

M6-5

M6-5 was prepared in the same way as M4-3, following the same preparation method of M4-3, using the same molar ratio, except that M4-2 was replaced by M6-4.

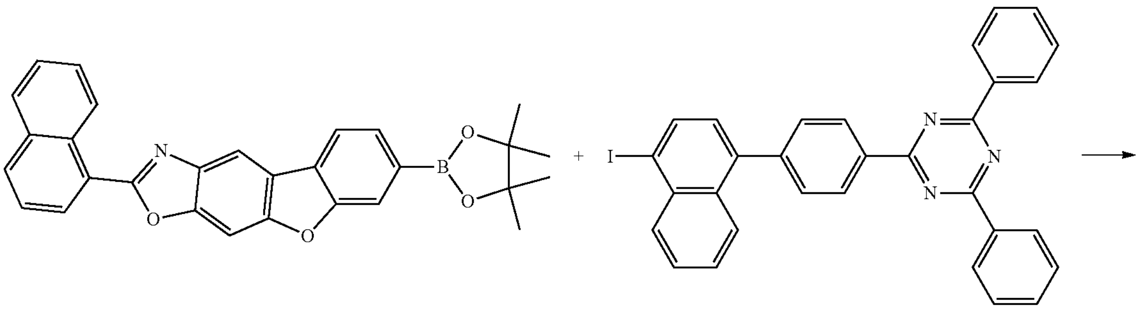

-continued

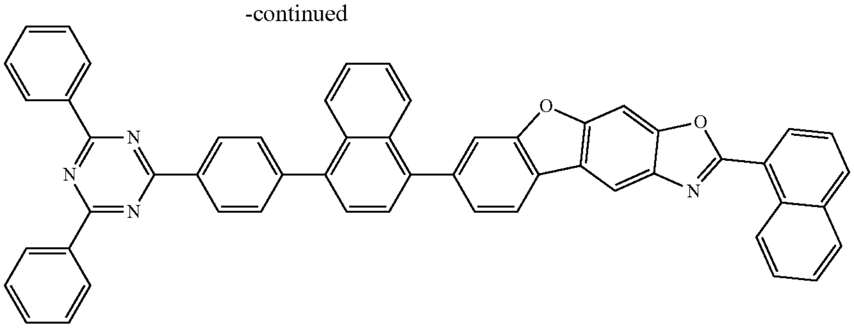

A24

A24 was prepared in the same way as A12, following the same preparation method of A12, using the same molar ratio, except that M4-4 was replaced by M6-5.

Preparation of B1

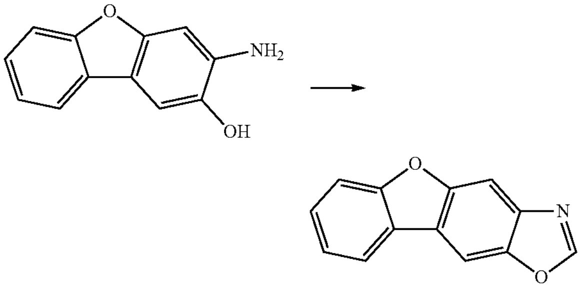

M7-1

M7-1 was prepared in the same way as M1-1, following the same preparation method of M1-1, using the same molar ratio, except that 2-amino-3-dibenzofuranol was replaced with 3-amino-2-dibenzofuranol.

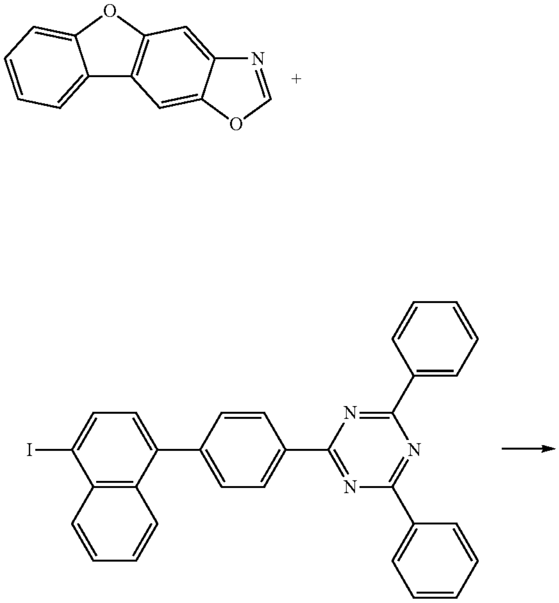

-continued

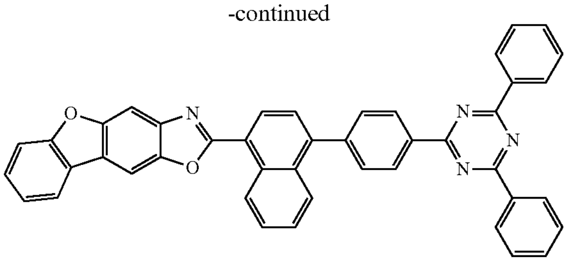

B1

B1 was prepared in the same way as A1, following the same preparation method of A1, using the same molar ratio, except that M1-1 was replaced by M7-1.

Preparation of B2

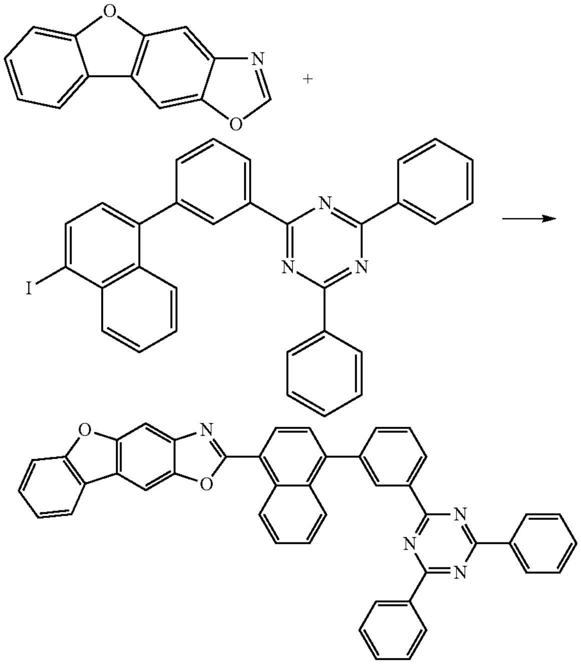

B2

B2 was prepared in the same way as A1, following the same preparation method of A1, using the same molar ratio, except that M1-1 was replaced with M7-1, and M1-2 was replaced with M2-1.

Preparation of B5

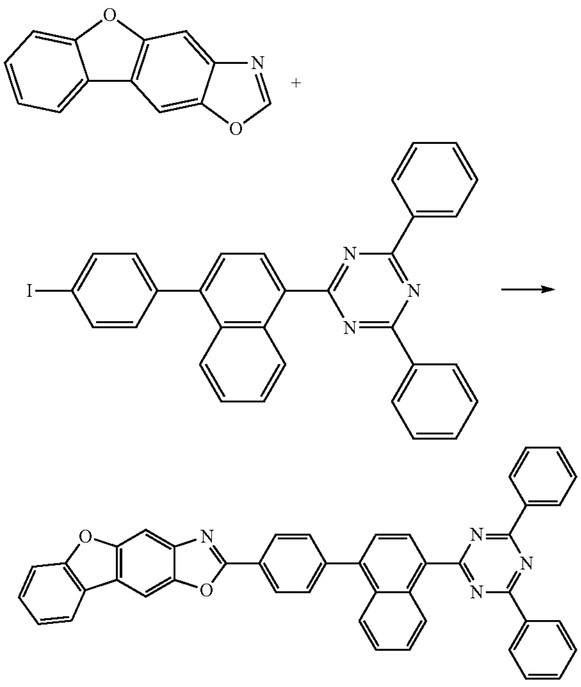

B5

B5 was prepared in the same way as A1, following the same preparation method of A1, using the same molar ratio, except that M1-1 was replaced by M7-1, and M1-2 was replaced by M3-1.

Preparation of B12

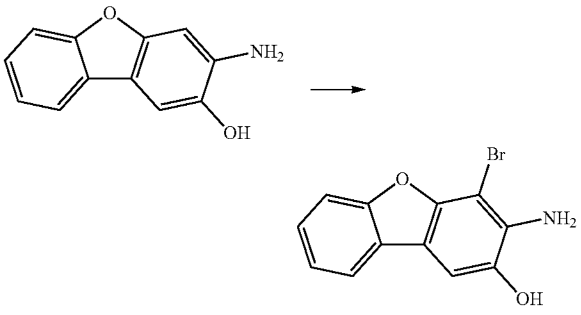

M8-1

M8-1 was prepared in the same way as M4-1, following the same preparation method of M4-1, using the same molar ratio, except that 2-amino-3-dibenzofuranol was replaced with 3-amino-2-dibenzofuranol.

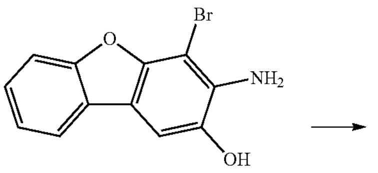

-continued

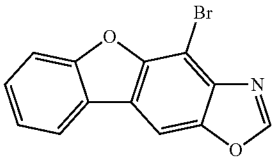

M8-2

M8-2 was prepared in the same way as M1-1, following the same preparation method of M1-1, using the same molar ratio, except that 2-amino-3-dibenzofuranol was replaced with M8-1.

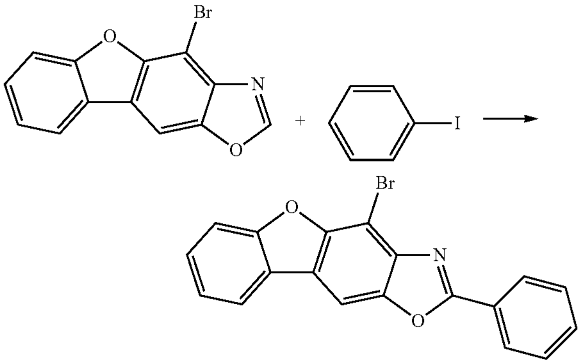

M8-3

M8-3 was prepared in the same way as A1, following the same preparation method of A1, using the same molar ratio, except that M1-1 was replaced by M8-2, and M1-2 was replaced by iodobenzene.

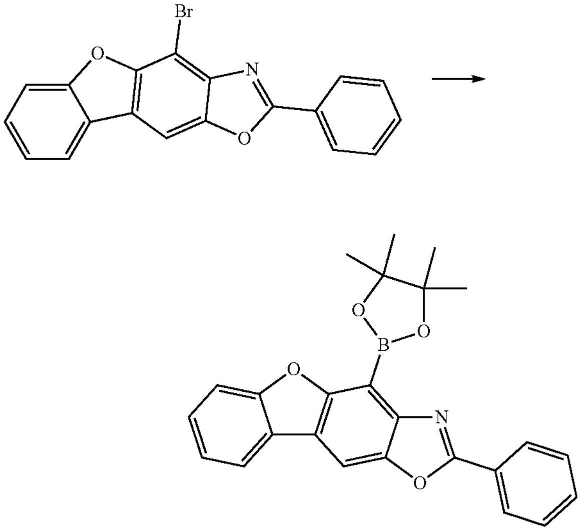

M8-4

M8-4 was the same as that of M4-4, following the same preparation method of M4-4, using the same molar ratio, except that M4-3 was replaced by M8-3.

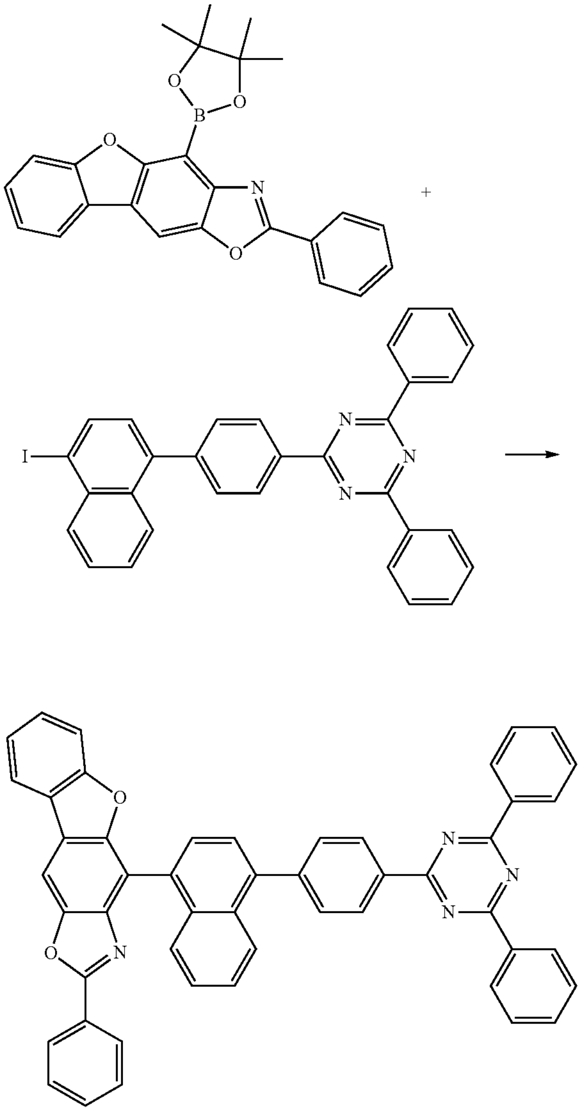

B12

B12 was prepared in the same way as A12, following the same preparation method of A12, using the same molar ratio, except that M4-4 was replaced by M8-4.

Preparation of B21

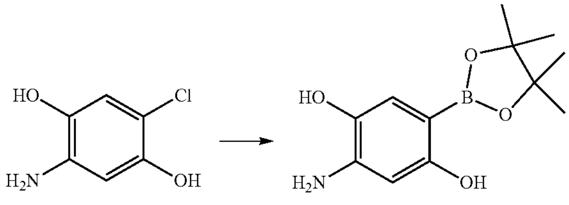

M9-1

M9-1 was prepared in the same way as M4-3, following the same preparation method of M4-3, using the same molar ratio, except that M4-2 was replaced by 2-amino-5-chloro-1,4-benzenediol.

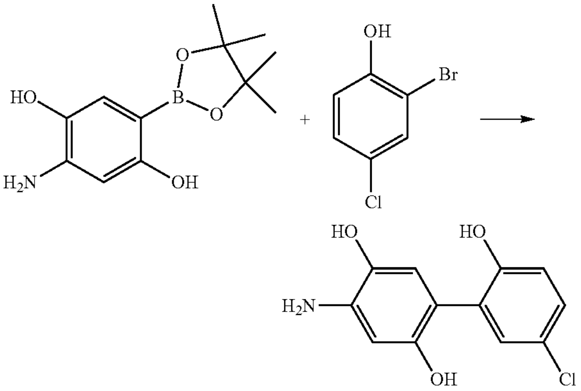

M9-2

M9-2 was prepared in the same way as A12, following the same preparation method of A12, using the same molar ratio, except that M4-3 was replaced by M9-1, and M1-2 was replaced by 2-bromo-4-chlorophenol.

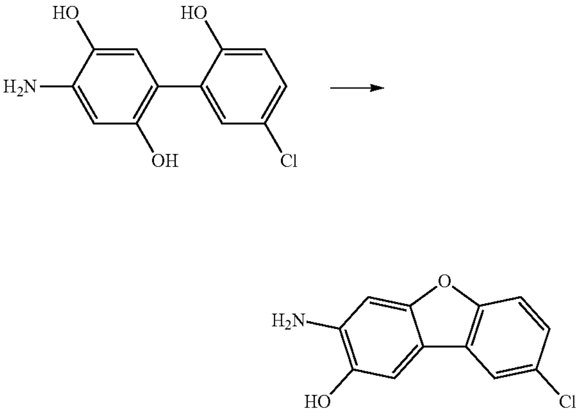

M9-3

M9-3 was prepared in the same way as M5-3, following the same preparation method of M5-3, using the same molar ratio, except that M5-2 was replaced by M9-2.

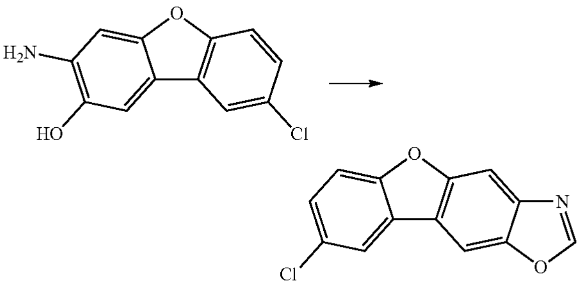

M9-4

M9-4 was prepared in the same way as M1-1, following the same preparation method of M1-1, using the same molar ratio, except that 2-amino-3-dibenzofuranol was replaced with M9-3.

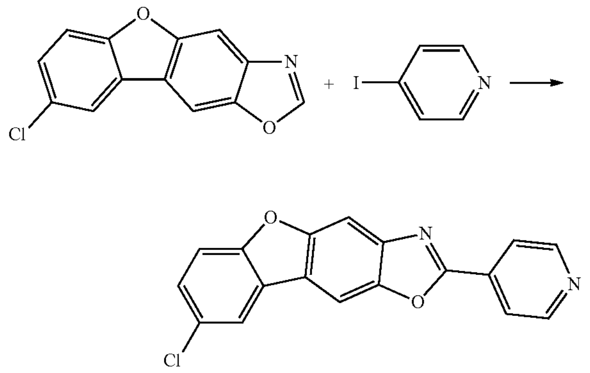
M9-5
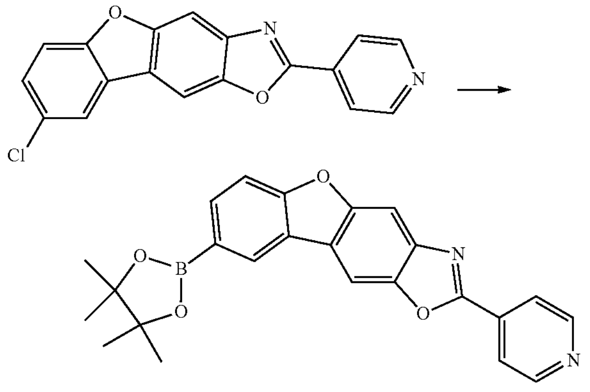
M9-6
M9-5 was prepared in the same way as A1, following the same preparation method of A1, using the same molar ratio, except that M1-1 was replaced by M9-4, and M1-2 was replaced by 4-iodopyridine.
M9-6 was prepared in the same way as M4-3, following the same preparation method of M4-3, using the same molar ratio, except that M4-2 was replaced by M9-5.
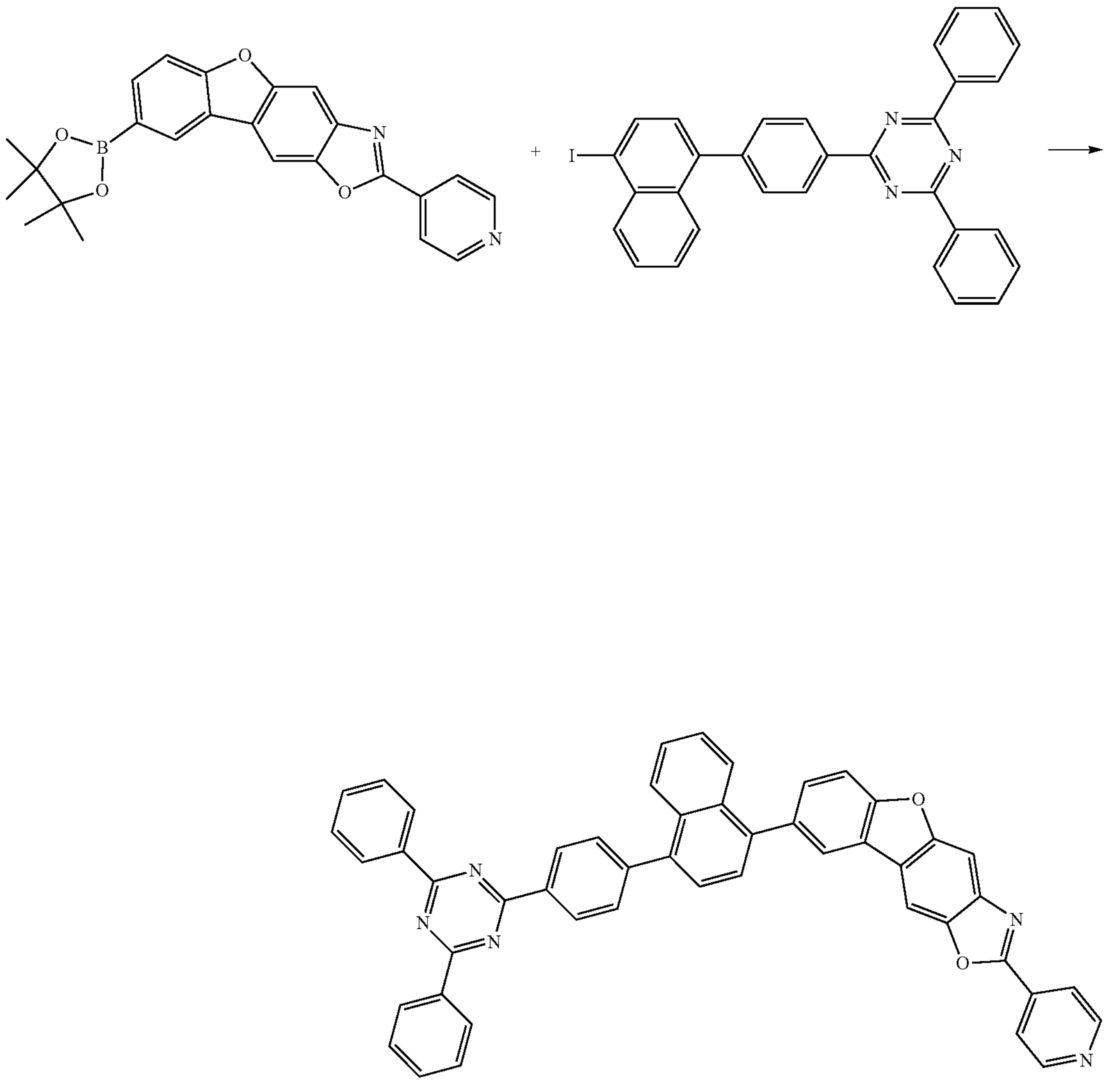
B21

B21 was prepared in the same way as A12, following the same preparation method of A12, using the same molar ratio, except that M4-4 was replaced by M9-6.

Preparation of B24

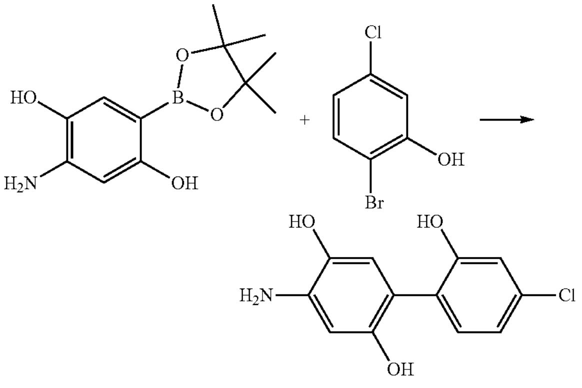

M10-1

M10-1 was prepared in the same way as A12, following the same preparation method of A12, using the same molar ratio, except that M4-3 was replaced by M9-1, and M1-2 was replaced by 2-bromo-5-chlorophenol.

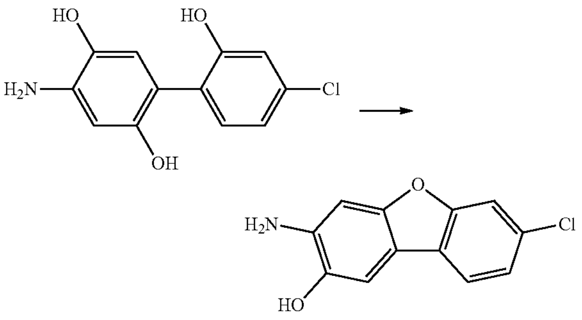

M10-2

M10-2 was prepared in the same way as M5-3, following the same preparation method of M5-3, using the same molar ratio, except that M5-2 was replaced by M10-1.

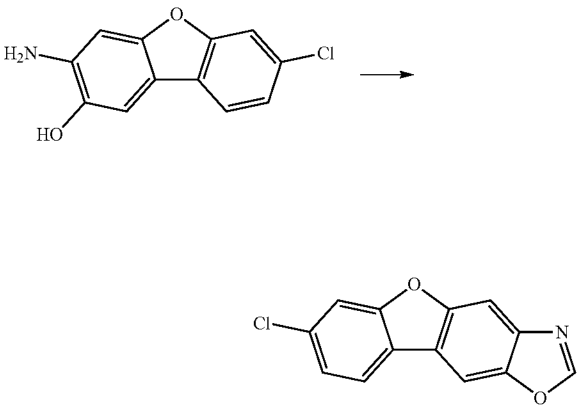

M10-3

M10-3 was prepared in the same way as M1-1, following the same preparation method of M1-1, using the same molar ratio, except that 2-amino-3-dibenzofuranol was replaced with M10-2.

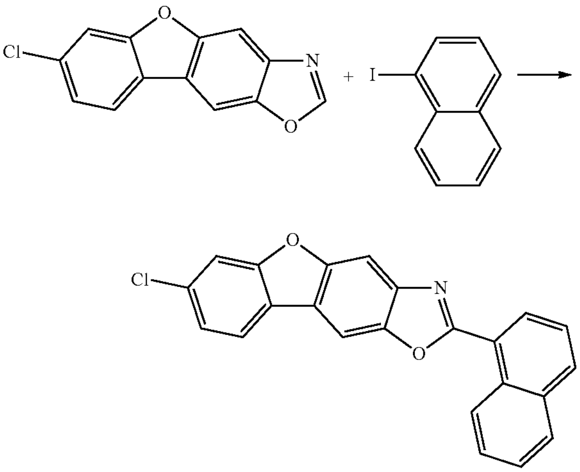

M10-4

M10-4 was prepared in the same way as A1, following the same preparation method of A1, using the same molar ratio, except that M1-1 was replaced by M10-3, and M1-2 was replaced by 1-iodonaphthalene.

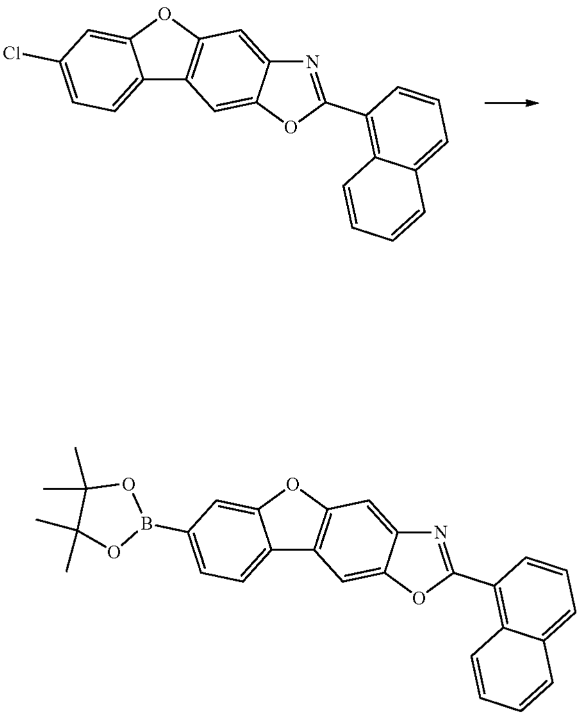

M10-5

M10-5 was prepared in the same way as M4-3, following the same preparation method of M4-3, using the same molar ratio, except that M4-2 was replaced by M10-4.

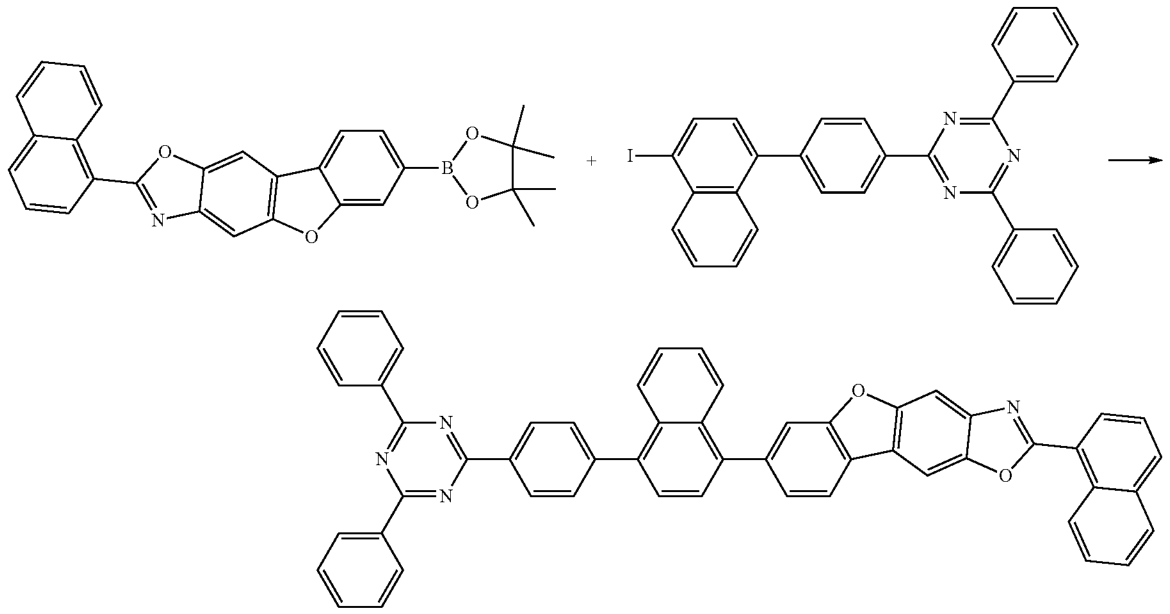

B24

B24 was prepared in the same way as A12, following the same preparation method of A12, using the same molar ratio, except that M4-4 was replaced by M10-5.

Preparation of C1

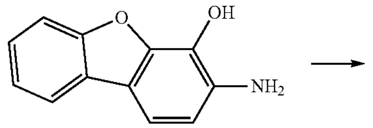

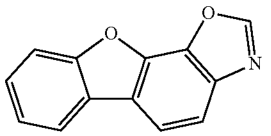

M11-1

M11-1 was prepared in the same way as M1-1, following the same preparation method of M1-1, using the same molar ratio, except that 2-amino-3-dibenzofuranol was replaced by 3-amino-4-dibenzofuranol.

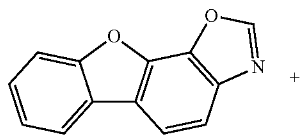

-continued

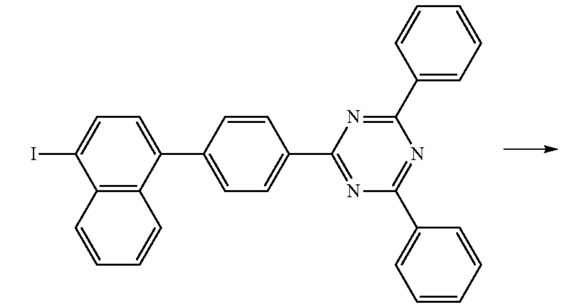

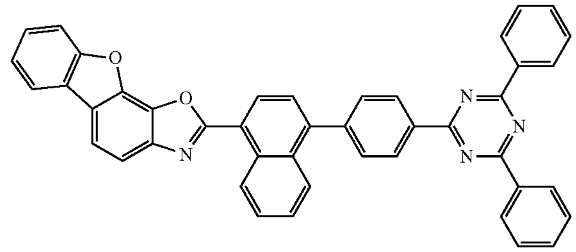

C1

C1 was prepared in the same way as A1, following the same preparation method of A1, using the same molar ratio, except that M1-1 was replaced by M11-1.

Preparation of C2

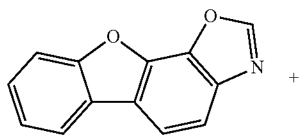

-continued

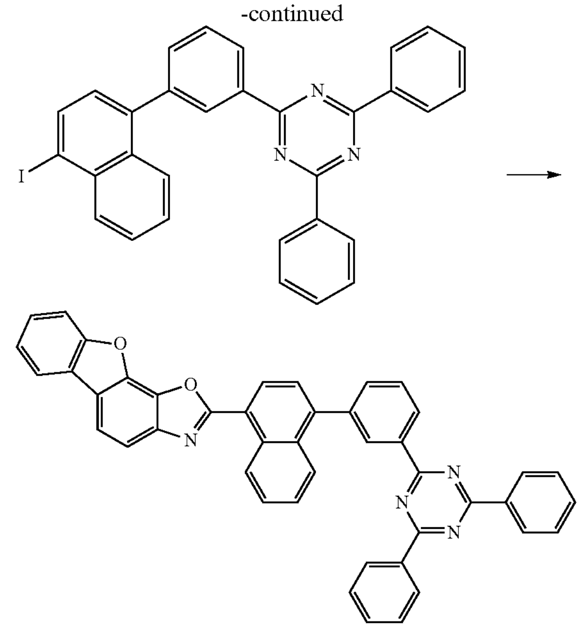

C2

C2 was prepared in the same way as A1, following the same preparation method of A1, using the same molar ratio, except that M1-1 was replaced with M11-1, and M1-2 was replaced with M2-1.

Preparation of C5

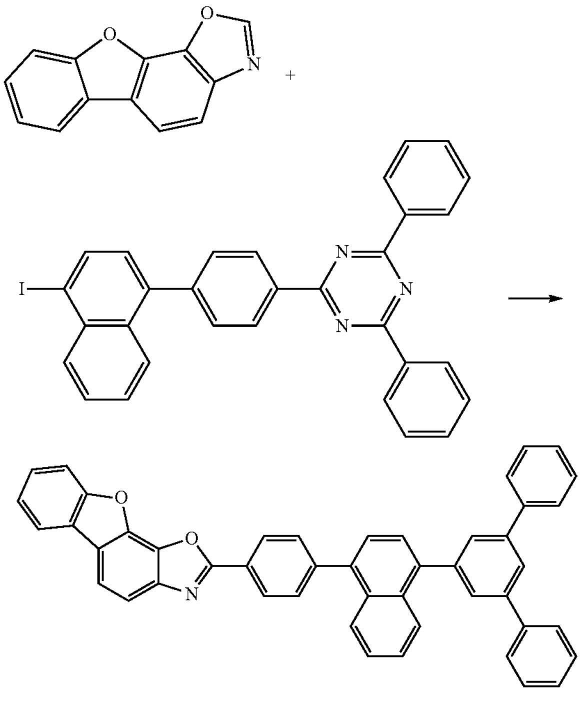

C5

C5 was prepared in the same way as A1, following the same preparation method of A1, using the same molar ratio, except that M1-1 was replaced by M11-1, and M1-2 was replaced by M3-1.

Preparation of C11

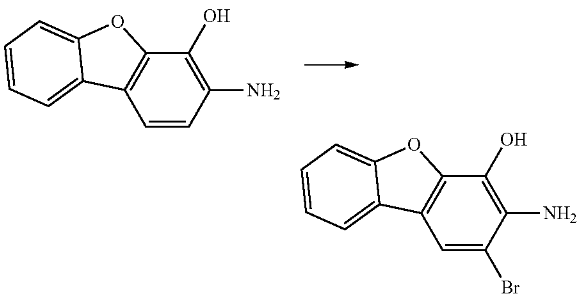

M12-1

M12-1 was prepared in the same way as M4-1, following the same preparation method of M4-1, using the same molar ratio, except that 2-amino-3-dibenzofuranol was replaced with 3-amino-4-dibenzofuranol.

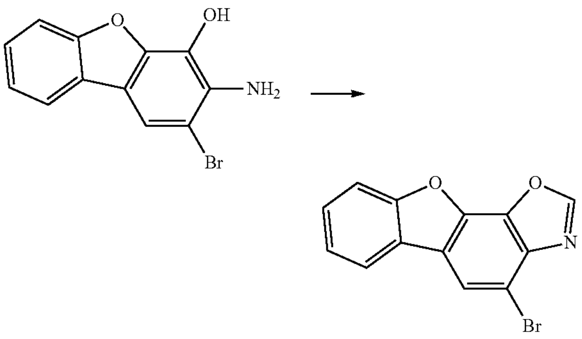

M12-2

M12-2 was prepared in the same way as M1-1, following the same preparation method of M1-1, using the same molar ratio, except that 2-amino-3-dibenzofuranol was replaced with M12-1.

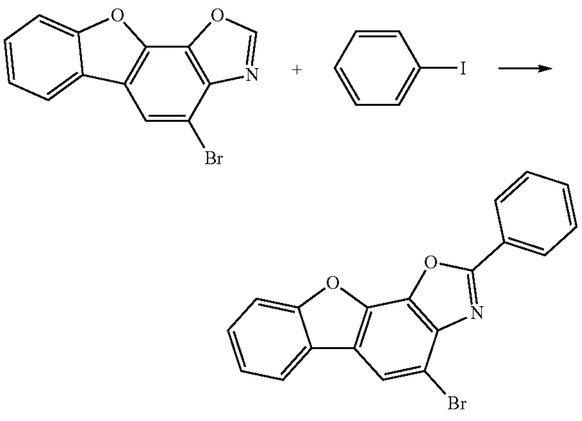

M12-3

M12-3 was prepared in the same way as A1, following the same preparation method of A1, using the same molar ratio, except that M1-1 was replaced by M12-2, and M1-2 was replaced by iodobenzene.

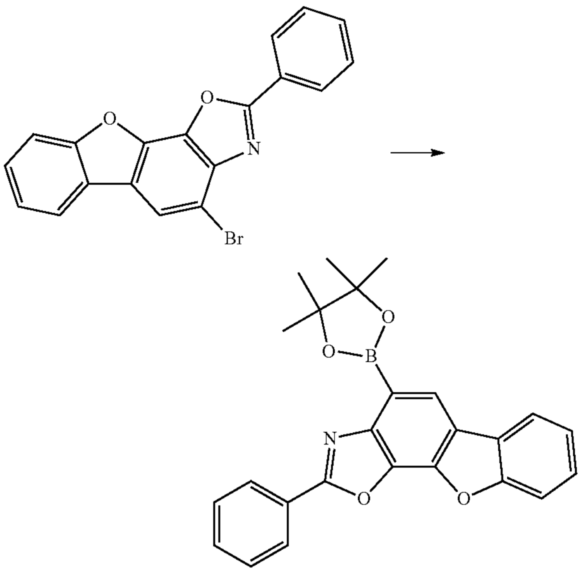

M12-4

M12-4 was prepared in the same way as M4-4, following the same preparation method of M4-4, using the same molar ratio, except that M4-3 was replaced by M12-3.

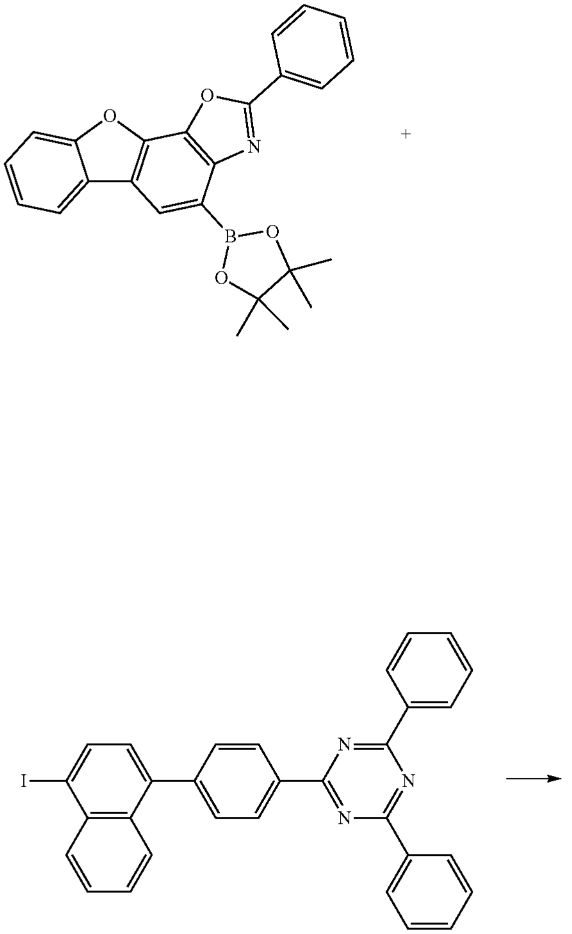

-continued

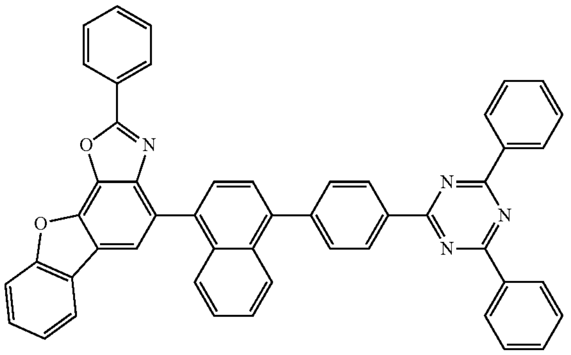

C11

C11 was prepared in the same way as A12, following the same preparation method of A12, using the same molar ratio, except that M4-4 was replaced by M12-4.

Preparation of C21

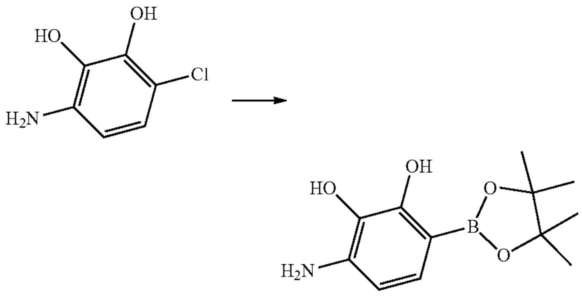

M13-1

M13-1 was prepared in the same way as M4-3, following the same preparation method of M4-3, using the same molar ratio, except that M4-2 was replaced with 3-amino-6-chloro-1,2-benzenediol.

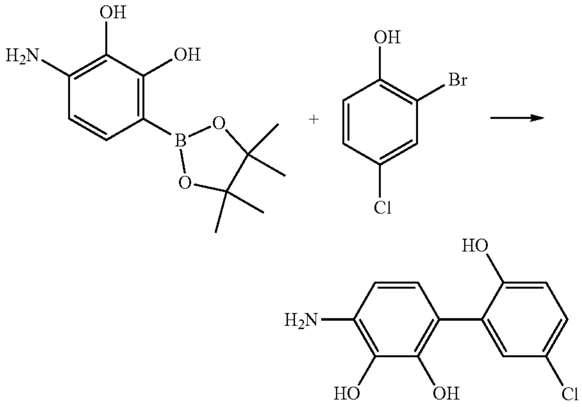

M13-2

M13-2 was prepared in the same way as A12, following the same preparation method of A12, using the same molar ratio, except that M4-3 was replaced by M13-1, and M1-2 was replaced by 2-bromo-4-chlorophenol.

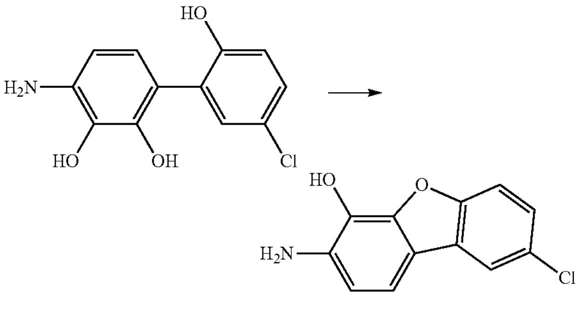

M13-3

M13-3 was prepared in the same way as M5-3, following the same preparation method of M5-3, using the same molar ratio, except that M5-2 was replaced by M13-2.

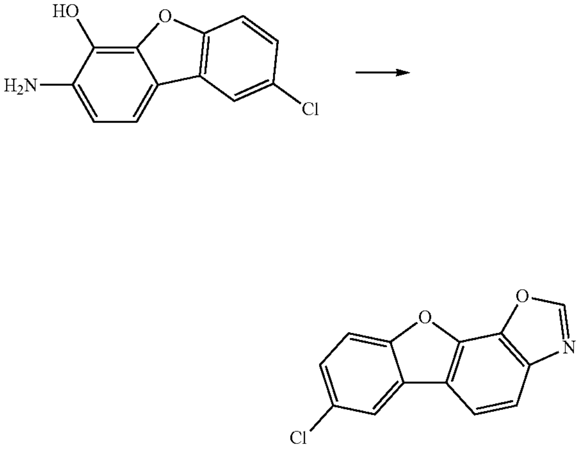

M13-4

M13-4 was prepared in the same way as M1-1, following the same preparation method of M1-1, using the same molar ratio, except that 2-amino-3-dibenzofuranol was replaced with M13-3.

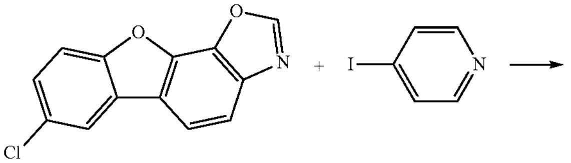

-continued

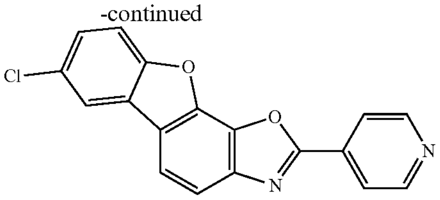

M13-5

M13-5 was prepared in the same way as A1, following the same preparation method of A1, using the same molar ratio, except that M1-1 was replaced by M13-4, and M1-2 was replaced by 4-iodopyridine.

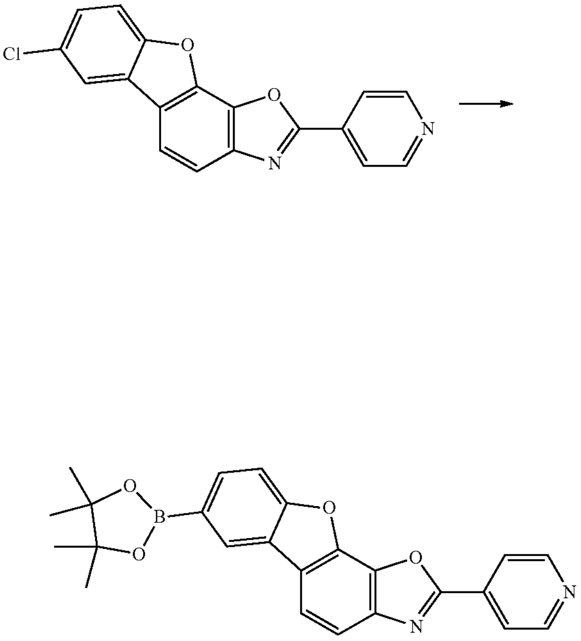

M13-6

M13-6 was prepared in the same way as M4-3, following the same preparation method of M4-3, using the same molar ratio, except that M4-2 was replaced by M13-5.

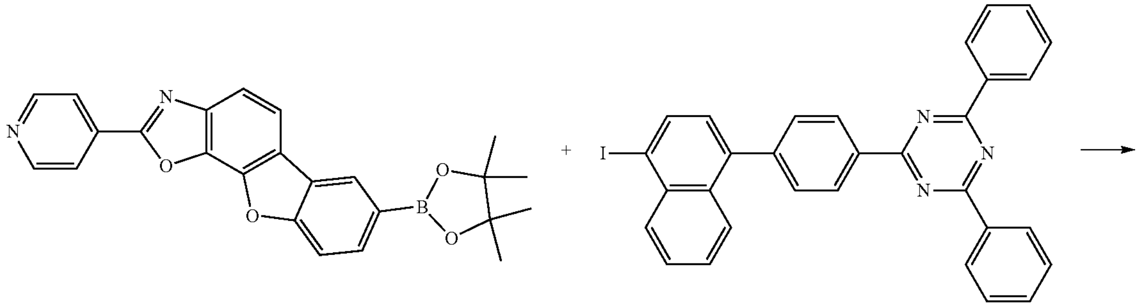

-continued

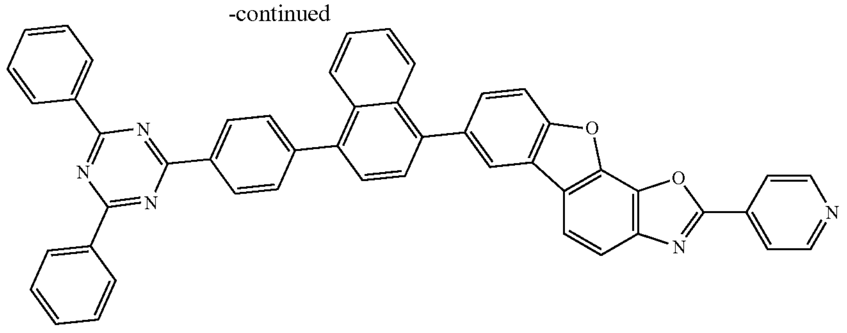

C21

C21 was prepared in the same way as A12, following the same preparation method of A12, using the same molar ratio, except that M4-4 was replaced by M13-6.

Preparation of C24

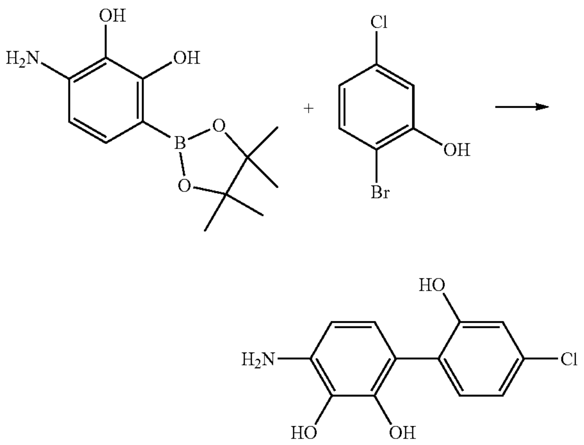

M14-1

M14-1 was prepared in the same way as A12, following the same preparation method of A12, using the same molar ratio, except that M4-3 was replaced by M13-1, and M1-2 was replaced by 2-bromo-5-chlorophenol.

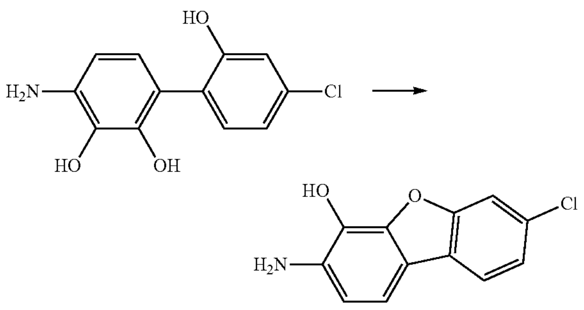

M14-2

M14-2 was prepared in the same way as M5-3, following the same preparation method of M5-3, using the same molar ratio, except that M5-2 was replaced by M14-1.

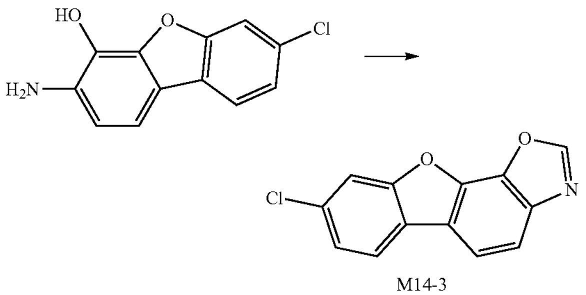

M14-3

M14-3 was prepared in the same way as M1-1, following the same preparation method of M1-1, using the same molar ratio, except that 2-amino-3-dibenzofuranol was replaced by M14-2.

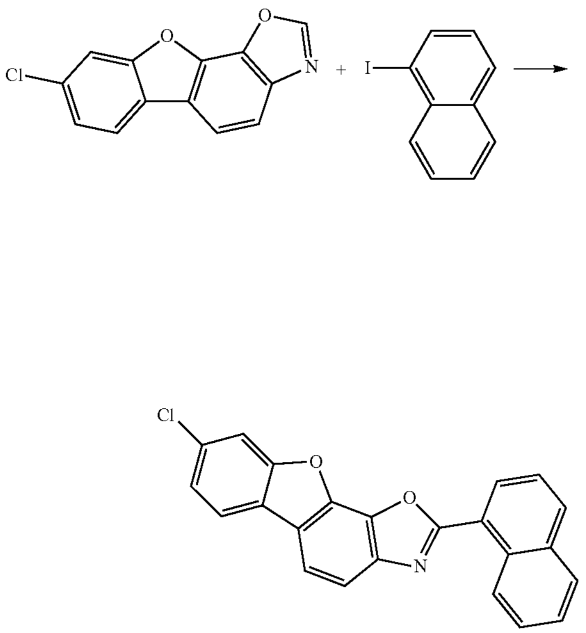

M14-4

M14-4 was prepared in the same way as A1, following the same preparation method of A1, using the same molar ratio, except that M1-1 was replaced by M14-3, and M1-2 was replaced by 1-iodonaphthalene.

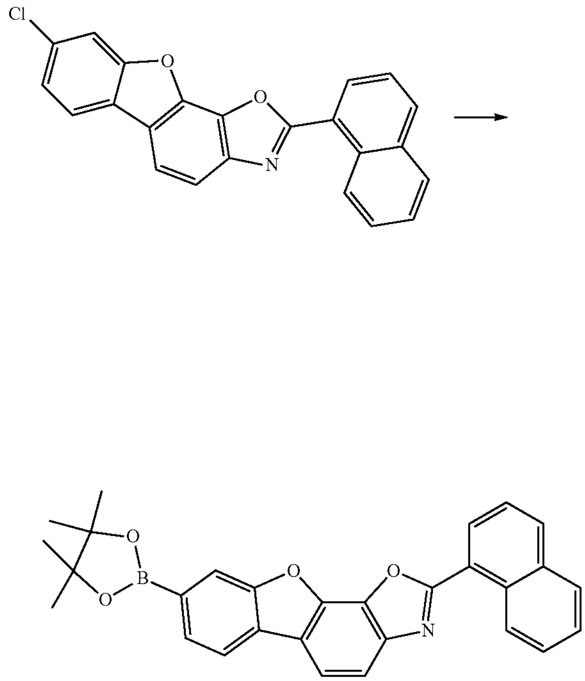

M14-5

M14-5 was prepared in the same way as M4-3, following the same preparation method of M4-3, using the same molar ratio, except that M4-2 was replaced by M14-4.

C24 was prepared in the same way as A12, following the same preparation method of A12, using the same molar ratio, except that M4-4 was replaced by M14-5.

Preparation of D1

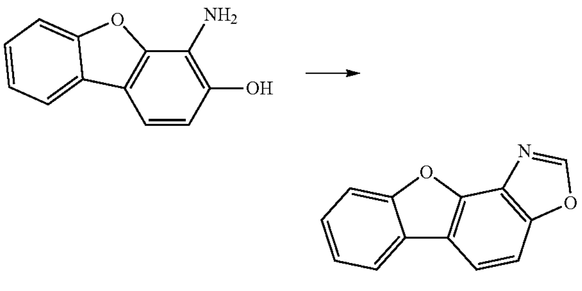

M15-1

M15-1 was prepared in the same way as M1-1, following the same preparation method of M1-1, using the same molar ratio, except that 2-amino-3-dibenzofuranol was replaced with 4-amino-3-dibenzofuranol.

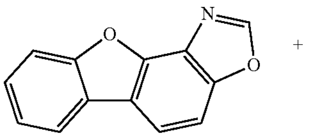

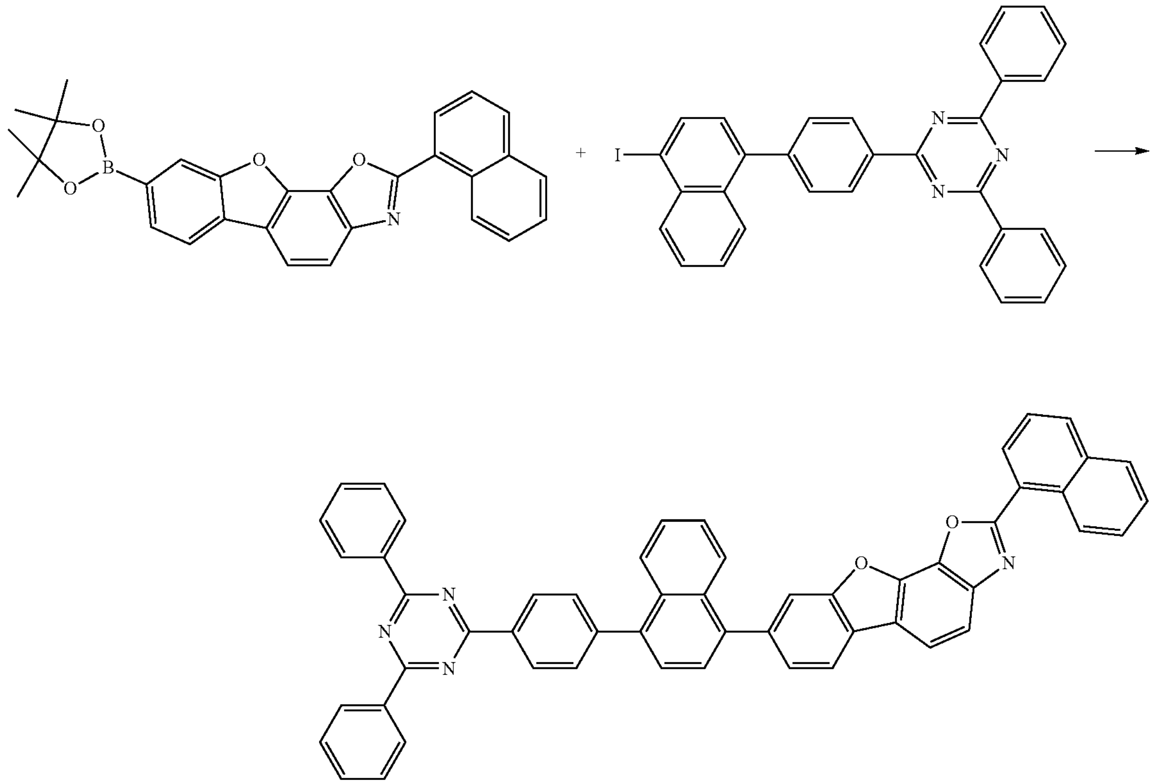

C24

-continued

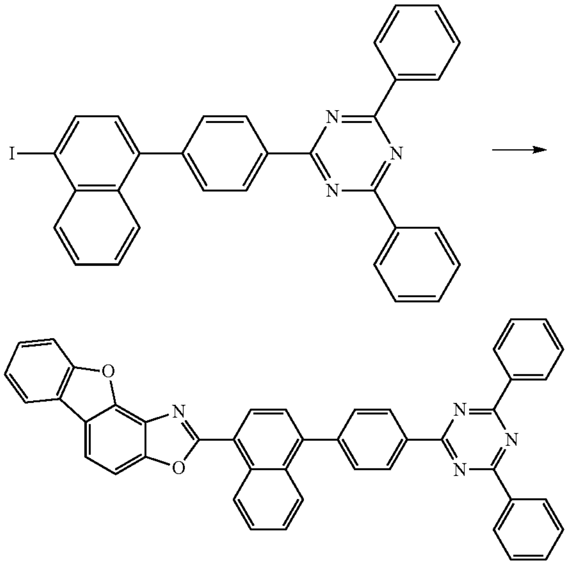

D1

D1 was prepared in the same way as A1, following the same preparation method of A1, using the same molar ratio, except that M1-1 was replaced by M15-1.

Preparation of D2

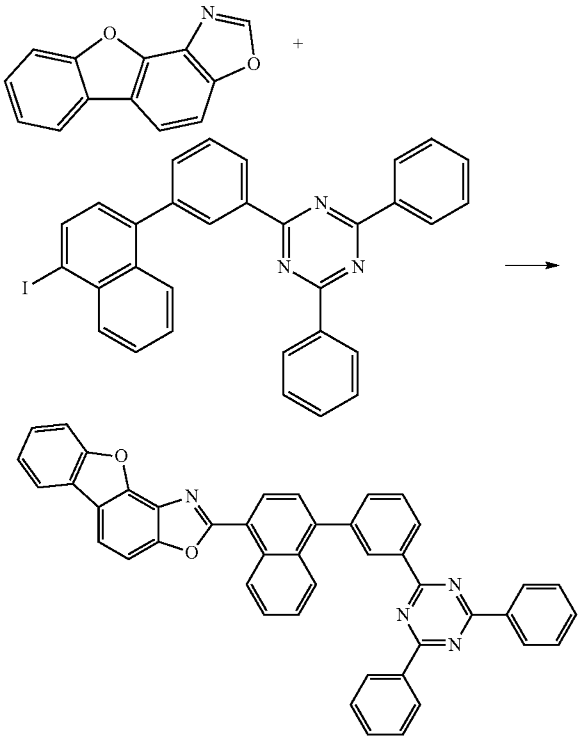

D2

D2 was prepared in the same way as A1, following the same preparation method of A1, using the same molar ratio, except that M1-1 was replaced by M15-1, and M1-2 was replaced by M2-1.

Preparation of D5

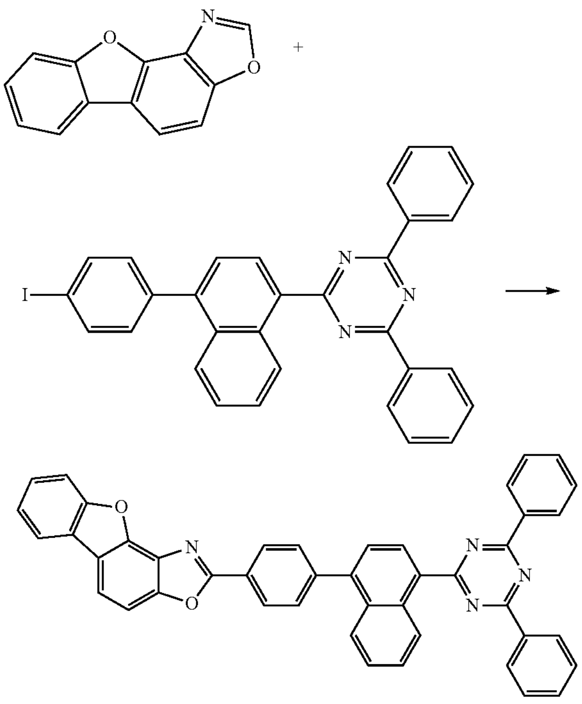

D5

D5 was prepared in the same way as A1, following the same preparation method of A1, using the same molar ratio, except that M1-1 was replaced by M15-1, and M1-2 was replaced by M3-1.

Preparation of D11

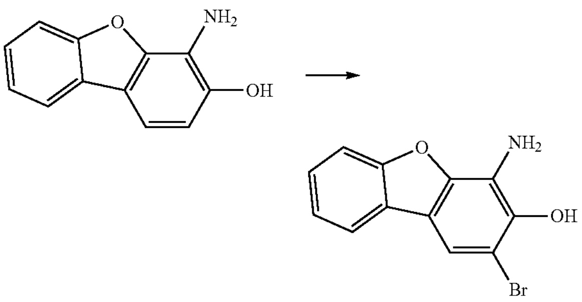

M16-1

M16-1 was prepared in the same way as M4-1, following the same preparation method of M4-1, using the same molar ratio, except that 2-amino-3-dibenzofuranol was replaced with 4-amino-3-dibenzofuranol.

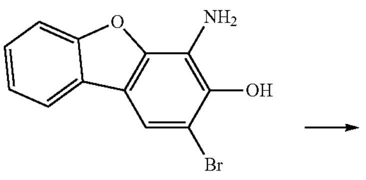

-continued

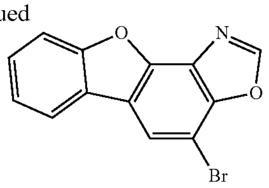

M16-2

M16-2 was prepared in the same way as M1-1, following the same preparation method of M1-1, using the same molar ratio, except that 2-amino-3-dibenzofuranol was replaced with M16-1.

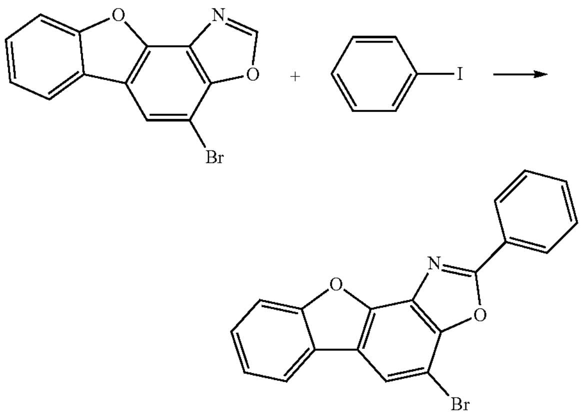

M16-3

M16-3 was prepared in the same way as A1, following the same preparation method of A1, using the same molar ratio, except that M1-1 was replaced by M16-2, and M1-2 was replaced by iodobenzene.

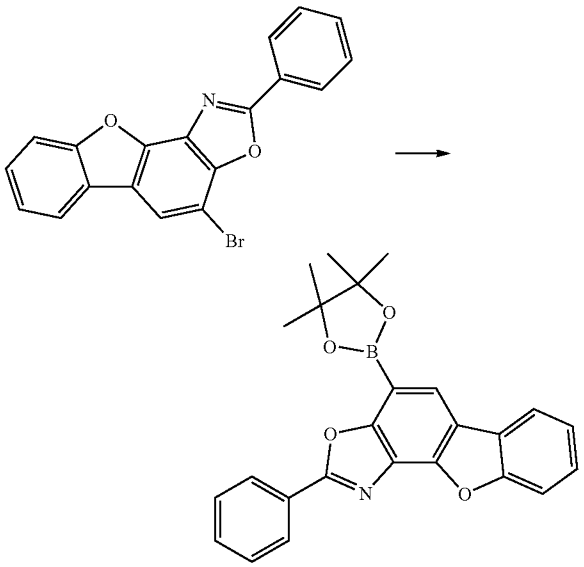

M16-4

M16-4 was prepared in the same way as M4-4, following the same preparation method of M4-4, using the same molar ratio, except that M4-3 was replaced by M16-3.

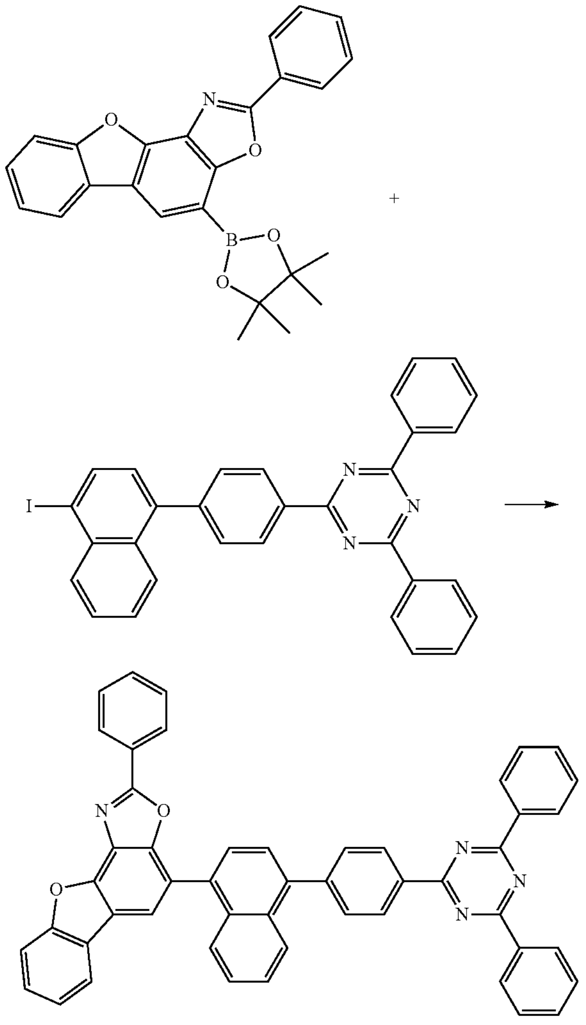

D11

D11 was prepared in the same way as A12, following the same preparation method of A12, using the same molar ratio, except that M4-4 was replaced by M16-4.

Preparation of D21

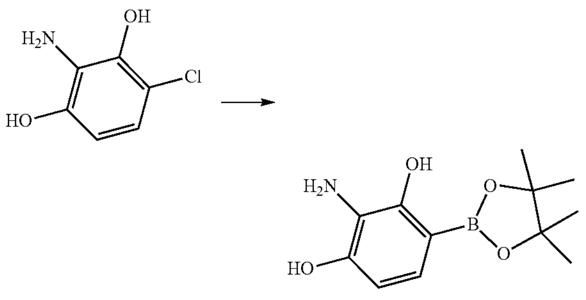

M17-1

M17-1 was prepared in the same way as M4-3, following the same preparation method of M4-3, using the same molar ratio, except that M4-2 was replaced with 2-amino-4-chloro-1,3-benzenediol.

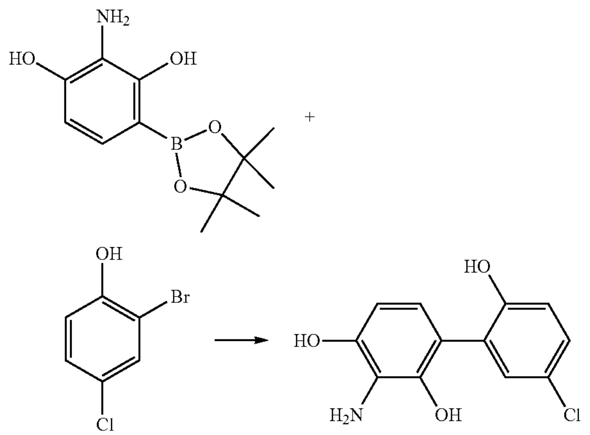

M17-2

M17-2 was prepared in the same way as A12, following the same preparation method of A12, using the same molar ratio, except that M4-3 was replaced with M17-1, and M1-2 was replaced with 2-bromo-4-chlorophenol.

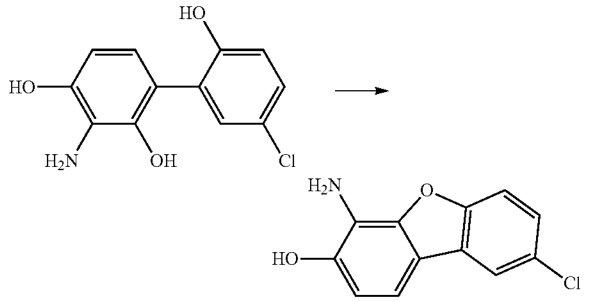

M17-3

M17-3 was prepared in the same way as M5-3, following the same preparation method of M5-3, using the same molar ratio, except that M5-2 was replaced by M17-2.

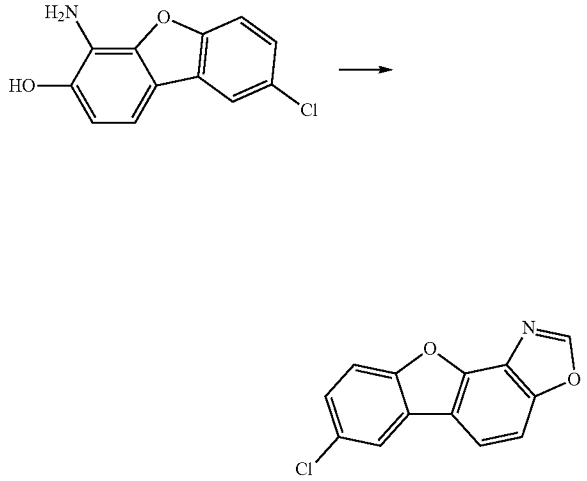

M17-4

M17-4 was prepared in the same way as M1-1, following the same preparation method of M1-1, using the same molar ratio, except that 2-amino-3-dibenzofuranol was replaced with M17-3.

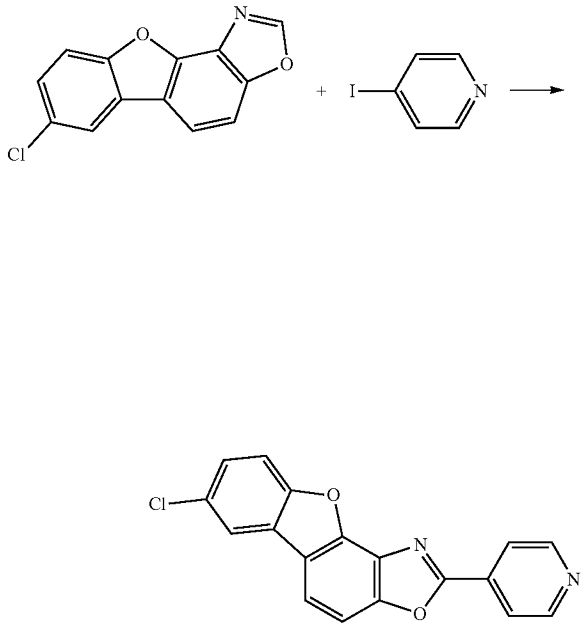

M17-5

M17-5 was prepared in the same way as A1, following the same preparation method of A1, using the same molar ratio, except that M1-1 was replaced by M17-4, and M1-2 was replaced by 4-iodopyridine.

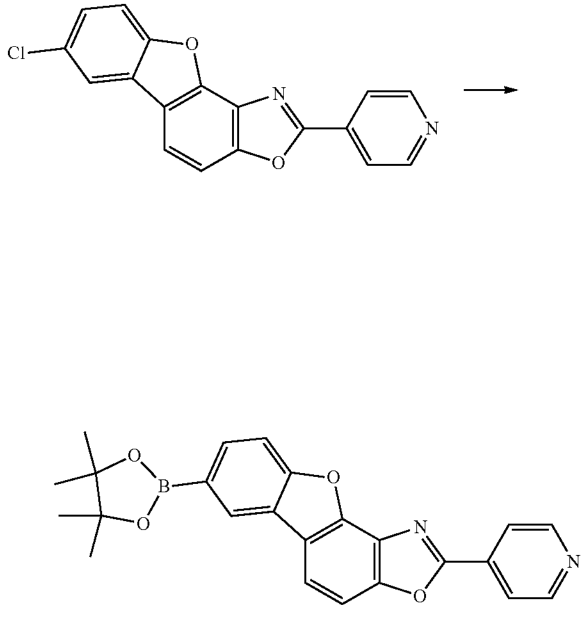

M17-6

M17-6 was prepared in the same way as M4-3, following the same preparation method of M4-3, using the same molar ratio, except that M4-2 was replaced by M17-5.

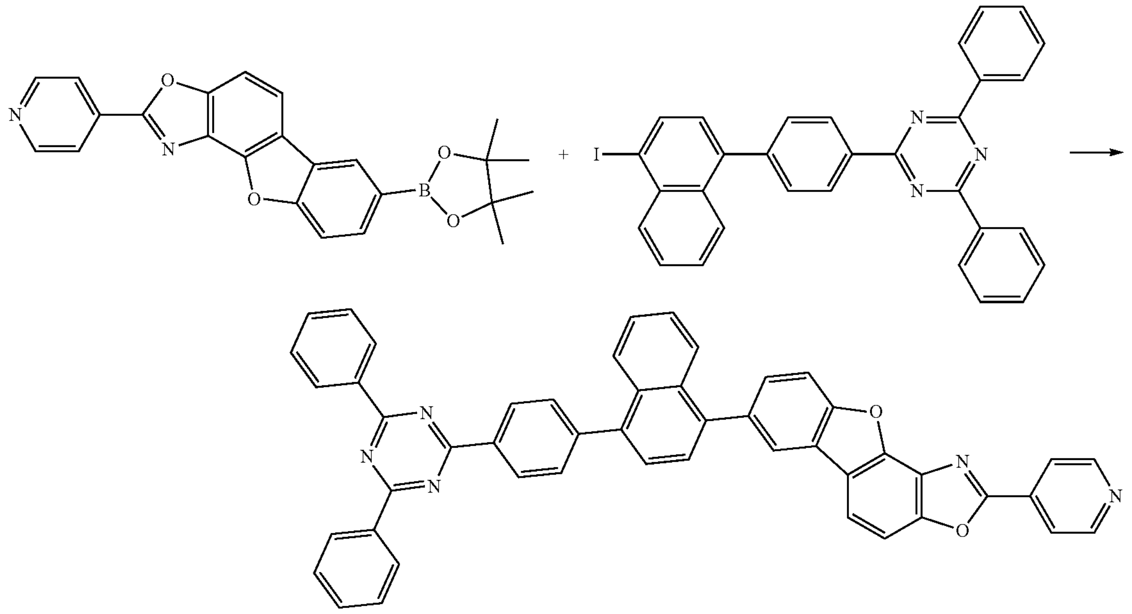

D21

D21 was prepared in the same way as A12, following the same preparation method of A12, using the same molar ratio, except that M4-4 was replaced by M17-6.

Preparation of D24

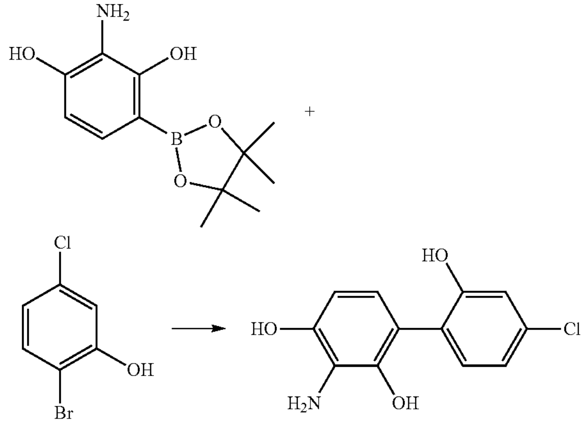

M18-1

M18-1 was prepared in the same way as A12, following the same preparation method of A12, using the same molar ratio, except that M4-3 was replaced by M18-1, and M1-2 was replaced by 2-bromo-5-chlorophenol.

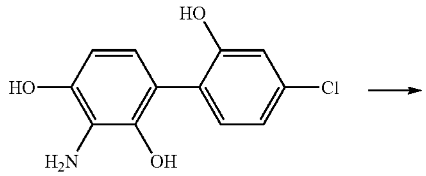

-continued

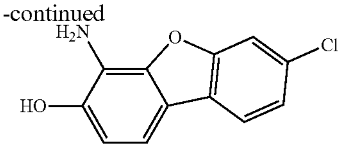

M18-2

M18-2 was prepared in the same way as M5-3, following the same preparation method of M5-3, using the same molar ratio, except that M5-2 was replaced by M18-1.

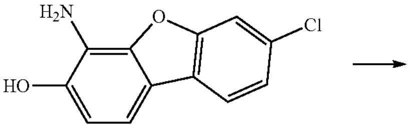

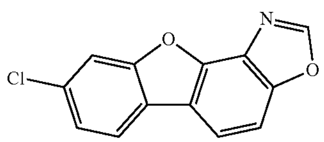

M18-3

M18-3 was prepared in the same way as M1-1, following the same preparation method of M1-1, using the same molar ratio, except that 2-amino-3-dibenzofuranol was replaced with M18-2.

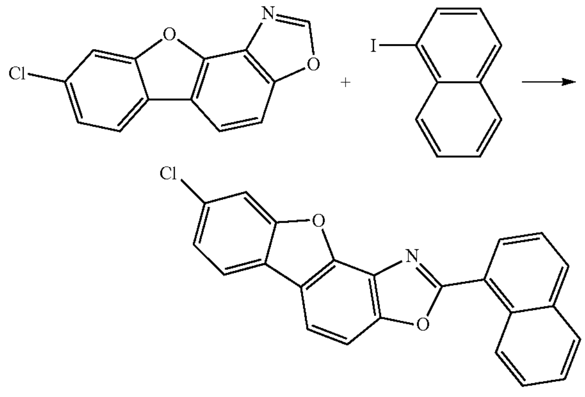

M18-4

M18-4 was prepared in the same way as A1, following the same preparation method of A1, using the same molar ratio, except that M1-1 was replaced by M18-3, and M1-2 was replaced by 1-iodonaphthalene.

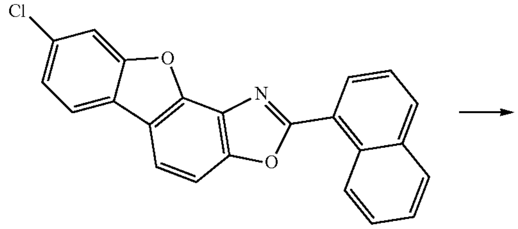

-continued

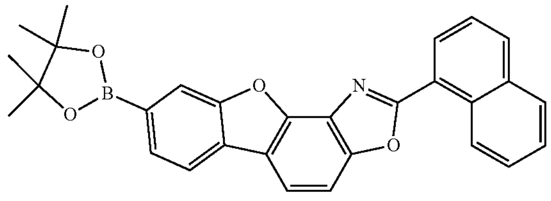

M18-5

M18-5 was prepared in the same way as M4-3, following the same preparation method of M4-3, using the same molar ratio, except that M4-2 was replaced by M18-4.

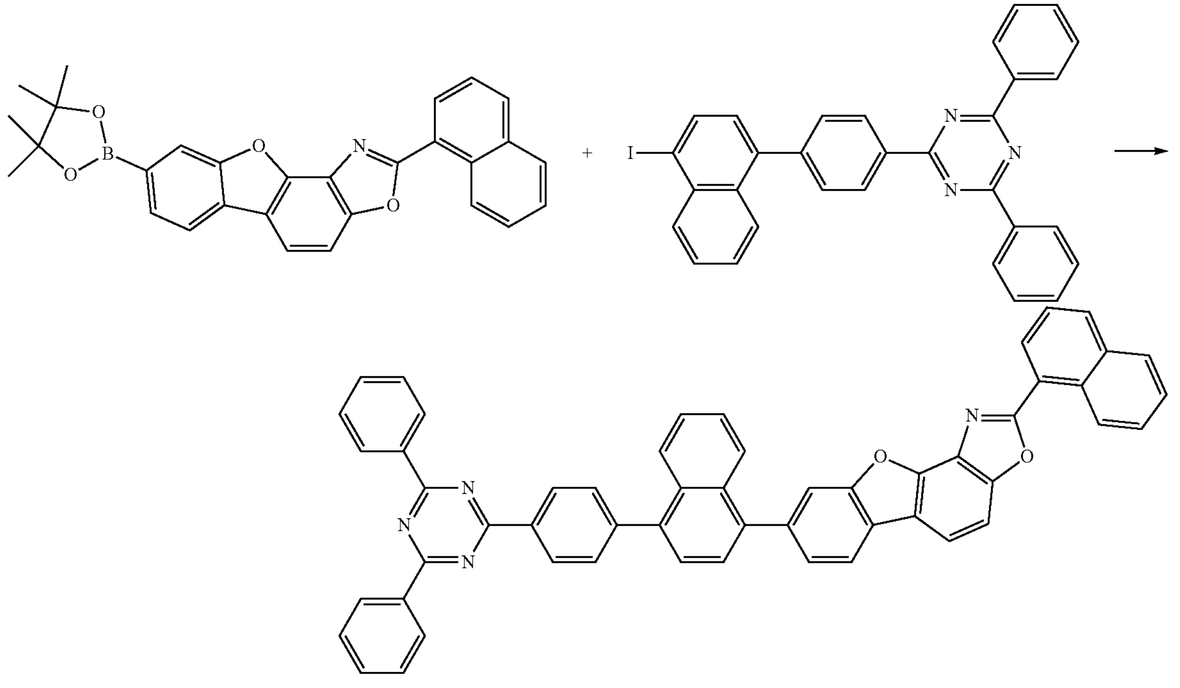

D24

D24 was prepared in the same way as A12, following the same preparation method of A12, using the same molar ratio, except that M4-4 was replaced by M18-5.

Preparation of E1

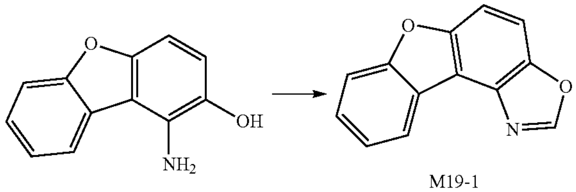 [SMILES: Nc1c(O)ccc2oc3ccccc3c12 ; c1ccc2c(c1)oc1ccc3ocnc3c12]

M19-1

M19-1 was prepared in the same way as M1-1, following the same preparation method of M1-1, using the same molar ratio, except that 2-amino-3-dibenzofuranol was replaced with 1-amino-2-dibenzofuranol.

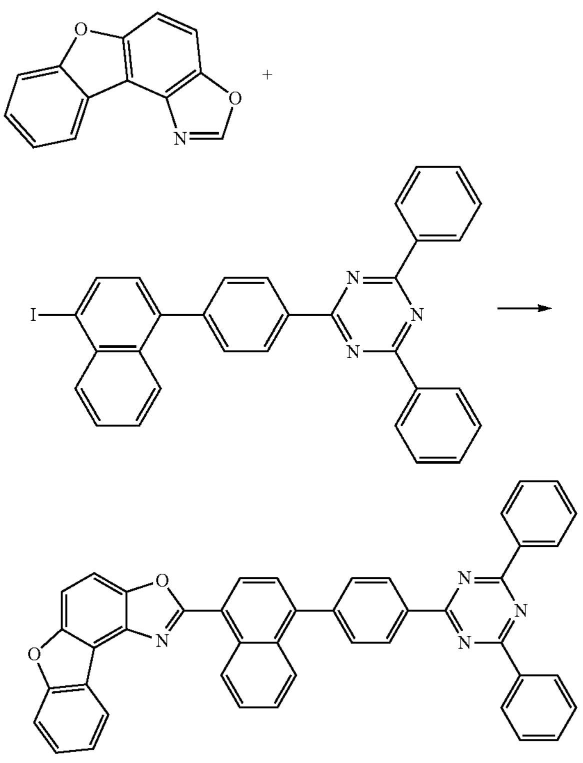

E1

E1 was prepared in the same way as A1, following the same preparation method of A1, using the same molar ratio, except that M1-1 was replaced by M19-1.

Preparation of E2

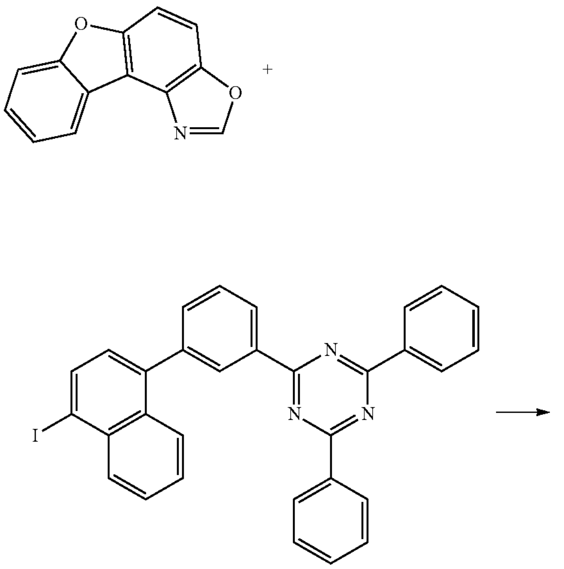

-continued

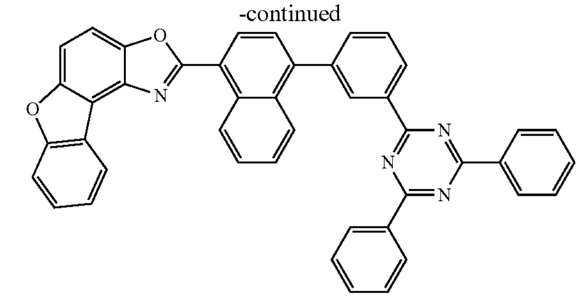

E2

E2 was prepared in the same way as A1, following the same preparation method of A1, using the same molar ratio, except that M1-1 was replaced by M19-1, and M1-2 was replaced by M2-1.

Preparation of E5

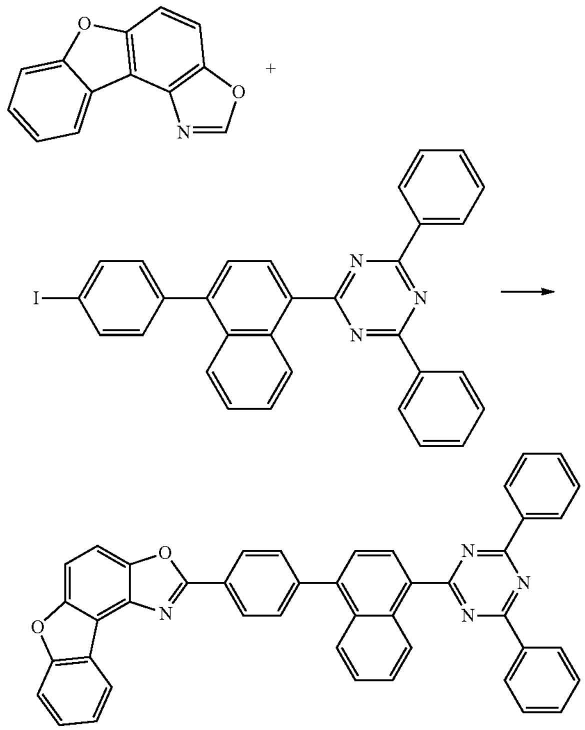

E5

E5 was prepared in the same way as A1, following the same preparation method of A1, using the same molar ratio, except that M1-1 was replaced by M19-1, and M1-2 was replaced by M3-1.

Preparation of E12

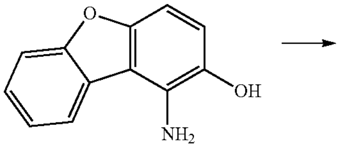

-continued

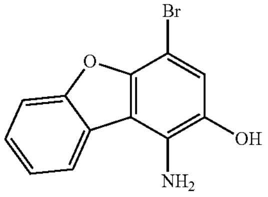

M20-1

M20-1 was prepared in the same way as M4-1, following the same preparation method of M4-1, using the same molar ratio, except that 2-amino-3-dibenzofuranol was replaced with 1-amino-2-dibenzofuranol.

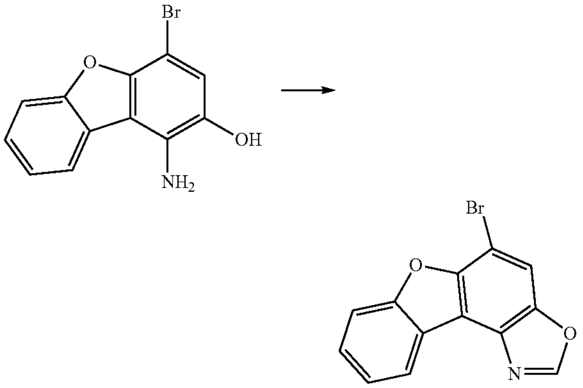

M20-2

M20-2 was prepared in the same way as M1-1, following the same preparation method of M1-1, using the same molar ratio, except that 2-amino-3-dibenzofuranol was replaced with M20-1.

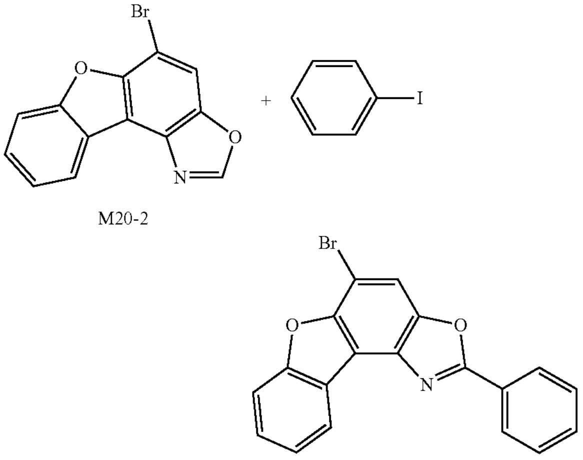

M20-2

M20-3

M20-3 was prepared in the same way as A1, following the same preparation method of A1, using the same molar ratio, except that M1-1 was replaced with M20-2, and M1-2 was replaced with iodobenzene.

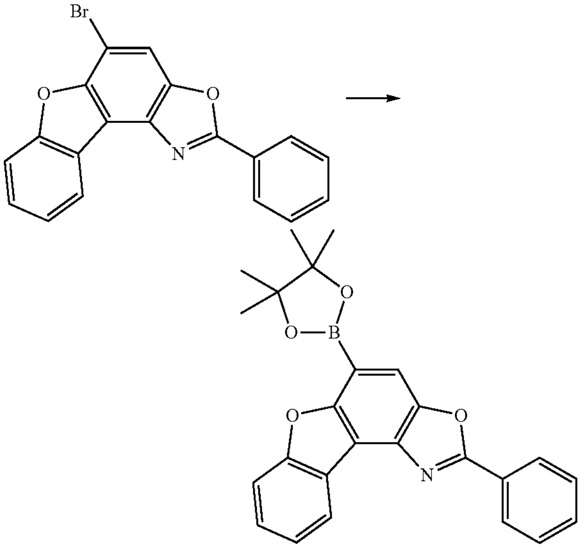

M20-4

M20-4 was prepared in the same way as M4-4, following the same preparation method of M4-4, using the same molar ratio, except that M4-3 was replaced by M20-3.

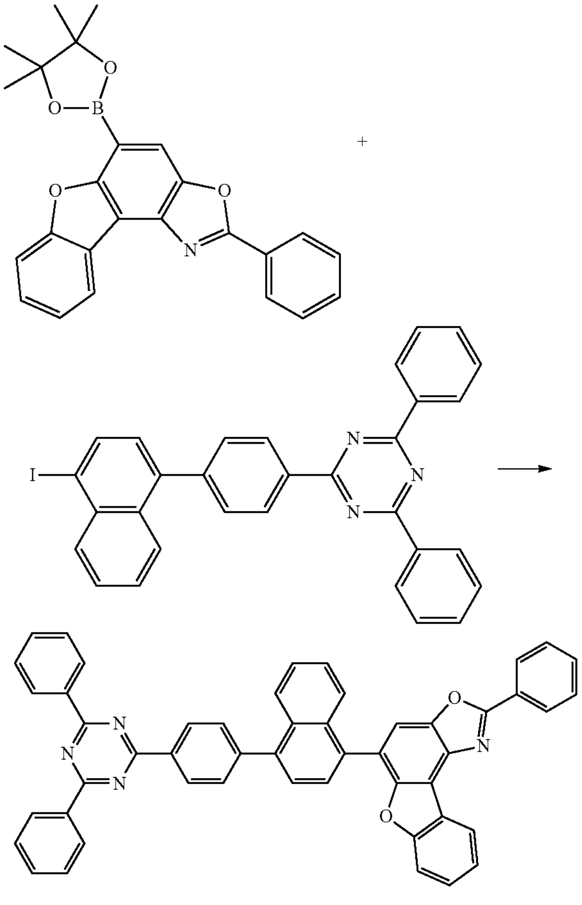

E12

E12 was prepared in the same way as A12, following the same preparation method of A12, using the same molar ratio, except that M4-4 was replaced by M20-4.

Preparation of E21

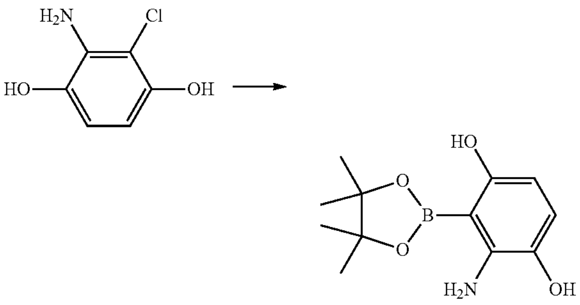

M21-1

M21-1 was prepared in the same way as M4-3, following the same preparation method of M4-3, using the same molar ratio, except that M4-2 was replaced with 2-amino-3-chloro-1,4-benzenediol.

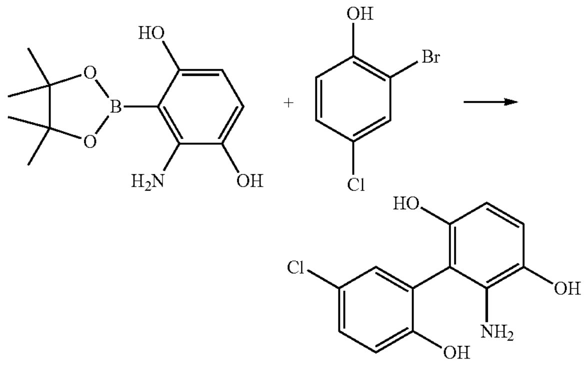

M21-2

M21-2 was prepared in the same way as A12, following the same preparation method of A12, using the same molar ratio, except that M4-3 was replaced by M21-1, and M1-2 was replaced by 2-bromo-4-chlorophenol.

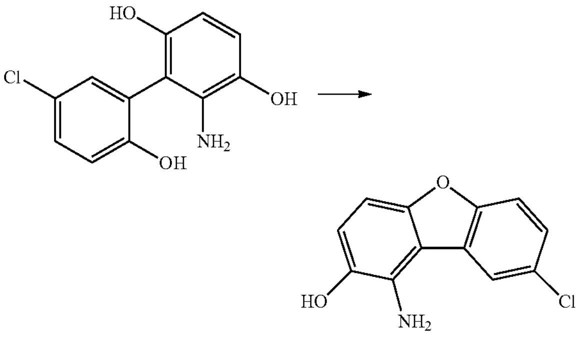

M21-3

M21-3 was prepared in the same way as M5-3, following the same preparation method of M5-3, using the same molar ratio, except that M5-2 was replaced by M21-2.

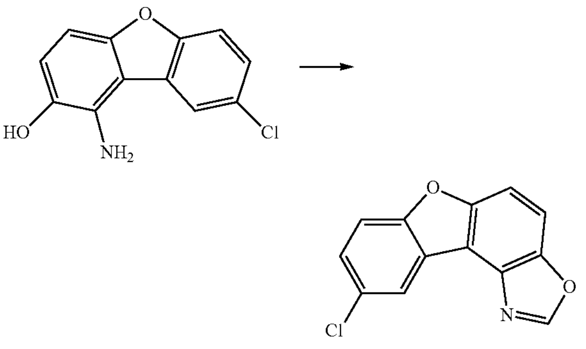

M21-4

M21-4 was prepared in the same way as M1-1, following the same preparation method of M1-1, using the same molar ratio, except that 2-amino-3-dibenzofuranol was replaced with M21-3.

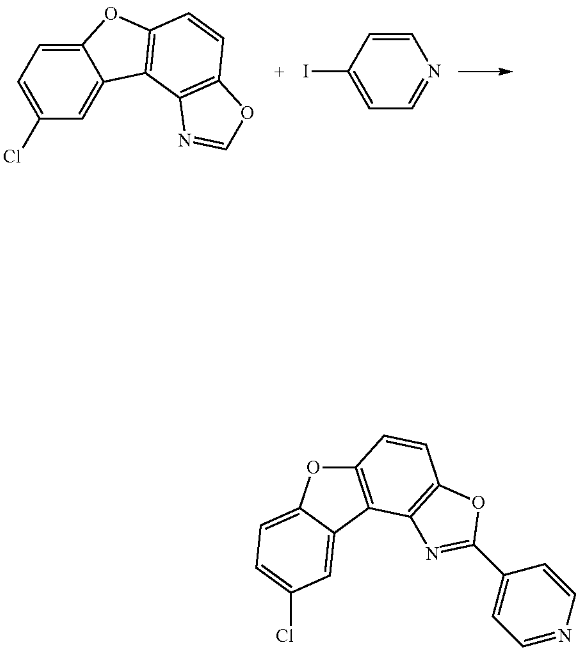

M21-5

M21-5 was prepared in the same way as A1, following the same preparation method of A1, using the same molar ratio, except that M1-1 was replaced by M21-4, and M1-2 was replaced by 4-iodopyridine.

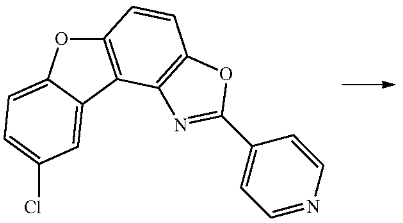

-continued

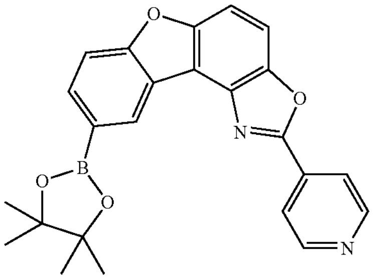

M21-6

M21-6 was prepared in the same way as M4-3, following the same preparation method of M4-3, using the same molar ratio, except that M4-2 was replaced by M21-5.

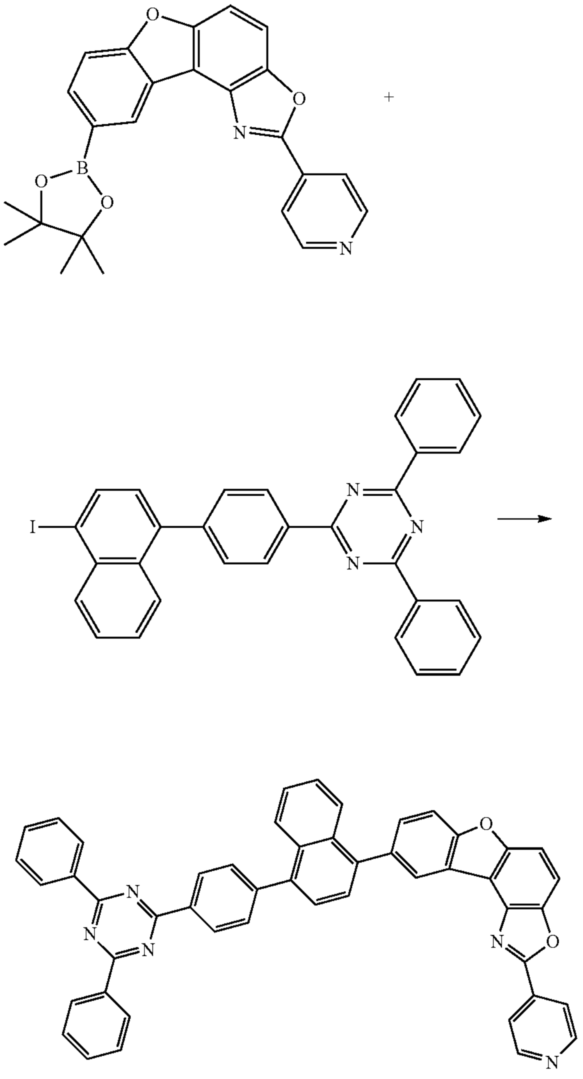

E21

E21 was prepared in the same way as A12, following the same preparation method of A12, using the same molar ratio, except that M4-4 was replaced by M21-6.

Preparation of E24

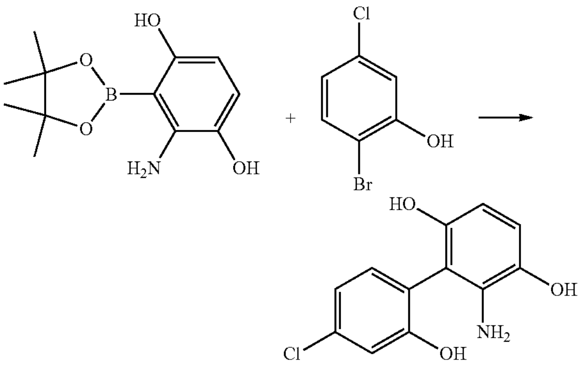

M22-1

M22-1 was prepared in the same way as A12, following the same preparation method of A12, using the same molar ratio, except that M4-3 was replaced by M21-1, and M1-2 was replaced by 2-bromo-5-chlorophenol.

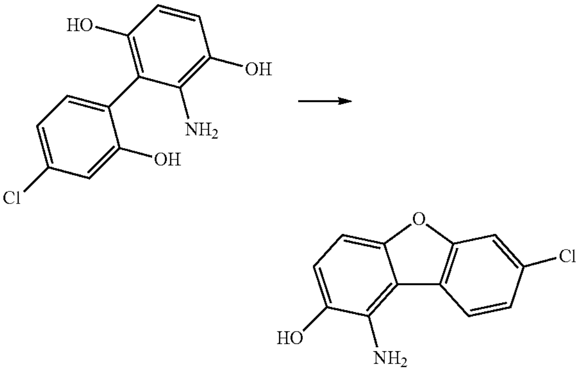

M22-2

M22-2 was prepared in the same way as A M5-3, following the same preparation method of M5-3, using the same molar ratio, except that M5-2 was replaced by M22-1.

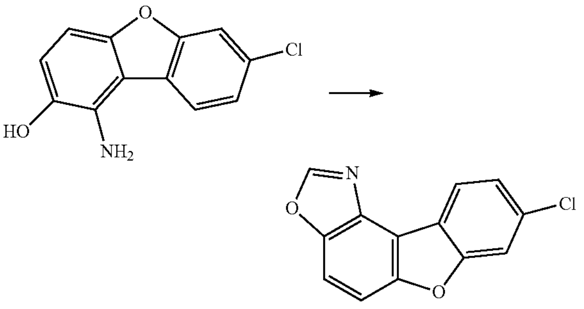

M22-3

M22-3 was prepared in the same way as M1-1, following the same preparation method of M1-1, using the same molar ratio, except that 2-amino-3-dibenzofuranol was replaced with M22-2.

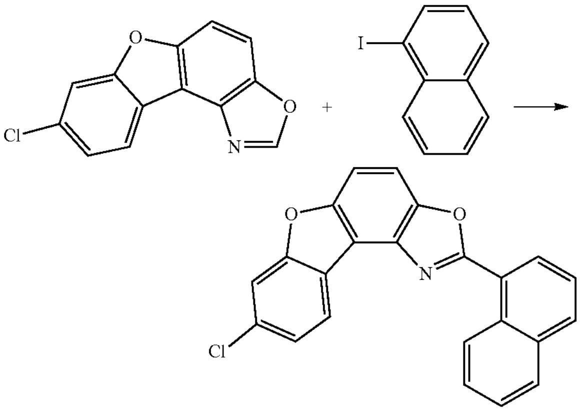

M22-4

M22-4 was prepared in the same way as A1, following the same preparation method of A1, using the same molar ratio, except that M1-1 was replaced by M22-3, and M1-2 was replaced by 1-iodonaphthalene.

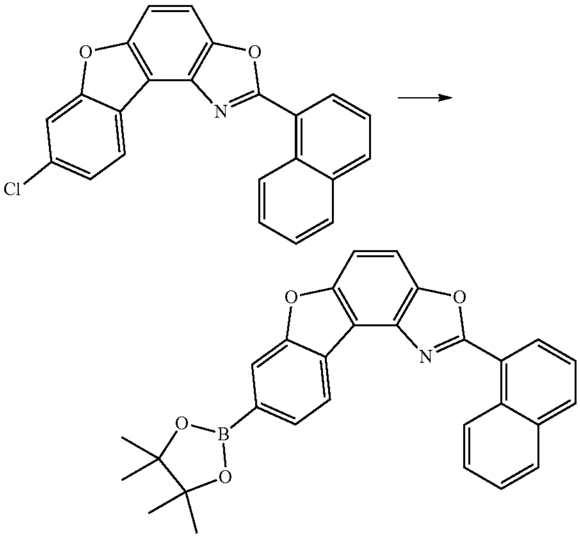

M22-5

M22-5 was prepared in the same way as M4-3, following the same preparation method of M4-3, using the same molar ratio, except that M4-2 was replaced by M22-4.

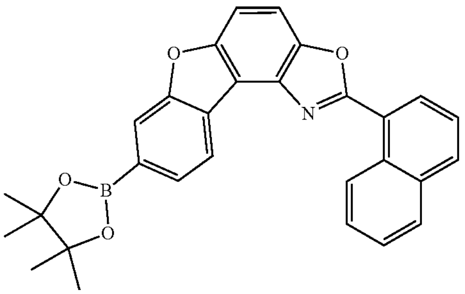

+

-continued

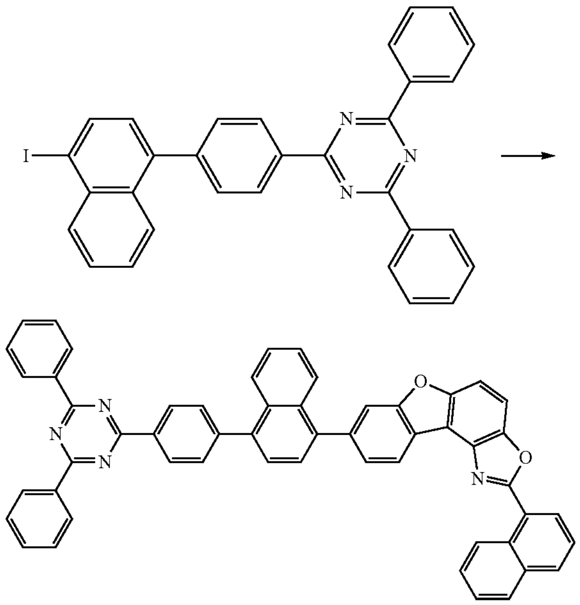

E24

E24 was prepared in the same way as A12, following the same preparation method of A12, using the same molar ratio, except that M4-4 was replaced by M22-5

Preparation of F1

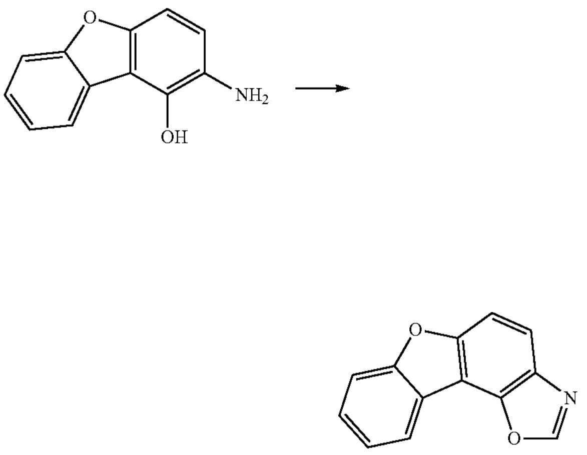

M23-1

M23-1 was prepared in the same way as M1-1, following the same preparation method of M1-1, using the same molar ratio, except that 2-amino-3-dibenzofuranol was replaced by 2-amino-1-dibenzofuranol.

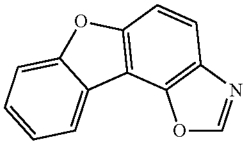

+

-continued

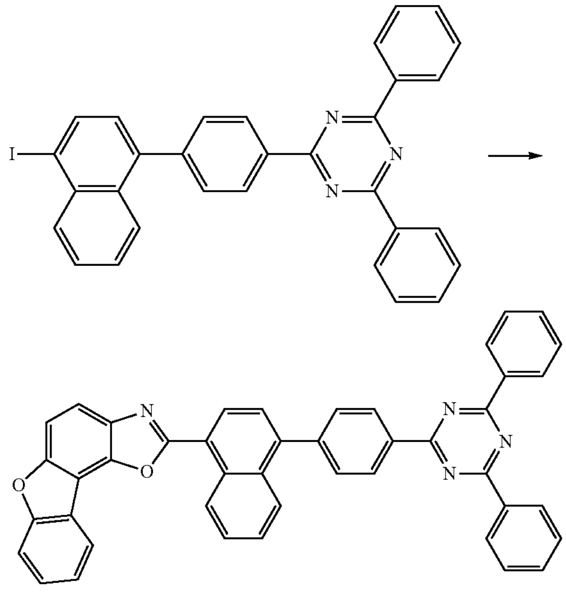

F1

F1 was prepared in the same way as A1, following the same preparation method of A1, using the same molar ratio, except that M1-1 was replaced by M23-1.

Preparation of F2

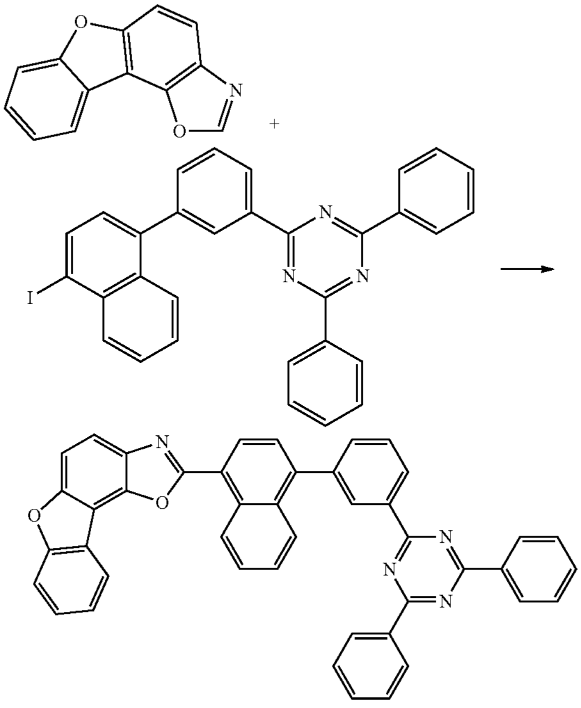

F2

F2 was prepared in the same way as A1, following the same preparation method of A1, using the same molar ratio, except that M1-1 was replaced by M23-1, and M1-2 was replaced by M2-1.

Preparation of F5

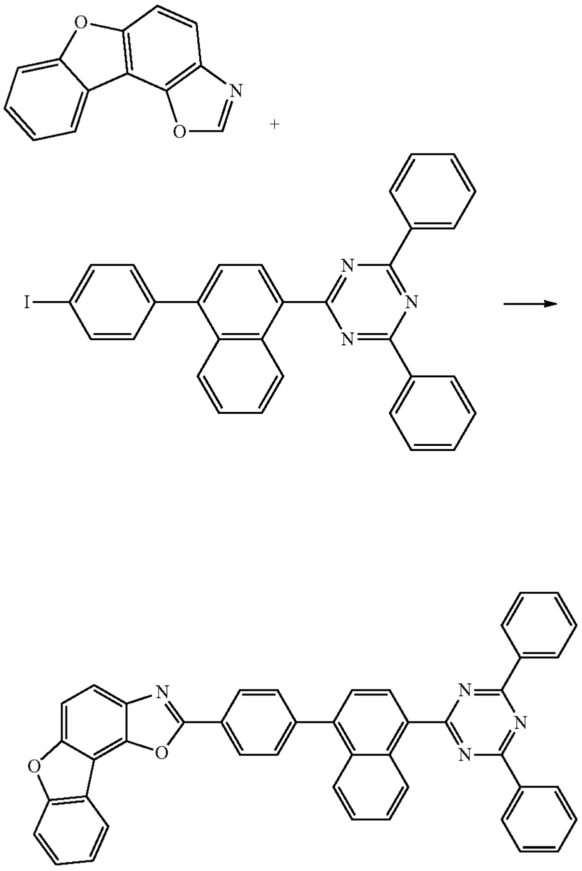

F5

F5 was prepared in the same way as A1, following the same preparation method of A1, using the same molar ratio, except that M1-1 was replaced by M23-1, and M1-2 was replaced by M3-1.

Preparation of F12

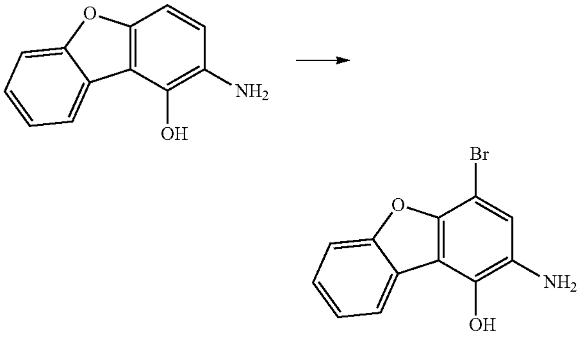

M24-1

M24-1 was prepared in the same way as M4-1, following the same preparation method of M4-1, using the same molar ratio, except that 2-amino-3-dibenzofuranol was replaced by 2-amino-1-dibenzofuranol.

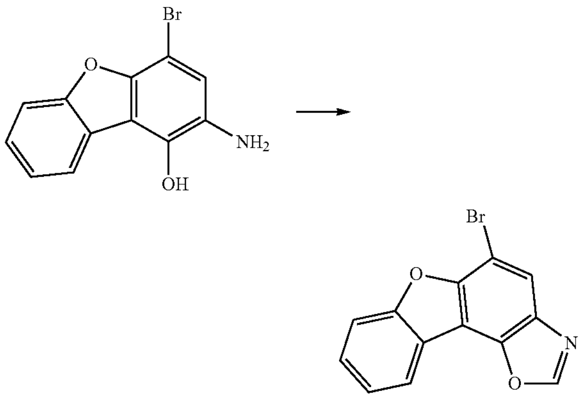

M24-2

M24-2 was prepared in the same way as M1-1, following the same preparation method of M1-1, using the same molar ratio, except that 2-amino-3-dibenzofuranol was replaced with M24-1.

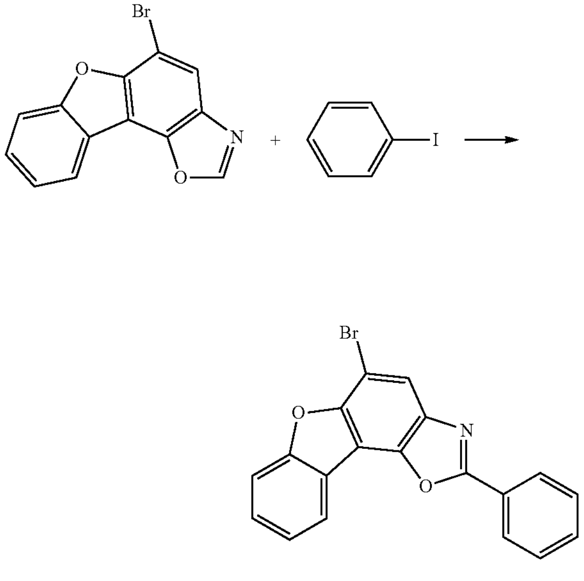

M24-3

M24-3 was prepared in the same way as A1, following the same preparation method of A1, using the same molar ratio, except that M1-1 was replaced with M24-2, and M1-2 was replaced with iodobenzene.

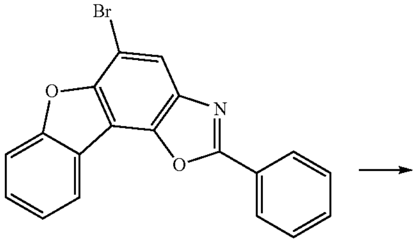

-continued

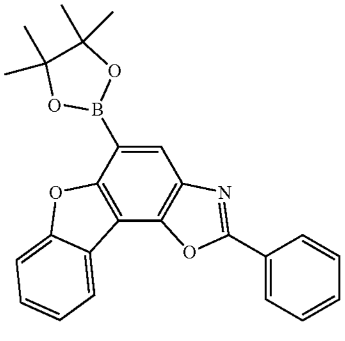

M24-4

M24-4 was prepared in the same way as M4-4, following the same preparation method of M4-4, using the same molar ratio, except that M4-3 was replaced by M24-3.

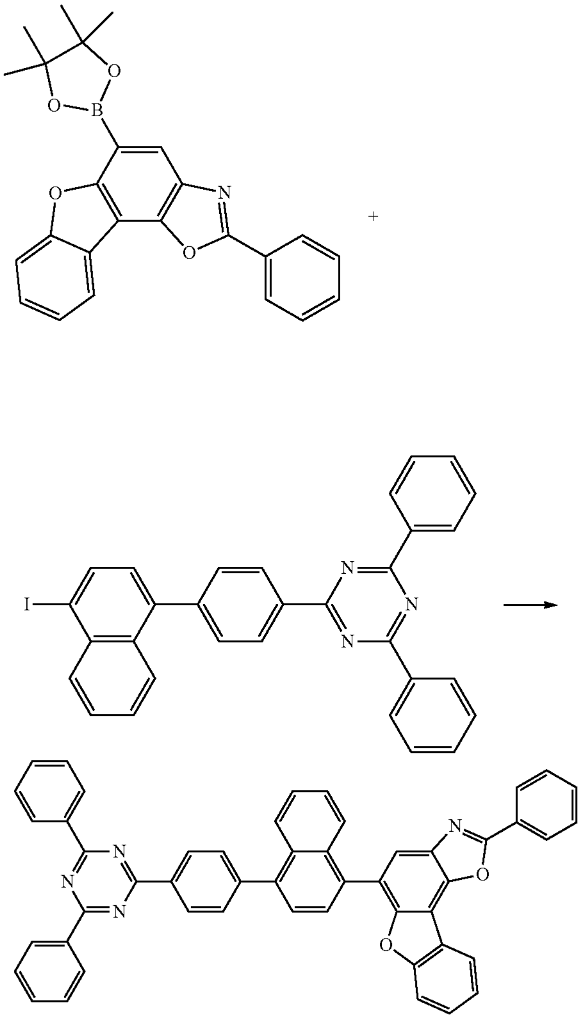

F12

F12 was prepared in the same way as A12, following the same preparation method of A12, using the same molar ratio, except that M4-4 was replaced by M24-4.

Preparation of F21

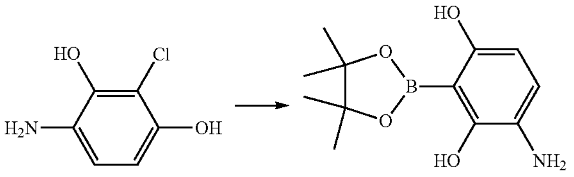

M25-1

M25-1 was prepared in the same way as M4-3, following the same preparation method of M4-3, using the same molar ratio, except that M4-2 was replaced by 4-amino-2-chloro-1,3-benzenediol.

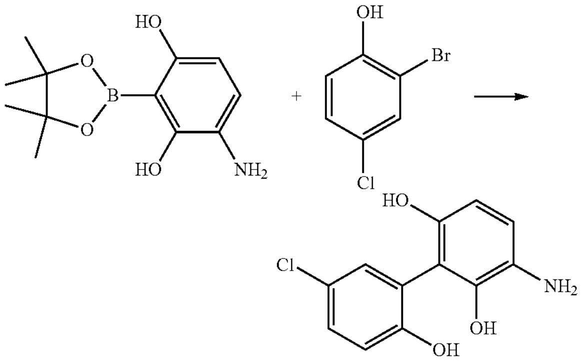

M25-2

M25-2 was prepared in the same way as A12, following the same preparation method of A12, using the same molar ratio, except that M4-3 was replaced by M25-1, and M1-2 was replaced by 2-bromo-4-chlorophenol.

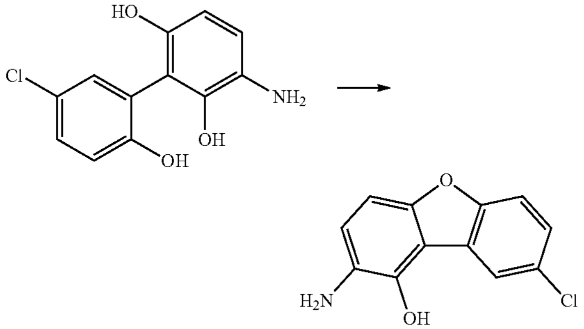

M25-3

M25-3 was prepared in the same way as M5-3, following the same preparation method of M5-3, using the same molar ratio, except that M5-2 was replaced by M25-2.

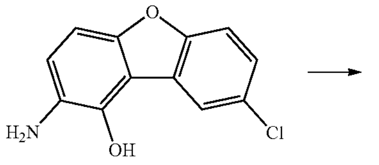

-continued

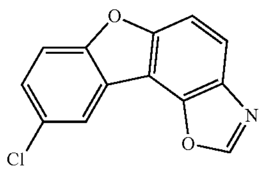

M25-4

M25-4 was prepared in the same way as M1-1, following the same preparation method of M1-1, using the same molar ratio, except that 2-amino-3-dibenzofuranol was replaced with M25-3.

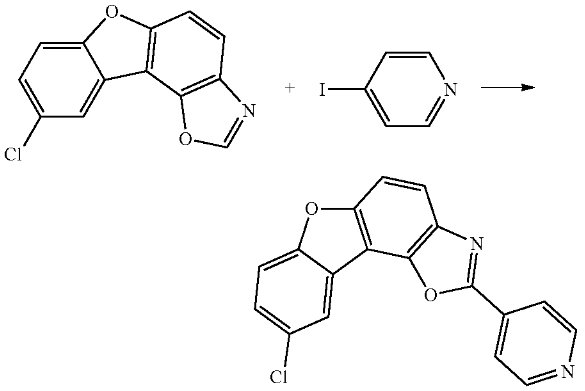

M25-5

M25-5 was prepared in the same way as A1, following the same preparation method of A1, using the same molar ratio, except that M1-1 was replaced by M25-4, and M1-2 was replaced by 4-iodopyridine.

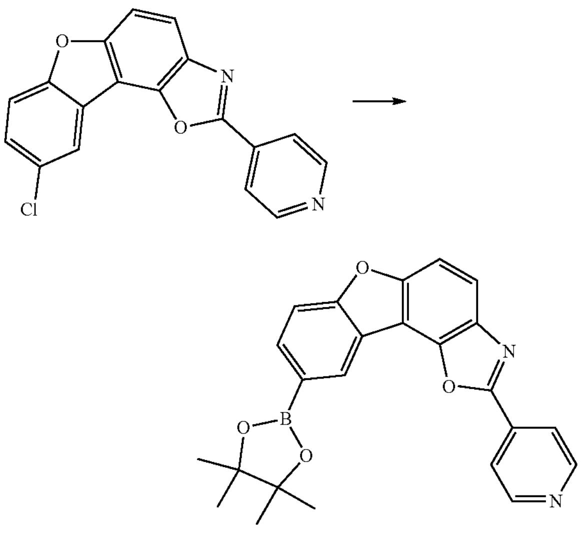

M25-6

M25-6 was prepared in the same way as M4-3, following the same preparation method of M4-3, using the same molar ratio, except that M4-2 was replaced by M25-5.

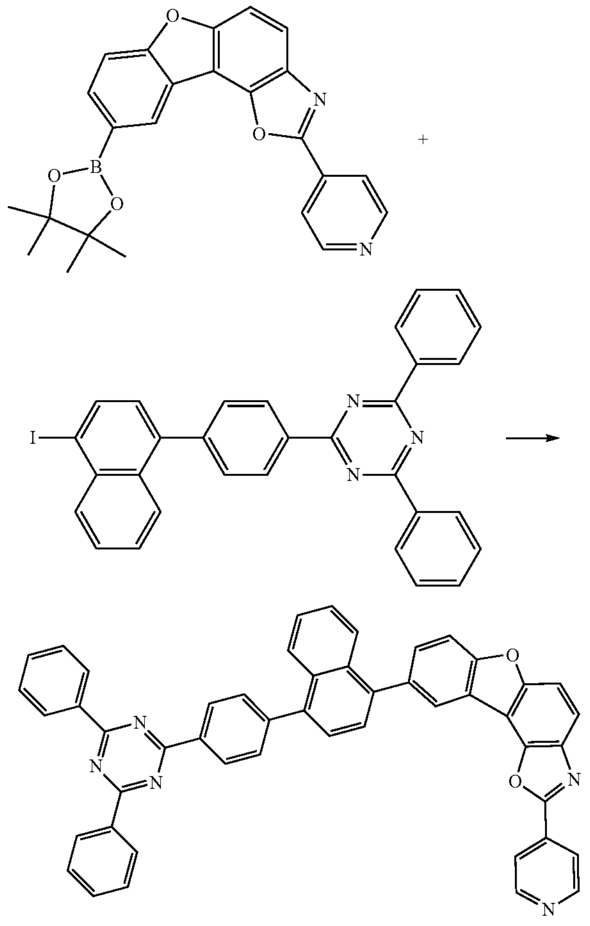

F21

F21 was prepared in the same way as A12, following the same preparation method of A12, using the same molar ratio, except that M4-4 was replaced by M25-6.

Preparation of F24

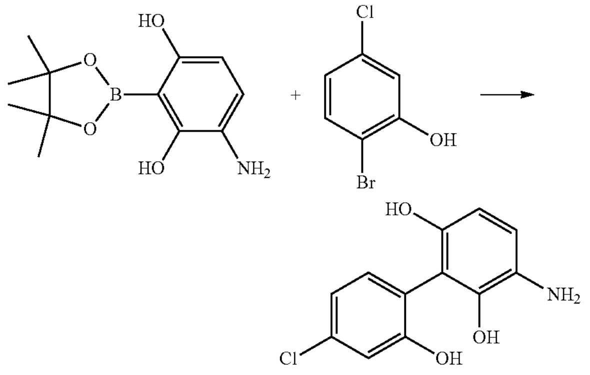

M26-1

M26-1 was prepared in the same way as A12, following the same preparation method of A12, using the same molar ratio, except that M4-3 was replaced by M25-1, and M1-2 was replaced by 2-bromo-5-chlorophenol.

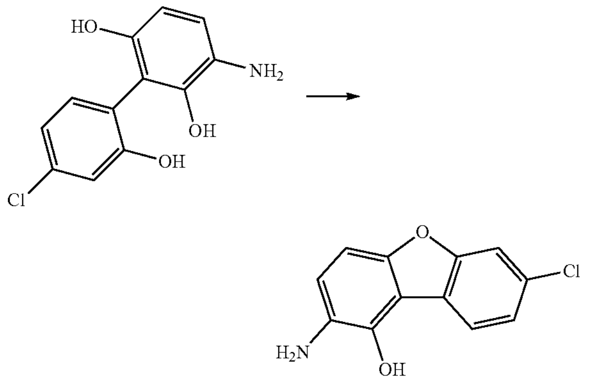

M26-2

M26-2 was prepared in the same way as M5-3, following the same preparation method of M5-3, using the same molar ratio, except that M5-2 was replaced by M26-1.

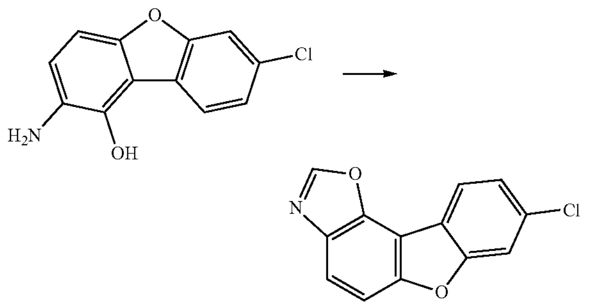

M26-3

M26-3 was prepared in the same way as M1-1, following the same preparation method of M1-1, using the same molar ratio, except that 2-amino-3-dibenzofuranol was replaced with M26-2.

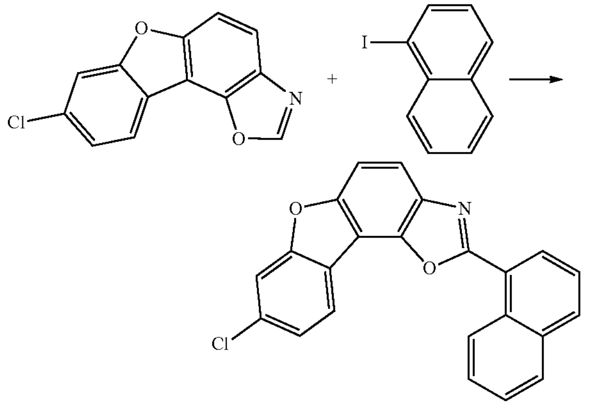

M26-4

M26-4 was prepared in the same way as A1, following the same preparation method of A1, using the same molar ratio, except that M1-1 was replaced by M26-3, and M1-2 was replaced by 1-iodonaphthalene.

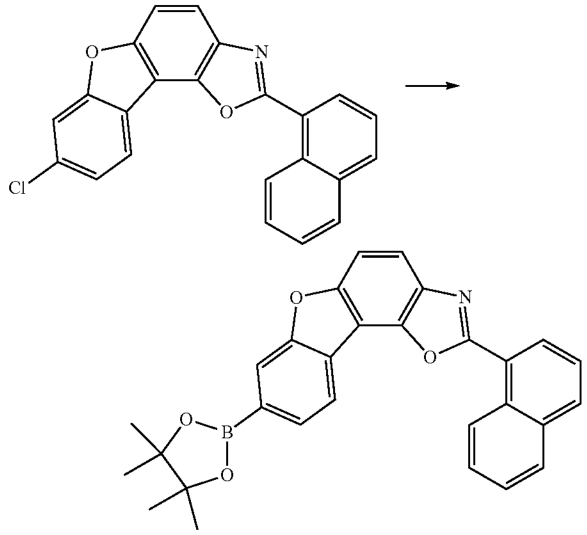

M26-5

M26-5 was prepared in the same way as M4-3, following the same preparation method of M4-3, using the same molar ratio, except that M4-2 was replaced by M26-4.

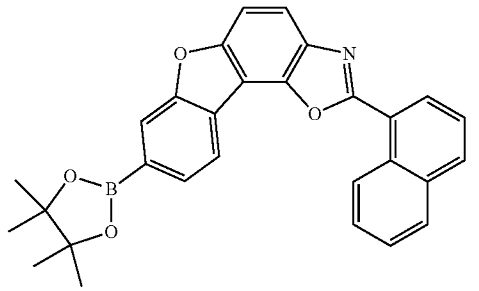

+

-continued

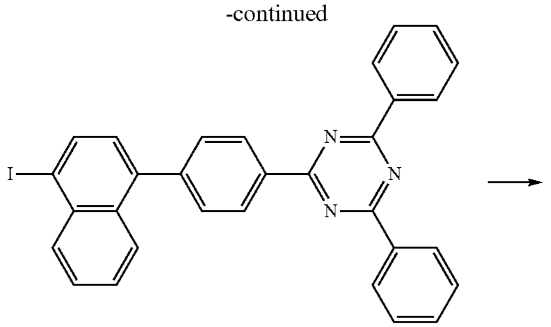

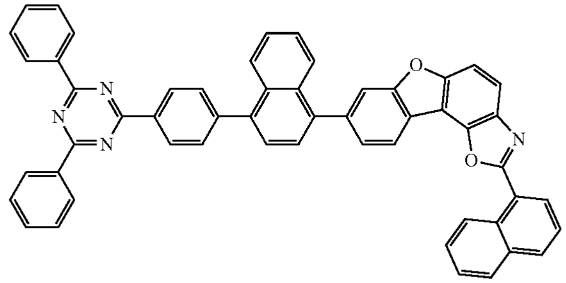

F24

F24 was prepared in the same way as A12, following the same preparation method of A12, using the same molar ratio, except that M4-4 was replaced by M26-5.

The compounds synthesized in the above examples were identified by matrix-assisted laser desorption ionization time-of-flight mass spectrometry and elemental analysis, and the results thereof are shown in Table 1 below.

TABLE 1

| Compound | MALDI-TOF MS theoretical value (m/z) | MALDI-TOF MS measured value (m/z) | UV absorption (nm) | Elemental analysis theoretical value | Elemental analysis measured value |
|---|---|---|---|---|---|
| A1 | 642.21 | 641.54 | 387 | C: 82.23; H: 4.08; N: 8.72; | C: 82.20; H: 4.12; N: 8.70; |
| A2 | 642.21 | 641.88 | 354 | C: 82.23; H: 4.08; N: 8.72; | C: 82.21; H: 4.08; N: 8.73; |
| A5 | 642.21 | 642.20 | 367 | C: 82.23; H: 4.08; N: 8.72; | C: 82.24; H: 4.09; N: 8.72; |
| A12 | 718.24 | 718.33 | 381 | C: 83.55; H: 4.21; N: 7.79; | C: 83.52; H: 4.23; N: 7.78; |
| A21 | 719.23 | 719.08 | 400 | C: 81.76; H: 4.06; N: 9.73; | C: 81.76; H: 4.06; N: 9.73; |
| A24 | 768.25 | 768.09 | 412 | C: 84.36; H: 4.20; N: 7.29; | C: 84.37; H: 4.18; N: 7.28; |
| B1 | 642.21 | 641.74 | 377 | C: 82.23; H: 4.08; N: 8.72; | C: 82.23; H: 4.08; N: 8.72; |
| B2 | 642.21 | 641.86 | 349 | C: 82.23; H: 4.08; N: 8.72; | C: 82.23; H: 4.10; N: 8.69; |
| B5 | 642.21 | 642.08 | 361 | C: 82.23; H: 4.08; N: 8.72; | C: 82.22; H: 4.09; N: 8.70; |
| B12 | 718.24 | 718.18 | 371 | C: 83.55; H: 4.21; N: 7.79; | C: 83.56; H: 4.23; N: 7.78; |
| B21 | 719.23 | 719.05 | 392 | C: 81.76; H: 4.06; N: 9.73; | C: 81.76; H: 4.06; N: 9.73; |
| B24 | 768.25 | 768.11 | 401 | C: 84.36; H: 4.20; N: 7.29; | C: 84.36; H: 4.22; N: 7.25; |

TABLE 1-continued

| Compound | MALDI-TOF MS theoretical value (m/z) | MALDI-TOF MS measured value (m/z) | UV absorption (nm) | Elemental analysis theoretical value | Elemental analysis measured value |
|---|---|---|---|---|---|
| C1 | 642.21 | 642.19 | 397 | C: 82.23; H: 4.08; N: 8.72; | C: 82.22; H: 4.09; N: 8.71; |
| C2 | 642.21 | 642.11 | 364 | C: 82.23; H: 4.08; N: 8.72; | C: 82.23; H: 4.08; N: 8.72; |
| C5 | 642.21 | 641.94 | 377 | C: 82.23; H: 4.08; N: 8.72; | C: 82.23; H: 4.08; N: 8.72; |
| C11 | 718.24 | 718.16 | 391 | C: 83.55; H: 4.21; N: 7.79; | C: 83.56; H: 4.19; N: 7.78; |
| C21 | 719.23 | 719.15 | 410 | C: 81.76; H: 4.06; N: 9.73; | C: 81.76; H: 4.06; N: 9.73; |
| C24 | 768.25 | 768.28 | 421 | C: 84.36; H: 4.20; N: 7.29; | C: 84.35; H: 4.22; N: 7.26; |
| D1 | 642.21 | 642.06 | 380 | C: 82.23; H: 4.08; N: 8.72; | C: 82.23; H: 4.08; N: 8.72; |
| D2 | 642.21 | 642.13 | 349 | C: 82.23; H: 4.08; N: 8.72; | C: 82.23; H: 4.08; N: 8.72; |
| D5 | 642.21 | 642.17 | 362 | C: 82.23; H: 4.08; N: 8.72; | C: 82.23; H: 4.08; N: 8.72; |
| D11 | 718.24 | 718.27 | 376 | C: 83.55; H: 4.21; N: 7.79; | C: 83.55; H: 4.21; N: 7.79; |
| D21 | 719.23 | 719.06 | 394 | C: 81.76; H: 4.06; N: 9.73; | C: 81.77; H: 4.07; N: 9.69; |
| D24 | 768.25 | 768.33 | 407 | C: 84.36; H: 4.20; N: 7.29; | C: 84.36; H: 4.20; N: 7.29; |
| E1 | 642.21 | 642.28 | 392 | C: 82.23; H: 4.08; N: 8.72; | C: 82.23; H: 4.08; N: 8.72; |
| E2 | 642.21 | 642.41 | 359 | C: 82.23; H: 4.08; N: 8.72; | C: 82.23; H: 4.08; N: 8.72; |
| E5 | 642.21 | 641.95 | 374 | C: 82.23; H: 4.08; N: 8.72; | C: 82.23; H: 4.08; N: 8.72; |
| E12 | 718.24 | 718.39 | 386 | C: 83.55; H: 4.21; N: 7.79; | C: 83.55; H: 4.22; N: 7.82; |
| E21 | 719.23 | 719.37 | 405 | C: 81.76; H: 4.06; N: 9.73; | C: 81.75; H: 4.08; N: 9.69; |
| E24 | 768.25 | 768.43 | 417 | C: 84.36; H: 4.20; N: 7.29; | C: 84.36; H: 4.20; N: 7.29; |
| F1 | 642.21 | 642..32 | 370 | C: 82.23; H: 4.08; N: 8.72; | C: 82.24; H: 4.10; N: 8.67; |
| F2 | 642.21 | 642.47 | 344 | C: 82.23; H: 4.08; N: 8.72; | C: 82.24; H: 4.06; N: 8.73; |
| F5 | 642.21 | 642.38 | 351 | C: 82.23; H: 4.08; N: 8.72; | C: 82.23; H: 4.08; N: 8.72; |
| F12 | 718.24 | 718.01 | 364 | C: 83.55; H: 4.21; N: 7.79; | C: 83.56; H: 4.23; N: 7.74; |
| F21 | 719.23 | 719.41 | 386 | C: 81.76; H: 4.06; N: 9.73; | C: 81.77; H: 4.05; N: 9.71; |
| F24 | 768.25 | 768.35 | 398 | C: 84.36; H: 4.20; N: 7.29; | C: 84.35; H: 4.23; N: 7.24; |

For the organic compounds provided by the present disclosure, the distribution of the molecular frontier orbitals HOMO and LUMO was optimized and calculated through the Gaussian 09 program package (Gaussian Inc.) at the B3LYP/6-31G(d) calculation level using density functional theory (DFT). In one embodiment, the singlet energy level $E_S$ and triplet energy level $E_T$ of compound molecules were simulated and calculated based on time-dependent density functional theory (TDDFT). The results are shown in Table 2.

TABLE 2

| Organic compound number | HOMO (eV) | LUMO (eV) | $E_S$ (eV) | $E_T$ (eV) |
|---|---|---|---|---|
| A1 | −5.67 | −1.86 | 3.20 | 2.77 |
| A2 | −5.71 | −1.91 | 3.51 | 2.86 |
| A5 | −5.65 | 1.89 | 3.38 | 2.71 |
| A12 | −5.75 | −1.95 | 3.25 | 2.66 |
| A21 | −5.60 | −1.97 | 3.10 | 2.80 |
| A24 | −5.64 | −1.83 | 3.01 | 2.81 |

TABLE 2-continued

| Organic compound number | HOMO (eV) | LUMO (eV) | $E_S$ (eV) | $E_T$ (eV) |
|---|---|---|---|---|
| B1 | −5.68 | −1.85 | 3.29 | 2.72 |
| B2 | −5.72 | −1.90 | 3.55 | 2.81 |
| B5 | −5.66 | 1.88 | 3.43 | 2.66 |
| B12 | −5.76 | −1.94 | 3.34 | 2.61 |
| B21 | −5.61 | −1.96 | 3.16 | 2.75 |
| B24 | −5.65 | −1.82 | 3.09 | 2.76 |
| C1 | −5.71 | −1.82 | 3.12 | 2.82 |
| C2 | −5.75 | −1.87 | 3.41 | 2.91 |
| C5 | −5.69 | 1.85 | 3.29 | 2.76 |
| C11 | −5.79 | −1.91 | 3.17 | 2.71 |
| C21 | −5.64 | −1.93 | 3.02 | 2.85 |
| C24 | −5.68 | −1.79 | 2.94 | 2.86 |
| D1 | −5.73 | −1.80 | 3.26 | 2.80 |
| D2 | −5.77 | −1.85 | 3.55 | 2.89 |
| D5 | −5.71 | 1.83 | 3.43 | 2.74 |
| D11 | −5.81 | −1.89 | 3.30 | 2.69 |
| D21 | −5.66 | −1.91 | 3.15 | 2.83 |
| D24 | −5.70 | −1.77 | 3.05 | 2.84 |
| E1 | −5.70 | −1.84 | 3.16 | 2.84 |

TABLE 2-continued

| Organic compound number | HOMO (eV) | LUMO (eV) | $E_S$ (eV) | $E_T$ (eV) |
|---|---|---|---|---|
| E2 | −5.74 | −1.89 | 3.45 | 2.93 |
| E5 | −5.68 | 1.87 | 3.32 | 2.78 |
| E12 | −5.78 | −1.93 | 3.21 | 2.73 |
| E21 | −5.63 | −1.95 | 3.06 | 2.87 |
| E24 | −5.67 | −1.81 | 2.97 | 2.88 |
| F1 | −5.69 | −1.83 | 3.35 | 2.86 |
| F2 | −5.73 | −1.88 | 3.60 | 2.95 |
| F5 | −5.67 | 1.86 | 3.33 | 2.80 |
| F12 | −5.77 | −1.92 | 3.41 | 2.75 |
| F21 | −5.62 | −1.94 | 3.21 | 2.89 |
| F24 | −5.66 | −1.80 | 3.12 | 2.90 |

Comparative Example

A glass substrate plate coated with ITO (indium tin oxide) in a thin film at a thickness of 1000 Å was put into distilled water in which a detergent was dissolved, and washed with ultrasonic waves. The ITO was washed for 30 minutes, ultrasonic washed for 10 minutes with distilled water twice. After the ITO was washed with distilled water, it was ultrasonic washed with a solvent of isopropanol, acetone, and methanol, dried, and then transported to a plasma cleaning machine. In one embodiment, after the above substrate plate was washed for 5 minutes by oxygen plasma, it was transported to a vacuum deposition machine.

On the ITO transparent electrode prepared above, the following compound [HI] was thermally vacuum-deposited to a thickness of 600 Å to form a hole injection layer. On the above hole injection layer, hexacyano hexaazatriphenylene (HAT) of the following chemical formula and the following compound [HT] were sequentially vacuum-deposited to 50 Å and 600 Å respectively to form a hole transport layer.

Next, on the above hole transport layer, the following compounds [BH] and [BD] were vacuum deposited at a weight ratio of 25:1 to a film thickness of 200 Å to form a light-emitting layer.

On the above light-emitting layer, the following compounds [ET] and [LiQ] (8-hydroxyquinolinolato-lithium) were vacuum-deposited at a weight ratio of 1:1 to form an electron injection and transport layer in a thickness of 150 Å. On the above electron injection and transport layer, lithium fluoride (LiF) and aluminum were sequentially vapor deposited to a thickness of 10 Å and 1000 Å respectively to form a cathode.

In the above process, the vapor deposition rate of organic substance was maintained at 0.4 to 0.9 Å/sec, the vapor deposition rate of lithium fluoride of the cathode was maintained at 0.3 Å/sec, and the vapor deposition rate of aluminum was maintained at 2 Å/sec, during vapor deposition, the vacuum degree was maintained at $1\times10^{-7}$ to $5\times10^{-8}$ Torr, to produce an organic light-emitting device.

[HAT]

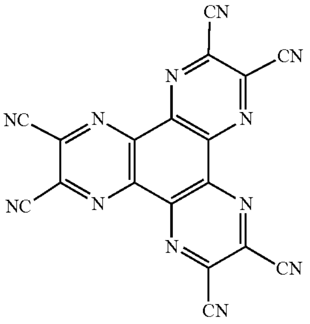

[HI-A]

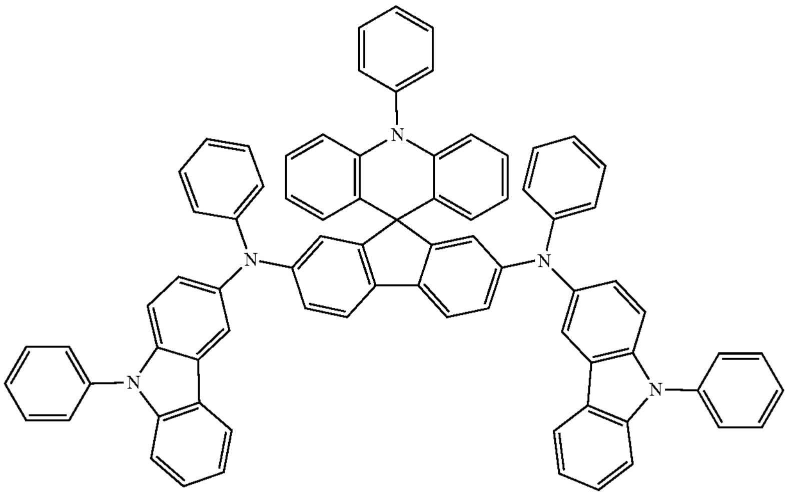

-continued
[HT-A]
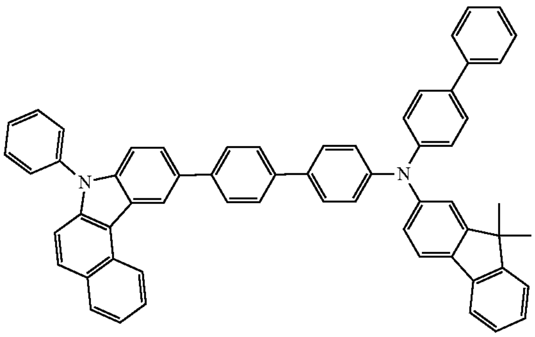
[LiQ]
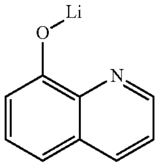
[BH]
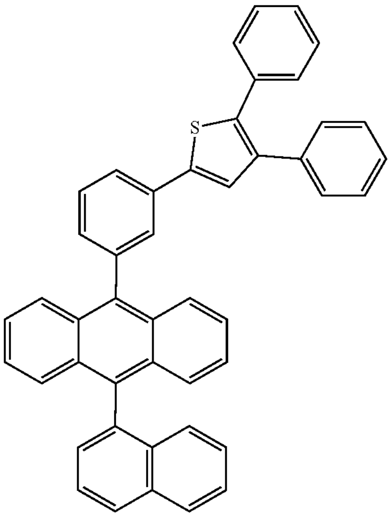
[BD]
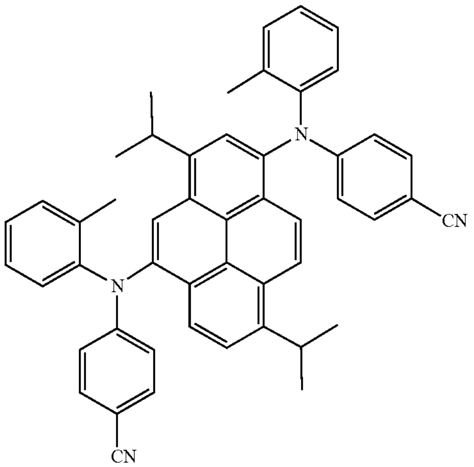
[ET]
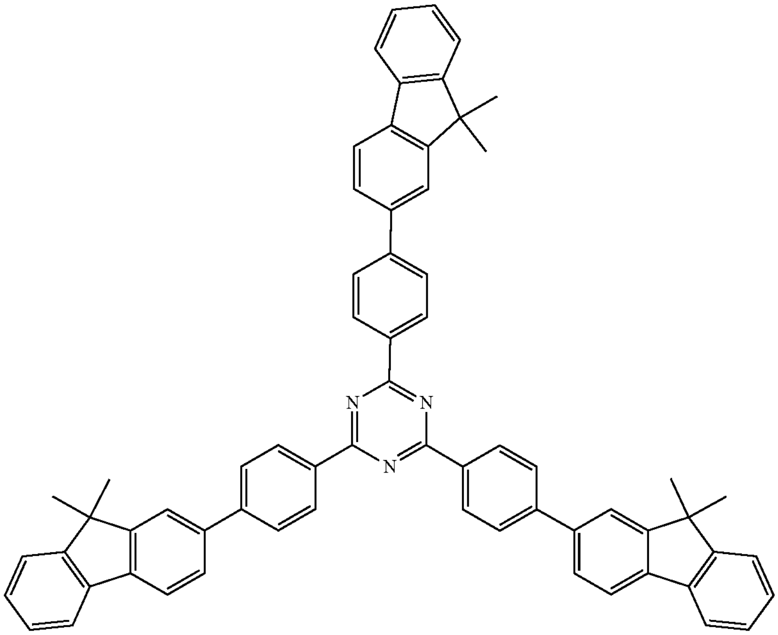

Experimental Example 1-36

Organic light-emitting devices were produced by the same method as in the Comparative Example, according to the above Comparative Example, except that the compound [ET] was replaced with the compounds synthesized in Example 1.

The driving voltage and luminous efficiency were measured at a current density of 10 mA/cm$^2$ for the organic light-emitting devices fabricated using the respective compounds as electron transport layers in the above-mentioned Experimental Examples and Comparative Example, and the time required to reach 95% of the initial brightness (LT95) was measured at a current density of 20 mA/cm$^2$. The results are shown in Table 3 below.

TABLE 3

| Name | Electron transport layer | Voltage (V) | Current efficiency (cd/A) | LT95(h) |
|---|---|---|---|---|
| Comparative Example | ET | 5.14 | 4.11 | 95 |
| Experimental Example 1 | A1 | 5.09 | 4.17 | 116 |
| Experimental Example 2 | A2 | 5.09 | 4.23 | 121 |
| Experimental Example 3 | A5 | 5.05 | 4.15 | 131 |
| Experimental Example 4 | A12 | 5.08 | 4.27 | 116 |
| Experimental Example 5 | A21 | 5.10 | 4.19 | 117 |
| Experimental Example 6 | A24 | 5.08 | 4.15 | 117 |
| Experimental Example 7 | B1 | 5.07 | 4.20 | 117 |
| Experimental Example 8 | B2 | 5.07 | 4.25 | 120 |
| Experimental Example 9 | B5 | 5.09 | 4.12 | 127 |
| Experimental Example 10 | B12 | 5.09 | 4.31 | 127 |
| Experimental Example 11 | B21 | 5.06 | 4.21 | 118 |
| Experimental Example 12 | B24 | 5.08 | 4.12 | 118 |
| Experimental Example 13 | C1 | 5.05 | 4.16 | 120 |
| Experimental Example 14 | C2 | 5.05 | 4.24 | 125 |
| Experimental Example 15 | C5 | 5.07 | 4.17 | 119 |
| Experimental Example 16 | C11 | 5.08 | 4.28 | 119 |
| Experimental Example 17 | C21 | 5.07 | 4.18 | 121 |
| Experimental Example 18 | C24 | 5.06 | 4.17 | 120 |
| Experimental Example 19 | D1 | 5.06 | 4.19 | 121 |
| Experimental Example 20 | D2 | 5.05 | 4.27 | 124 |
| Experimental Example 21 | D5 | 5.07 | 4.14 | 116 |
| Experimental Example 22 | D11 | 5.08 | 4.31 | 120 |
| Experimental Example 23 | D21 | 5.06 | 4.21 | 122 |
| Experimental Example 24 | D24 | 5.07 | 4.14 | 119 |
| Experimental Example 25 | E1 | 5.07 | 4.16 | 119 |
| Experimental Example 26 | E2 | 5.06 | 4.22 | 119 |
| Experimental Example 27 | E5 | 5.09 | 4.14 | 130 |

TABLE 3-continued

| Name | Electron transport layer | Voltage (V) | Current efficiency (cd/A) | LT95(h) |
|---|---|---|---|---|
| Experimental Example 28 | E12 | 5.09 | 4.30 | 126 |
| Experimental Example 29 | E21 | 5.06 | 4.21 | 116 |
| Experimental Example 30 | E24 | 5.05 | 4.15 | 129 |
| Experimental Example 31 | F1 | 5.08 | 4.20 | 117 |
| Experimental Example 32 | F2 | 5.07 | 4.26 | 119 |
| Experimental Example 33 | F5 | 5.05 | 4.13 | 118 |
| Experimental Example 34 | F12 | 5.08 | 4.34 | 116 |
| Experimental Example 35 | F21 | 5.06 | 4.25 | 116 |
| Experimental Example 36 | F24 | 5.07 | 4.15 | 116 |

As shown in Table 3, the organic light-emitting devices of Experimental Examples using the compounds provided by the present disclosure as electron transport layer materials exhibited superior device characteristics compared to the organic light-emitting device prepared in Comparative Example using the compound that was not included in formula 1.

In general, considering that the luminous efficiency and lifetime characteristics of organic light-emitting devices have a trade-off relationship with each other, it can be seen that compared with the device of the Comparative Example, when the substituents in formula 1 are changed, the electron transport rate can be adjusted, and the balance of current carrier of the device can be adjusted, which shows a marked improvement.

The descriptions of the above examples are only used to help understand the method and the embodiments of the present disclosure. It should be noted that several improvements and modifications can be made to the present disclosure, and these improvements and modifications also fall within the claims and the embodiments of the present disclosure.

What is claimed is:

1. A compound having a structure as shown in formula I:

formula I

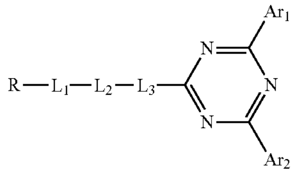

;

wherein R is selected from the group consisting of:

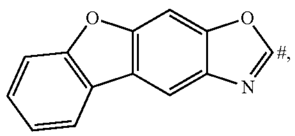

,

-continued

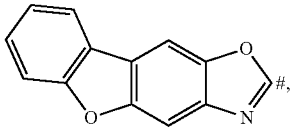

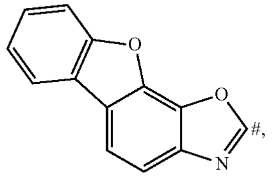

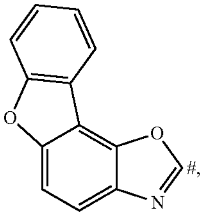

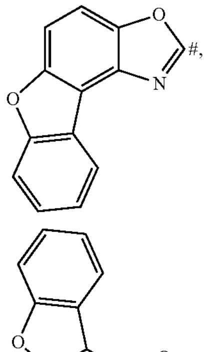

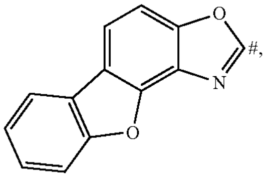

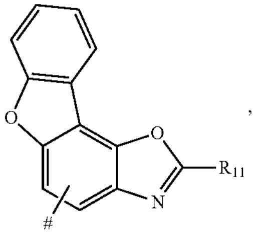

,

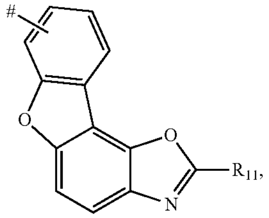

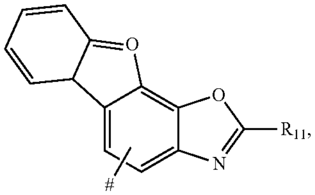

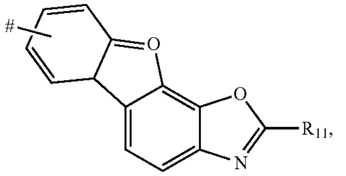

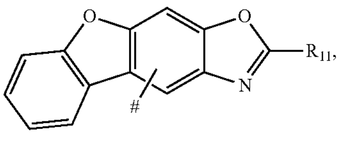

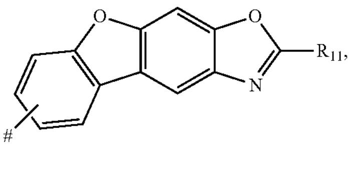

-continued

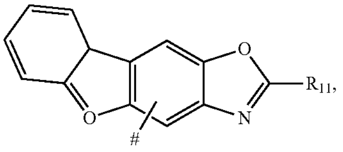

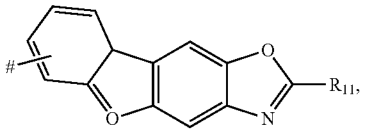

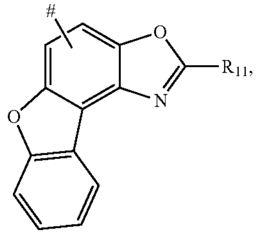

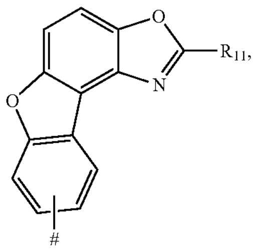

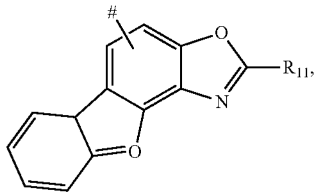

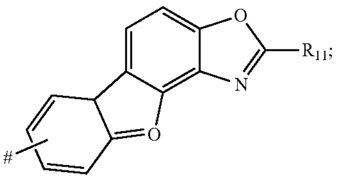

$L_1$, $L_2$, $L_3$ are independently selected from the group consisting of single bonds, phenyl, pyridyl, pyrimidinyl, pyrazinyl, pyridazinyl, naphthyl, anthracenyl, phenanthryl, 1,10-phenanthrolinyl, quinolinyl, isoquinolinyl quinoxalinyl, quinazolinyl and 1,5-naphthyridinyl, and at least two of $L_1$, $L_2$, and $L_3$ are not single bonds;

$Ar_1$ and $Ar_2$ are independently selected from the group consisting of phenyl, pyridyl, pyrimidinyl, pyrazinyl, pyridazinyl naphthyl, anthracenyl, phenanthryl, 1,10-phenanthrolinyl, quinolinyl, isoquinolinyl, quinoxalinyl, quinazolinyl and 1,5-naphthyridinyl;

# indicates the linking site.

2. The compound according to claim 1, which is selected from the group consisting of:

A1
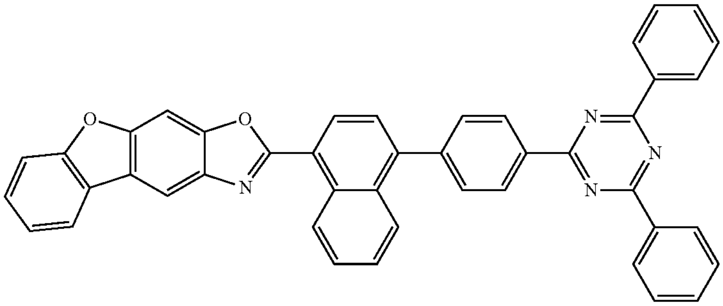
A2
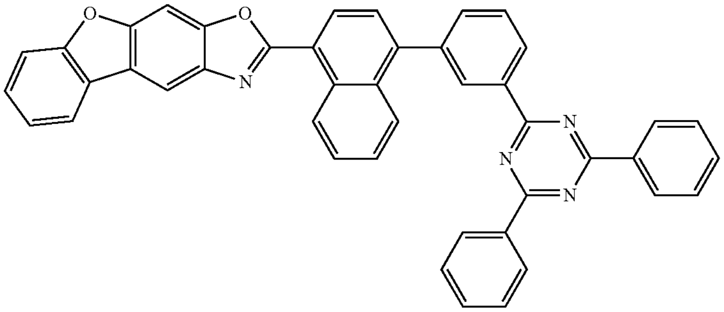
A3
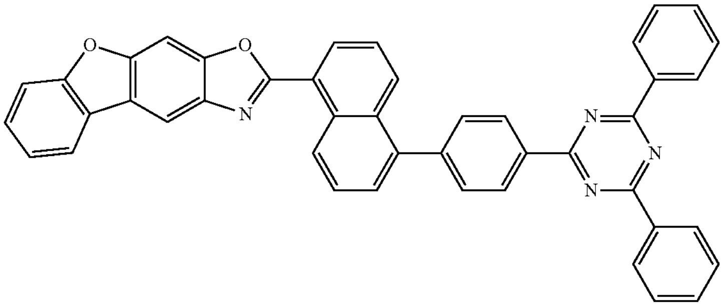
A4
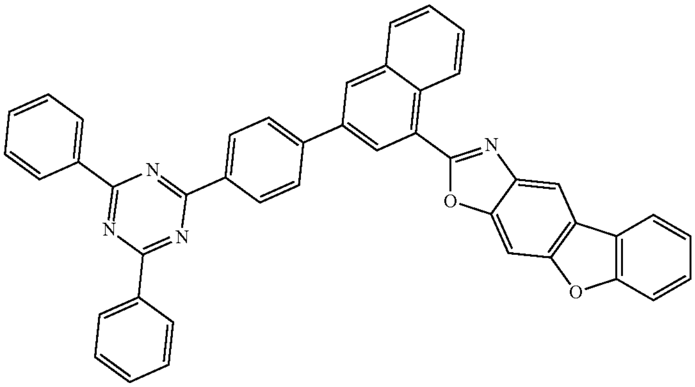
A5
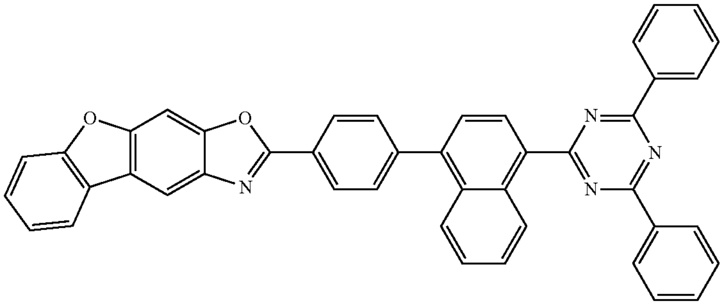

-continued
A6
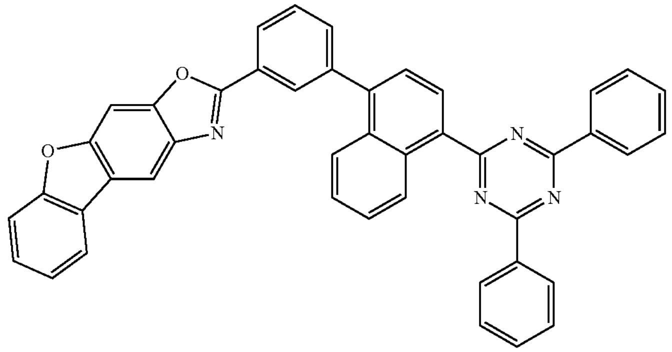
A7
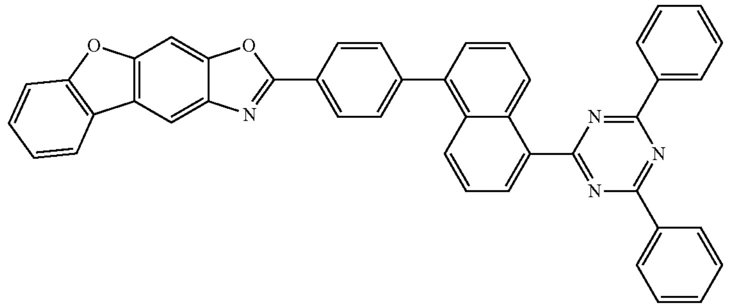
A8
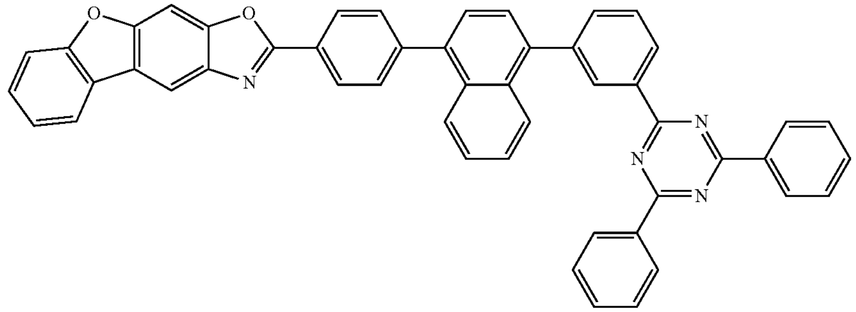
A9
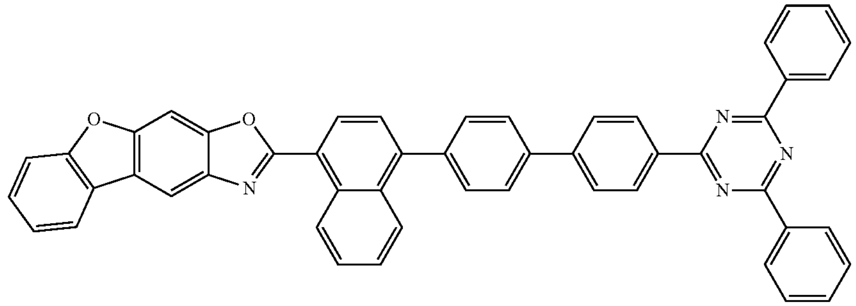
A10
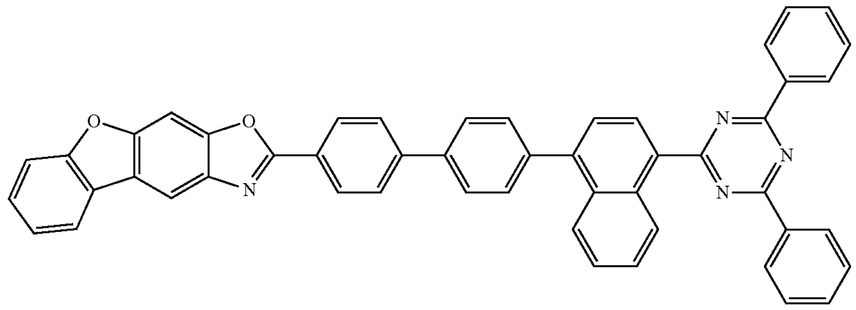

-continued
A11
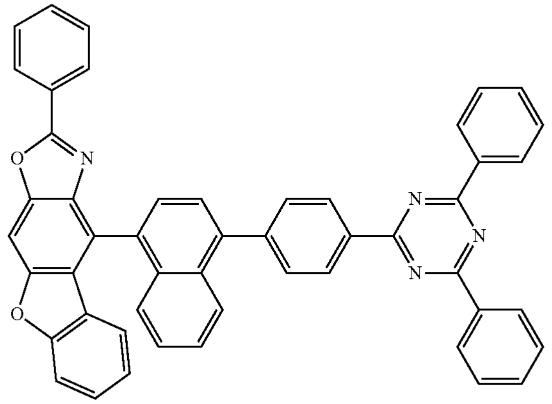
A12
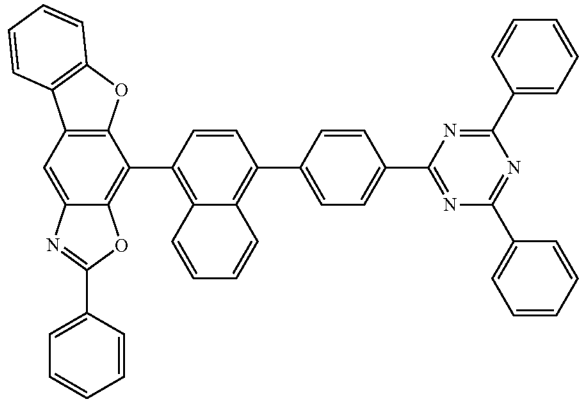
A13
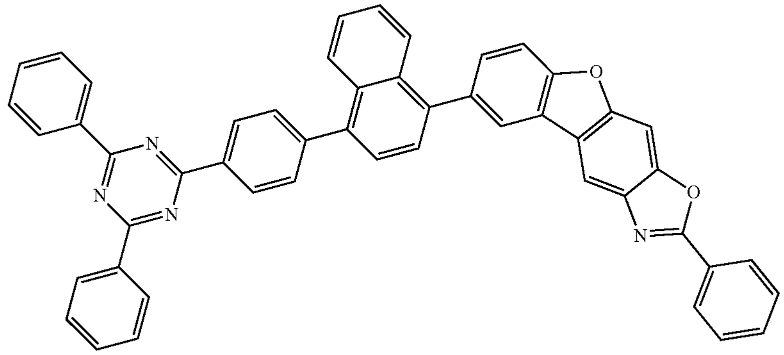
A14
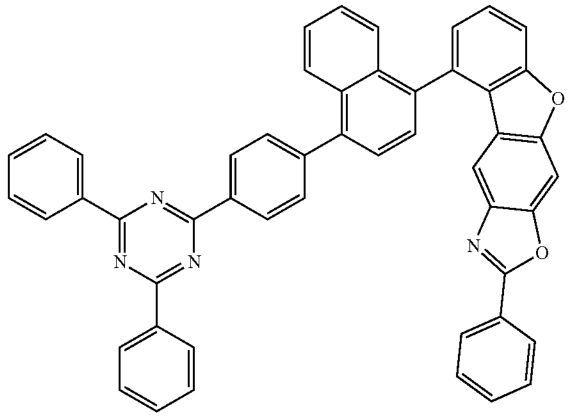

-continued
A15
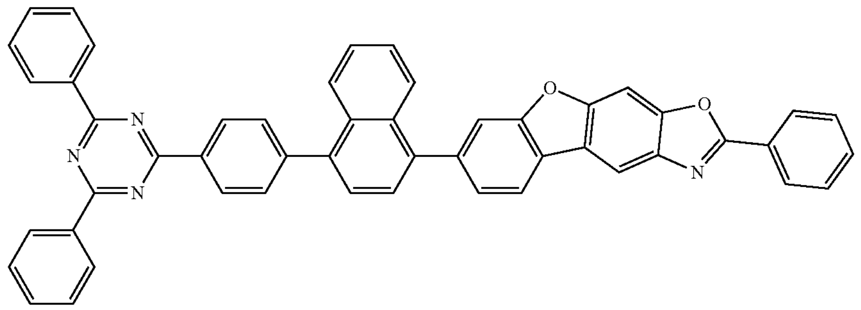
A16
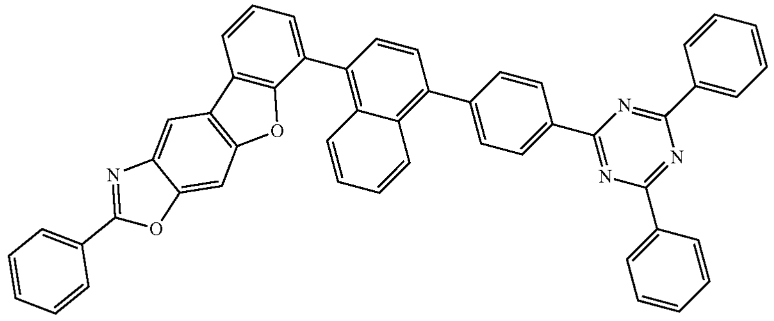
A17
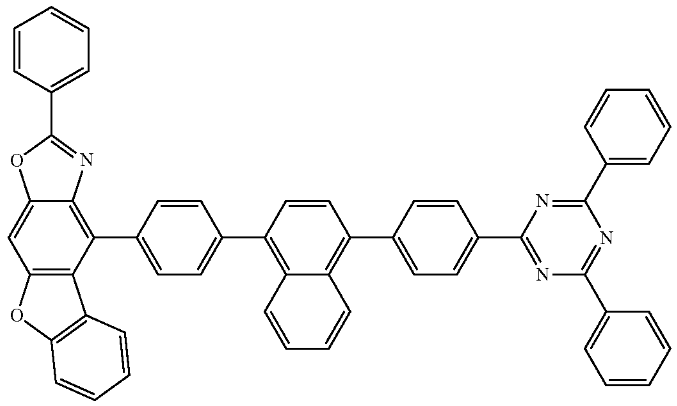
A18
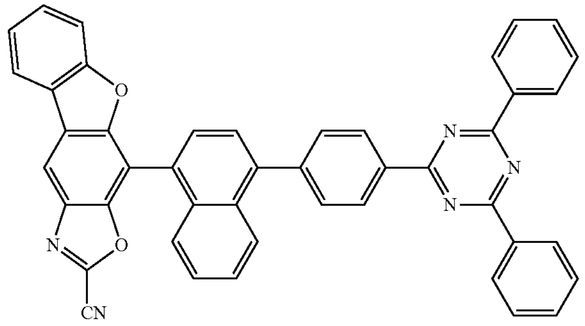

-continued
A19
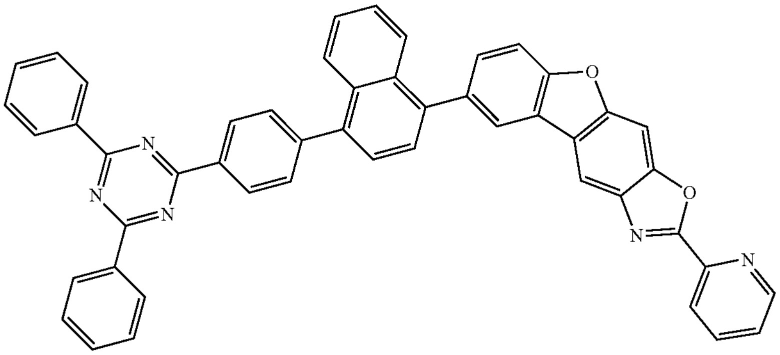
A20
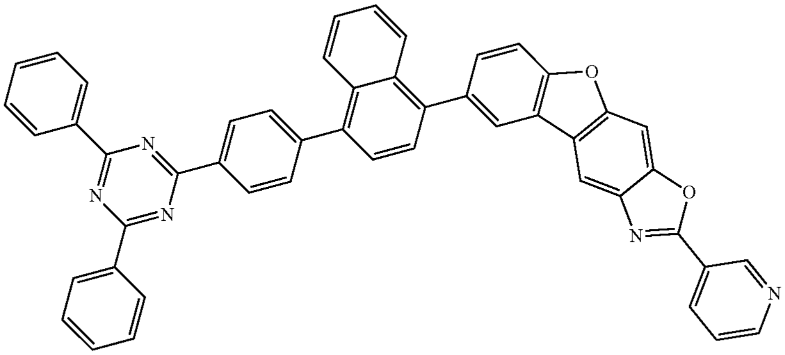
A21
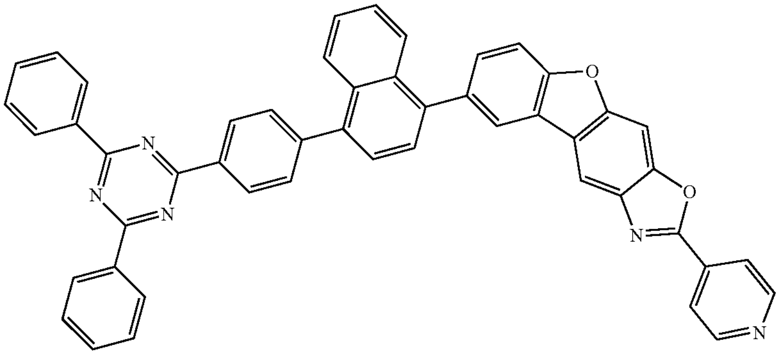
A22
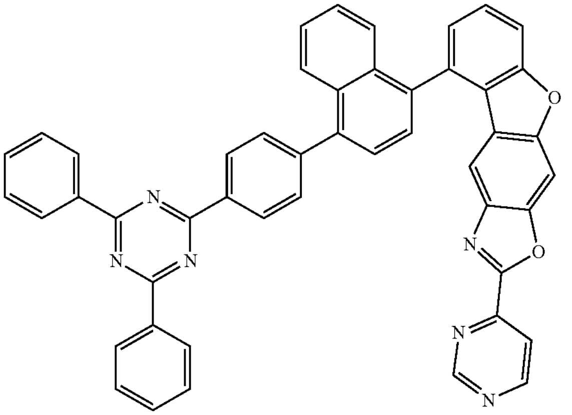

-continued
A23
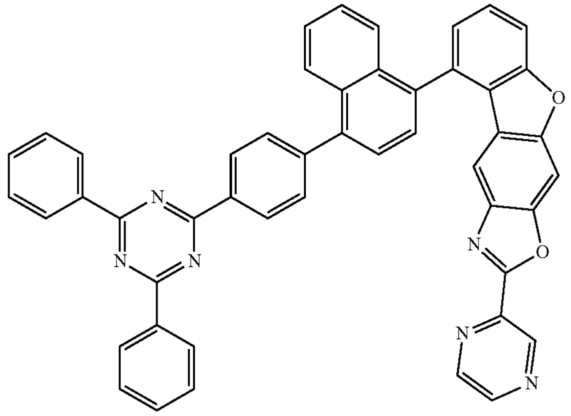
A24
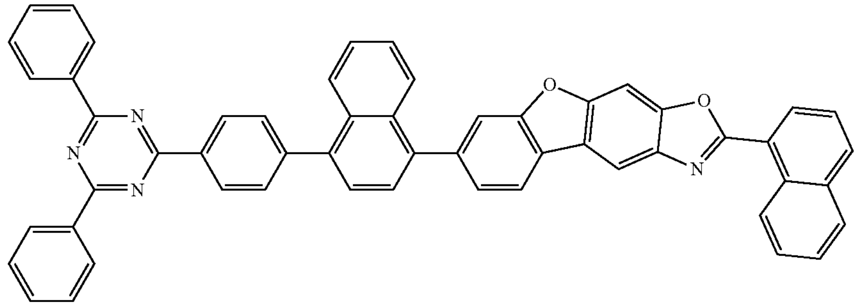
A25
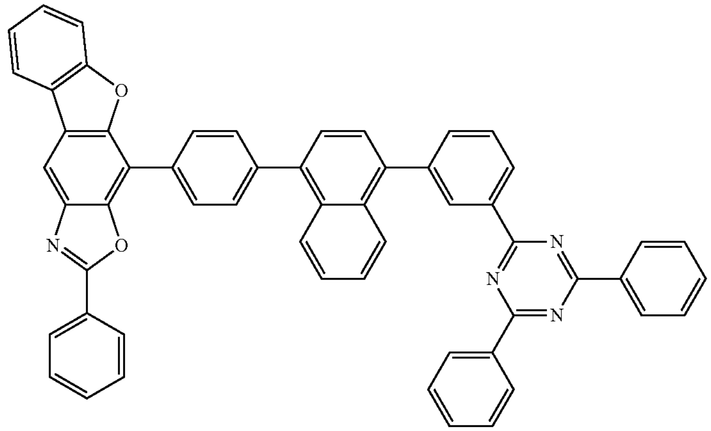
A26
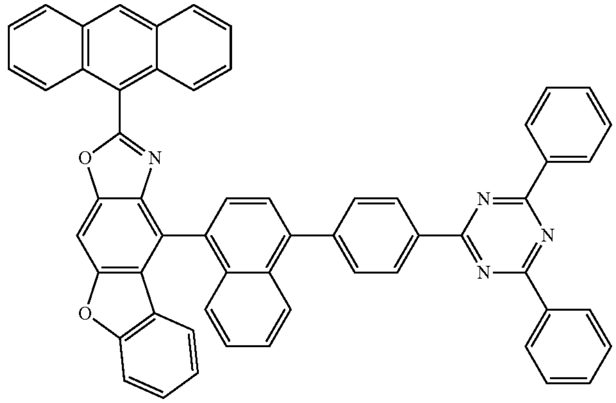

-continued
A27
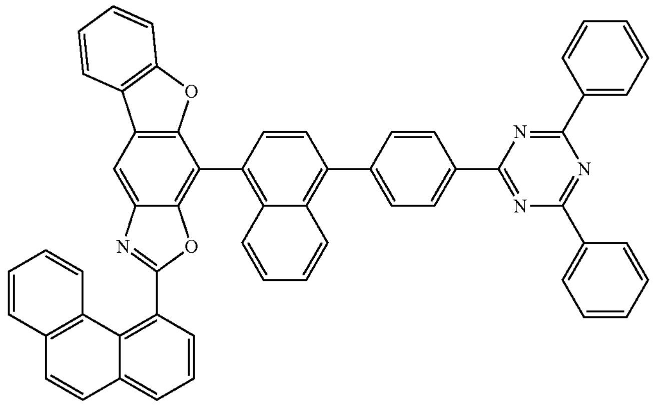
A28
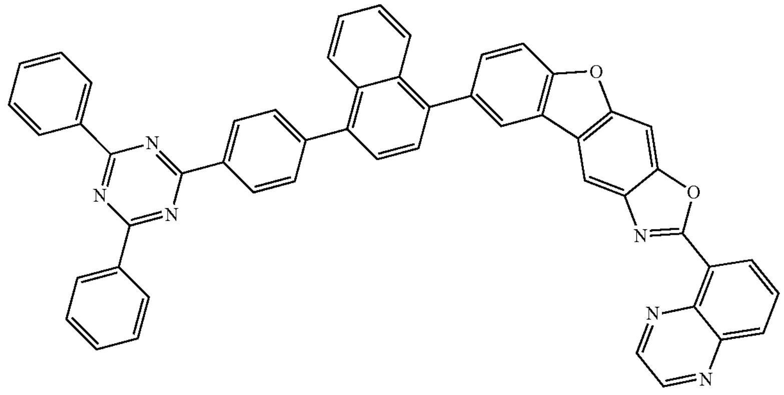
A29
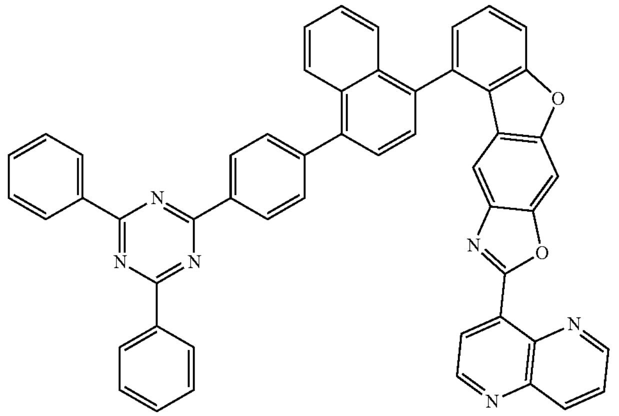
A30
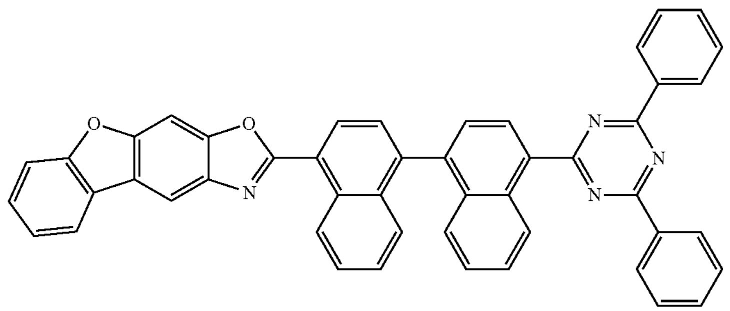

-continued
A31
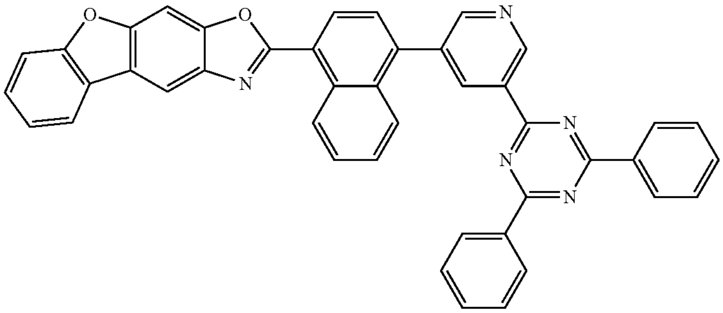
A32
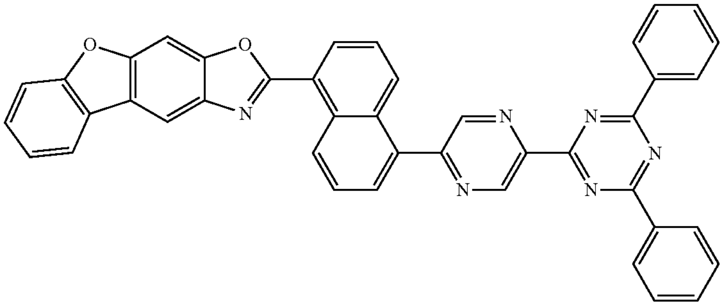
A33
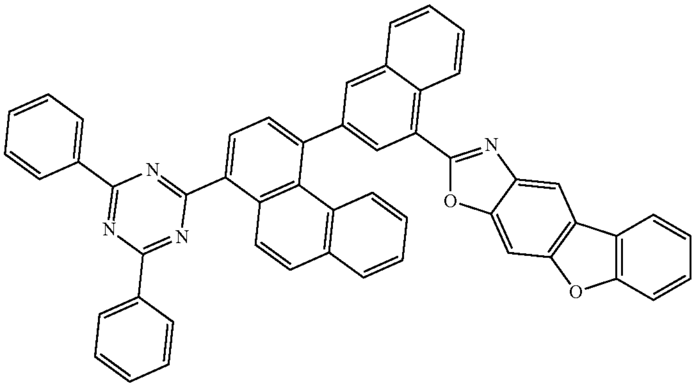
A34
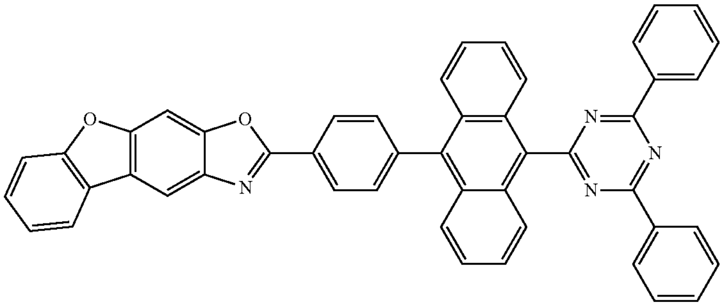

-continued
A35
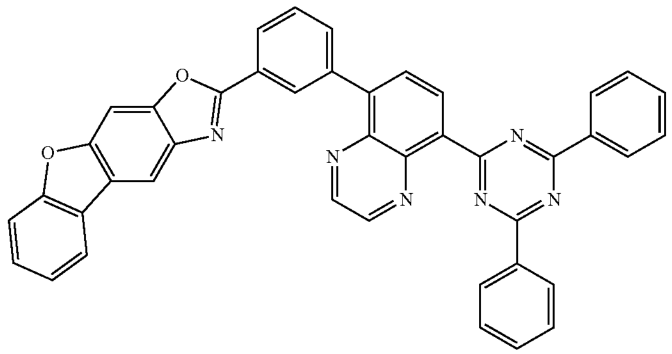
A36
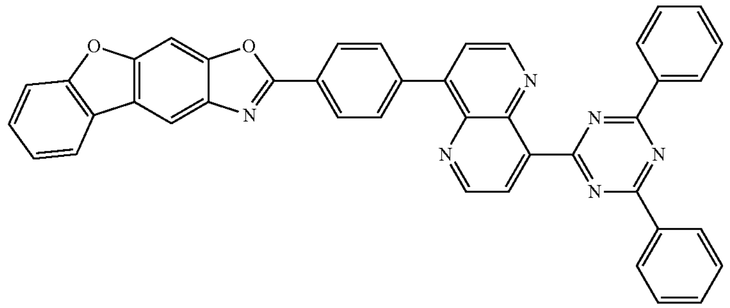
A37
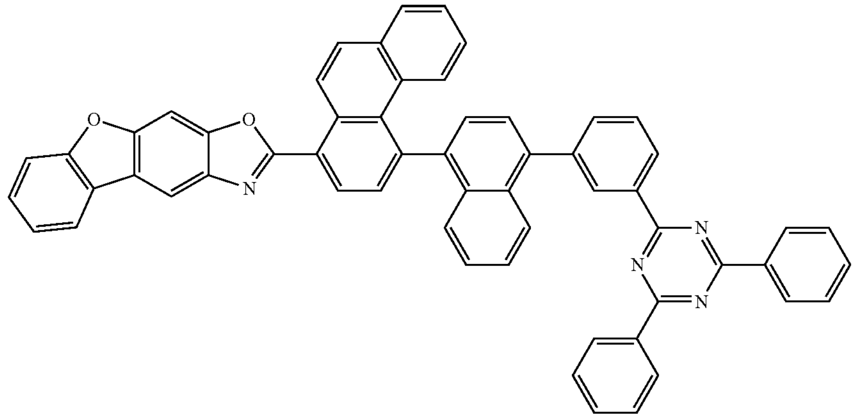
A38
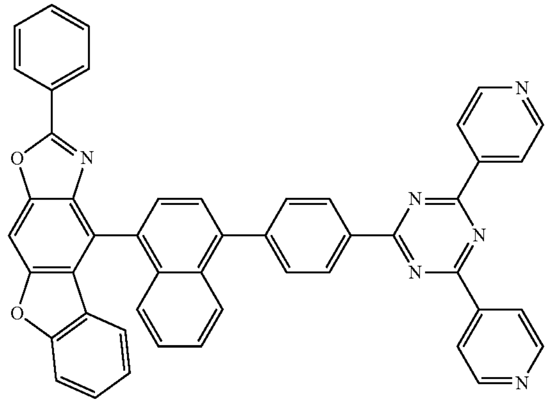

-continued
A39
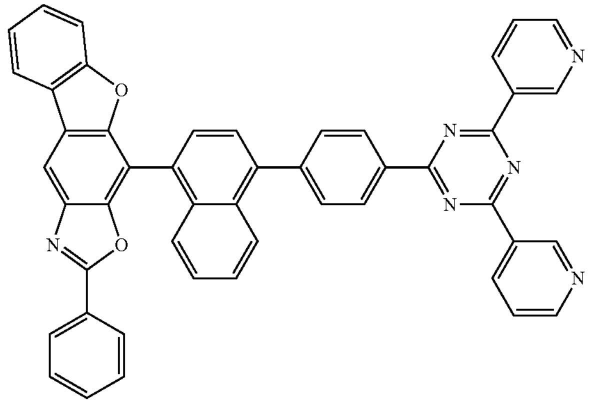
A40
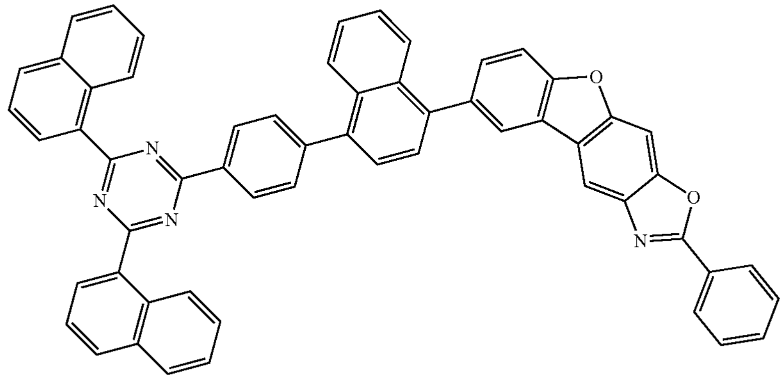
A41
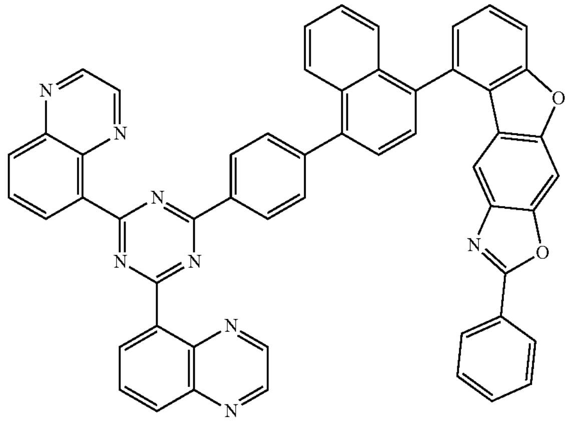
A42
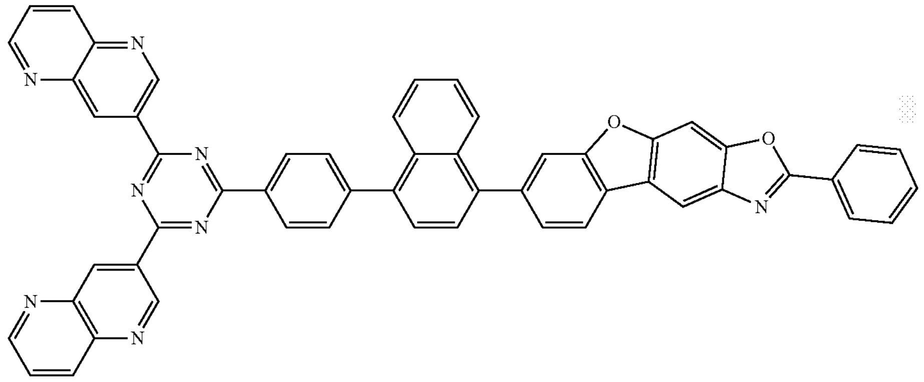

-continued
A43
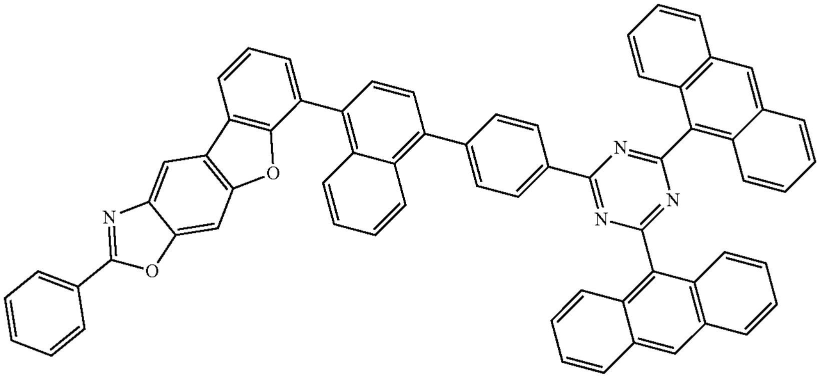
A44
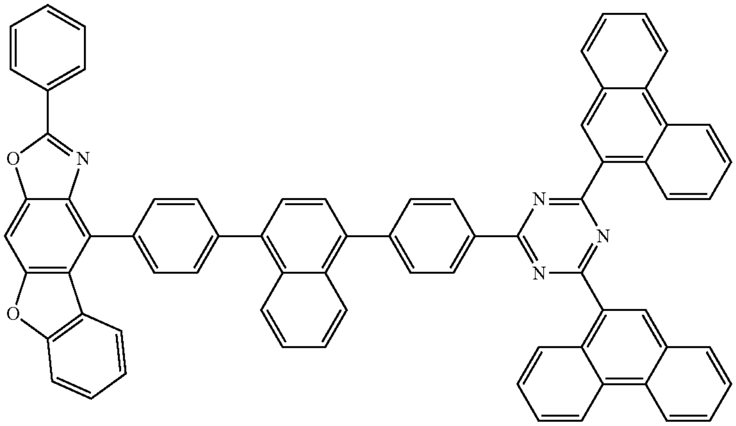
A45
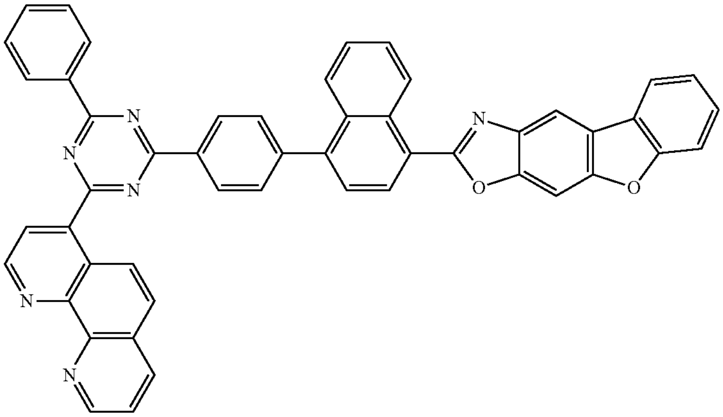
A46
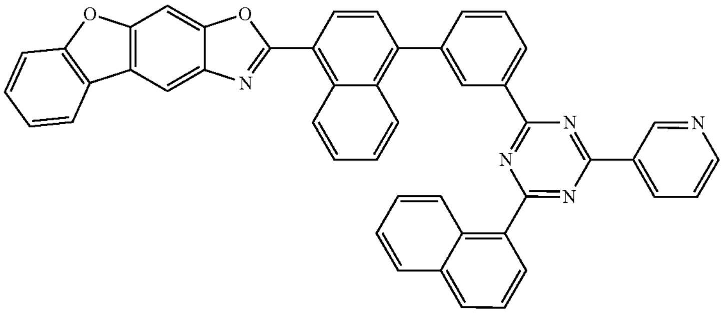

-continued
A47
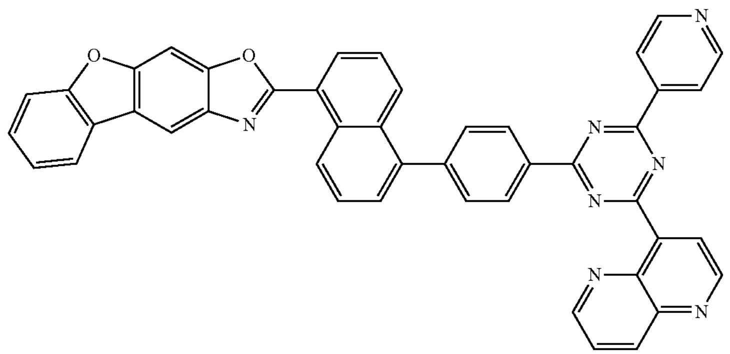
A48
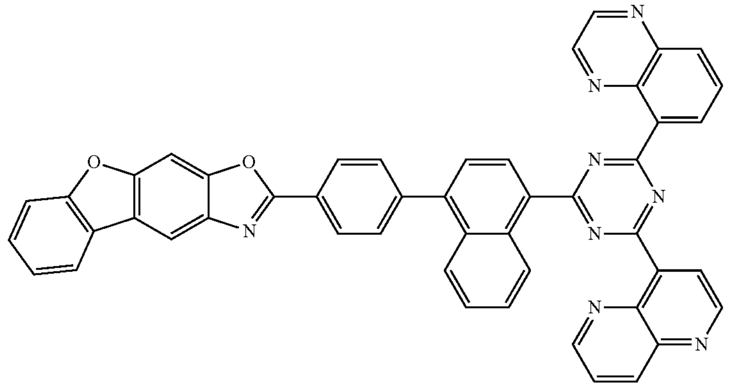
B1
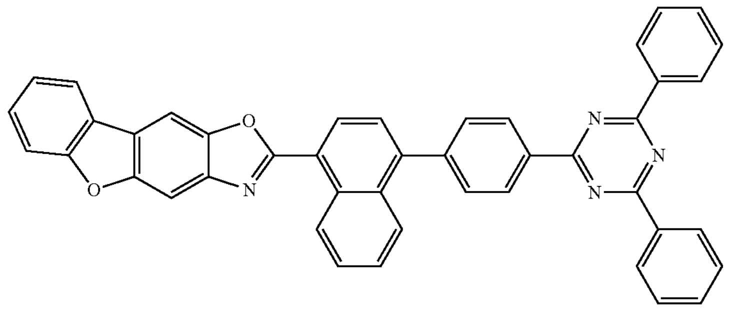
B2
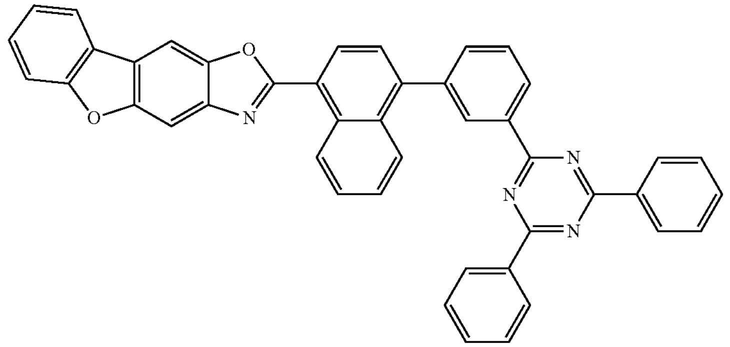

-continued
B3
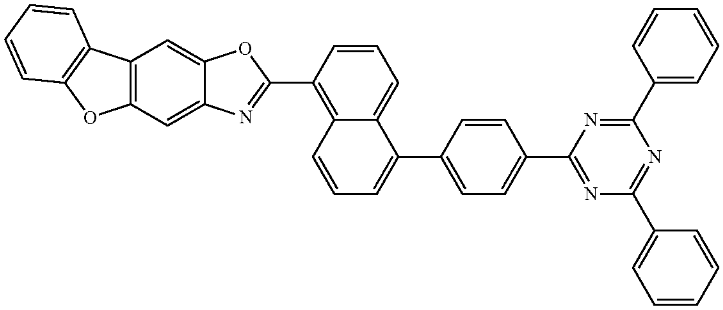
B4
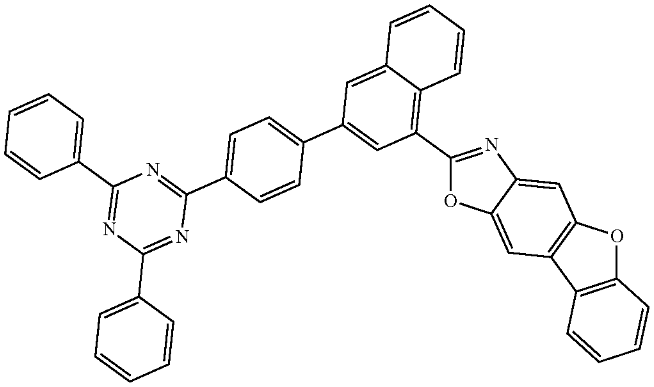
B5
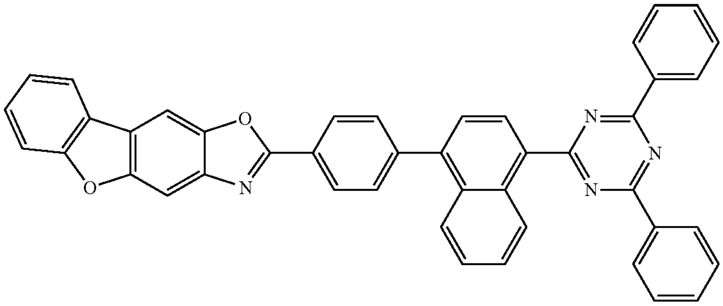
B6
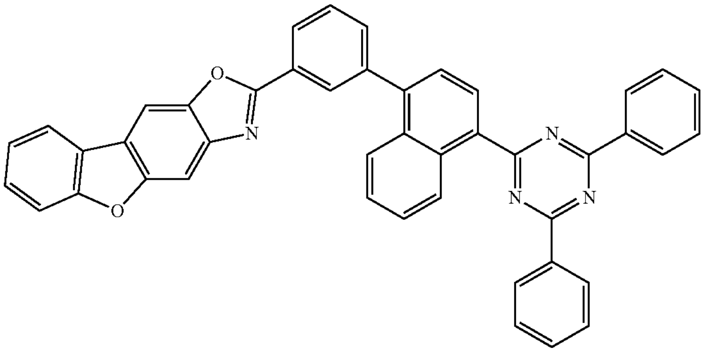

-continued
B7
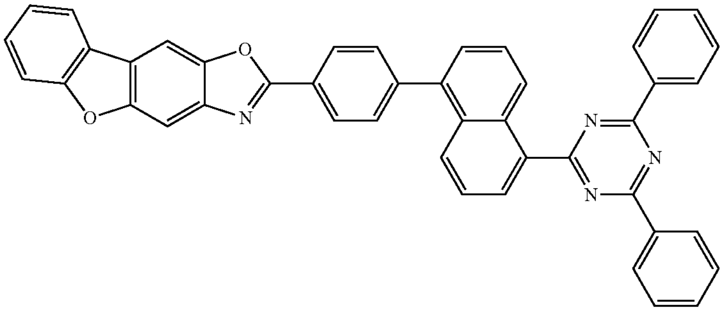
B8
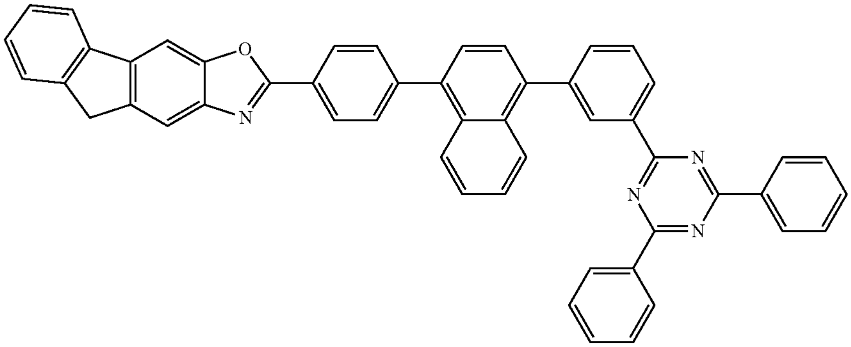
B9
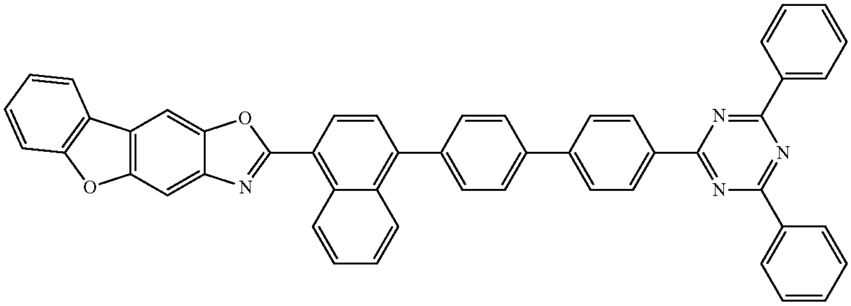
B10
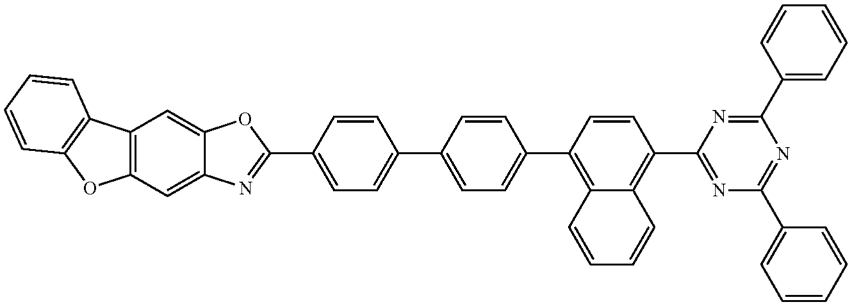

-continued
B11
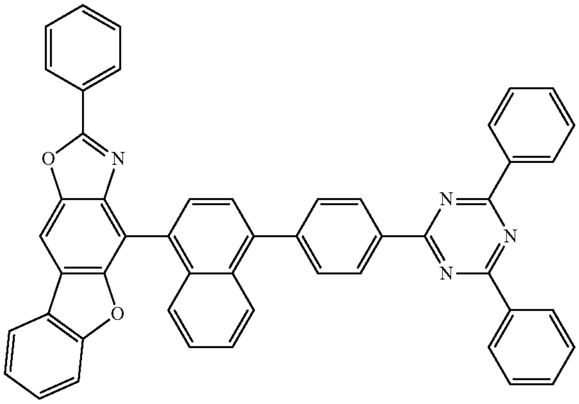
B12
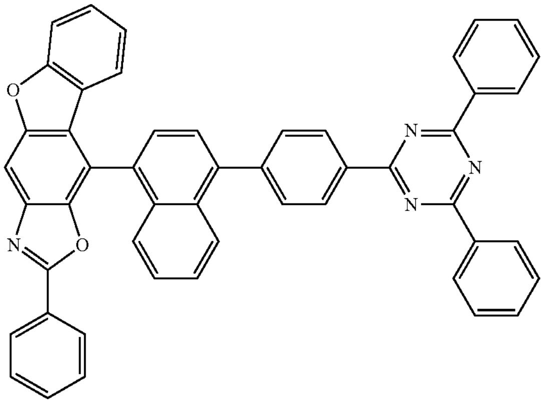
B13
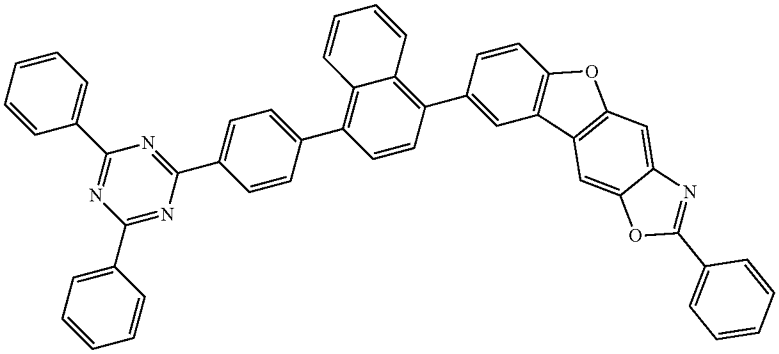
B14
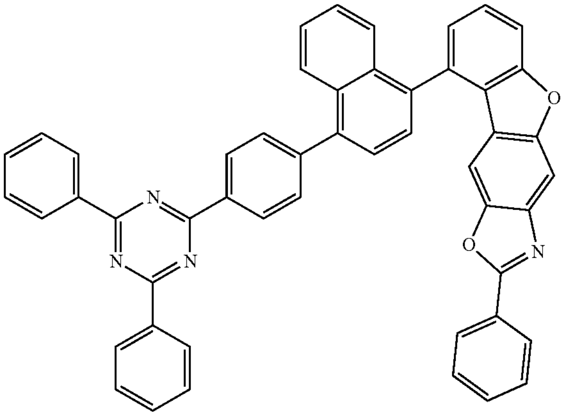

-continued
B15
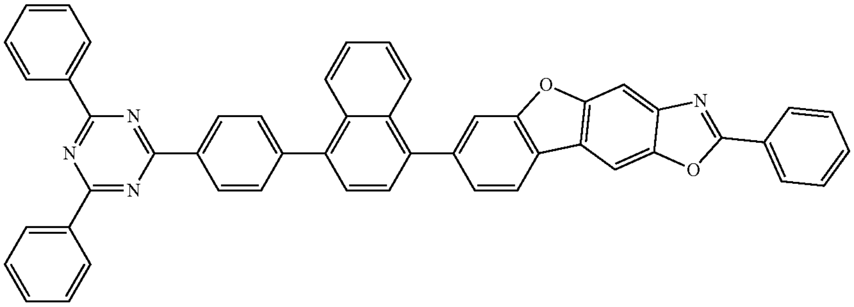
B16
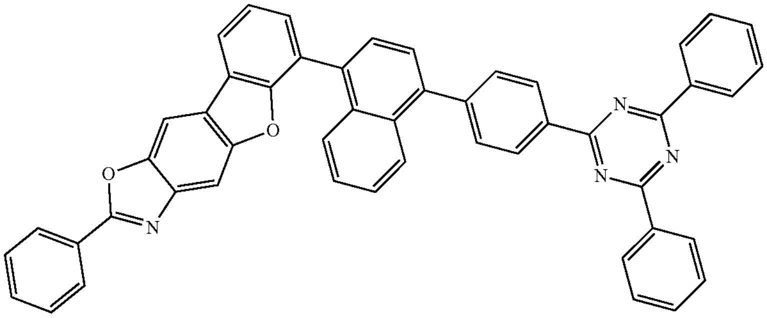
B17
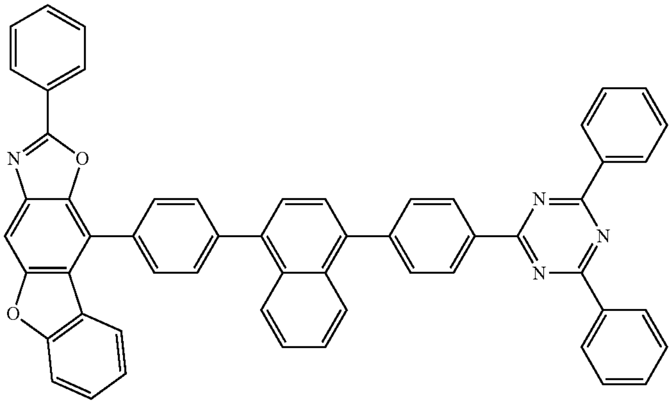
B18
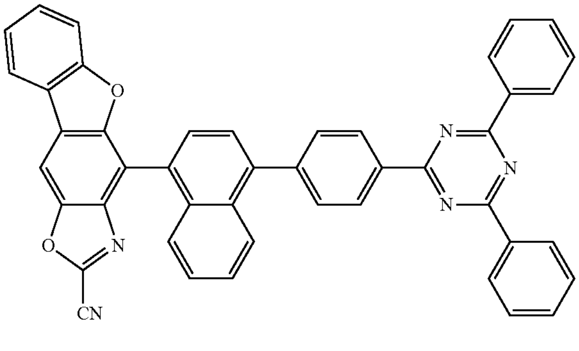

-continued
B19
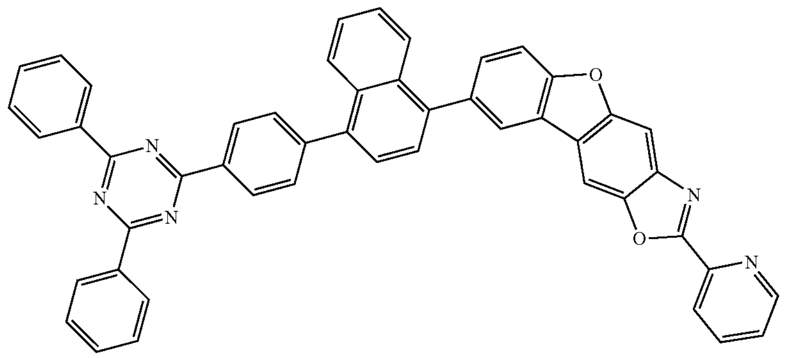
B20
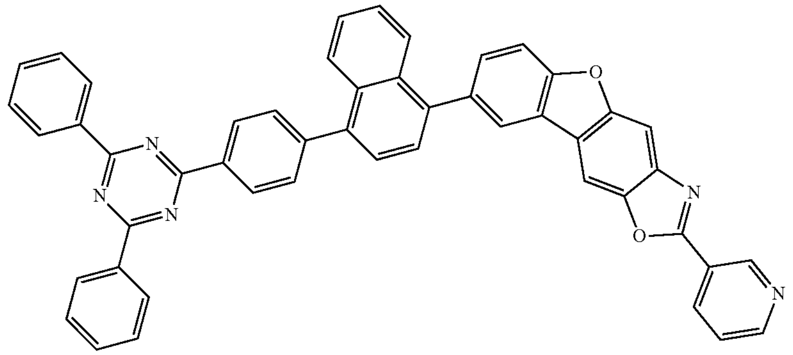
B21
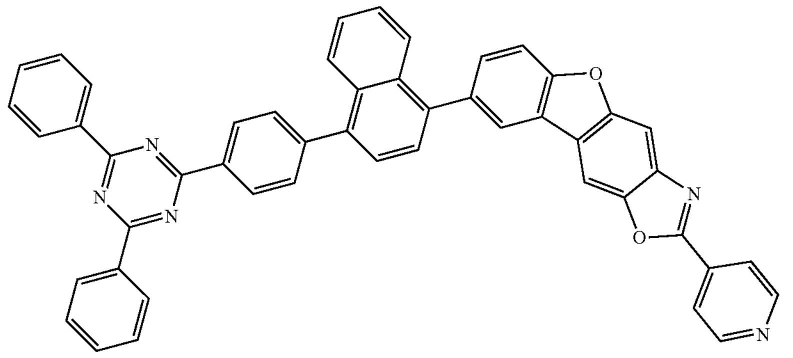
B22
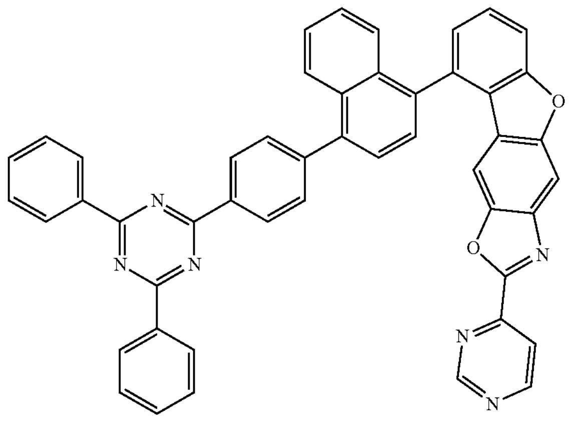

-continued
B23
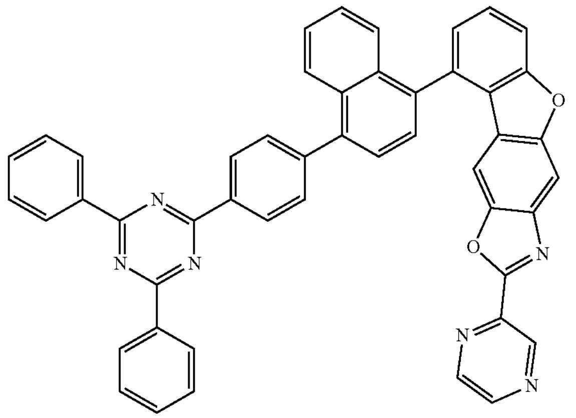
B24
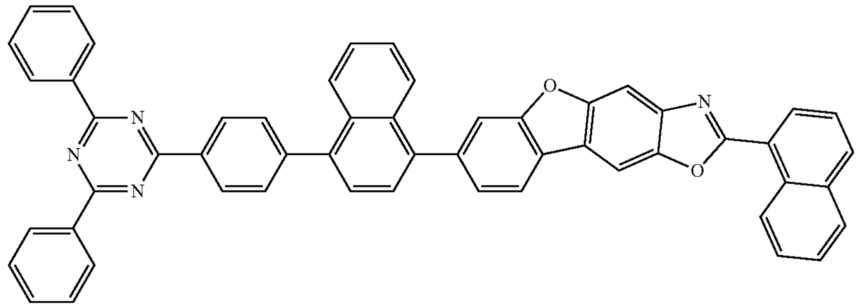
B25
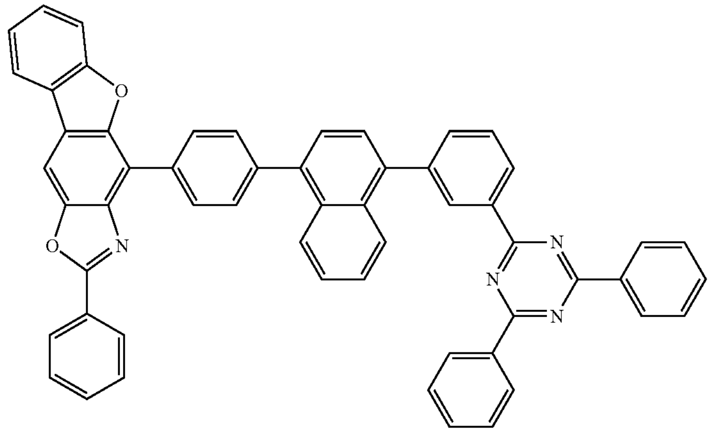
B26
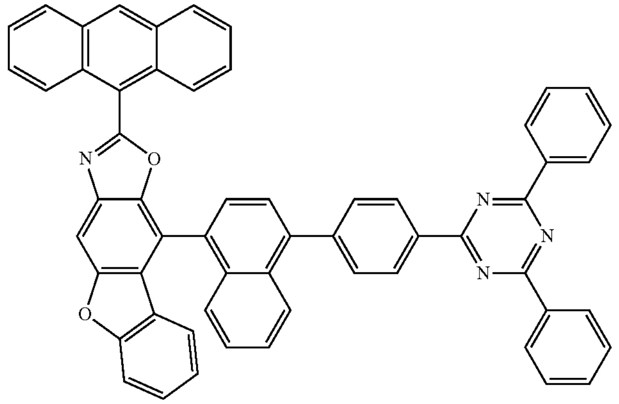

-continued
B27
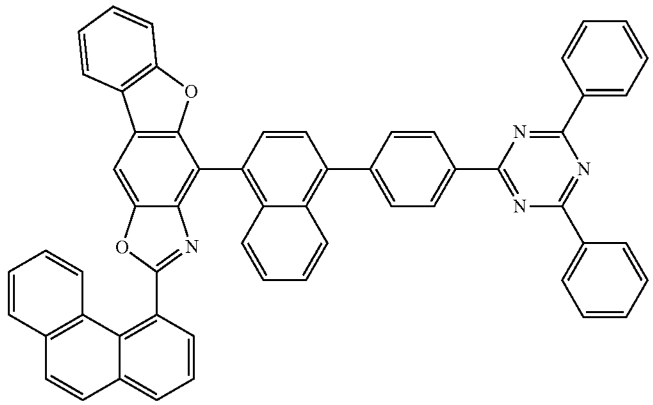
B28
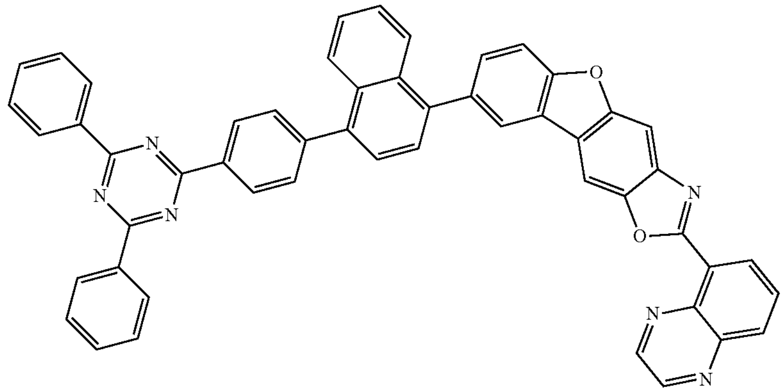
B29
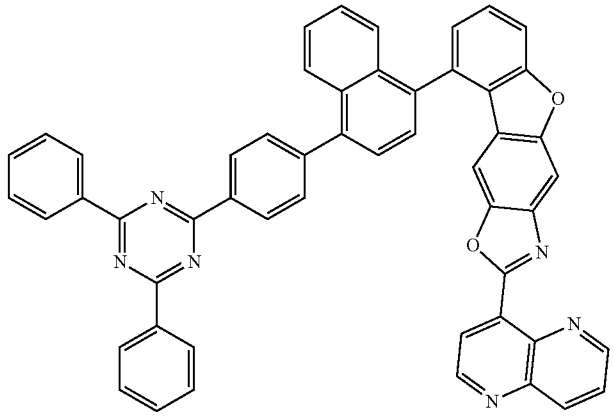
B30
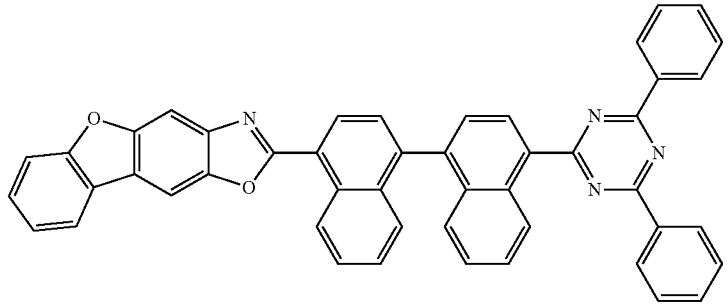

-continued
B31
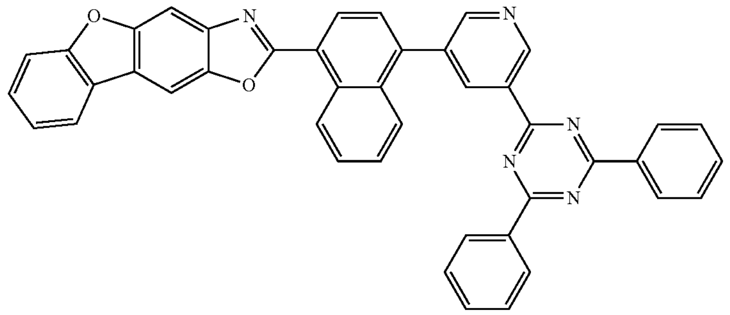
B32
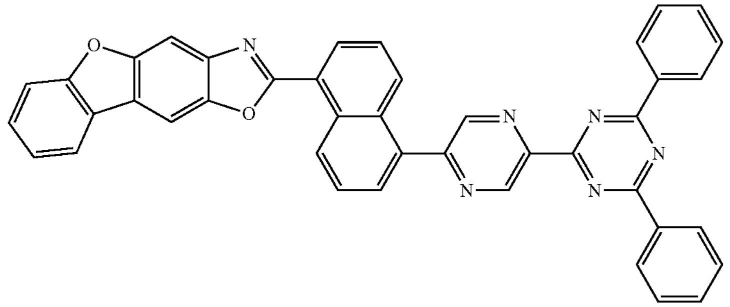
B33
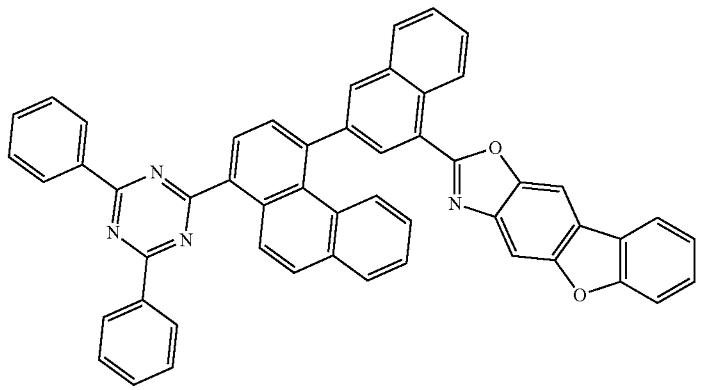
B34
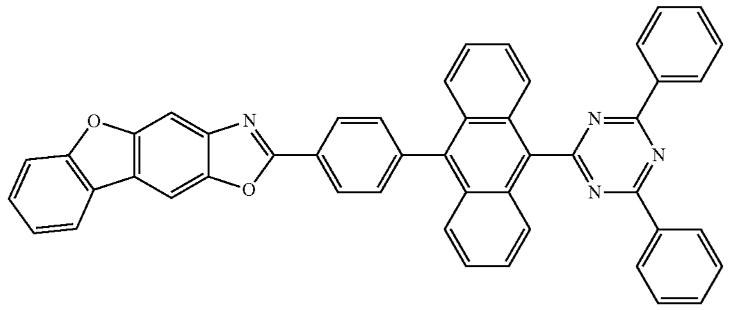

-continued
B35
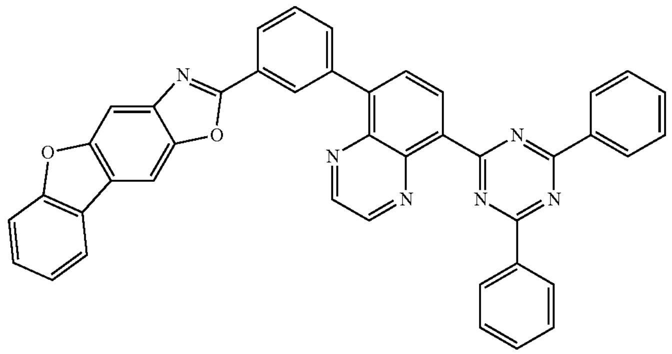
B36
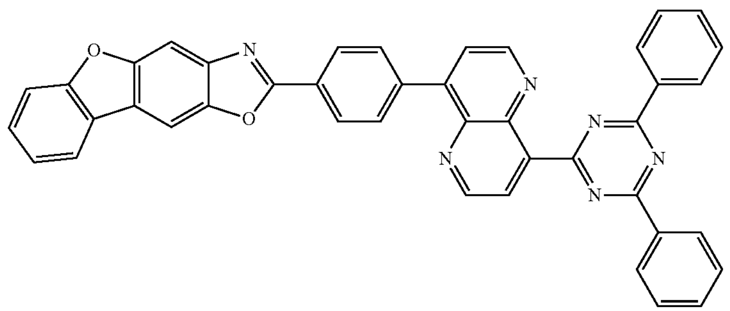
B37
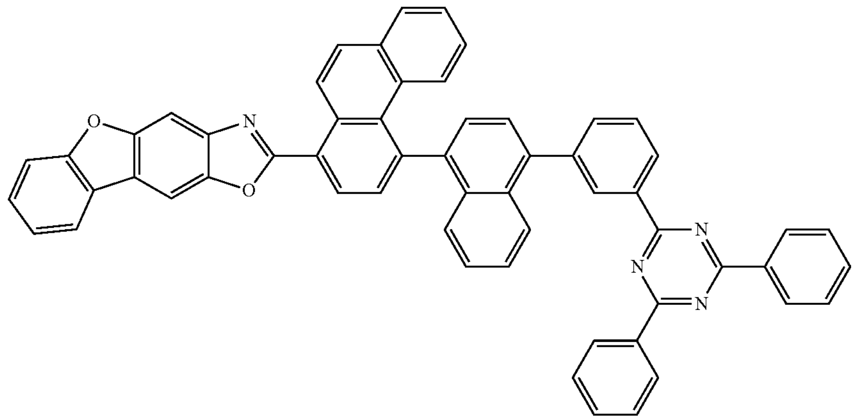
B38
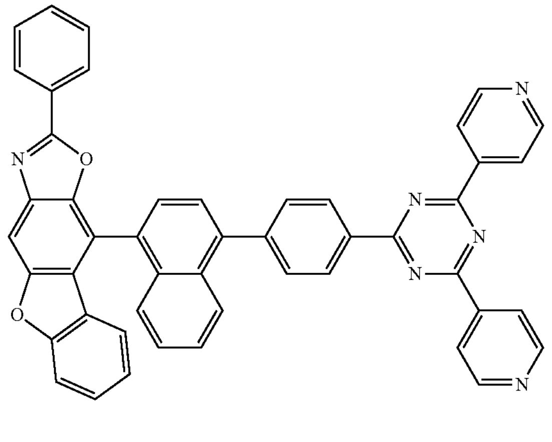

-continued
B39
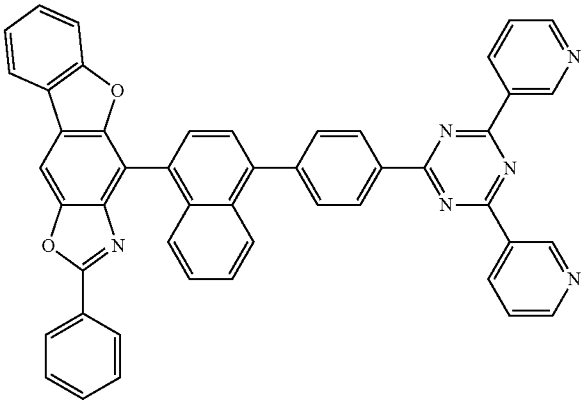
B40
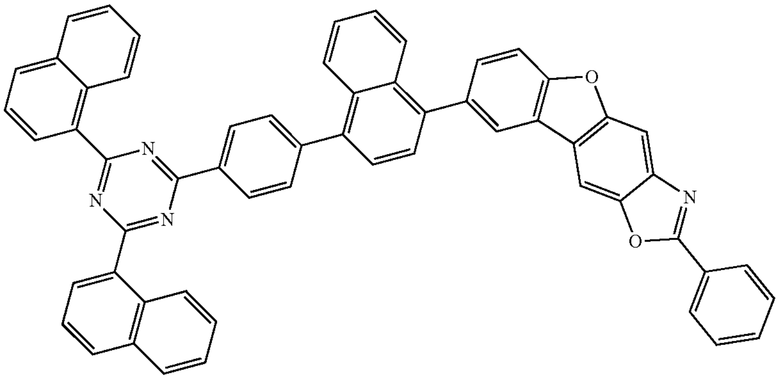
B41
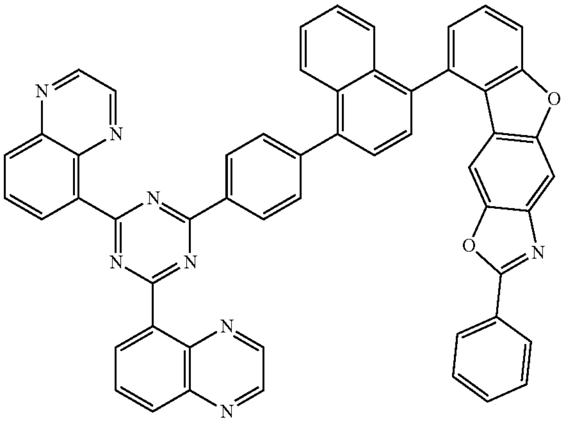
B42
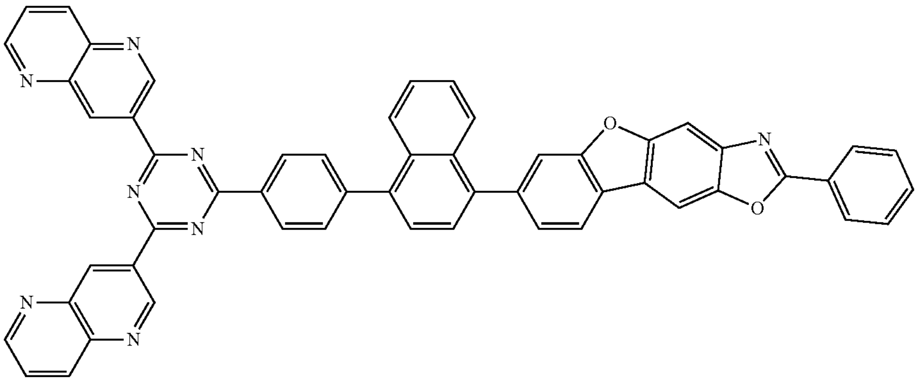

-continued
B43
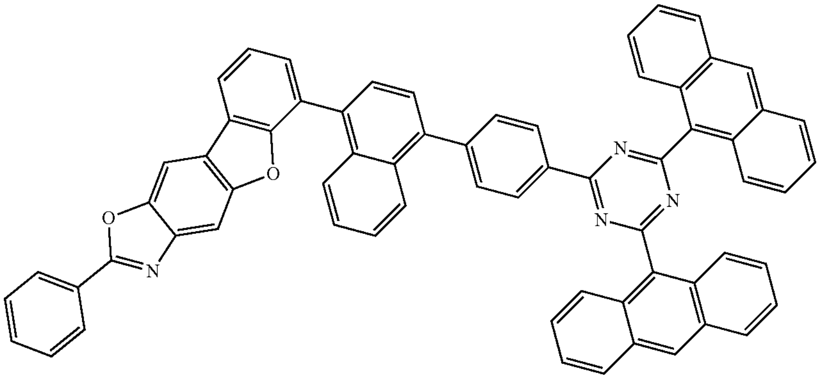
B44
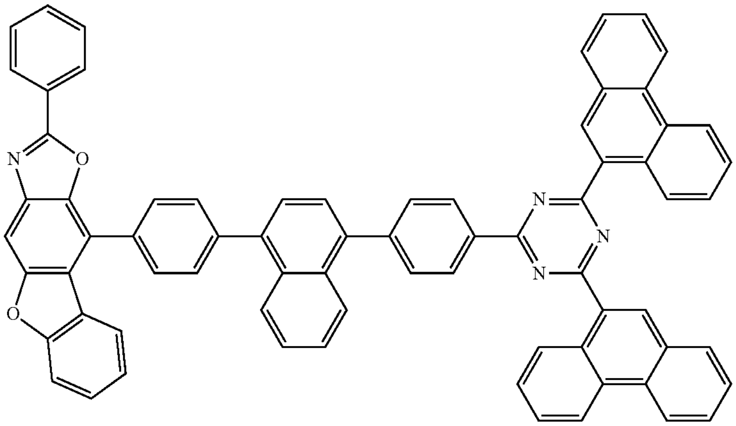
B45
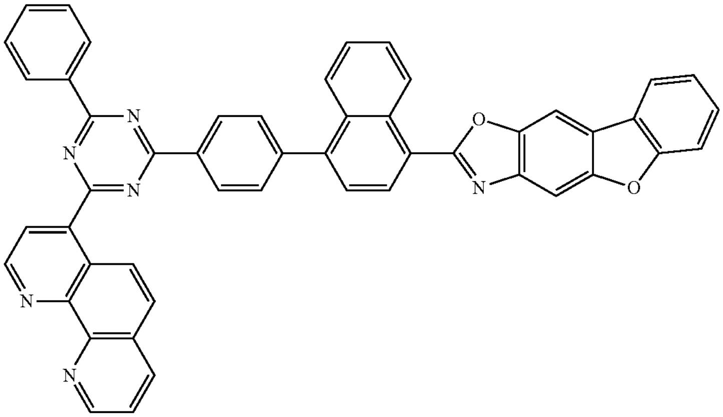
B46
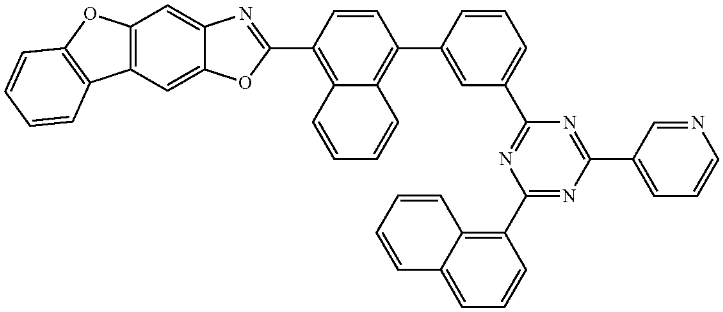

-continued
B47
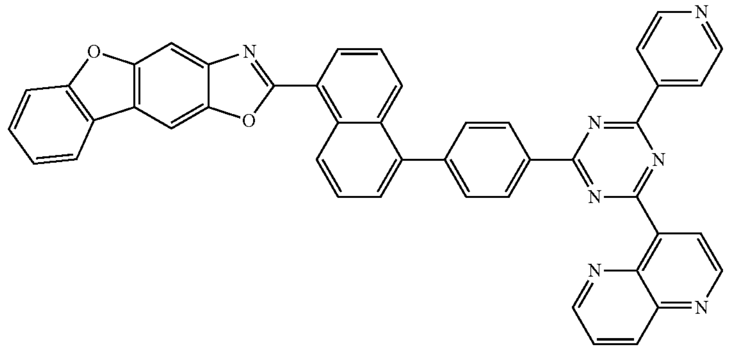
B48
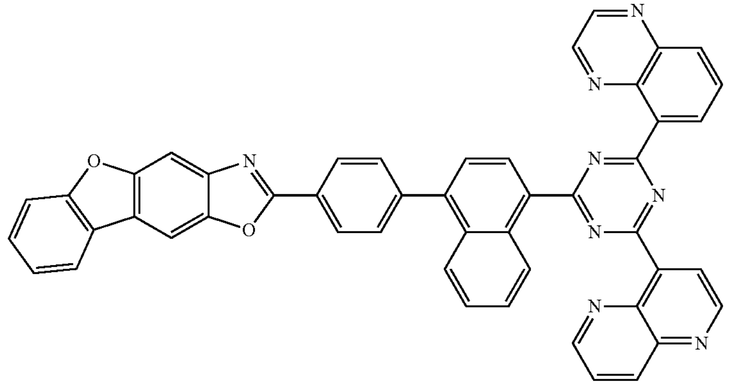
C1
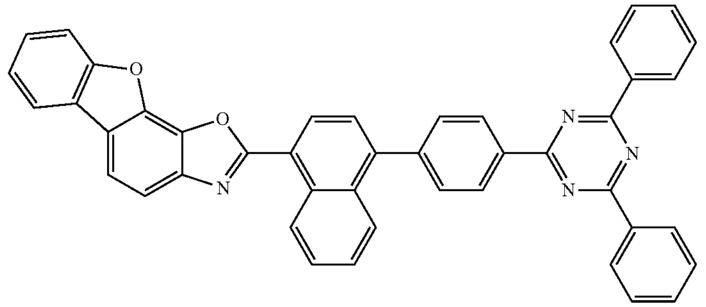
C2
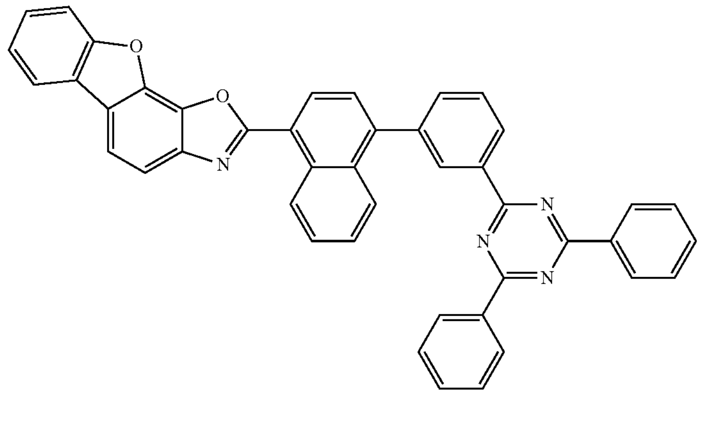

-continued
C3
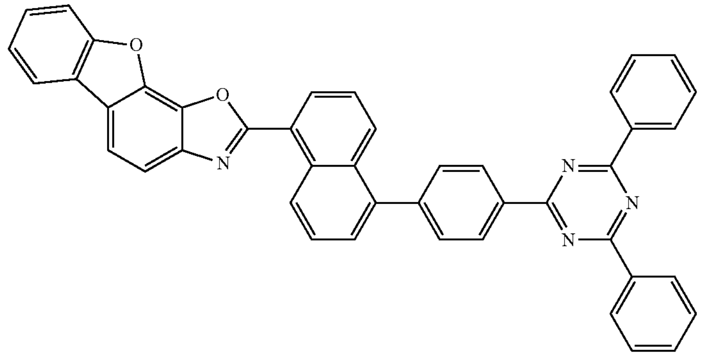
C4
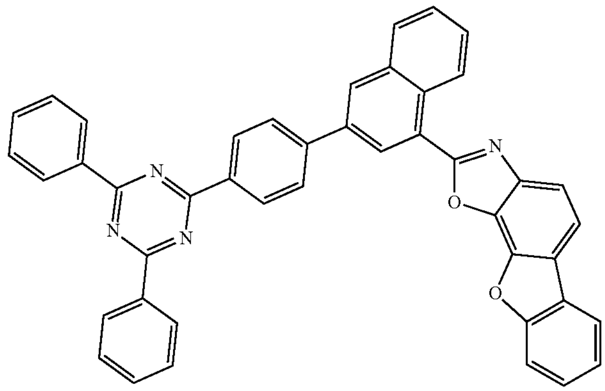
C5
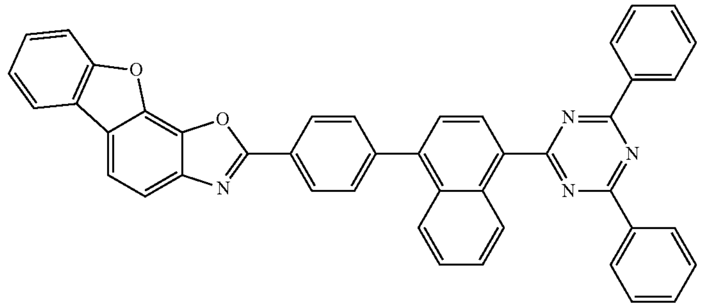
C6
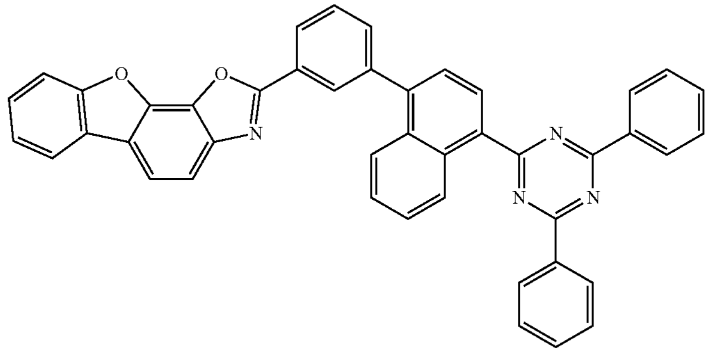

-continued
C7
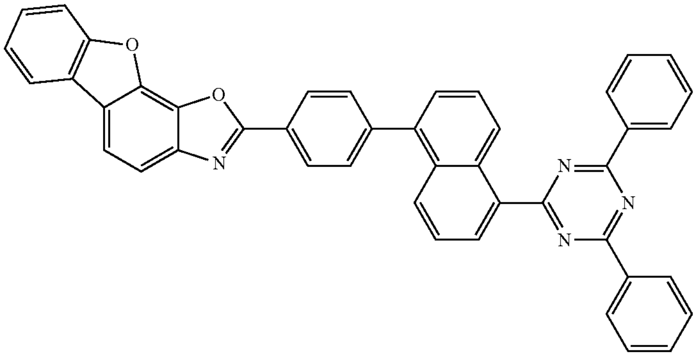
C8
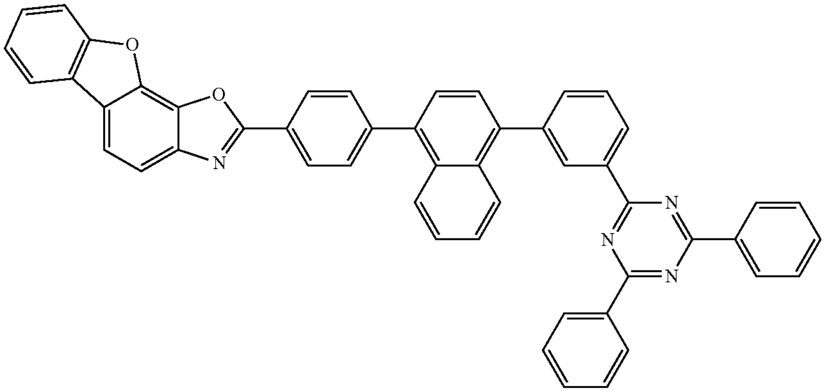
C9
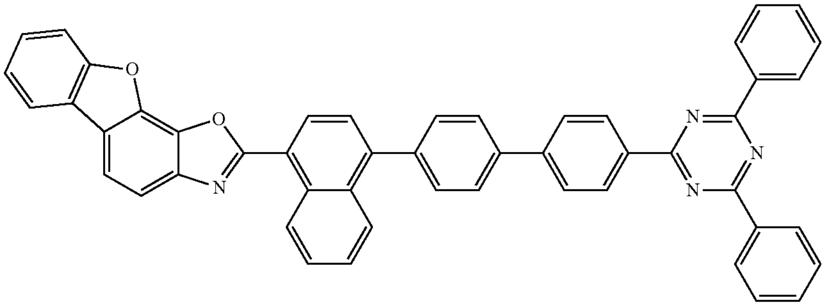
C10
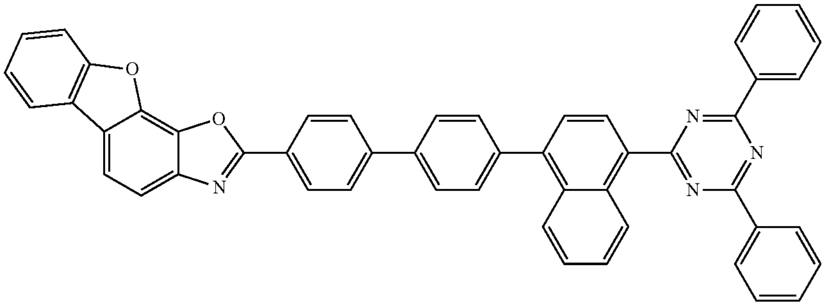

-continued
C11
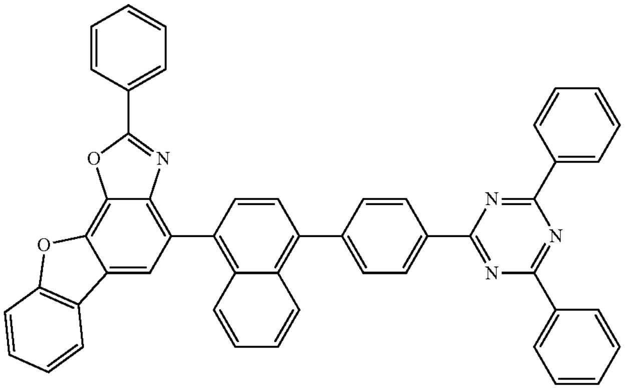
C12
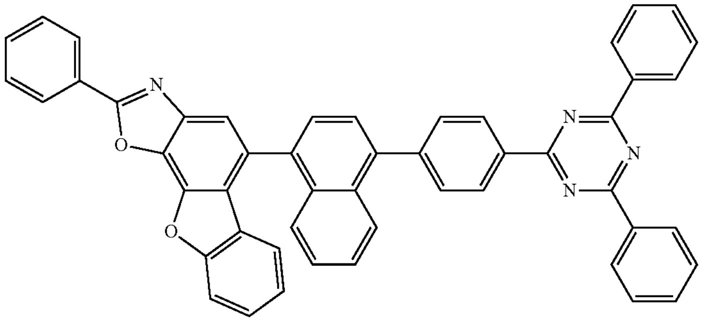
C13
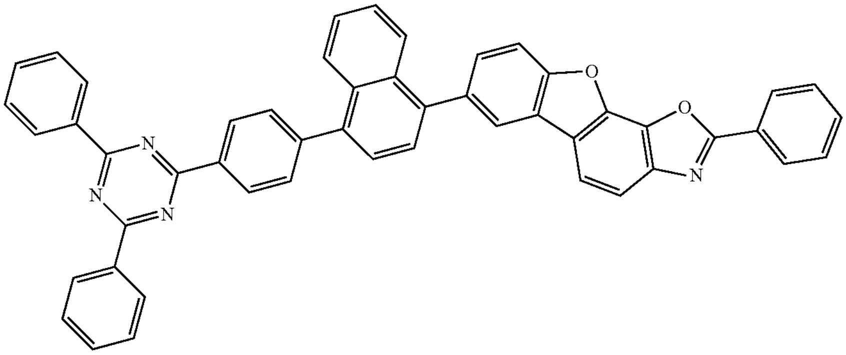
C14
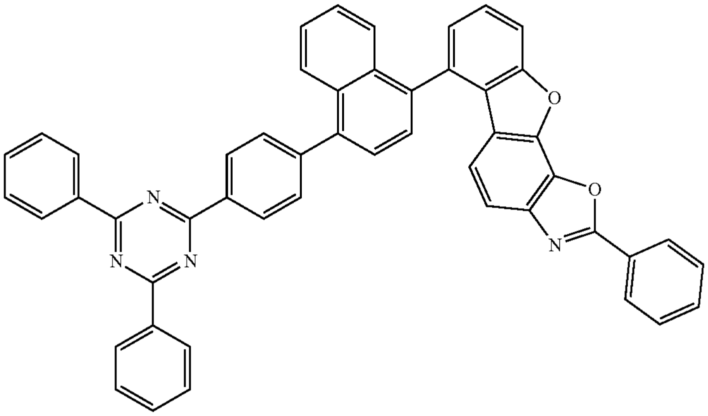

-continued
C15
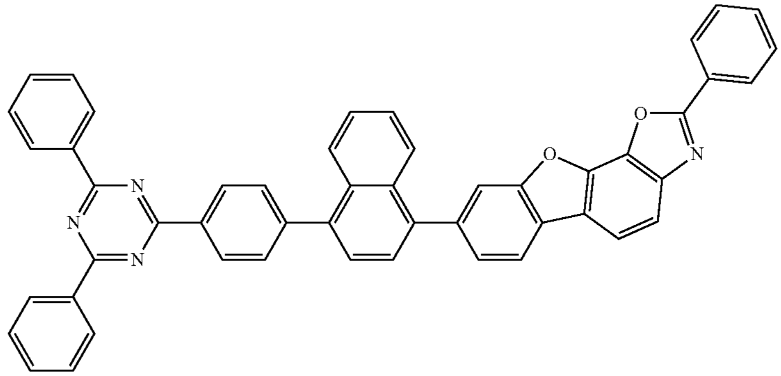
C16
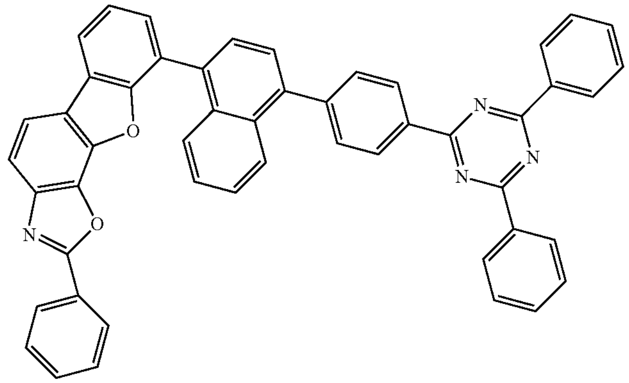
C17
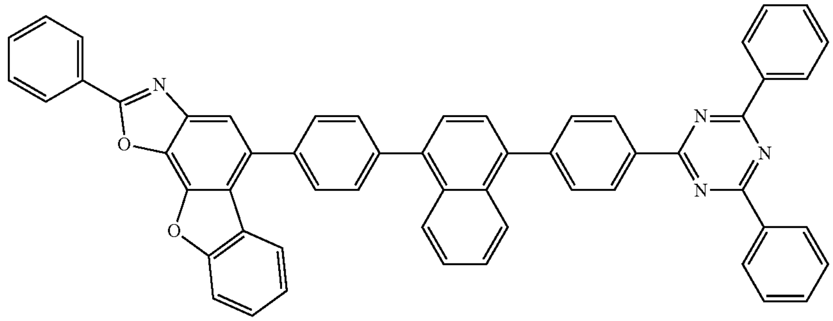
C18
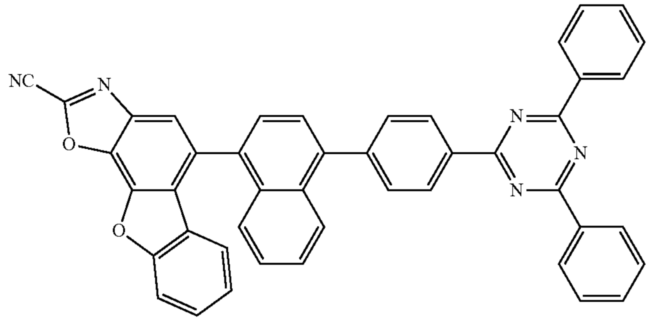

-continued
C19
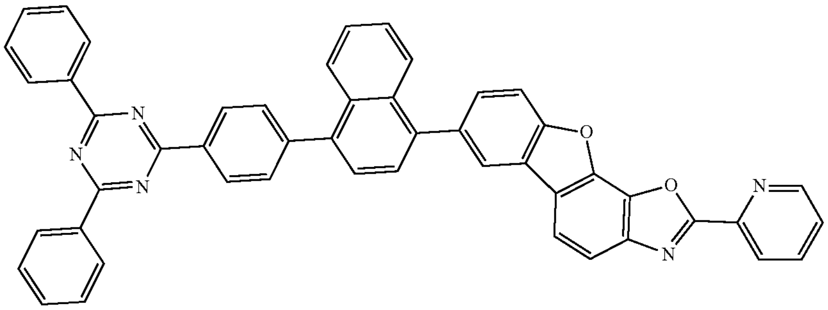
C20
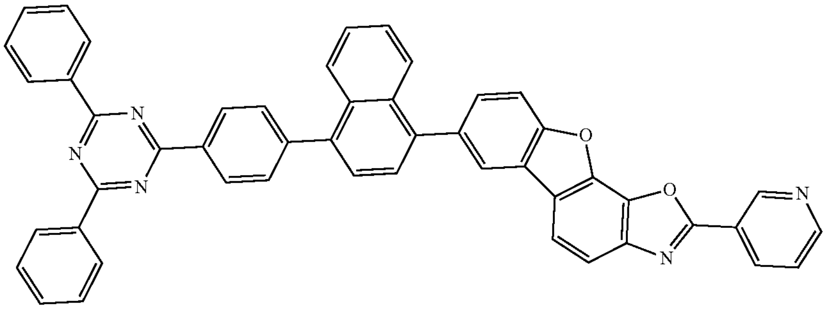
C21
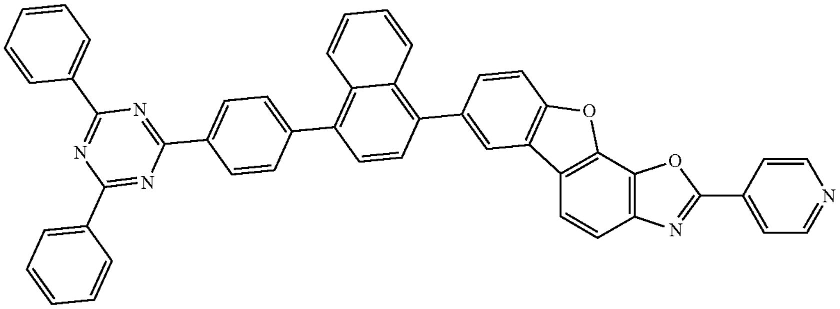
C22
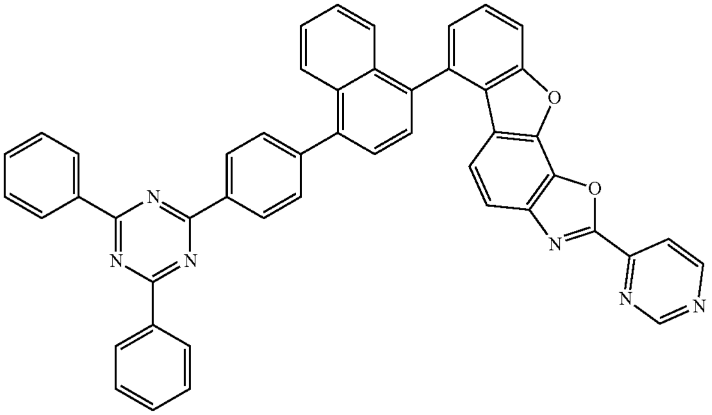

-continued
C23
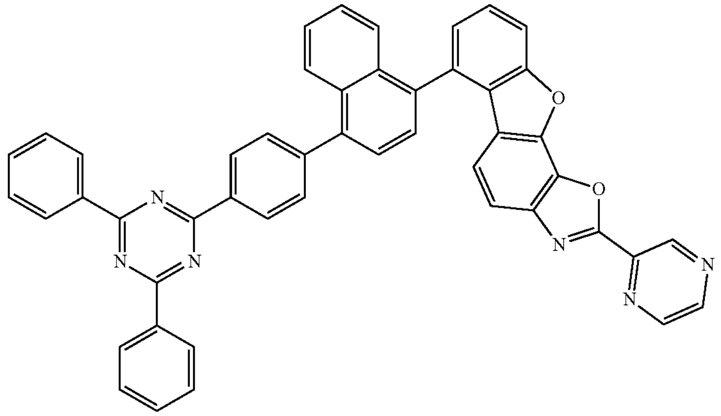
C24
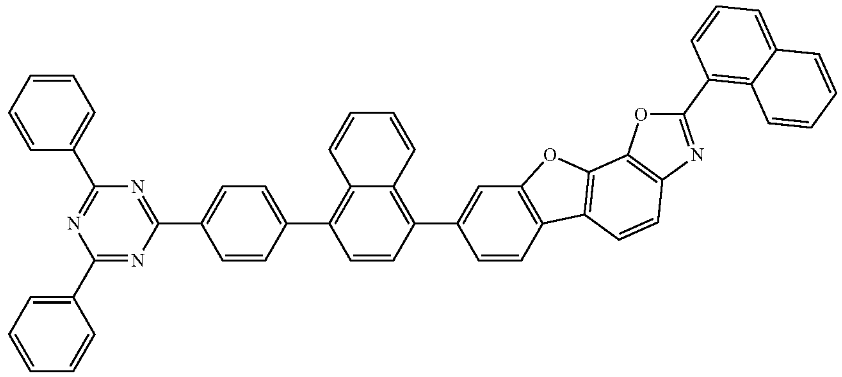
C25
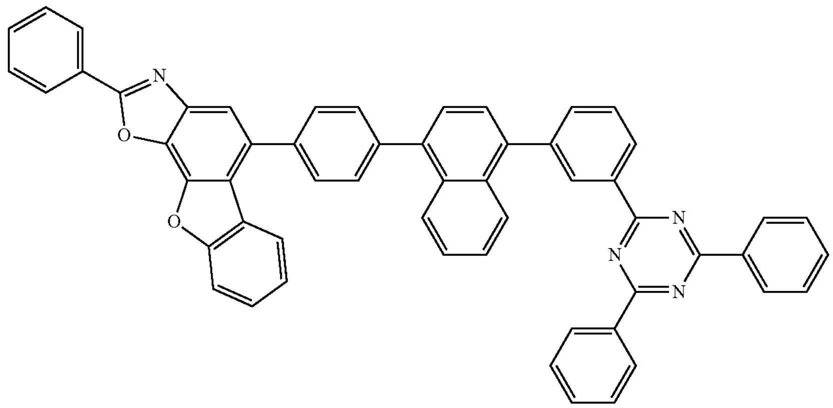
C26
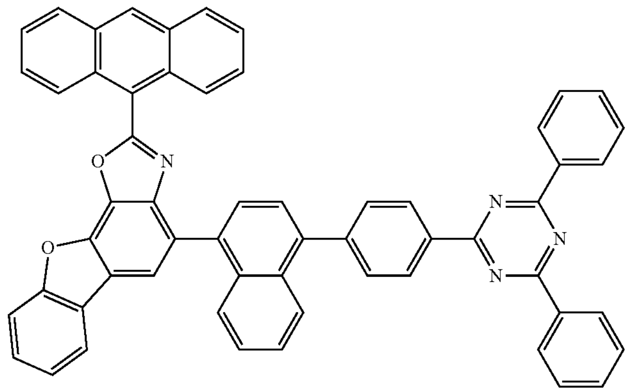

-continued
C27
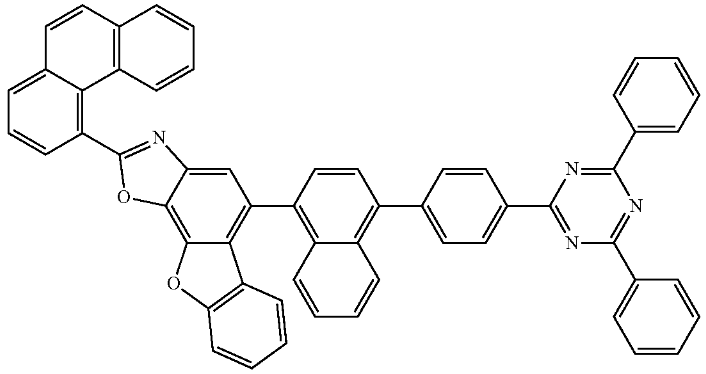
C28
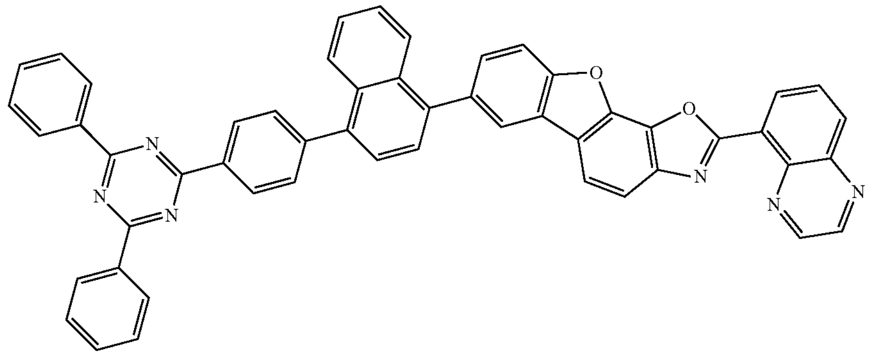
C29
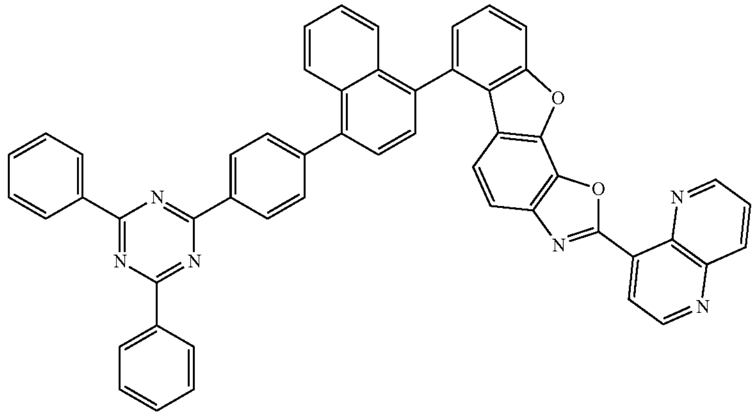
C30
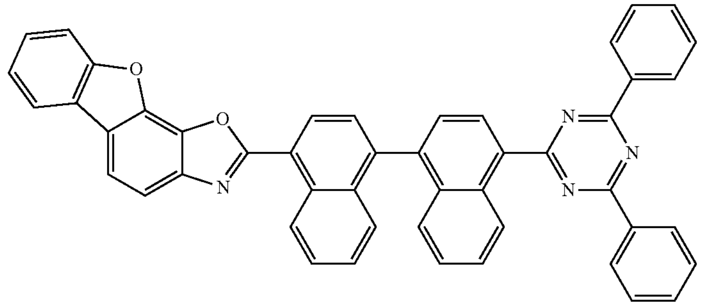

-continued
C31
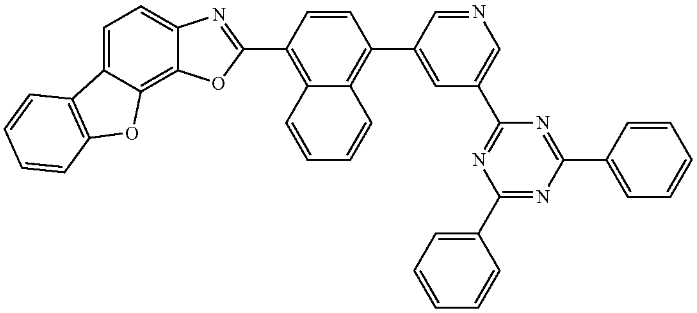
C32
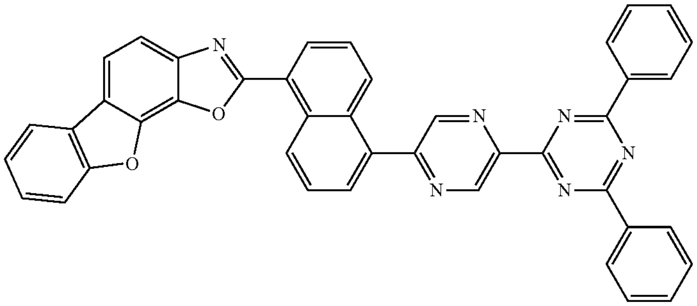
C33
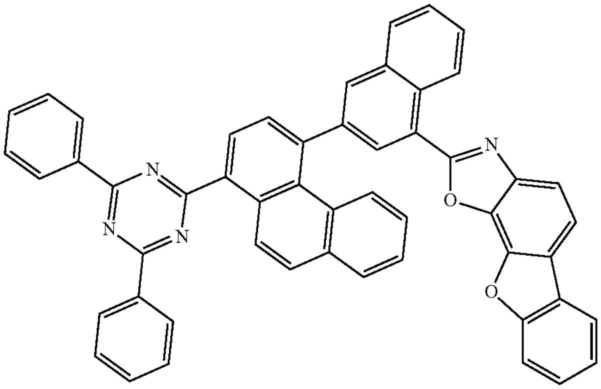
C34
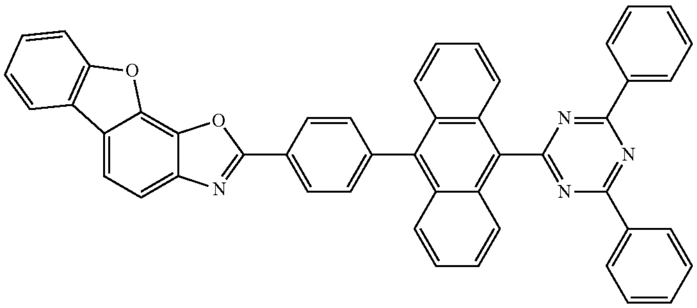

-continued
C35
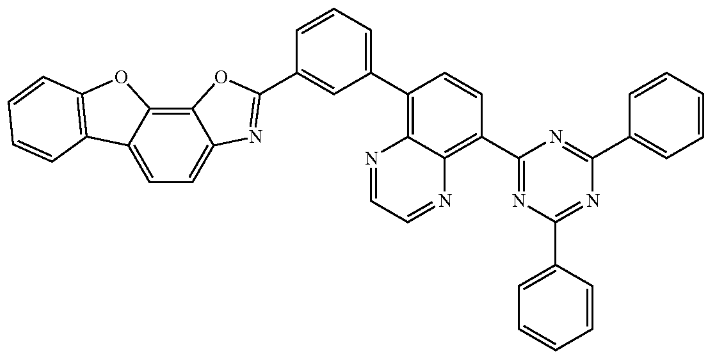
C36
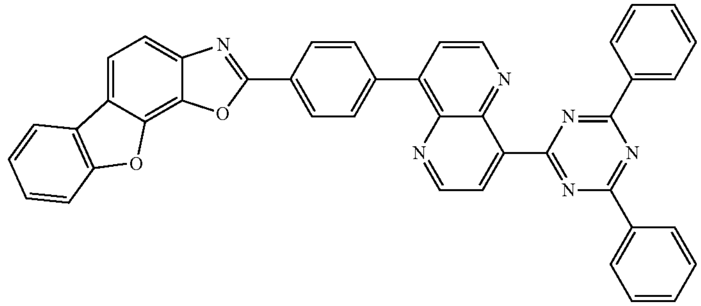
C37
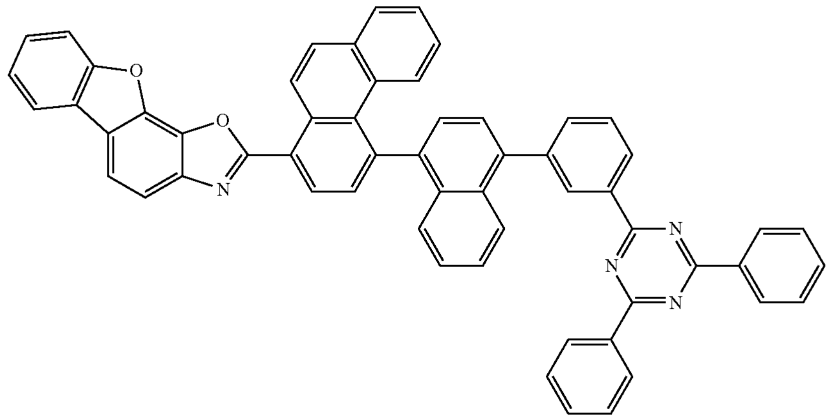
C38
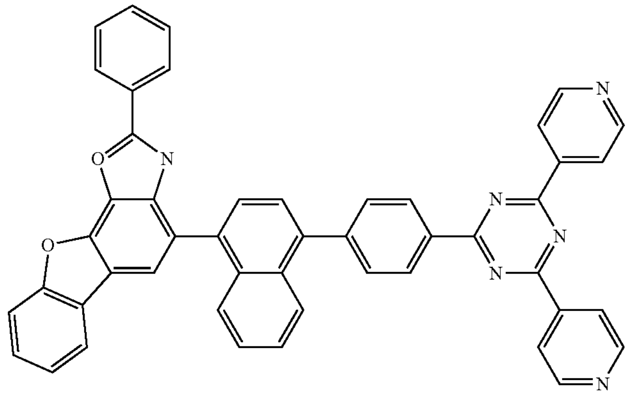

-continued
C39
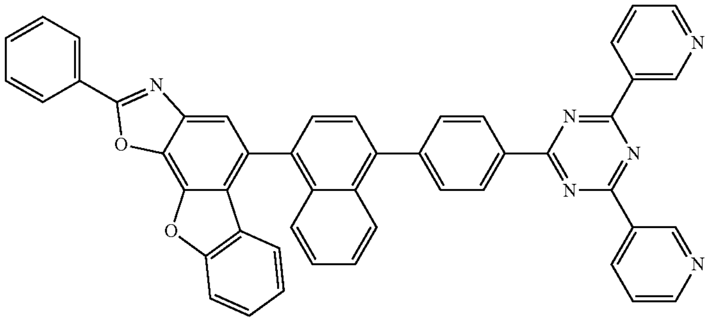
C40
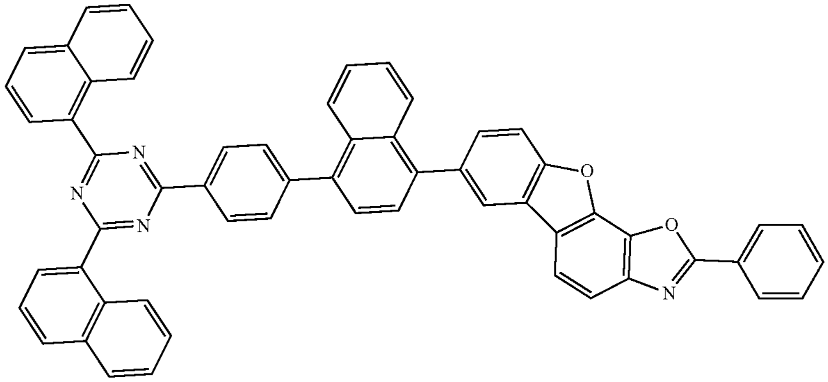
C41
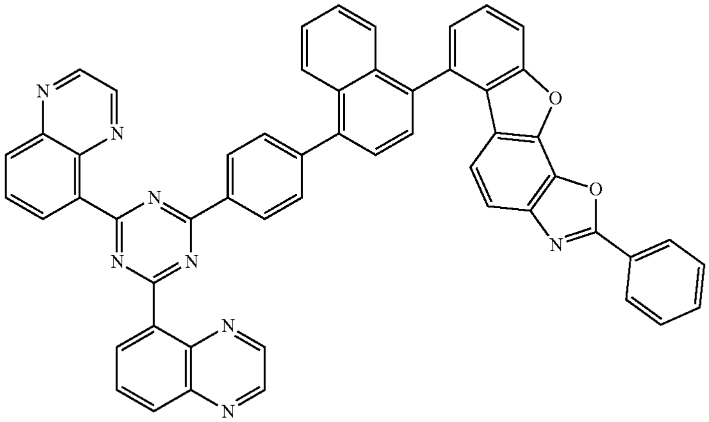
C42
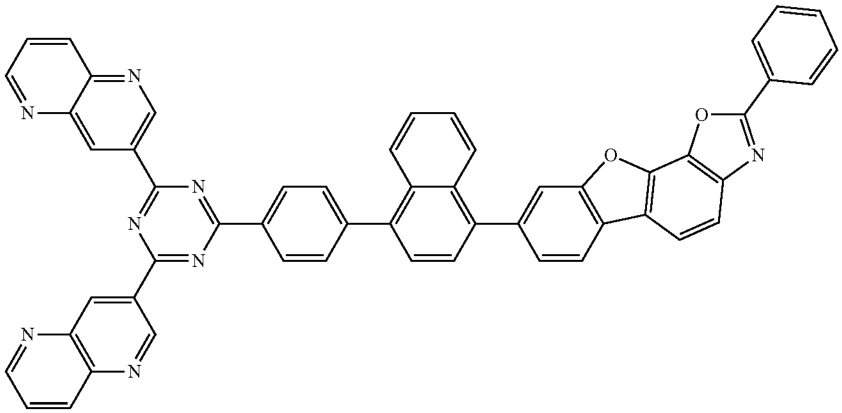

-continued
C43
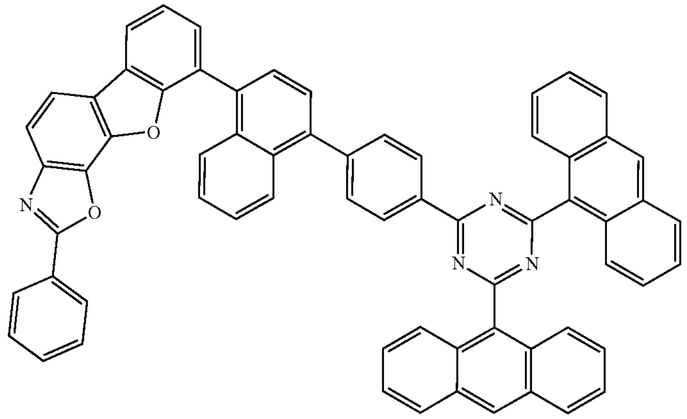
C44
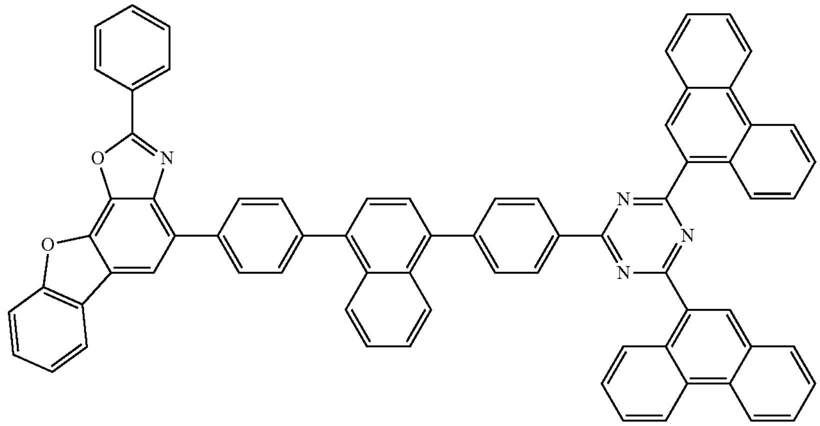
C45
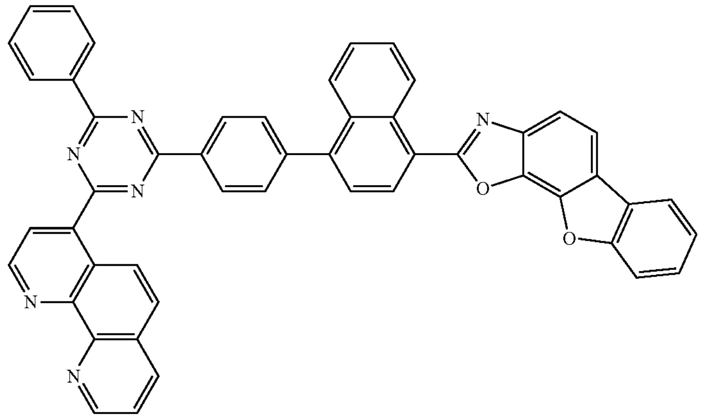
C46
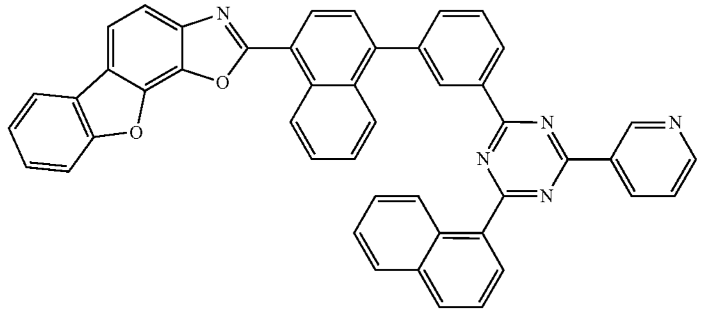

-continued
C47
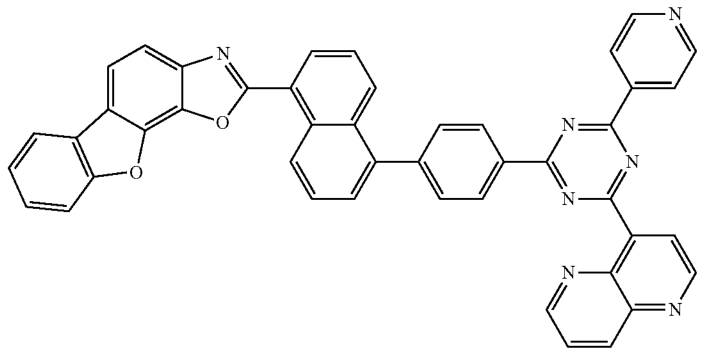
C48
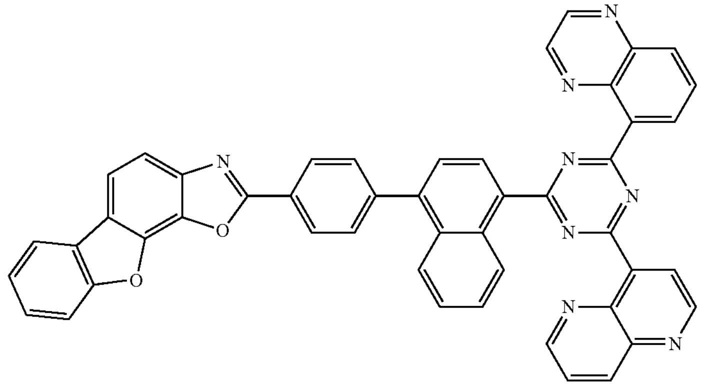
D1
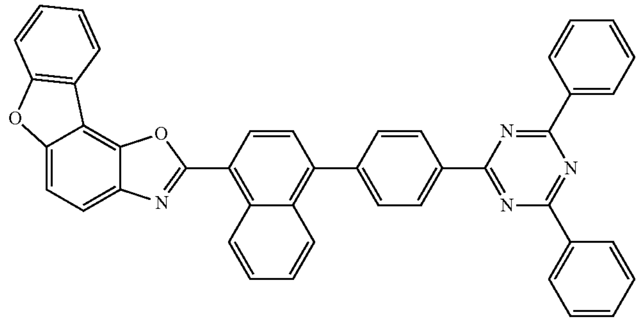
D2
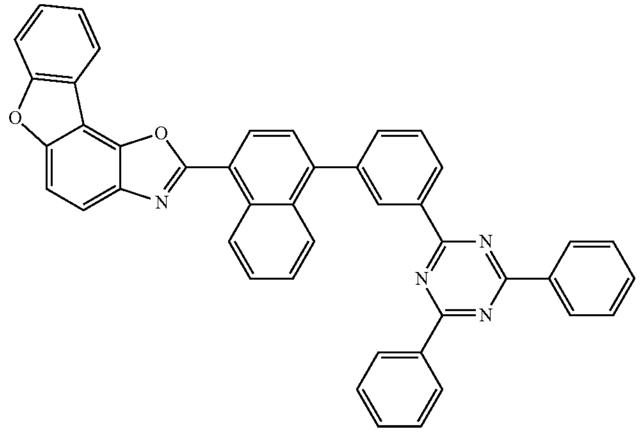

-continued
D3
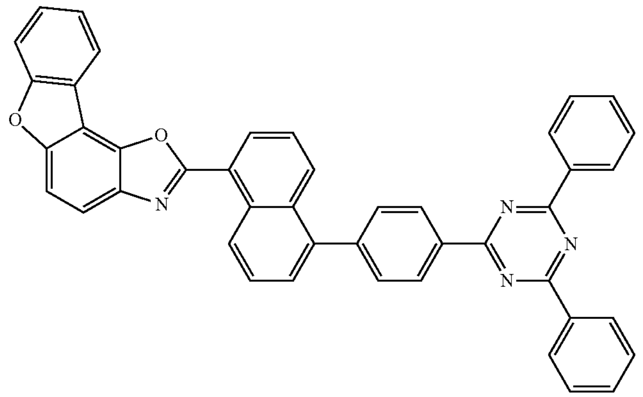
D4
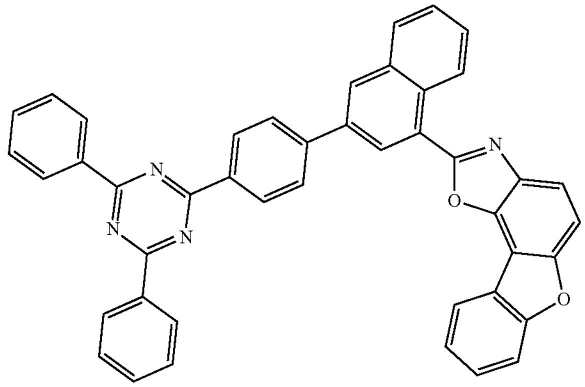
D5
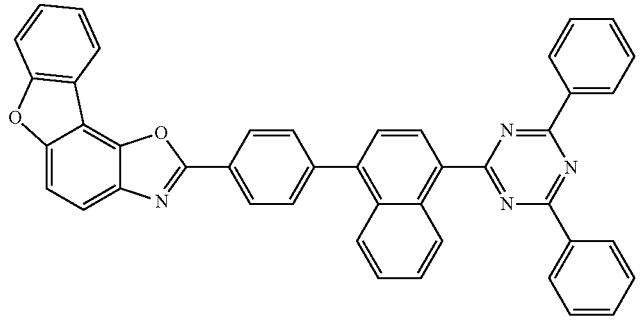
D6
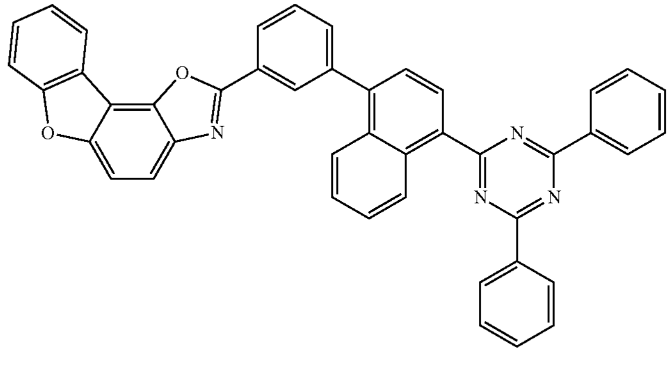

D7
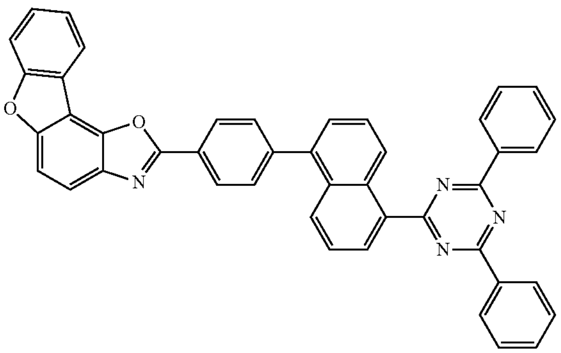
D8
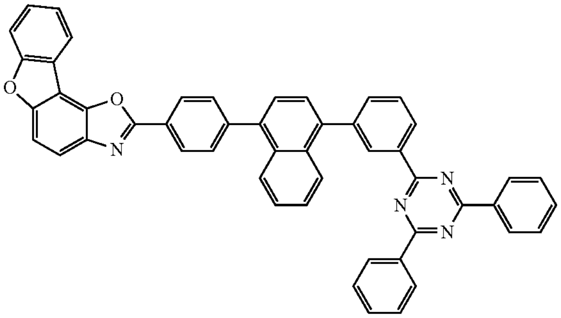
D9
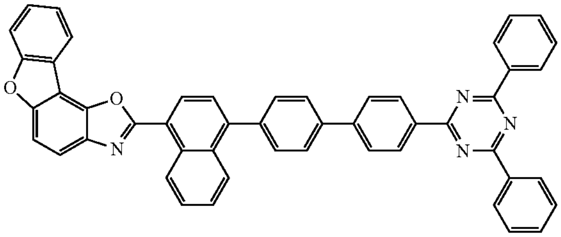
D10
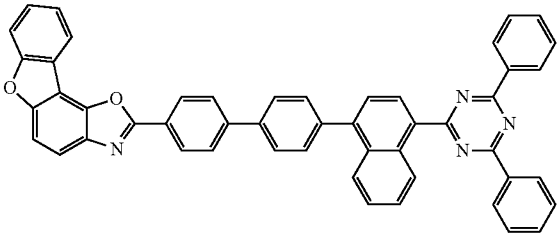
D11
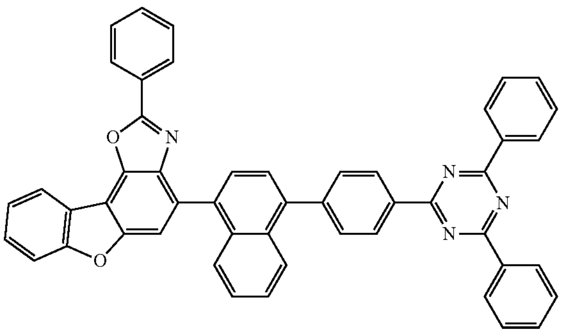
D12
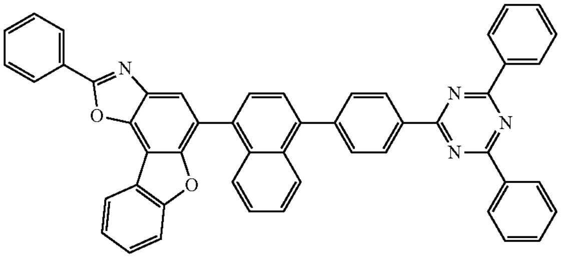
D13
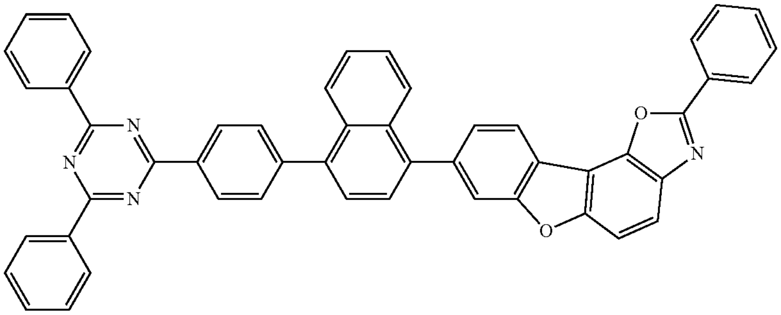
D14
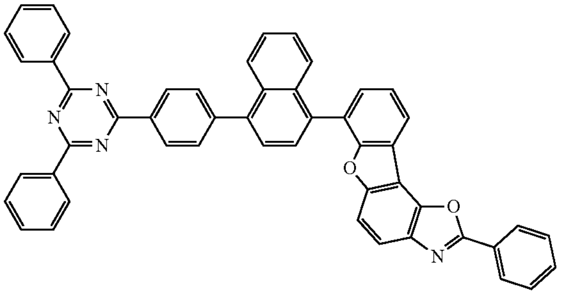
D15
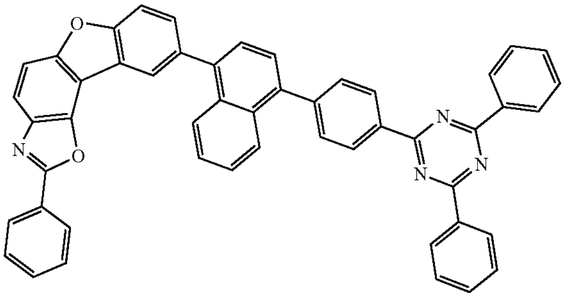

-continued
D16
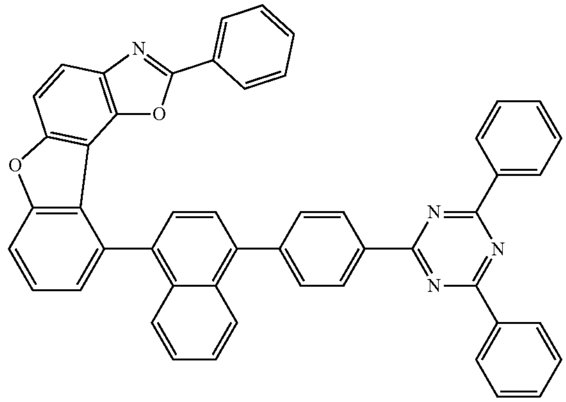
D17
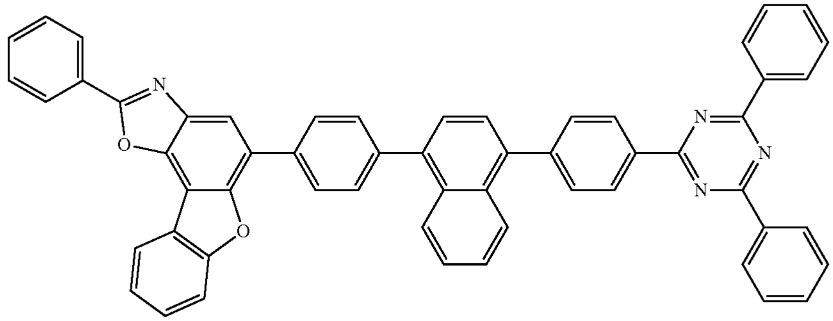
D18
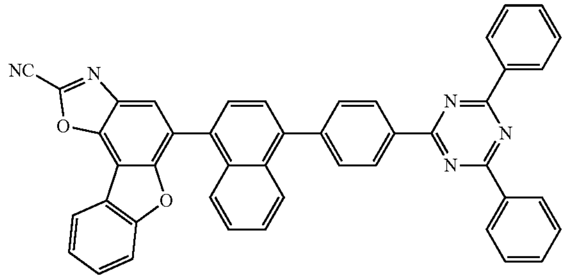
D19
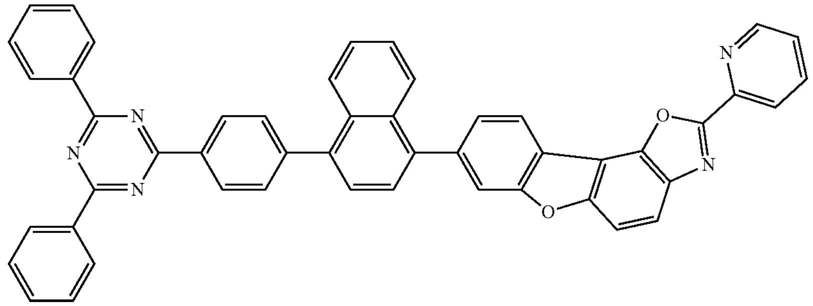
D20
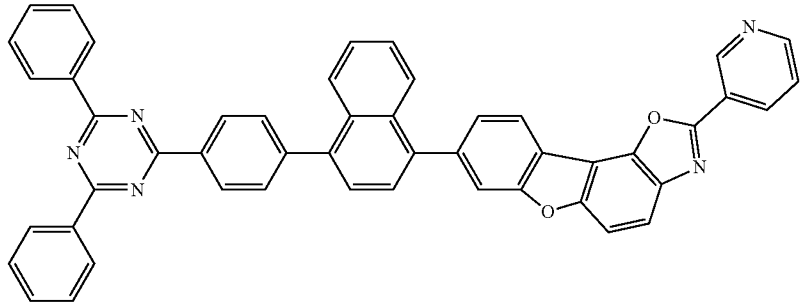

-continued
D21
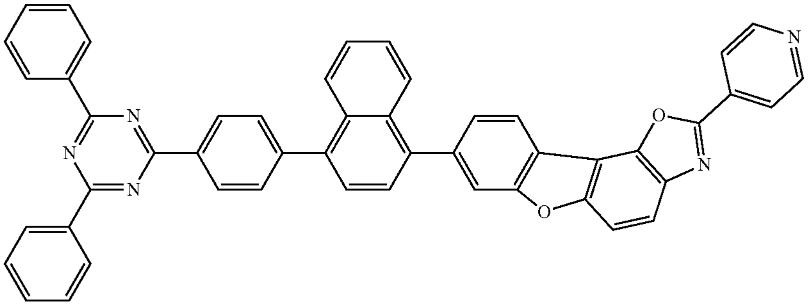
D22
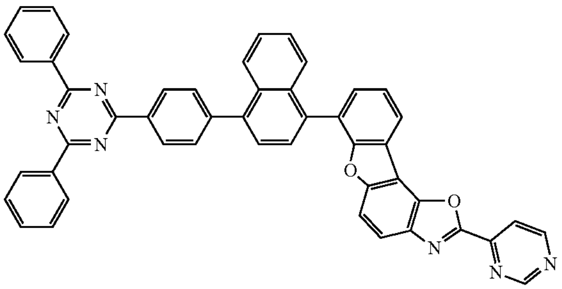
D23
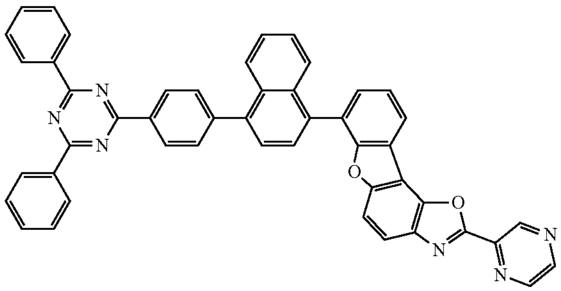
D24
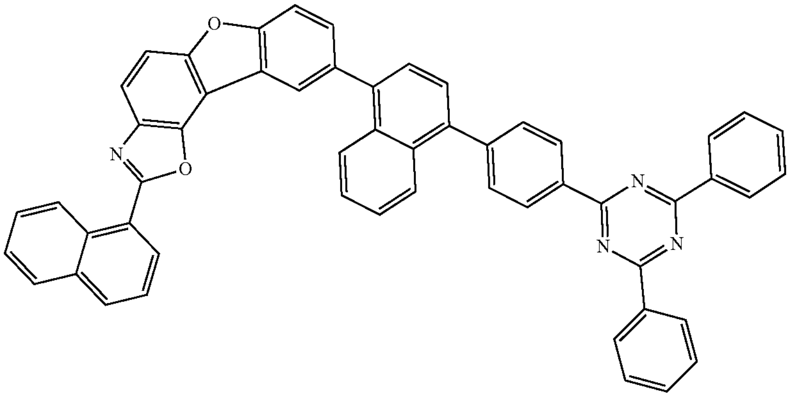
D25
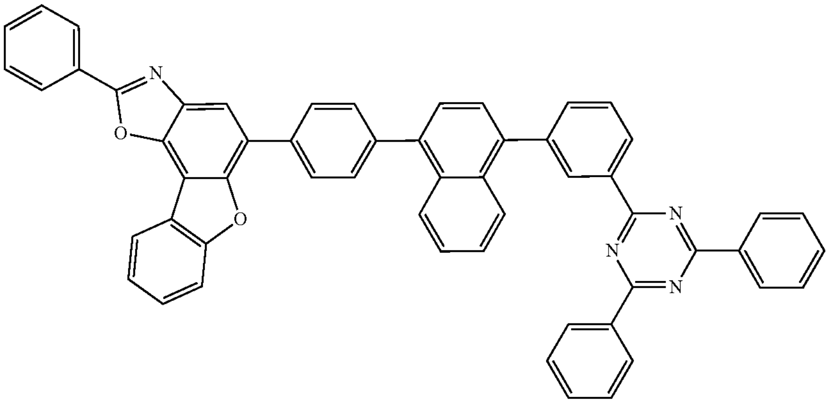

-continued
D26
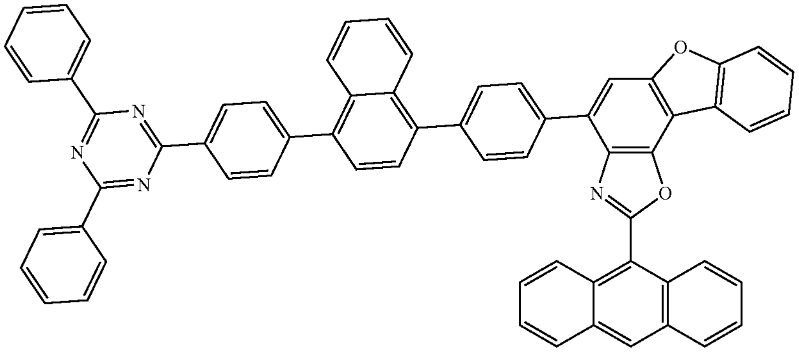
D27
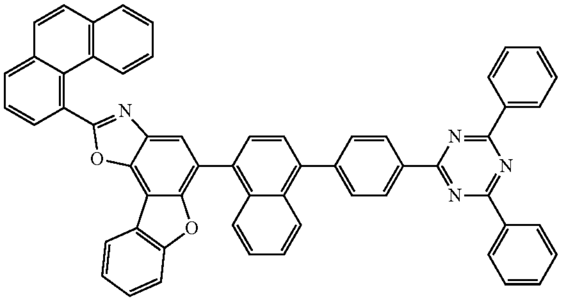
D28
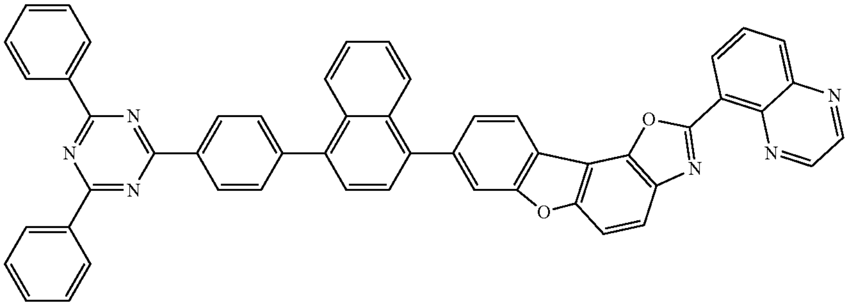
D29
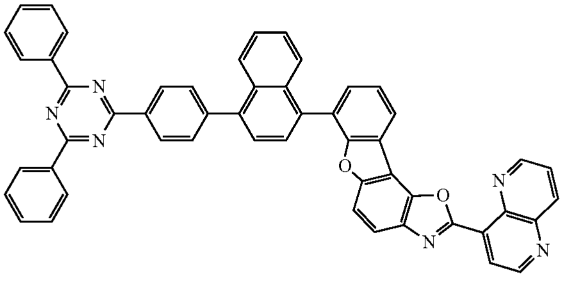
D30
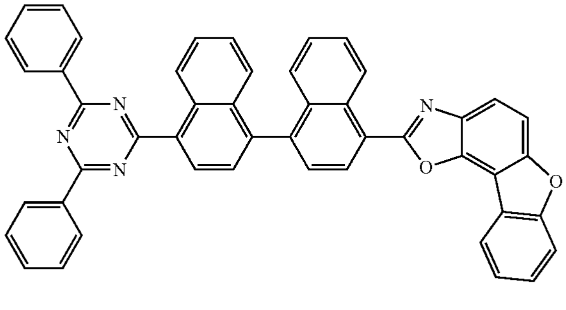
D31
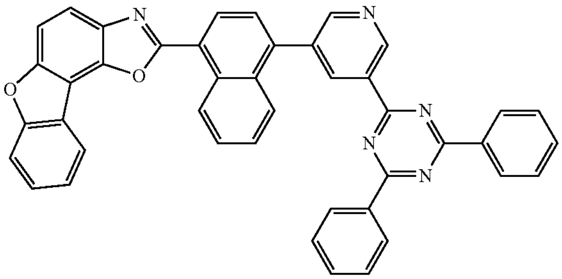
D32
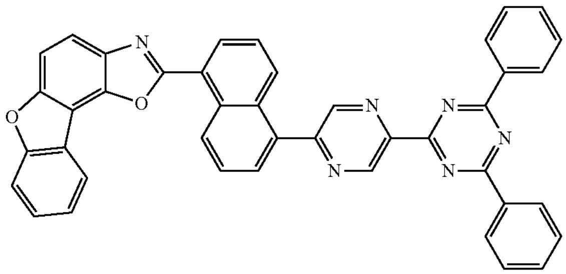

-continued
D33
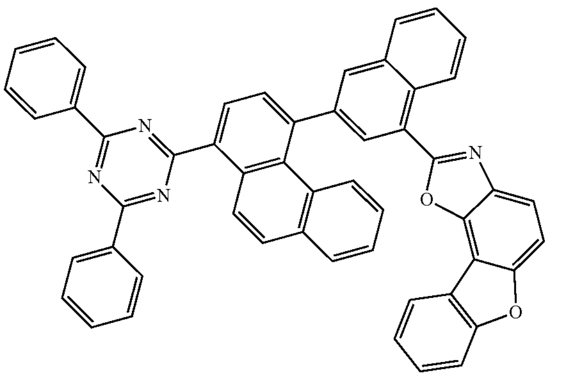
D34
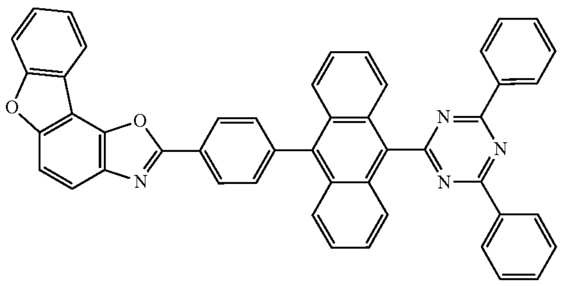
D35
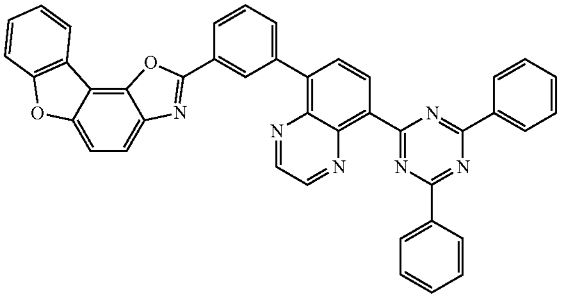
D36
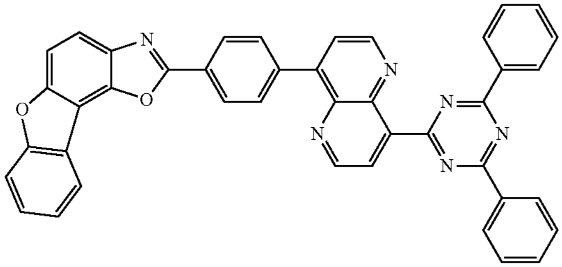
D37
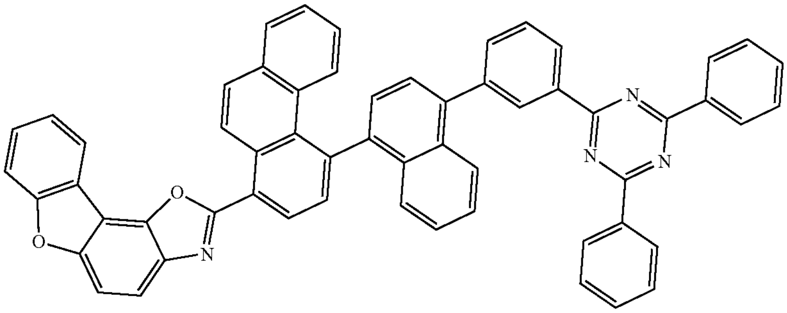
D38
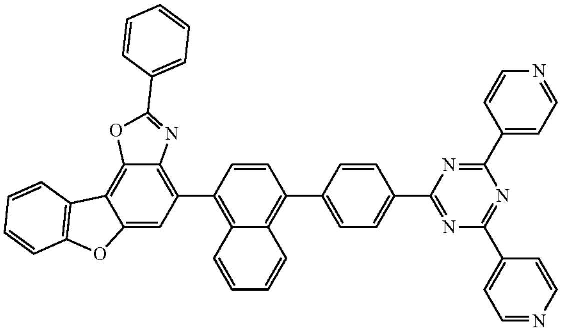
D39
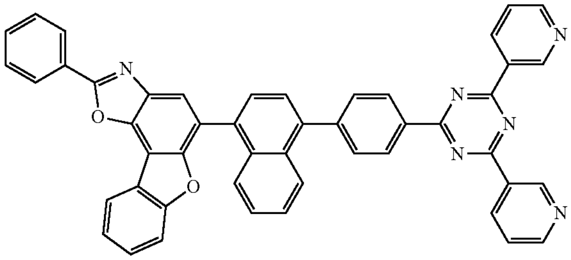

-continued
D40
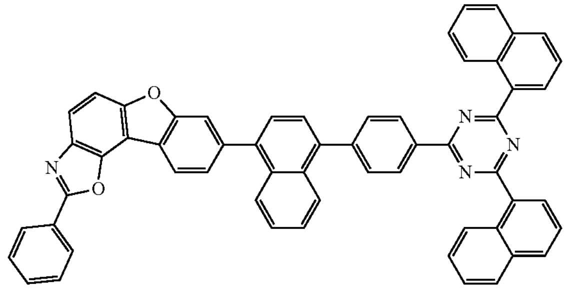
D41
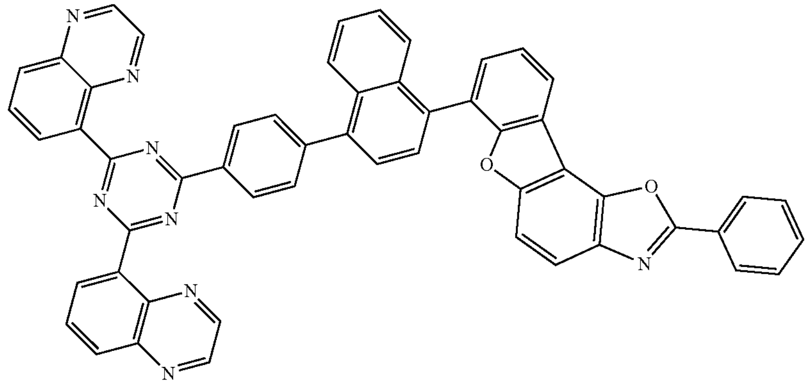
D42
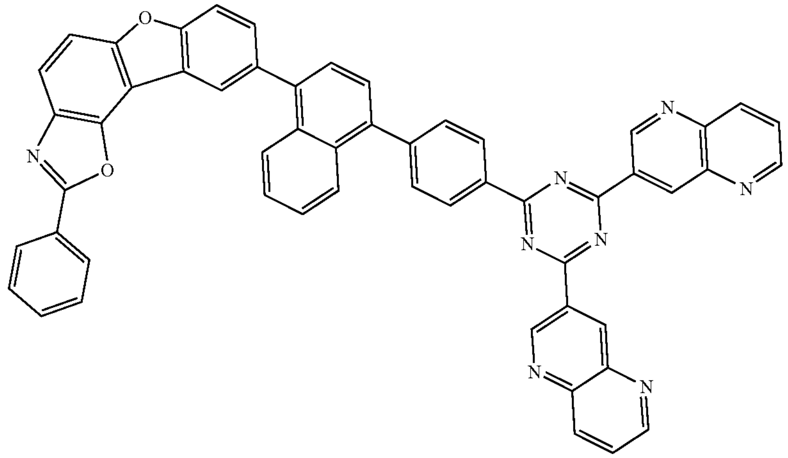
D43
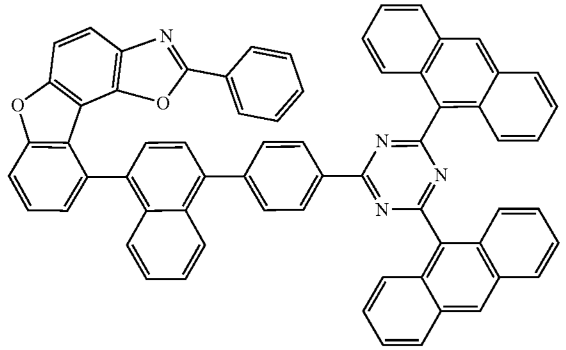

-continued
D44
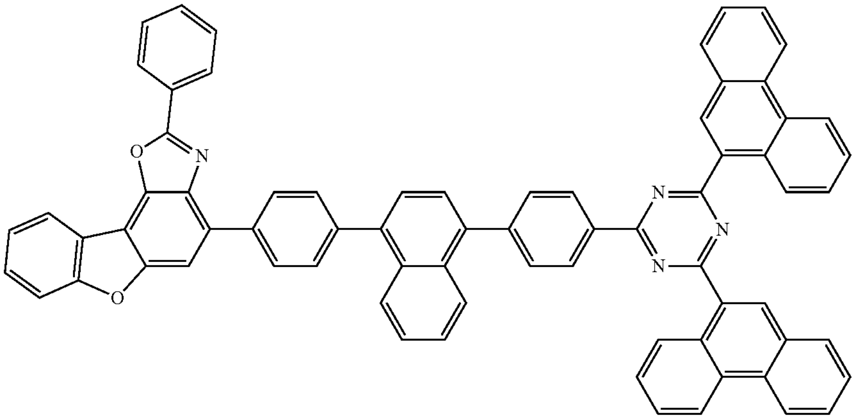
D45
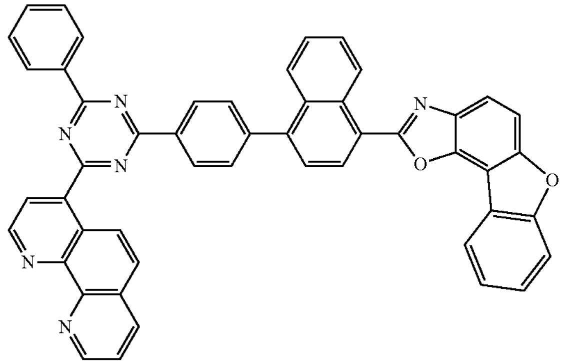
D46
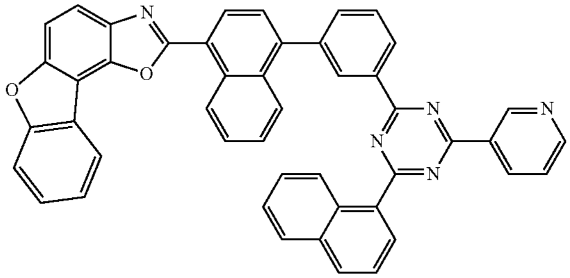
D47
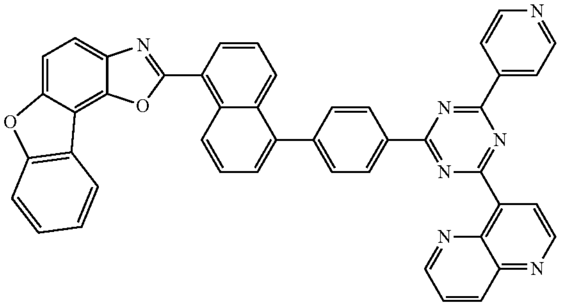
D48
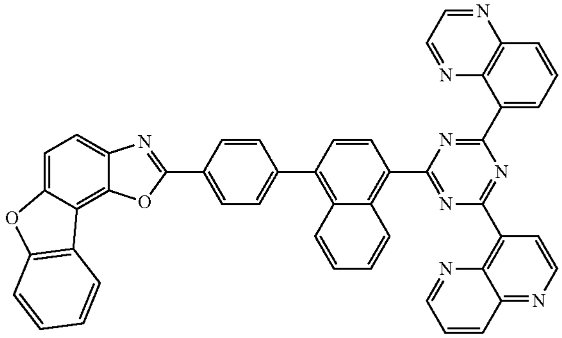
E1
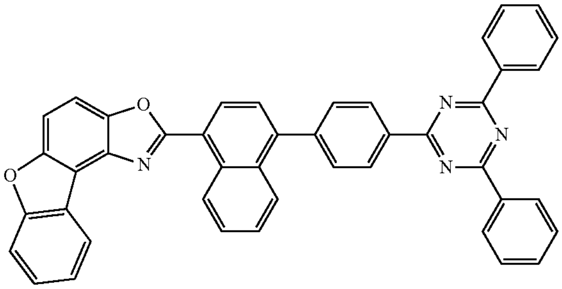
E2
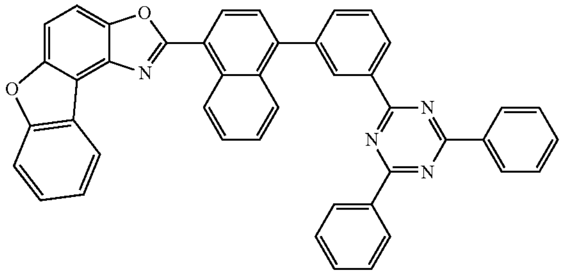

-continued
E3
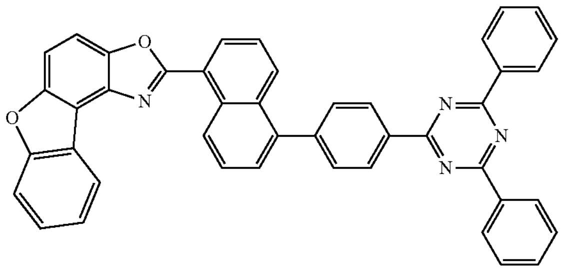
E4
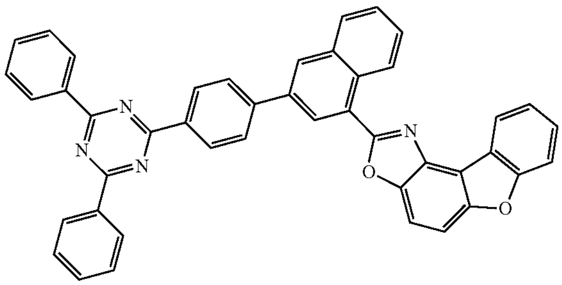
E5
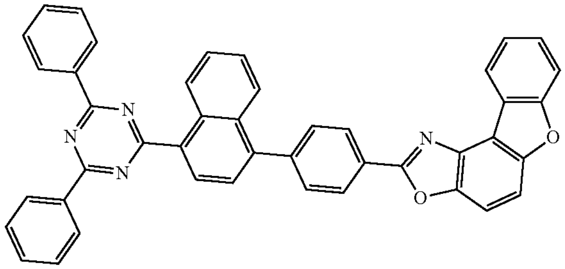
E6
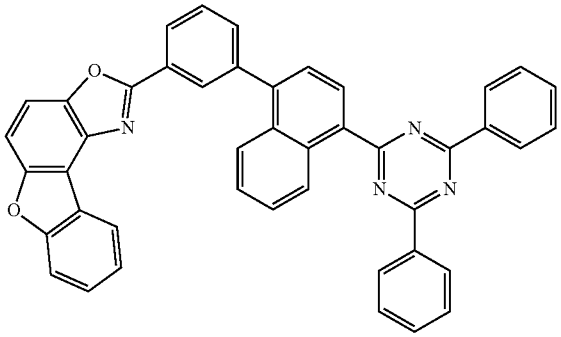
E7
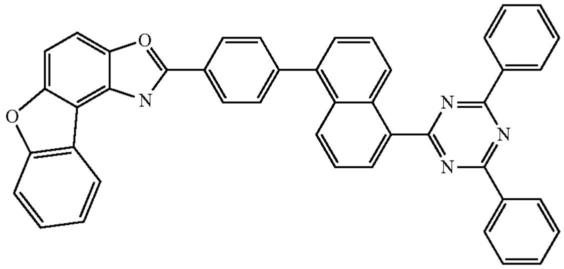
E8
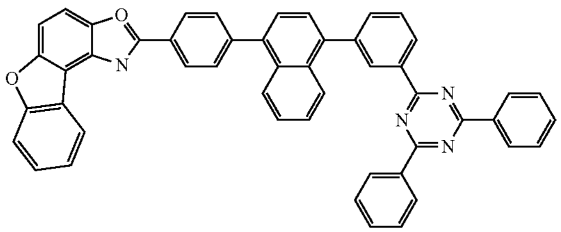
E9
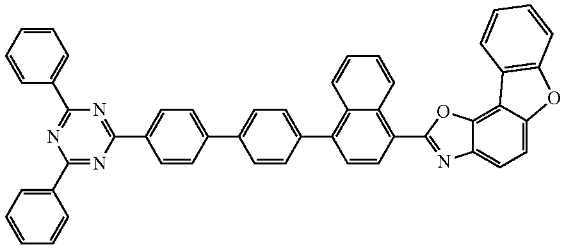
E10
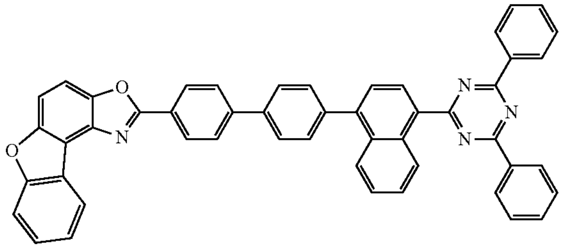
E11
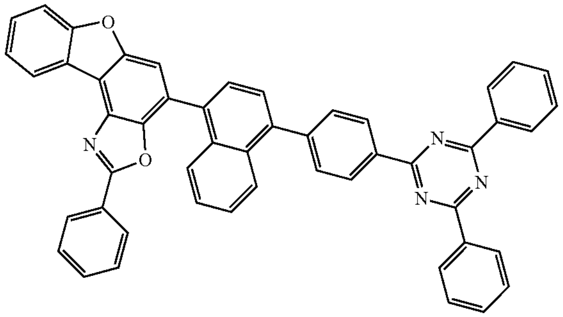
E12
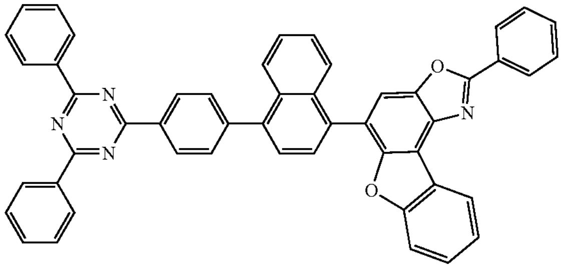

-continued
E13
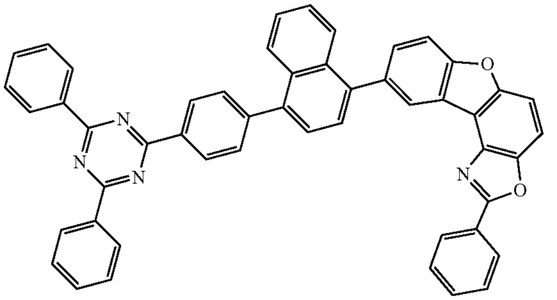
E14
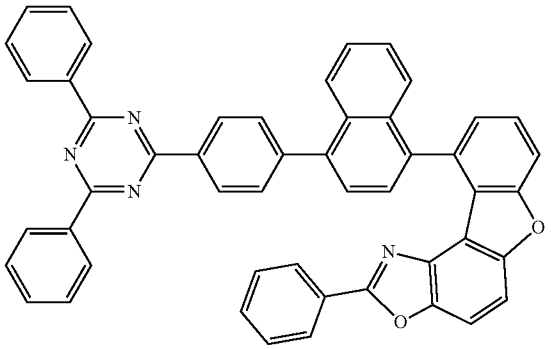
E15
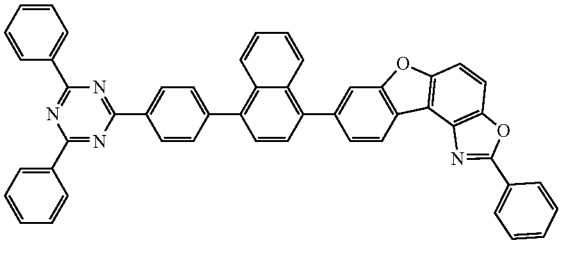
E16
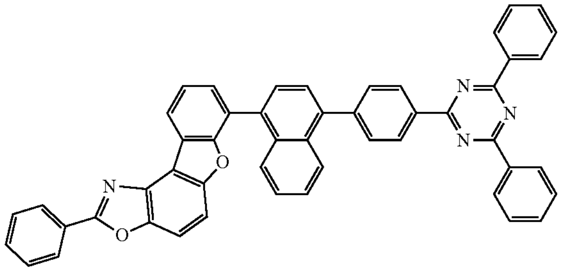
E17
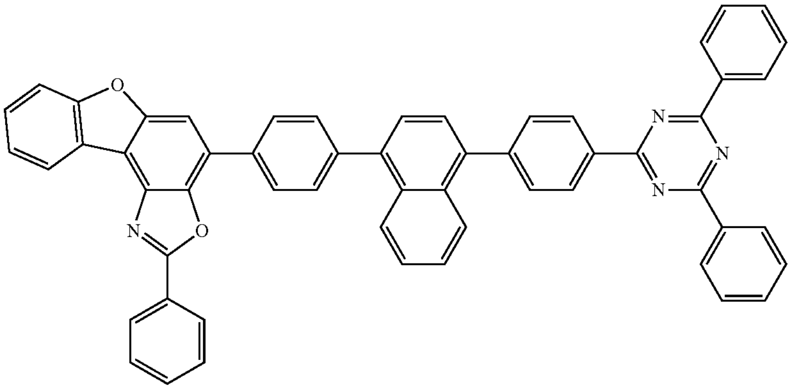
E18
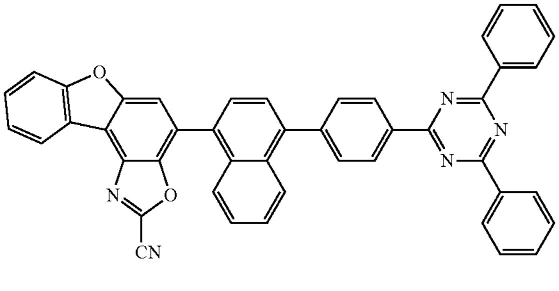
E19
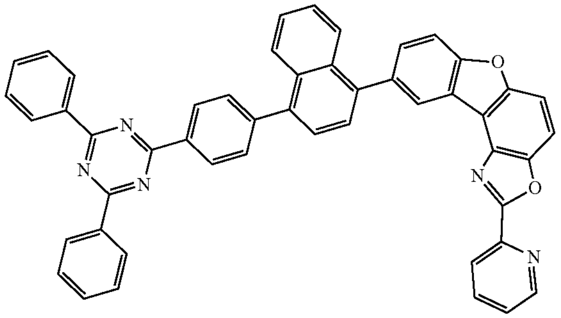

-continued
E20
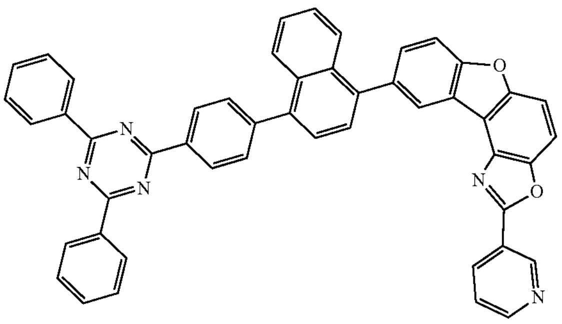
E21
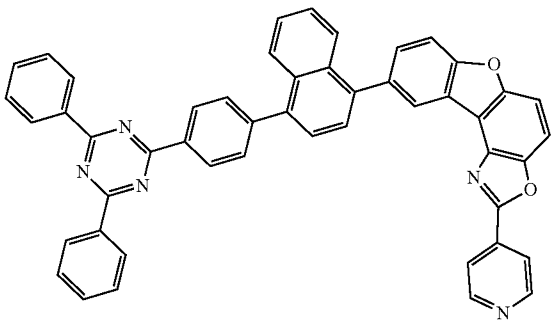
E22
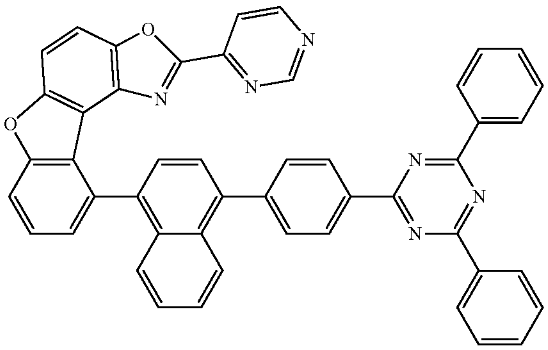
E23
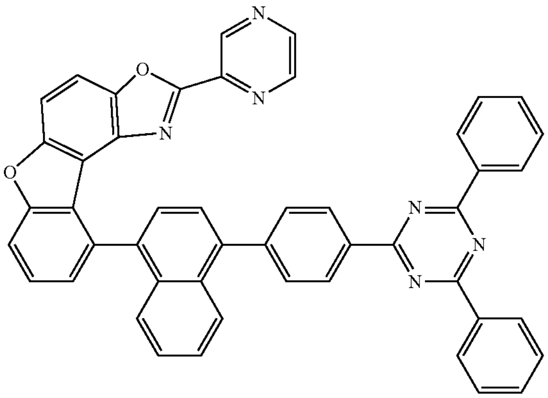
E24
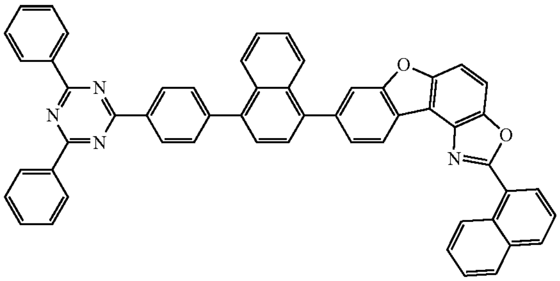
E25
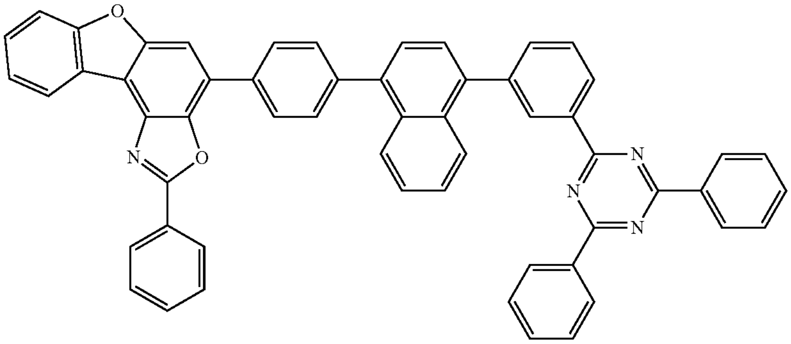

-continued
E26
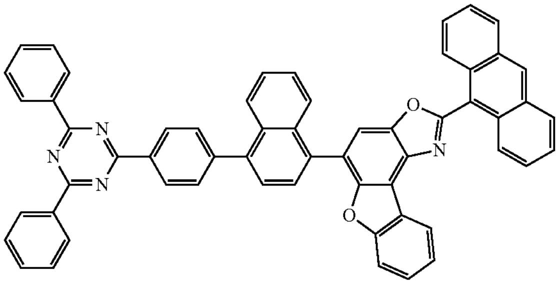
E27
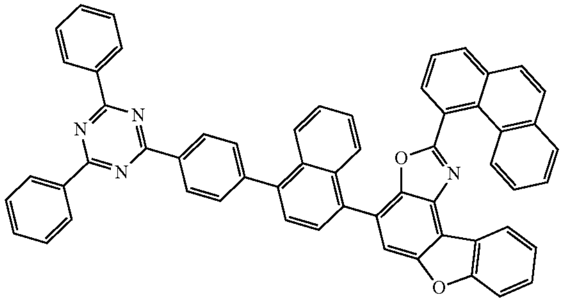
E28
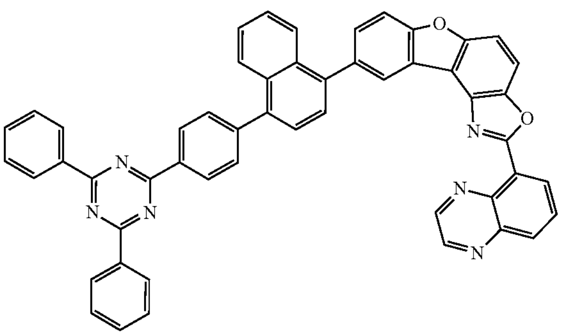
E29
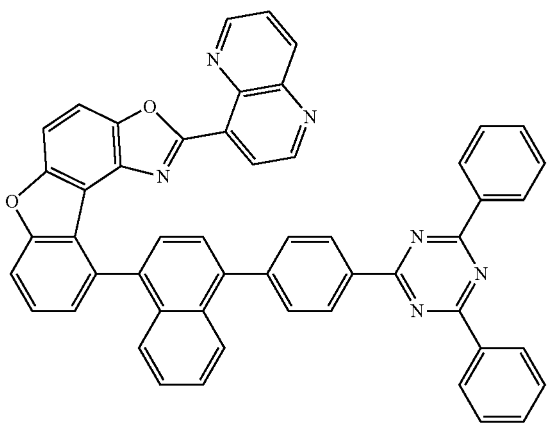
E30
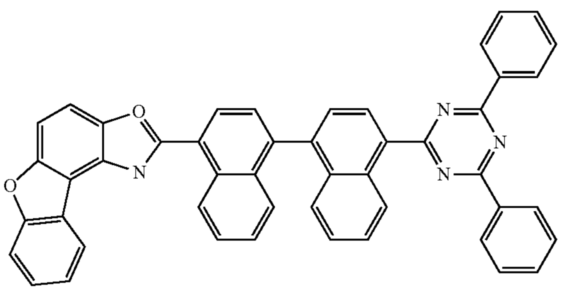
E31
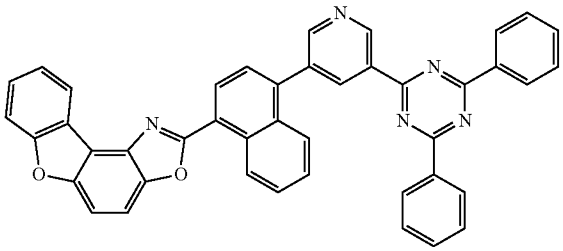
E32
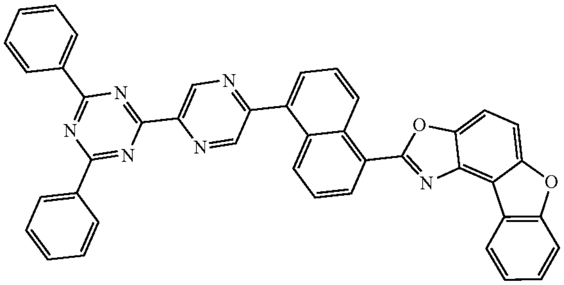
E33
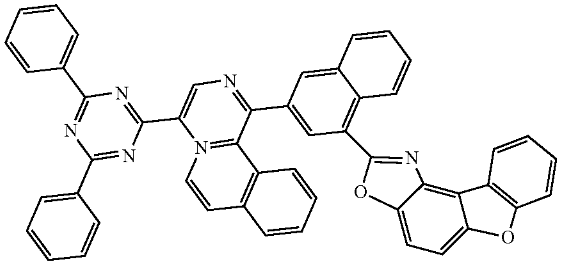

-continued
E34
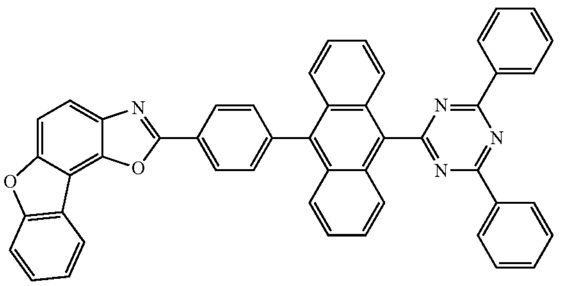
E35
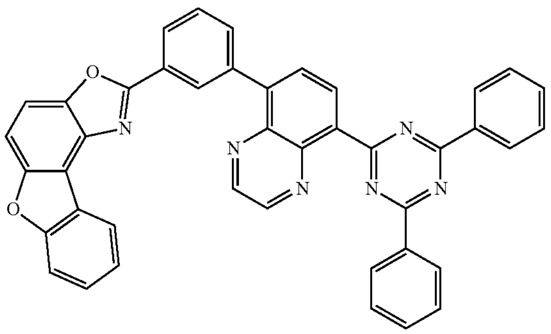
E36
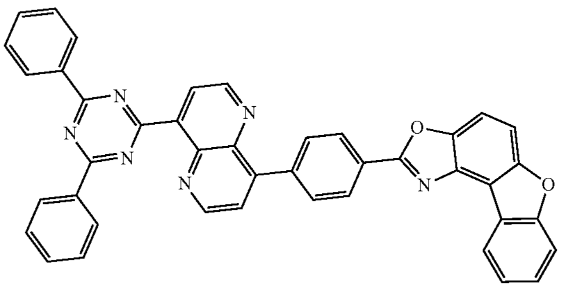
E37
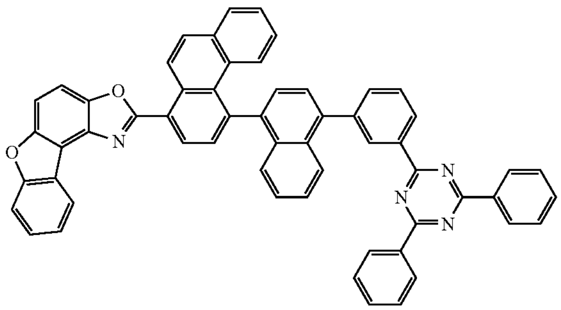
E38
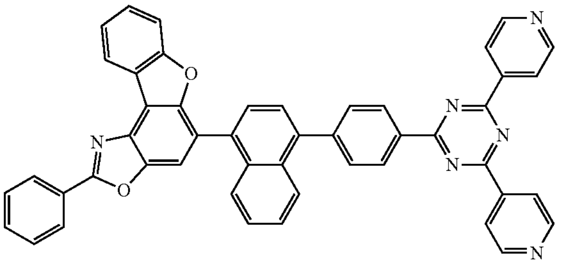
E39
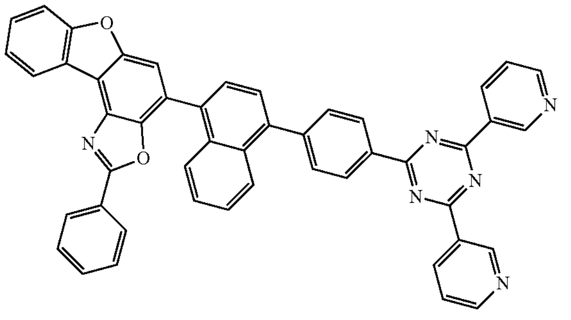
E40
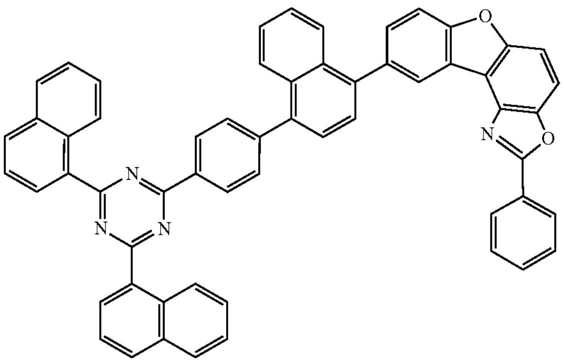
E41
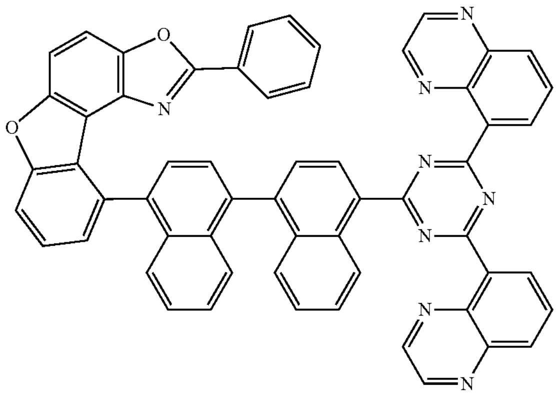

-continued
E42
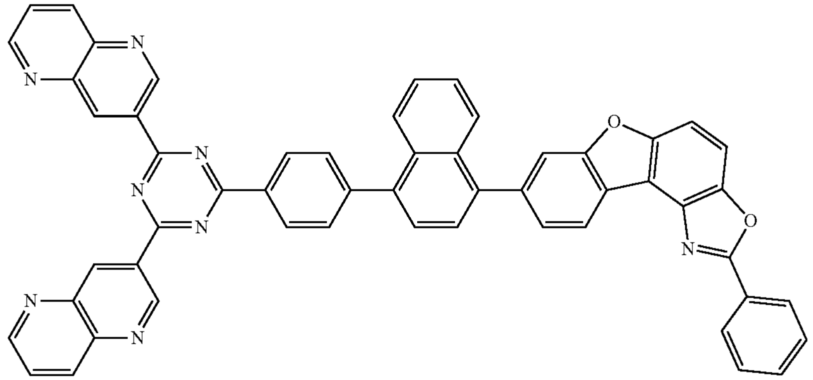
E43
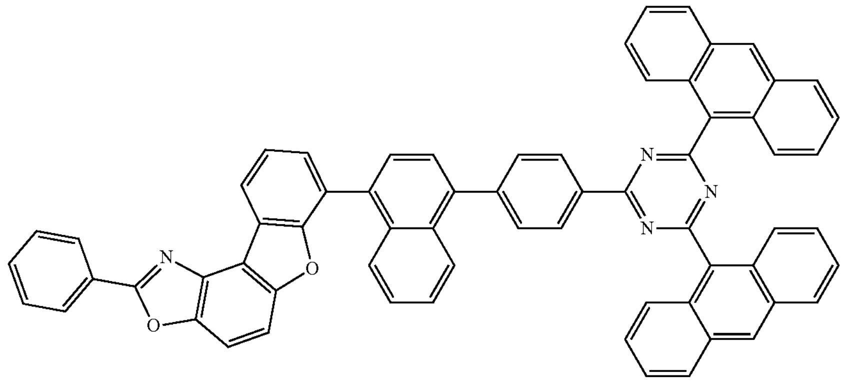
E44
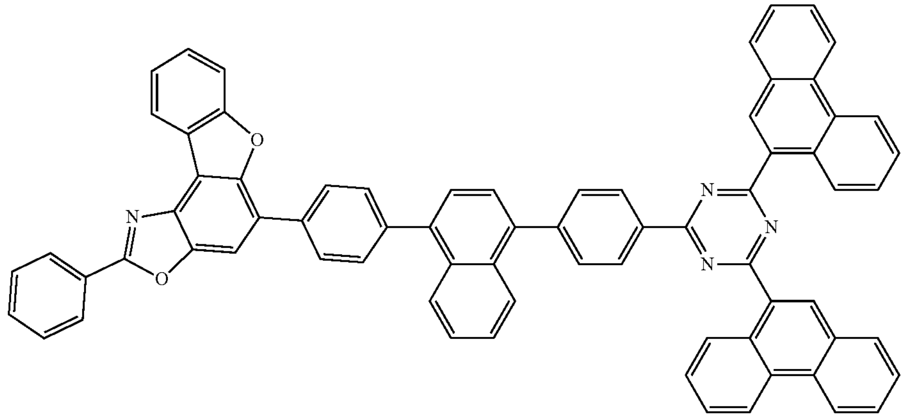
E45
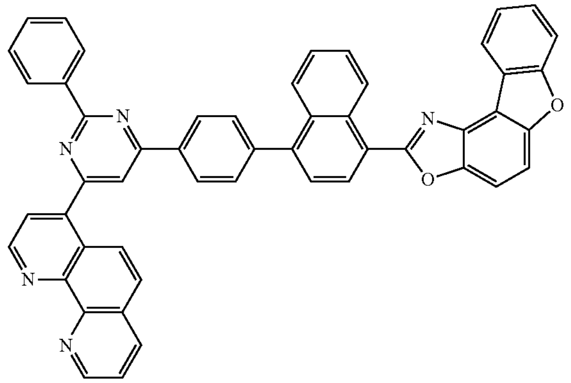
E46
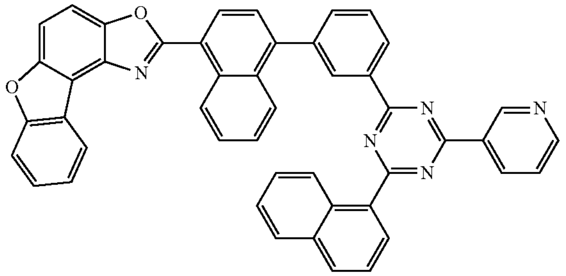

-continued
E47
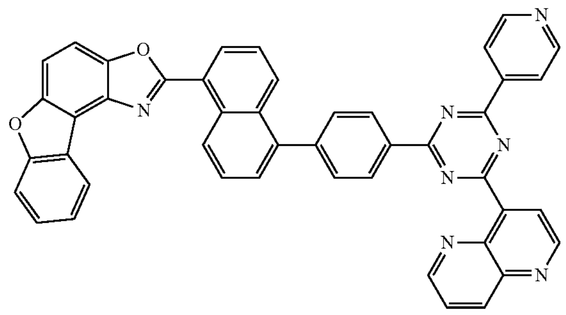
E48
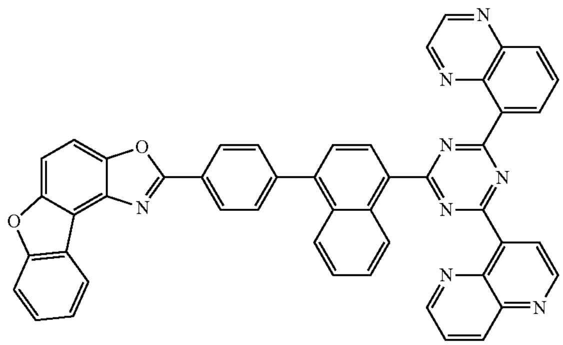
F1
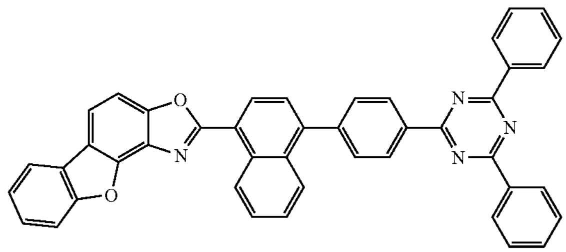
F2
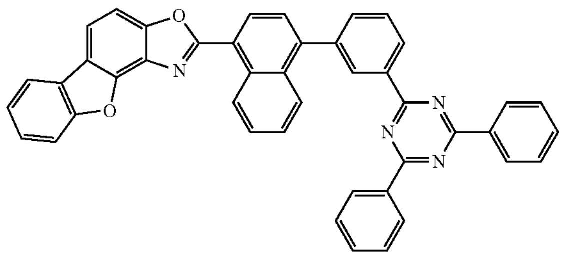
F3
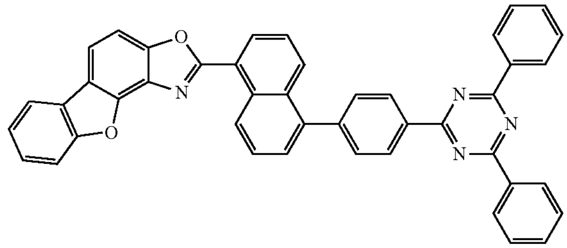
F4
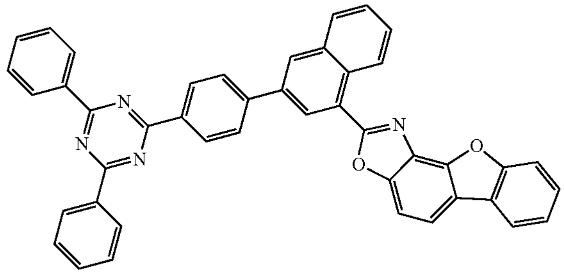
F5
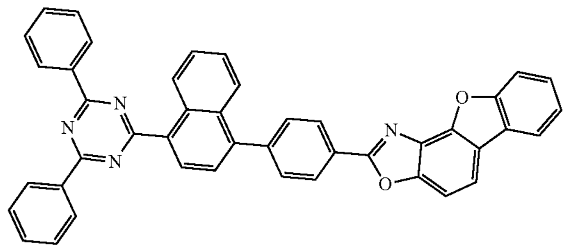
F6
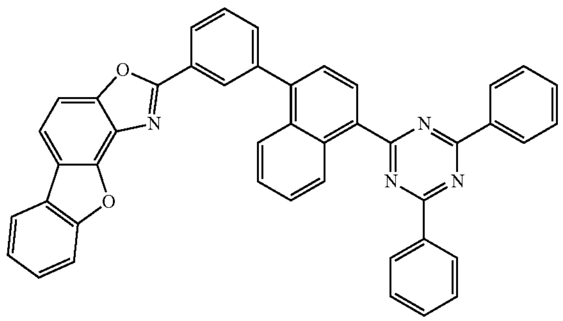
F7
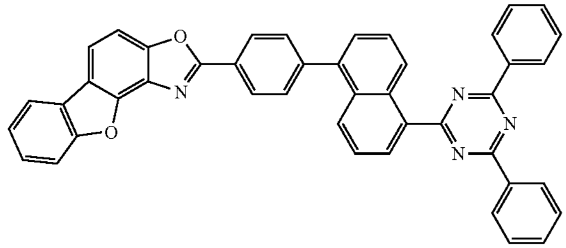

-continued
F8
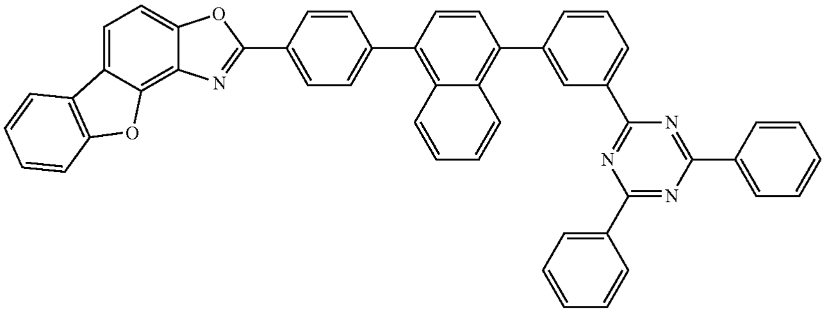
F9
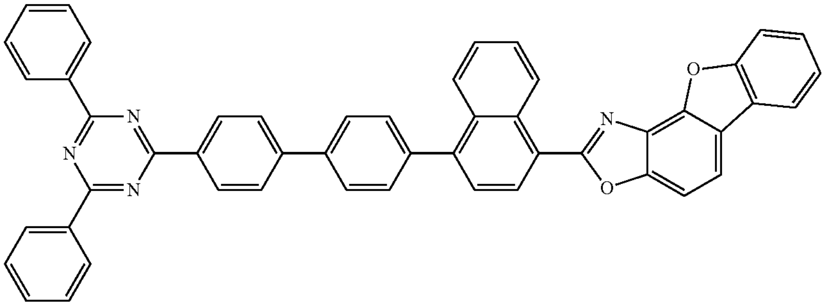
F10
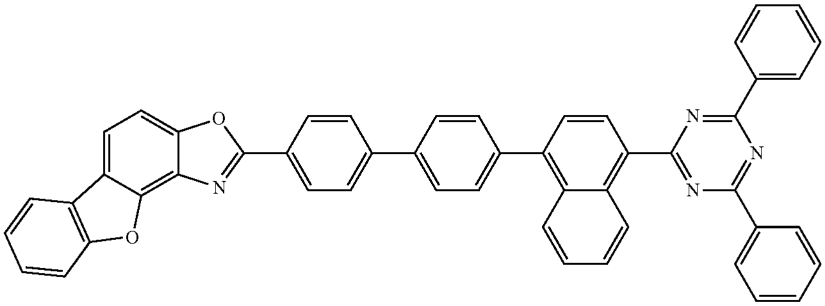
F11
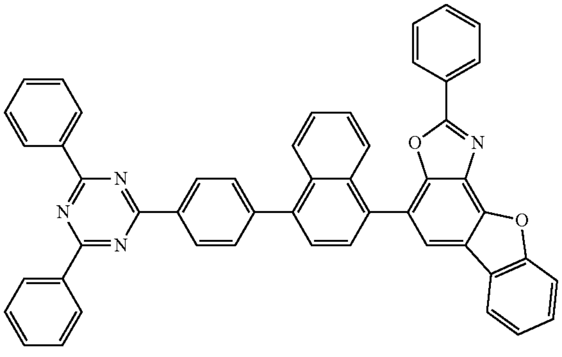
F12
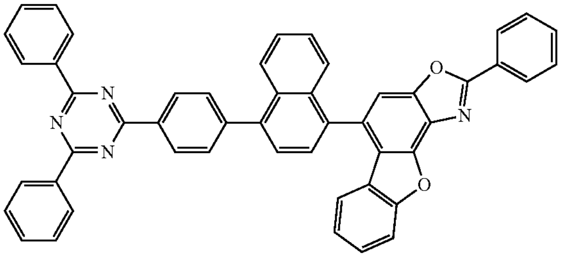
F13
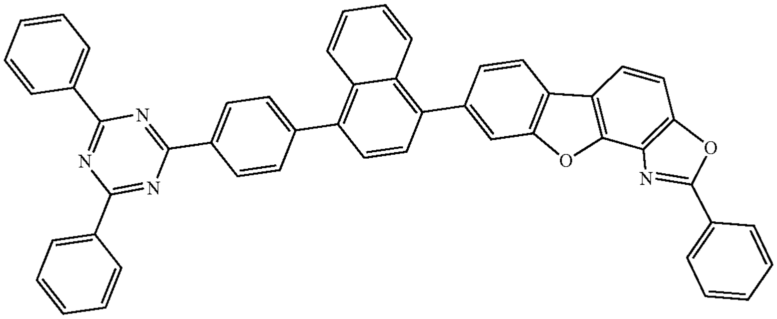

-continued
F14
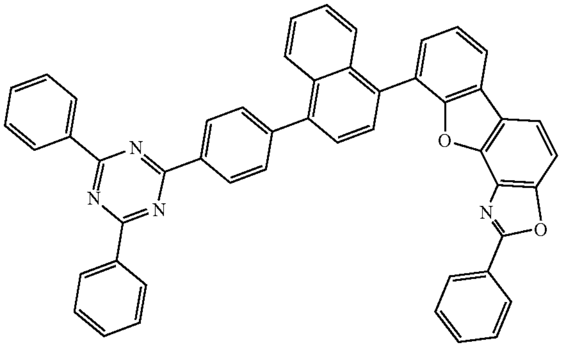
F15
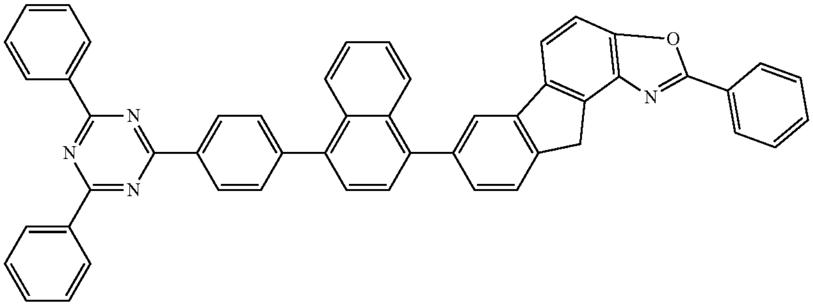
F16
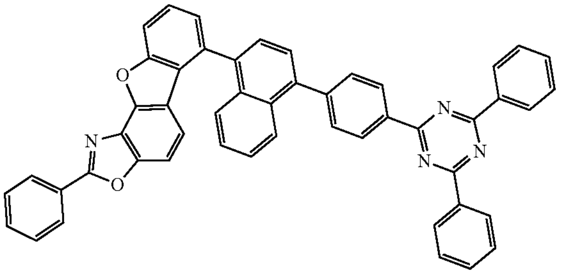
F17
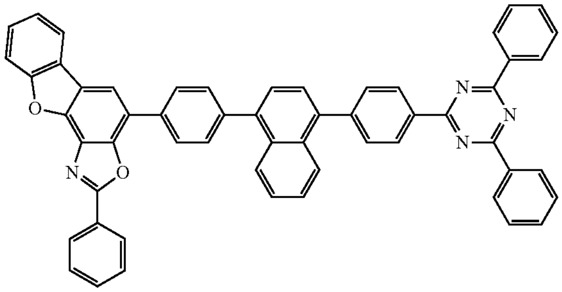
F18
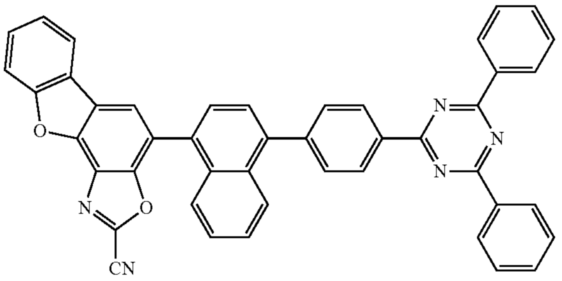
F19
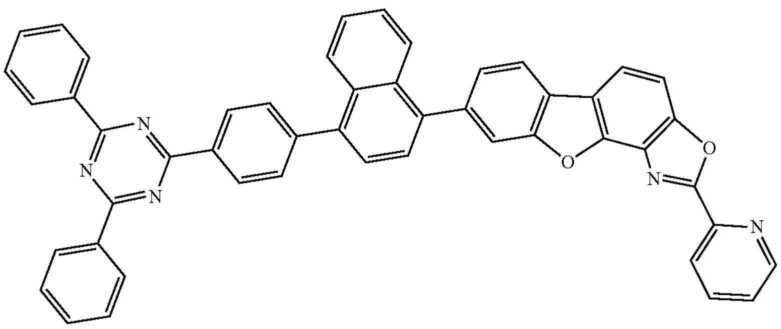

-continued
F20
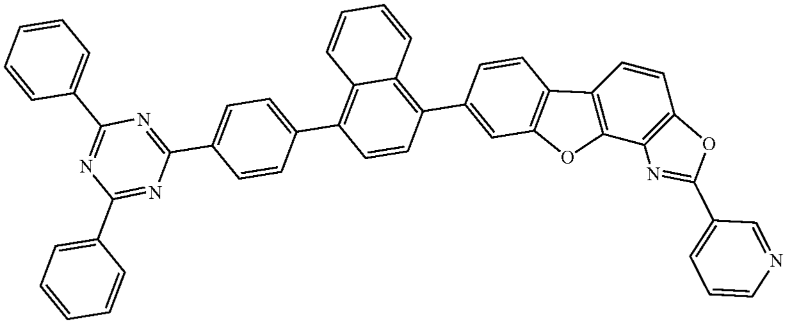
F21
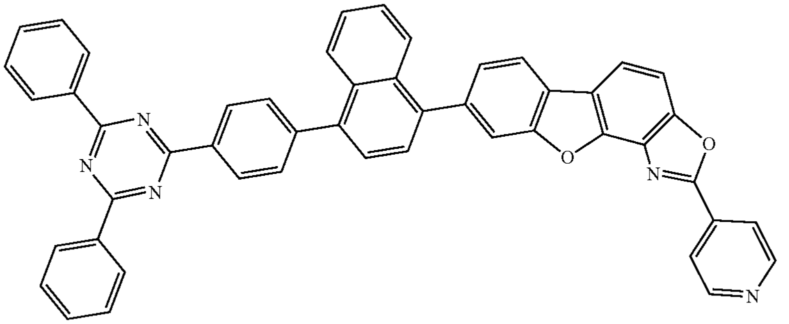
F22
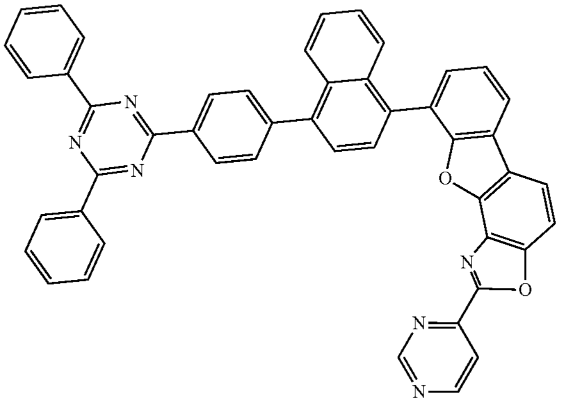
F23
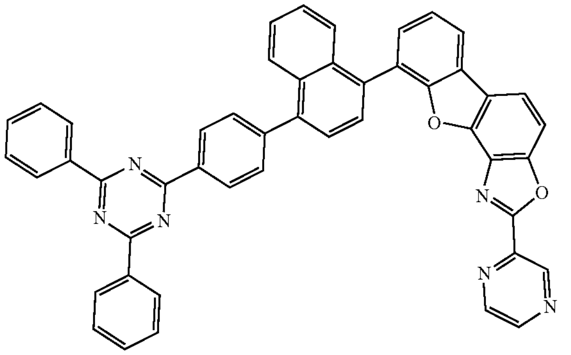
F24
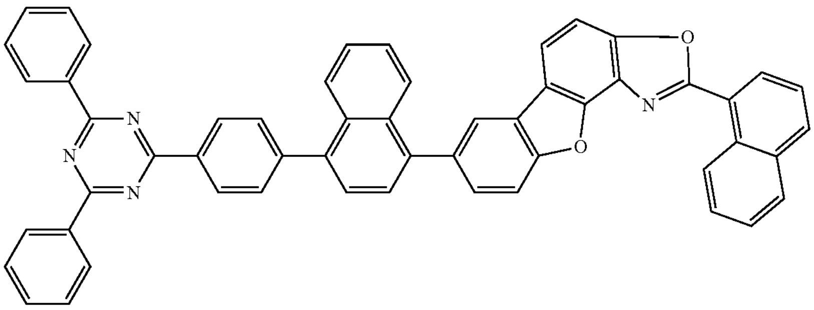

-continued
F25
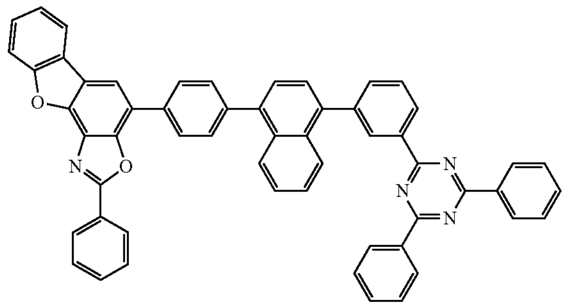
F26
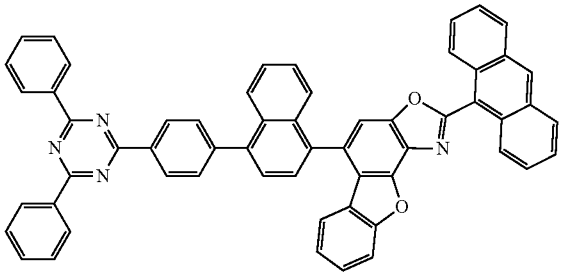
F27
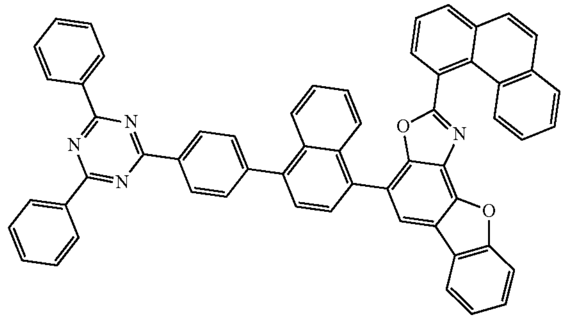
F28
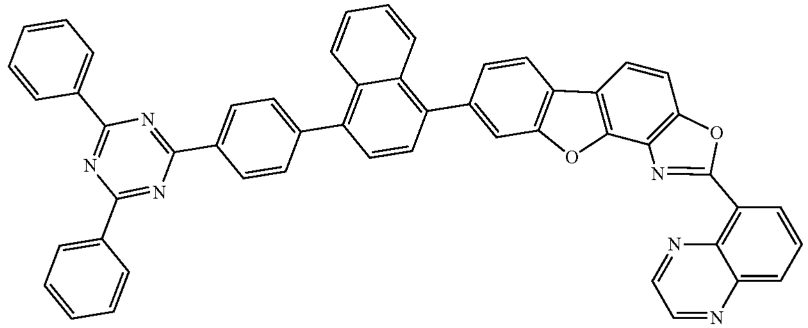
F29
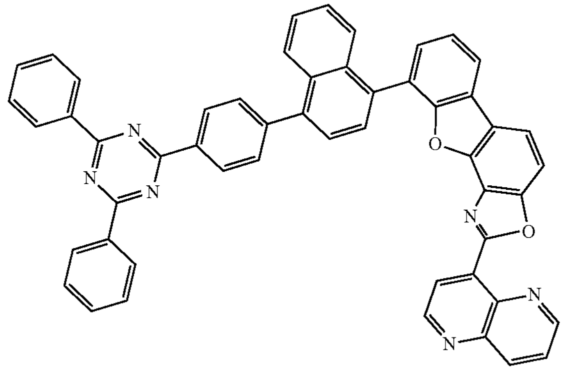
F30
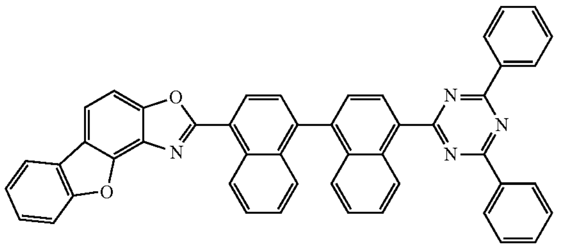
F31
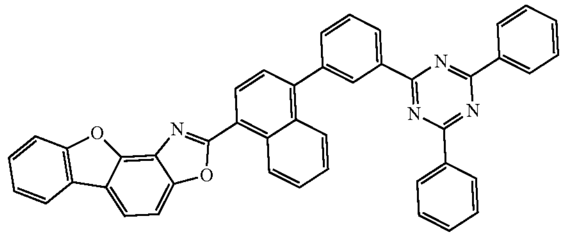
F32
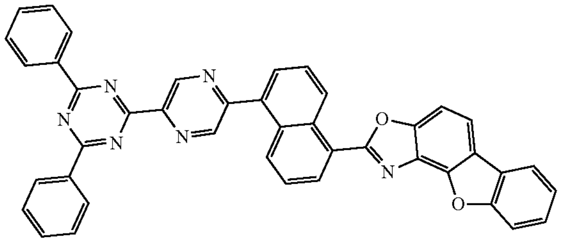

-continued
F33
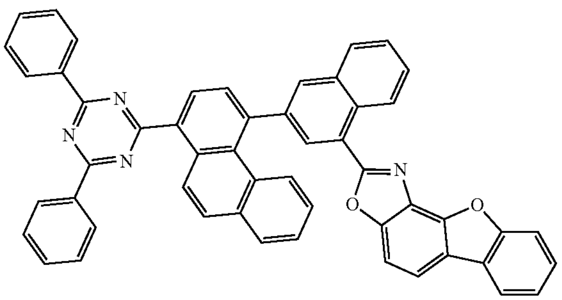
F34
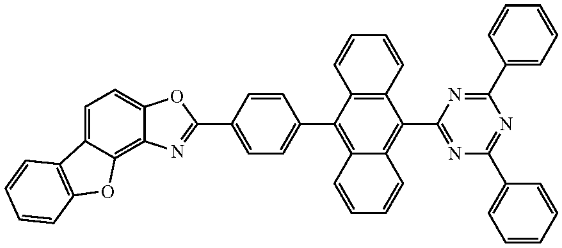
F35
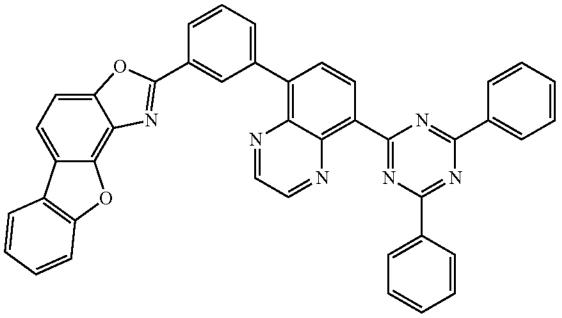
F36
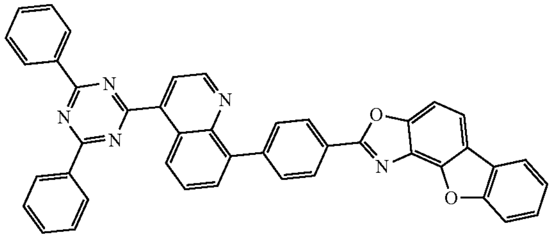
F37
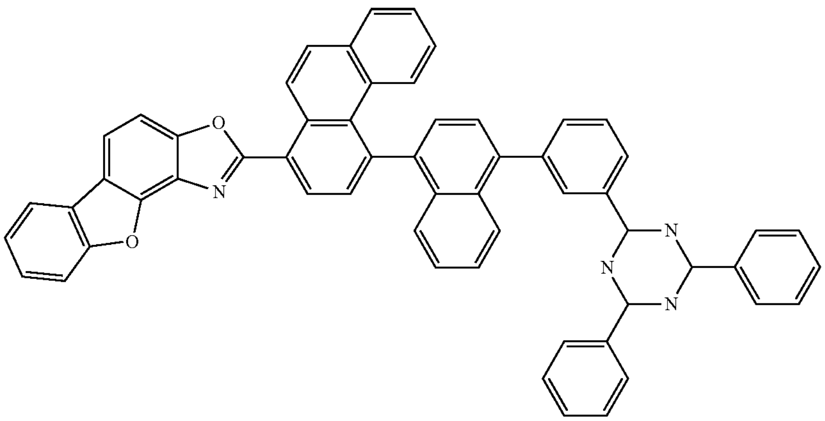
F38
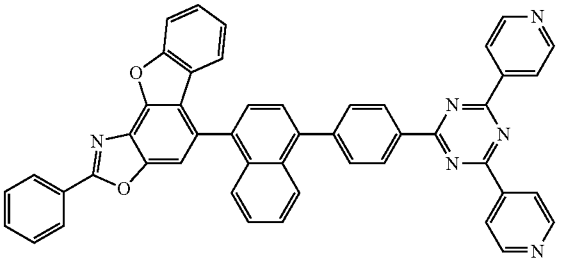
F39
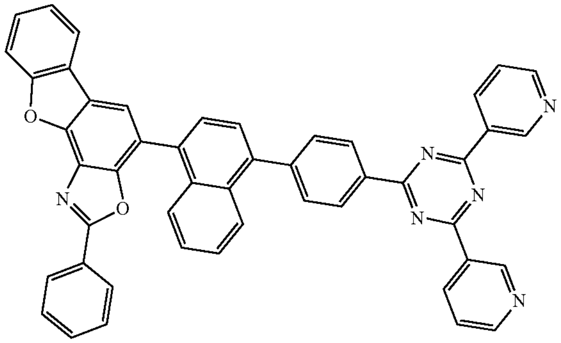

-continued
F40
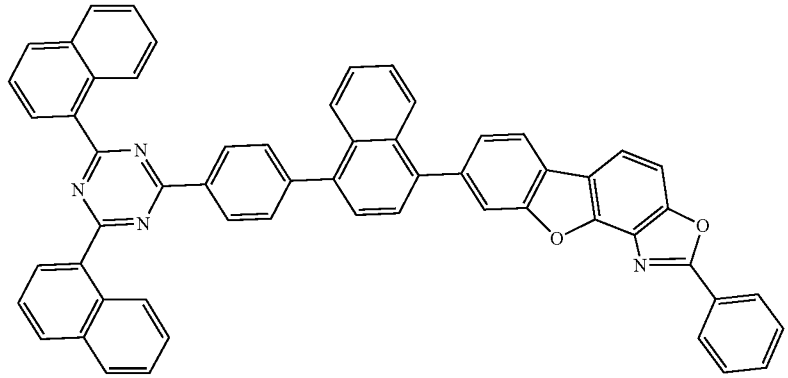
F41
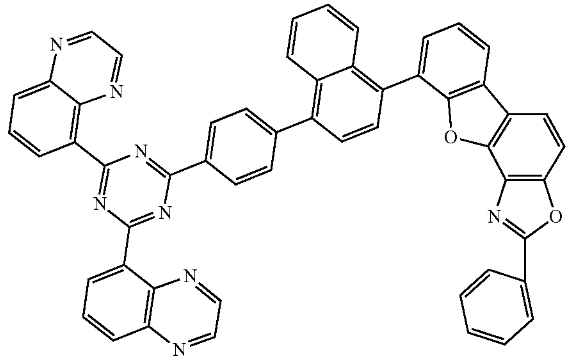
F42
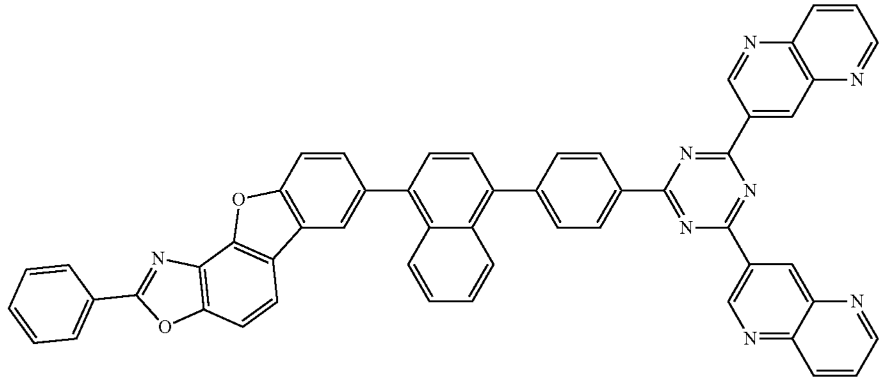
F43
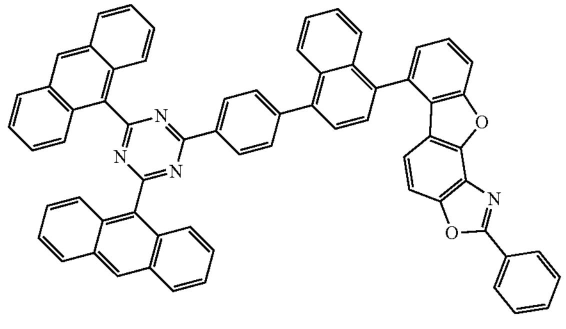

-continued
F44
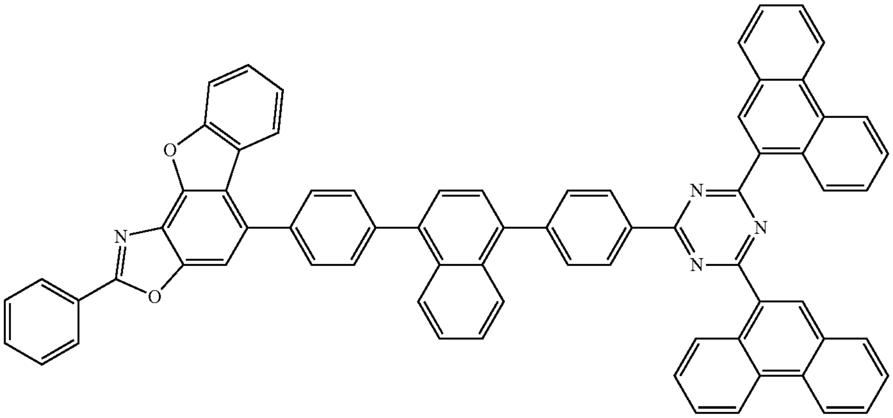
F45
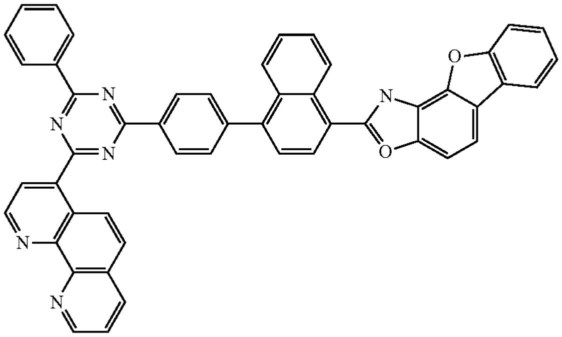
F46
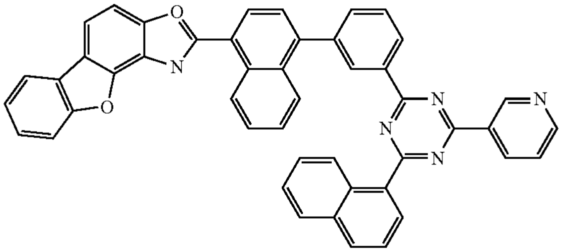
F47
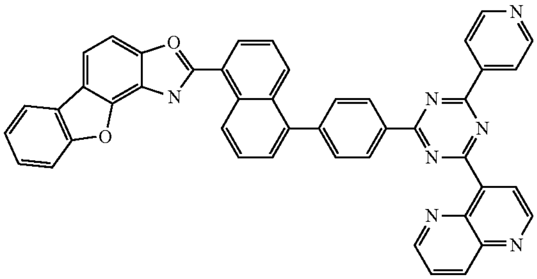
and
F48
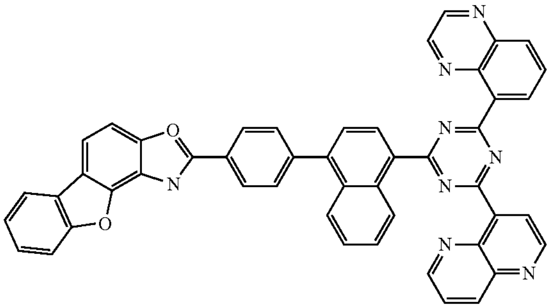
.
* * * * *